United States Patent
Zhao et al.

(10) Patent No.: US 12,065,658 B2
(45) Date of Patent: Aug. 20, 2024

(54) STERILE MUTANT AND TWO LINE BREEDING SYSTEM

(71) Applicants: UWM Research Foundation, Inc., Milwaukee, WI (US); United States of America, As Represented by the Secretary of Agriculture, Washington, DC (US)

(72) Inventors: Dazhong Zhao, Whitefish Bay, WI (US); Zhanguo Xin, Lubbock, TX (US)

(73) Assignees: UWM Research Foundation, Inc., Milwaukee, WI (US); United States of America, As Represented by the Secretary of Agriculture, Washington, DC (US)

(*) Notice: Subject to any disclaimer, the term of this patent is extended or adjusted under 35 U.S.C. 154(b) by 783 days.

(21) Appl. No.: 16/959,928

(22) PCT Filed: Jan. 3, 2019

(86) PCT No.: PCT/US2019/012217
§ 371 (c)(1),
(2) Date: Jul. 2, 2020

(87) PCT Pub. No.: WO2019/136174
PCT Pub. Date: Jul. 11, 2019

(65) Prior Publication Data
US 2021/0130844 A1    May 6, 2021

Related U.S. Application Data

(60) Provisional application No. 62/613,305, filed on Jan. 3, 2018.

(51) Int. Cl.
*C12N 15/82* (2006.01)

(52) U.S. Cl.
CPC .................. *C12N 15/8289* (2013.01)

(58) Field of Classification Search
None
See application file for complete search history.

(56) References Cited

U.S. PATENT DOCUMENTS

| | | |
|---|---|---|
| 4,945,050 A | 7/1990 | Sanford et al. |
| 5,240,855 A | 8/1993 | Tomes |
| 5,322,783 A | 6/1994 | Tomes et al. |
| 5,324,646 A | 6/1994 | Buising et al. |
| 5,563,055 A | 10/1996 | Townsend et al. |
| 5,736,369 A | 4/1998 | Bowen et al. |
| 5,750,867 A | 5/1998 | Williams et al. |
| 5,879,918 A | 3/1999 | Tomes et al. |
| 5,886,244 A | 3/1999 | Tomes et al. |
| 5,932,782 A | 8/1999 | Bidney |
| 5,981,840 A | 11/1999 | Zhao et al. |
| 2006/0015968 A1 | 1/2006 | Albertsen et al. |
| 2014/0215647 A1* | 7/2014 | Lenz ............... A01H 6/4666 800/278 |
| 2014/0234930 A1* | 8/2014 | Portereiko ......... C12N 15/8289 800/303 |
| 2015/0315607 A1 | 11/2015 | Ko et al. |
| 2016/0040184 A1 | 2/2016 | Cong et al. |

FOREIGN PATENT DOCUMENTS

| | | |
|---|---|---|
| CN | 104611364 A | 5/2015 |
| WO | WO2019136174 A2 | 7/2019 |

OTHER PUBLICATIONS

Xin et al. Morphological Characterization of a New and Easily Recognizable Nuclear Male Sterile Mutant of Sorghum (Sorghum bicolor). PLoS One, Jan. 4, 2017;12(1):e0165195. (Year: 2017).*
Akiba T, et al. "Organ fusion and defective shoot development in oni3 mutants of rice," Plant Cell Physiol 55(1):42-51, (2014).
Allen RL, et al., "Molecular characterization of one of the maize polygalacturonase gene family members which are expressed during late pollen development," Plant J 3(2):261-271, (1993).
Altschul et al., "Gapped BLAST and PSI-BLAST: a new generation of protein database search programs," Nucl. Acids Res. 25: 3389-3402 (1997).
Andrews DJ, et al., "A new factor for genetic male sterility in Sorghum bicolor (L.) Moench," Crop Sci. 1971; vol. 11, 308-9.
Aoyama T, et al., "A glucocorticoid-mediated transcriptional induction system in transgenic plants," Plant J. 1997;11(3):605-12.
Ariizumi T, et al., "Genetic regulation of sporopollenin synthesis and pollen exine development," Annu Rev Plant Biol 62:437-460, 2011.
Aya K, et al. "Gibberellin modulates anther development in rice via the transcriptional regulation of GAMYB," Plant Cell 21(5):1453-1472, 2009.
Barabas Z. "Observation of sex differentiation in sorghum by use of induced male-sterile mutants," Nature. 1962;195:257-9.
Budar F, et al., "Male sterility in plants: occurrence, determinism, significance and use," Life Sci. 2001; 324:543-50.
Bytebier et al., "T-DNA organization in tumor cultures and transgenic plants of the monocotyledon Asparagus officinalis," Proc. Natl. Acad. Sci. USA 84:5345-5349 (1987).
Casa, et al. "Community resources and strategies for association mapping in sorghum," Crop Sci. 2008;48:30-40.
Chang et al., "Construction of a male sterility system for hybrid rice breeding and seed production using a nuclear male sterility gene," PNAS, Dec. 2016, 113(49):14145-14150.
Chen L, et al., "Male sterility and fertility restoration in crops," Annu Rev Plant Biol 65:579-606, (2014).
Chen L, et al., "Thoughts and practice on some problems about research and application of two-line hybrid rice," Rice Science 18(2):79-85, (2011).
Chen Z, et al. "Cloning of a rice male sterility gene by a modified MutMap method," Hereditas (Beijing) 36(1):85-93 (2014).

(Continued)

*Primary Examiner* — Cynthia E Collins
(74) *Attorney, Agent, or Firm* — Michael Best & Friedrich LLP

(57) ABSTRACT

Disclosed herein are nuclear male sterile sorghum mutants, three-component genetic constructs, and methods of using said mutants and genetic constructs, such as in a two-line male sterility system for hybrid breeding.

17 Claims, 21 Drawing Sheets

Specification includes a Sequence Listing.

(56) References Cited

OTHER PUBLICATIONS

Cheng SH, et al., "Progress in research and development on hybrid rice: A super-domesticate in China," Ann Bot (Lond) 100(5):959-966, (2007).
Christou et al., "Parameters influencing stable transformation of rice immature embryos and recovery of transgenic plants using electric discharge particle acceleration," Annals of Botany 75:407-413 (1995).
Christou et al., "Stable Transformation of Soybean Callus by DNA-coated Gold Particles," Plant Physiol. 87:671-674 (1988).
Clément C, et al., "Anther plastids in angiosperms," The Botanical Review. 2001;67(1):54-73, retrieved from Gale Academic OneFile.
Crossway et al., "Micromanipulation techniques in plant biotechnology," Biotechniques 4:320-334 (1986).
Datta et al., "Genetically Engineered Fertile Indica-Rice Recovered from Protoplasts," Biotechnology 8: 736-740(1990).
De Siqueira Ferreira S, et al., "Biofuel and energy crops: high-yield Saccharinae take center stage in the post-genomics era," Genome Biol. 2013;14:210.
De Storme N, et al., "The impact of environmental stress on male reproductive development in plants: biological processes and molecular mechanisms," Plant Cell Environ. 2014;37(1):1-18.
D'Halluin et al., "Transgenic Maize Plants by Tissue Electroporation," Plant Cell 4: 1495-1505 (1992).
Ding J, et al. "A long noncoding RNA regulates photoperiod-sensitive male sterility, an essential component of hybrid rice," Proc Natl Acad Sci USA, 2012, 109(7):2654-2659.
Ding J, et al. "Validation of a rice specific gene, sucrose phosphate synthase, used as the endogenous reference gene for qualitative and real-time quantitative PCR detection of transgenes," J Agric Food Chem., 2004, 52(11):3372-3377.
Dong NV, et al. "Molecular mapping of a rice gene conditioning thermosensitive genic male sterility using AFLP, RFLP and SSR techniques," Theor Appl Genet. 2000, 100:727-34.
Dudley JW, et al. "Effects of Random Mating on Marker—QTL Associations in the Cross of the Illinois High Protein × Illinois Low Protein Maize Strains," Crop Sci. 2004;44(4), 1419-1428.
Ellstrand NC, et al., "Impact of population structure on the apparent outcrossing rate of grain sorghum (Sorghum bicolor)," Theor Appl Genet. 1983;66(3):323-7.
Fang Y, et al. "Identification and characterization of Mini1, a gene regulating rice shoot development," J Integr Plant Biol, 2015, 57(2):151-161.
Finer et al., "Transformation of Soybean via Particle Bombardment of Embryogenic Suspension Culture Tissue," In Vitro Cell Dev. Biol. 27P: 175-182 (1991).
Fromm et al., "Inheritance and Expression of Chimeric Genes in the Progeny of Transgenic Maize Plants," Biotechnology 8:833-839 (1990).
Goldberg RB, et al., "Anther development: basic principles and practical applications," Plant Cell. 1993;5(10):1217-29.
Guo JX, et al., "Molecular control of male reproductive development and pollen fertility in rice," J Integr Plant Biol, 2012, 54(12):967-978.
Hejátko J, et al. "In situ hybridization technique for mRNA detection in whole mount *Arabidopsis* samples," Nat Protoc, 2006, 1(4):1939-1946.
Hiei Y, et al., "Efficient transformation of rice (*Oryzasativa* L.) mediated by Agrobacterium and sequence analysis of the boundaries of the T-DNA," Plant J, 1994, 6(2):271-282.
Hooykaas-Van Slogteren et al., "Expression of Ti plasmid genes in monocotyledonous plants infected with Agrobacterium tumefaciens," Nature (London) 311 763-764 (1984).
Hsieh K, et al., "Tapetosomes in Brassica tapetum accumulate endoplasmic reticulum-derived flavonoids and alkanes for delivery to the pollen surface," Plant Cell. 2007;19(2):582-96.
Huang J, et al., "Creating completely both male and female sterile plants by specifically ablating microspore and megaspore mother cells," Front Plant Sci. 2016;7.
Huang JZ, et al., "Workable male sterility systems for hybrid rice: Genetics, biochemistry, molecular biology, and utilization," Rice, 2014, 7:13.
Huang, et al. (2016) Control of Anther Cell Differentiation by the Small Protein Ligand TPD1 and Its Receptor EMS1 in *Arabidopsis*. PLoS Genet 12(8): e1006147.
International Preliminary Report on Patentability for Application No. PCT/US2019/012217 dated Jul. 16, 2020 (9 pages).
International Search Report and Written Opinion for Application No. PCT/US2019/012217 dated Aug. 19, 2019 (14 pages).
Ishida, et al., "High efficiency transformation of maize (*Zea mays* L.) mediated by Agrobacterium tumefaciens," Nature Biotechnology 14:745-750 (1996).
Ishiguro S, et al., "The Defective in Anther Dehiscence1 Gene Encodes a Novel Phospholipase A1 Catalyzing the Initial Step of Jasmonic Acid Biosynthesis, Which Synchronizes Pollen Maturation, Anther Dehiscence, and Flower Opening in *Arabidopsis*," The Plant Cell., 2001, 13:2191-2209.
Jia G, et al., "Signaling of cell fate determination by the TPD1 small protein and EMS1 receptor kinase," Proc Natl Acad Sci, 2008;105(6):2220-5.
Jordan DR, et al., "Mapping and characterization of Rf 5: A new gene conditioning pollen fertility restoration in A 1 and A 2 cytoplasm in sorghum (Sorghum bicolor (L.) Moench)," Theor Appl Genet. 2011;123(3):383-96.
Kaeppler et al., "Silicon carbide fiber-mediated DNA delivery into plant cells," Plant Cell Reports 9:415-418 (1990).
Kaeppler et al., "Silicon carbide fiber-mediated stable transformation of plant cells," Theor. Appl. Genet. 84: 560-566 (1992).
Kalla R, et al. "The promoter of the barley aleurone-specific gene encoding a putative 7 kDa lipid transfer protein confers aleurone cell-specific expression in transgenic rice," Plant J 6(6):849-860, (1994).
Karlin, "Methods for assessing the statistical significance of molecular sequence features by using general scoring schemes," Proc. Natl. Acad. Sci. USA vol. 87, pp. 2264-2268, Mar. 1990.
Klein et al., "Factors Influencing Gene Delivery into *Zea mays* Cells by High-Velocity microprojectiles," Biotechnology 6:559-563 (1988).
Klein et al., "Genetic Transformation of Maize Cells by Particle Bombardment," Plant Physiol. 91:440-444 (1989).
Klein et al., "Transfer of foreign genes into intact maize cells with high-velocity microprojectiles," Proc. Natl. Acad. Sci. USA 85:4305-4309 (1988).
Kurdyukov S, et al. "Genetic and biochemical evidence for involvement of Hothead in the biosynthesis of long-chain α-, ω-dicarboxylic fatty acids and formation of extracellular matrix," Planta 224(2):315-329, (2006).
Kyte et al, "A Simple Method for Displaying the Hydropathic Character of a Protein," J. Mol. Biol. 157: I05-132 (1982).
Lee SB, et al., "Advances in the understanding of cuticular waxes in *Arabidopsis thaliana* and crop species," Plant Cell Rep 34(4):557-572, (2015).
Li et al., "An improved rice transformation system using the biolistic method," Plant Cell Reports 12:250-255 (1993).
Li H, et al. "Cytochrome P450 family member CYP704B2 catalyzes the ω-hydroxylation of fatty acids and is required for anther cutin biosynthesis and pollen exine formation in rice," Plant Cell 22:173-190, (2010).
Li N, et al. "The rice tapetum degeneration retardation gene is required for tapetum degradation and anther development," Plant Cell 18(11):2999-3014, (2006).
Liu YG, et al., "High-efficiency thermal asymmetric interlaced PCR for amplification of unknown flanking sequences," Biotechniques 43(5):649-656, (2007).
Lochlainn SO, et al. "High Resolution Melt (HRM) analysis is an efficient tool to genotype EMS mutants in complex crop genomes," Plant Methods 7:43, (2011). Retrieved from Gale Academic OneFile.
Mariani C, et al., "Induction of male sterility in plants by a chimaeric ribonuclease gene," Nature 374:737-741, (1990).
Matz MV, et al. "Fluorescent proteins from nonbioluminescent *Anthozoa* species," Nat Biotechnol 17:969-973, (1999).
McCabe et al., "Stable Transformation of Soybean (*Glycine max*) by Particle Acceleration," Biotechnology 6:923-926(1988).

(56) References Cited

OTHER PUBLICATIONS

McCormick et al., "Leaf disc transformation of cultivated tomato (*L. esculentum*) using Agrobacterium tumefaciens," Plant Cell Reports 5:81-84 (1986).
Morris GP, et al., "Population genomic and genome-wide association studies of agroclimatic traits in sorghum," Proc Natl Acad Sci USA. 2013;110(2):453-8.
Pacini E, et al., "The tapetum: Its form, function, and possible phylogeny in Embryophyta," Plant Syst Evol. 1985; vol. 149, No. 3-4, pp. 155-185.
Packer DJ, et al., "A comparison of inbred line and F1 testers for evaluating sorghum experimental lines in testcrosses," Field Crops Res. 2011;123:47-50.
Parish RW, et al., "Death of a tapetum: A programme of developmental altruism," Plant Sci. 2010;178:73-89.
Parish RW, et al., "Tapetal development and abiotic stress: a centre of vulnerability," Functional Plant Biology. 2012;39:553-9.
Paszkowski et al., "Direct Gene Transfer to Plants," EMBO Journal, 3(12):2717-2722 (1984).
Paterson AH, et al. "The Sorghum bicolor genome and the diversification of grasses," Nature. 2009;457(7229):551-6. Retrieved from Gale Academic OneFile.
Pearson, "Improved tools for biological sequence comparison," Proc. Natl. Acad. Sci. USA 85: 2444-2448, 1988.
Pedersen JF, et al., "Registration of N316-N320 Sorghum Nuclear Male-Sterility Genetic Stocks Joint contribution of the USDA-ARS and the Dep. of Agronomy," Univ. of Nebraska—Lincoln, as Journal Series Paper No. 12886. Registration by CSSA. Crop Sci. 2001;41(2), p. 607.
Perez-Prat E, et al., "Hybrid seed production and the challenge of propagating male-sterile plants," Trends Plant Sci 7(5):199-203, (2002).
Pérez-Vich B, et al., "Molecular mapping of nuclear male sterility genes in sunflower," Crop Sci. 2005;45(5):1851-7.
Praveen M, et al., "Inheritance and molecular mapping of Rf6 locus with pollen fertility restoration ability on A1 and A2 cytoplasms in sorghum," Plant Sci. 2015;238:73-80.
Recker JR, et al., "Analysis of Quantitative Traits in Two Long-Term Randomly Mated Soybean Populations: I. Genetic Variances," Crop Sci. 2013;53:1375.
Rhodes DH, et al., "Genome-wide association study of grain polyphenol concentrations in global sorghum [Sorghum bicolor (L.) Moench] germplasm," J Agric Food Chem. 2014;62:10916-27.
Riggs et al., "Stable transformation of tobacco by electroporation: Evidence for plasmid concatenation," Proc. Natl. Acad. Sc1. USA 83:5602-5606 (1986).
Rooney WL, et al., "Designing sorghum as a dedicated bioenergy feedstock," Biofuel Bioprod Bior. 2007; 1:147-57.
Rooney WL. "Sorghum Improvement-Integrating Traditional and New Technology to Produce Improved Genotypes," Adv Agron. 2004; 83: 37-109.
Samuels L, et al., "Sealing plant surfaces: Cuticular wax formation by epidermal cells," Annu Rev Plant Biol 59:683-707, (2008).
Sanford et al., "Delivery of substances into cells and tissues using a particle bombardment process," Particulate Science and Technology 5:1, 27-37 (1987).
Scott RJ, et al., "Stamen structure and function," Plant Cell. 2004;16 Suppl: S46-60.
Shan Q, et al. "Targeted genome modification of crop plants using a CRISPR-Cassystem," Nat Biotechnol 31(8):686-688, (2013).
Shi J, et al. (2011) Defective pollen wall is required for anther and microspore development in rice and encodes a fatty acyl carrier protein reductase. Plant Cell 23:2225-2246.
Shi J, et al., "Genetic and biochemical mechanisms of pollen wall development," Trends Plant Sci 20(11):741-753, (2015).
Shimada, et al. A non-destructive screenable marker, OsFAST, for identifying transgenic rice seeds. Plant Signal Behav. Oct. 2011, vol. 6, No. 10, pp. 1454-1456.
Singh et al., "Cytological characterization of transgenic soybean," Theor. Appl. Genet. 96: 319-324 (1998).

Sullivan TD, et al., "Analysis of maize brittle-1 alleles and a defective Suppressor-mutator-induced mutable allele," Plant Cell 3:1337-1348, (1991).
Tamura K, et al., "MEGA6: Molecular Evolutionary Genetics Analysis version 6.0," Mol Biol Evol 30(12):2725-2729, (2013).
Tang X, et al., "Pistil-specific and ethylene-regulated expression of 1-aminocyclopropane-1-carboxylate oxidase genes in petunia flowers," Plant Cell 6:1227-1239, (1994).
Ullstrup AJ. The Impacts of the Southern Corn Leaf Blight Epidemics of 1970-1971. Annu Rev Phytopathol. 1972; 10:37-50.
Upadhyaya HD, et al., "Developing a Mini Core Collection of Sorghum for Diversified Utilization of Germplasm," Crop Sci. 2009;49:1769-80.
Walbot V, et al., "Pre-Meiotic Anther Development: Cell Fate Specification and Differentiation," Annu Rev Plant Biol. 2016;67:365-95.
Weising, et al., "Foreign Genes in Plants: Transfer, Structure, Expression, and Applications," Annual review of genetics, 1988, vol. 22, p. 421-477.
Wongnate T, et al., "The substrate oxidation mechanism of pyranose 2-oxidase and other related enzymes in the glucose-methanol-choline superfamily," FEBS J 280:3009-3027, (2013).
Wu Y, et al. "Development of a novel recessive genetic male sterility system for hybrid seed production in maize and other cross-pollinating crops," Plant Biotechnol J 14:1046-1054, (2016).
Xin et al., "Morphological Characterization of a New and Easily Recognizable Nuclear Male Sterile Mutant of Sorghum (Sorghum bicolor)," PLOS One, Jan. 2017, 12(1):e0165195.
Xin Z, et al. "Applying genotyping (Tilling) and phenotyping analyses to elucidate gene function in a chemically induced sorghum mutant population," BMC Plant Biol. 2008; 8:103.
Xin Z, et al., "Gene mutagenesis systems and resources for the Saccharinae," In: Jorgensen RA, editor. Plant genetics and genomics. Genomics of the Saccharinae. New York: Springer; 2012., chp. 8, p. 169-85.
Xu X, et al., "Progress and discussion in breeding of indica rice CMS lines in China," Chin Agr Sci Bul 3:176-180, (2007).
Yan, et al. Functional architecture of two exclusively late stage pollen-specific promoters in rice (*Oryza sativa* L.). Plant Mol Biol. 2015, vol. 88, pp. 415-428.
Zhang D, et al., "Cytological analysis and genetic control of rice anther development," J Genet Genomics 38:379-390, (2011).
Zhang D, et al., "Specification of tapetum and microsporocyte cells within the anther," Curr Opin Plant Biol. 2014; 17:49-55.
Zhang H, et al. "Mutation in CSA creates a new photoperiod-sensitive genic male sterile line applicable for hybrid rice seed production," PNAS, 2013;110(1):76-81.
Zhang H, et al., "Carbon starved anther encodes a MYB domain protein that regulates sugar partitioning required for rice pollen development," Plant Cell. 2010; 22:672-89.
Zhang W, et al., "Regulation of *Arabidopsis* tapetum development and function by Dysfunctional Tapetum1 (DYT1) encoding a putative bHLH transcription factor," Development. 2006;133(16):3085-95.
Zhang, et al. Construction of a multicontrol sterility system for a maize male-sterile line and hybrid seed production based on the ZmMs7 gene encoding a PHD finger transcription factor, Plant Biotechnol J., 2018, vol. 16, pp. 459-471.
Zhao D., "Control of anther cell differentiation: a teamwork of receptor-like kinases," Sex Plant Reprod. 2009;22:221-8.
Zhao DZ, et al., "The excess microsporocytes1 gene encodes a putative leucine-rich repeat receptor protein kinase that controls somatic and reproductive cell fates in the *Arabidopsis* anther," Genes Dev. 2002;16:2021-31.
Zhao G, et al. "Two ATP binding cassette G transporters, rice ATP Binding Cassette G26 and ATP Binding Cassette G15, collaboratively regulate rice male reproduction," Plant Physiol 169:2064-2079, (2015).
Zhou D, et al. "Pedigree-based analysis of derivation of genome segments of an elite rice reveals key regions during its breeding," Plant Biotechnol J 14:638-648, (2016).

(56) References Cited

OTHER PUBLICATIONS

Zhou H, et al. "Photoperiod- and thermo-sensitive genic male sterility in rice are caused by a point mutation in a novel noncoding RNA that produces a small RNA," Cell Res 22(4):649-660, (2012).

Zhou H, et al. "RNase Z(S1) processes UbL40 mRNAs and controls thermosensitive genic male sterility in rice," Nat Commun 5:4884, (2014).

\* cited by examiner

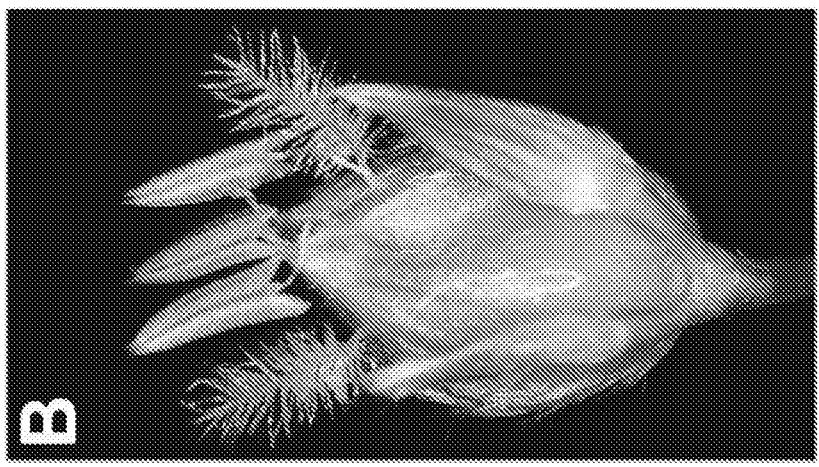 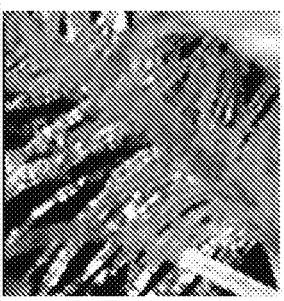
FIG. 3B
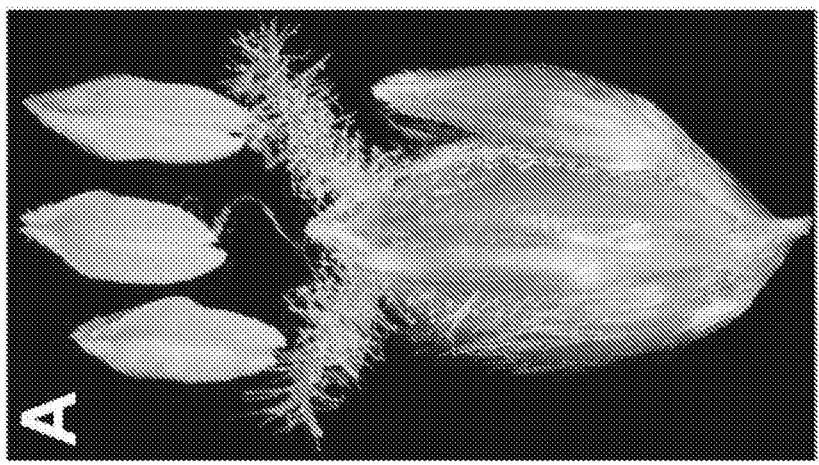 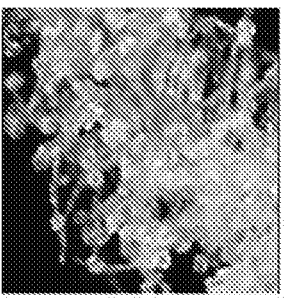
FIG. 3A

```
MS8      MIKGSYPDGSHDRIIMFGSMTHDSSQSSI-YDNTDVEQQMERLAPFTIEDHSMPAMLTS
OsEAT1   MIVGAGYFEDSHDQSLMAGSLIHDSMQAPASSENTSIDLQKEKVHPYSTEALSNTAMLA-
         **..*.****.***:**:.** **::*****    *     *        *      :

MS8      EEARKVIEQIIEHQLGIDMEQDHSDHMIQGVEPAETAMLVPVYGVQDRILSHQI-EGEHNI
OsEAT1   EEARKAIEHLCHQLEIDLEQ------EVPEVETAMWDPAICTIPDHIIMHQFSEDFQHI
         *****:::::**** **:**      :**.******  *.: :*.:*::.**  .*.:*

MS8      TVEQNLEYDEASYGMSTYAAAHDILNSLQIQRCSLIFEFPSTEHIFEGDPAQMMVMELDI
OsEAT1   LVEQQIEQYDSALYPKGVTTPAPDLLML----MQCTMAPAFPATSVFEGDTTLMGTEYLDI
         **:*::* :*:* * . ..   .*:::*    :*   .* *.*:::***    :  :**

MS8      IMDILGYATH----ESGMM-FSDSTLPLGYHATQSHMLKDLYESLPQMYGIFTSDDERDGM
OsEAT1   NGRLITSVAAVPDSGSSGIMFASDSALQLGYHGTQSHLIKDICHSLPQMYGLPFTSEDEREVI
          :.:: . *:    *. .: *:***:*:*** ****::**: .******:  :*.:**:.:

MS8      VSVAGVSGMIRQEIDGEQTQSFVLGTERQQGGFSKGKGKAMFATEERREQLMVYGALR
OsEAT1   IGVG--SGDLFQEIDDROPDS-VIECERGKGEFGKGKGKANFATEKERREQLNVKFPTLR
         :.*.  **:::****..:*.  *:    .*.* *******:*****:******:* .**

MS8      SLIFMPIAMDRASIVGDAIDYIMELMRTVELKTILLERKEMSTDRRKTIELDEEAADGEE
OsEAT1   MLFEMFTEMDRASIVGDAIEYIDELMRTVKELMIIVEQKEHGMHRREVLKLDQERALDGEE
         .*.: *  ***********:** ******:* :::::** .. ** ::.**:*.  *******

MS8      SSSMIPVSPVQNHDHMCAIESSSWVQERSKECQVDVRIVDQEINIKFETEKKRANSLLCAAK
OsEAT1   SSSMRPVTRDQDMQLHGAIESSSWVQERSKECHVDVRIVDDEVMLKLTEKKKANSLIRAAK
         ****.**:  :::  ..*************::*******:*::::: ***::****: ***

MS8      VLEEFRLELIHVVGGIIGDEHIFMFMTKIPKGSSVYACAVAKKLLEAVEIKKCQALMIFM*
OsEAT1   VLEEVQLELIHVVGGIIGDHIEMFNTKVSEGSAVYACAVAKKLLQAVDVQHQALDIFM*
         ****.*************::*:* **:.:**:************:**::: *** ***
```

FIG. 7

```
SbTDR    MGGG--------GHSCVAAAGDGAGASMEAALRTLVGVDAWDYCIYWRLSPDQRFLEMTG
OsTDR    MGRQDRLLMKNSNAAAAAAVNGGGTSLDAALRPLVGSDGWDYCIYWRLSPDQRFLEMTG
         **  *       , :,,*** ;*,*:*::**** *** *,*******************

SbTDR    FCCSSEFRAQLSALGDLPPSIQLDSSSAGMHAEAMVSNQPIWQSSRVSELQTSYSSEPIG
OsTDR    FCCSSELRAQVSALLDLPSSIPLDSSSIGMHAQALLSNQPIWQSSSER--------ERAD
         ******:***;*** *** ** ***** ****;*;:**********          *  ,

SbTDR    SGGGPRTRLLVPVAGGLVELFAARYMAERQMAELVMAQCGVPGGAEAGEGGGGVHAWQP
OsTDR    GGGGAKTRLLVPVAGGLVELFASRYMAEREQMAELVMAQCGGGGAGDDGGGQAWPPPETP
         .*** ;****************;******;*********** *.,;  *  * .    *

SbTDR    GFAWDGAADASRGMMYGGAAVPPSLGLFDAAGSVAADPFQAVVVQQAPGAGGGGG------
OsTDR    SFQWDGGADAQR-LMYGGSS-----LNLFDAAAA-DDDPF-----------LGGGGGDAVGD
         .* ***,***,*  ;****;;     *,*****,;    ***           *****

SbTDR    ---VDDAGWQYAAAAAAAGSELAAVQQEPQPQPQPRGADSGSEGSDMQ-VDPEDDGDGDG
OsTDR    EAAAAGAWPYAGMAVSEPSVA--VAQEQMQHAAGGGVAEESGSEGRKLHGGDPEDDGD---
             ,,* **,*,; *   * **         *;*****  ;;;  *******

SbTDR    DVDAQERGGGGGGGKGGGKRQQCKHLVAERRRRKKLNDRLYKLRSLVPNISKMDRASILG
OsTDR    ----------GEGRSGGAKRQQCKHLEAERKRRKKLNGHLYKLRSLVPNITKMDRASILG
                   * *  ,**,******** ***;*****,;***********;*********

SbTDR    DAIDYIVGLQMQVKALQDELEDPA-DGGAFDVLLDHPPASLVGLENDDSPRTSHHL----
OsTDR    DAIDYIVGLQKQVKELQDELEDNEVHHKPPDVLIDHPPASLVGLNDQASPPNSHQQQF
         **********;*** ******    ,  ;****;***********;***;  , *

SbTDR    ---PLAGSKRSRAAV-----------QAAEREKGHDMEPQVEVRQVRANEFFIQMLCERKPGRF
OsTDR    PLAVSGSSSRRSHKDPAMTDDKVGGGGGGHRMEPQLEVRQVQGNELPVQVLWEHKPGGF
            ;:**,  *;           ,, ** ****;*****;;**;*;;* *;*** *

SbTDR    VQIMDSIAALGLEVTNVNVTSHESLVLNVFRAABRDSEVAVQADRVRDSLLEVTREPY-G
OsTDR    VRLMDAMNALGLEVINVNVTTYKTLVLNVFRVMVRDSEVAVQADRVRDSLLEVTRETYPG
         *;;**;; ****** ***** ;;;*******, ********************** * *

SbTDR    VWSSAAPPVGVQMSGGGIVDVKLDGVDVKLDGIIDGQAAPGVAVA------VGEDQYGGYNH
OsTDR    VWPSPQEEDDAK-------------------FDGGDGGQAAAAAAAAGGERYHDEVGGGYRQ
         ** *   ,,                       ;**  ,****  ,* ,*    ;;  ***;;

SbTDR    LLQYLA*--
OsTDR    HLSYLAFD*
         ** ****
```

FIG. 8

>Sb04G030850 cDNA:KNOWN_protein_coding
ATGATTGCTGGGGGAGGCTATTTTGATGGTTCTCATGATCATATTCTCATGGAAGGATCG
ATGATCCATGATTCTTCCAATCTTCCATCTATGACAATACAGATGTTGAACAGCAGAAC
TTCAGACTTGCGCCCTTTATCATAGAAGATCACTCCAATCCAGCCAACCTTACCTCTGAG
CCTGCAAGGGTGATCGACCAAATTCATCACCAGCTTGGGATTGACATGGAGCAGGACCAT
AGTGATCACATGATCCAAGGAGTTCCTCCAGCAGAAACTGCAAATTTAGTTCCTGTTGTC
TATGGTGTCCAAGATCGTATCCTCAGCCACCAGATAGAAGGTCCACATAACATAACTGTG
GAACAACAGGTCCTGGACTACGACCCTGCATCATATGGAAATGGCACTTATGCAGCTGCA
CATGATCTTCTAAATTCTACAGATCCAAAGGTGCAGTTTGATTCCTGAATTTCCTTCG
ACAGAACATATCTTTGGTGATCCAGCACAGAACATGGTCAATCCTTTGGACATTACCAAT
GACCTTCAAGGAGTAGCAACTCATGAAAGTGGAATGATGTTCAGCGATTCAACTCTACCA
TTAGGTATCATGCTACTCAATCTCATATGTTGAAGGATCTCTATCATTCACTACCACAA
AACTATGGATATTTACCAGTGATGATGAGAGAGATGGGATGGTCGGGGTAGCAGGGGTC
TCAGGAAATATTTTCCAGGAGATAGATGGGAGACAGTTCGACAGCCCAGTACTGGGGACT
AGAAGACAGAAAGGTGGATTTGGCAAGGGCAAGGGAAAAGCTAACTTTGCAACTGAAAGA
GAGAGGAGGGAGCAGCTAAATGTGAAGTATGGGCTTTAAGATCACTGTTCCCAAACCCT
ACTAAGAATGACAGGGCCTCTATAGTTGGAGATGCCATTGACTACATCAATGAGCTTAAT
AGAACAGTGAAAGAACTGAAGATCTTACTGGAAAAGAAGAGGAACAGCACTGACAGGAGG
AAGATACTGAAGTTGGATGATGAAGCAGCTGATGATGGGGAAAGCTCTTCAATGCAGCCA
GTAAGTGATGACCAAAACAATCAGATGAATGGGGCTATAAGGAGCTCCTGGGTTCAAAGA
AGGTCCAAGGAGTGCGATGTTGATGTCCGCATAGTTGATGATGAAATAAATATCAAGTTC
ACAGAGAAGAAGAGAGCCAACTCTTTGCTTTGTGCTGCAAAGGTTCTAGAGGAGTTTCGT
CTTGAGCTCATCCATGTTGTTGGGGGAATCATAGGAGATCACCATATATTCATGTTCAAT
ACAAAGATACCTAAGGGCTCTTCGGTGTACGCGTGCGCGGTGGCTAAGAAGCTCCTTGAA
GCTGTGGAGATAAAGAAGCAGGCTCTTAATATCTTCAACTAG

FIG. 9A

```
Sb04G030850 peptide: Sb04g030850.1 pep:KNOWN_protein_coding

MIAGGGYEDGSHDHILMEGSMIHDSQSSIYDMTDVEQQNERLAPFIEDHSMPANLTSE
PARVIDQIHHQLGIDMEQDHSDHMIQGVPPAETANLVPVYGVQDRILSHQIEGPHNITV
EQQVLDYDPASYGNGTYAAAHDLLNSLQIQRCSLIPEFPSTEHIFGDPAQMMVNPLDITN
                       *  *
DLQGVATHESGMMFSDSTLPLGYHATQSHMLKDLYHSLPQNYGIFTSDDERDGMVGVAGV
SGNIFQEIDGRQFDSPVLGTRRQKGGFGKGKGKANPATERERREQLNVKYGALRSLFPNP
TKNDRASIVGDAIDYINELNRTVKELKILLEKKRNSTDRKKILKLDDEAADDGESSSMQP
VSDDQNNQMNGAIRSSWVQRRSKECDVDVRIVDDEINIKFTEKKRANSLLCAAKVLEEFR
LELIHVVGGIIGDHHIFMFMNTKIPKGSSVIACAVAKKLLEAVEIKKQALNIFM
```

FIG. 9B

SEQUENCE LISTING

<160> NUMBER OF SEQ ID NOS: 35

<210> SEQ ID NO 1
<211> LENGTH: 473
<212> TYPE: PRT
<213> ORGANISM: Sorghum bicolor

<400> SEQUENCE: 1

```
Met Ile Ala Gly Gly Gly Tyr Phe Asp Gly Ser His Asp His Ile Leu
1               5                   10                  15

Met Glu Gly Ser Met Ile His Asp Ser Ser Gln Ser Ser Ile Tyr Asp
            20                  25                  30

Asn Thr Asp Val Glu Gln Gln Asn Phe Arg Leu Ala Pro Phe Ile Ile
        35                  40                  45

Glu Asp His Ser Asn Pro Ala Asn Leu Thr Ser Glu Pro Ala Arg Val
    50                  55                  60

Ile Asp Gln Ile His His Gln Leu Gly Ile Asp Met Glu Gln Asp His
65                  70                  75                  80

Ser Asp His Met Ile Gln Gly Val Pro Pro Ala Glu Thr Ala Asn Leu
                85                  90                  95

Val Pro Val Val Tyr Gly Val Gln Asp Arg Ile Leu Ser His Gln Ile
            100                 105                 110

Glu Gly Pro His Asn Ile Thr Val Glu Gln Gln Val Leu Asp Tyr Asp
        115                 120                 125

Pro Ala Ser Tyr Gly Asn Gly Thr Tyr Ala Ala Ala His Asp Leu Leu
    130                 135                 140

Asn Ser Leu Gln Ile Gln Arg Cys Ser Leu Ile Pro Glu Phe Pro Ser
145                 150                 155                 160

Thr Glu His Ile Phe Gly Asp Pro Ala Gln Asn Met Val Asn Pro Leu
                165                 170                 175

Asp Ile Thr Asn Asp Leu Gln Gly Val Ala Thr His Glu Ser Gly Met
            180                 185                 190

Met Phe Ser Asp Ser Thr Leu Pro Leu Gly Tyr His Ala Thr Gln Ser
        195                 200                 205

His Met Leu Lys Asp Leu Tyr His Ser Leu Pro Gln Asn Tyr Gly Ile
    210                 215                 220

Phe Thr Ser Asp Asp Glu Arg Asp Gly Met Val Gly Val Ala Gly Val
225                 230                 235                 240

Ser Gly Asn Ile Phe Gln Glu Ile Asp Gly Arg Gln Phe Asp Ser Pro
                245                 250                 255

Val Leu Gly Thr Arg Arg Gln Lys Gly Gly Phe Gly Lys Gly Lys Gly
            260                 265                 270

Lys Ala Asn Phe Ala Thr Glu Arg Glu Arg Arg Glu Gln Leu Asn Val
        275                 280                 285

Lys Tyr Gly Ala Leu Arg Ser Leu Phe Pro Asn Pro Thr Lys Asn Asp
    290                 295                 300

Arg Ala Ser Ile Val Gly Asp Ala Ile Asp Tyr Ile Asn Glu Leu Asn
305                 310                 315                 320

Arg Thr Val Lys Glu Leu Lys Ile Leu Leu Glu Lys Lys Arg Asn Ser
                325                 330                 335

Thr Asp Arg Arg Lys Ile Leu Lys Leu Asp Asp Glu Ala Ala Asp Asp
            340                 345                 350

Gly Glu Ser Ser Ser Met Gln Pro Val Ser Asp Asp Gln Asn Asn Gln
        355                 360                 365
```

```
Met Asn Gly Ala Ile Arg Ser Ser Trp Val Gln Arg Arg Ser Lys Glu
            370                 375                 380

Cys Asp Val Asp Val Arg Ile Val Asp Glu Ile Asn Ile Lys Phe
385                 390                 395                 400

Thr Glu Lys Lys Arg Ala Asn Ser Leu Leu Cys Ala Ala Lys Val Leu
                405                 410                 415

Glu Glu Phe Arg Leu Glu Leu Ile His Val Val Gly Gly Ile Ile Gly
                420                 425                 430

Asp His His Ile Phe Met Phe Asn Thr Lys Ile Pro Lys Gly Ser Ser
            435                 440                 445

Val Tyr Ala Cys Ala Val Ala Lys Lys Leu Leu Glu Ala Val Glu Ile
450                 455                 460

Lys Lys Gln Ala Leu Asn Ile Phe Asn
465                 470

<210> SEQ ID NO 2
<211> LENGTH: 464
<212> TYPE: PRT
<213> ORGANISM: Oryza Sativa

<400> SEQUENCE: 2

Met Ile Val Gly Ala Gly Tyr Phe Glu Asp Ser His Asp Gln Ser Leu
1               5                   10                  15

Met Ala Gly Ser Leu Ile His Asp Ser Asn Gln Ala Pro Ala Ser Ser
                20                  25                  30

Glu Asn Thr Ser Ile Asp Leu Gln Lys Phe Lys Val His Pro Tyr Ser
            35                  40                  45

Thr Glu Ala Leu Ser Asn Thr Ala Asn Leu Ala Glu Ala Ala Arg Ala
50                  55                  60

Ile Asn His Leu Gln His Gln Leu Glu Ile Asp Leu Glu Gln Glu Val
65                  70                  75                  80

Pro Pro Val Glu Thr Ala Asn Trp Asp Pro Ala Ile Cys Thr Ile Pro
                85                  90                  95

Asp His Ile Ile Asn His Gln Phe Ser Glu Asp Pro Gln Asn Ile Leu
            100                 105                 110

Val Glu Gln Gln Ile Gln Gln Tyr Asp Ser Ala Leu Tyr Pro Asn Gly
        115                 120                 125

Val Tyr Thr Pro Ala Pro Asp Leu Leu Asn Leu Met Gln Cys Thr Met
    130                 135                 140

Ala Pro Ala Phe Pro Ala Thr Thr Ser Val Phe Gly Asp Thr Thr Leu
145                 150                 155                 160

Asn Gly Thr Asn Tyr Leu Asp Leu Asn Gly Glu Leu Thr Gly Val Ala
                165                 170                 175

Ala Val Pro Asp Ser Gly Ser Gly Leu Met Phe Ala Ser Asp Ser Ala
            180                 185                 190

Leu Gln Leu Gly Tyr His Gly Thr Gln Ser His Leu Ile Lys Asp Ile
        195                 200                 205

Cys His Ser Leu Pro Gln Asn Tyr Gly Leu Phe Pro Ser Glu Asp Glu
    210                 215                 220

Arg Asp Val Ile Ile Gly Val Gly Ser Gly Asp Leu Phe Gln Glu Ile
225                 230                 235                 240

Asp Asp Arg Gln Phe Asp Ser Val Leu Glu Cys Arg Arg Gly Lys Gly
                245                 250                 255

Glu Phe Gly Lys Gly Lys Gly Lys Ala Asn Phe Ala Thr Glu Arg Glu
            260                 265                 270
```

```
Arg Arg Glu Gln Leu Asn Val Lys Phe Arg Thr Leu Arg Met Leu Phe
        275                 280                 285

Pro Asn Pro Thr Lys Asn Asp Arg Ala Ser Ile Val Gly Asp Ala Ile
290                 295                 300

Glu Tyr Ile Asp Glu Leu Asn Arg Thr Val Lys Glu Leu Lys Ile Leu
305                 310                 315                 320

Val Glu Gln Lys Arg His Gly Asn Asn Arg Arg Lys Val Leu Lys Leu
                325                 330                 335

Asp Gln Glu Ala Ala Ala Asp Gly Glu Ser Ser Met Arg Pro Val
                340                 345                 350

Arg Asp Asp Gln Asp Asn Gln Leu His Gly Ala Ile Arg Ser Ser Trp
        355                 360                 365

Val Gln Arg Arg Ser Lys Glu Cys His Val Asp Val Arg Ile Val Asp
    370                 375                 380

Asp Glu Val Asn Ile Lys Leu Thr Glu Lys Lys Lys Ala Asn Ser Leu
385                 390                 395                 400

Leu His Ala Ala Lys Val Leu Asp Glu Phe Gln Leu Glu Leu Ile His
                405                 410                 415

Val Val Gly Gly Ile Ile Gly Asp His His Ile Phe Met Phe Asn Thr
                420                 425                 430

Lys Val Ser Glu Gly Ser Ala Val Tyr Ala Cys Ala Val Ala Lys Lys
                435                 440                 445

Leu Leu Gln Ala Val Asp Val Gln His Gln Ala Leu Asp Ile Phe Asn
                450                 455                 460

<210> SEQ ID NO 3
<211> LENGTH: 571
<212> TYPE: PRT
<213> ORGANISM: Sorghum bicolor

<400> SEQUENCE: 3

Met Gly Gly Gly Gly His Ser Cys Val Ala Ala Ala Gly Asp Gly Ala
1               5                   10                  15

Gly Ala Ser Met Glu Ala Ala Leu Arg Thr Leu Val Gly Val Asp Ala
                20                  25                  30

Trp Asp Tyr Cys Ile Tyr Trp Arg Leu Ser Pro Asp Gln Arg Phe Leu
            35                  40                  45

Glu Met Thr Gly Phe Cys Cys Ser Ser Glu Phe Glu Ala Gln Leu Ser
    50                  55                  60

Ala Leu Gly Asp Leu Pro Pro Ser Ile Gln Leu Asp Ser Ser Ser Ala
65                  70                  75                  80

Gly Met His Ala Glu Ala Met Val Ser Asn Gln Pro Ile Trp Gln Ser
                85                  90                  95

Ser Arg Val Ser Glu Leu Gln Thr Ser Tyr Ser Ser Glu Pro Ile Gly
            100                 105                 110

Ser Gly Gly Gly Pro Arg Thr Arg Leu Leu Val Pro Val Ala Gly Gly
        115                 120                 125

Leu Val Glu Leu Phe Ala Ala Arg Tyr Met Ala Glu Glu Glu Gln Met
    130                 135                 140

Ala Glu Leu Val Met Ala Gln Cys Gly Val Pro Gly Gly Ala Glu Ala
145                 150                 155                 160

Gly Glu Gly Gly Gly Gly Val His Ala Trp Gln Pro Gly Phe Ala Trp
                165                 170                 175
```

```
Asp Gly Ala Ala Asp Ala Ser Arg Gly Met Met Tyr Gly Gly Ala Ala
            180                 185                 190

Val Pro Pro Ser Leu Gly Leu Phe Asp Ala Ala Gly Ser Val Ala Ala
            195                 200                 205

Asp Pro Phe Gln Ala Val Val Gln Gln Ala Pro Gly Ala Gly Gly
            210                 215                 220

Gly Gly Gly Val Asp Asp Ala Gly Trp Gln Tyr Ala Ala Ala Ala
225                 230                 235                 240

Ala Ala Gly Ser Glu Leu Ala Ala Val Gln Gln Pro Gln Pro Pro
                245                 250                 255

Gln Pro Gln Pro Arg Gly Ala Asp Ser Gly Ser Glu Gly Ser Asp Met
            260                 265                 270

Gln Val Asp Pro Glu Asp Asp Gly Asp Gly Asp Gly Asp Val Asp Ala
            275                 280                 285

Gln Gly Arg Gly Gly Gly Gly Gly Gly Lys Gly Gly Lys Arg
            290                 295                 300

Gln Gln Cys Lys Asn Leu Val Ala Glu Arg Arg Arg Lys Lys Leu
305                 310                 315                 320

Asn Asp Arg Leu Tyr Lys Leu Arg Ser Leu Val Pro Asn Ile Ser Lys
            325                 330                 335

Met Asp Arg Ala Ser Ile Leu Gly Asp Ala Ile Asp Tyr Ile Val Gly
            340                 345                 350

Leu Gln Asn Gln Val Lys Ala Leu Gln Asp Glu Leu Glu Asp Pro Ala
            355                 360                 365

Asp Gly Gly Ala Pro Asp Val Leu Leu Asp His Pro Pro Ala Ser
            370                 375                 380

Leu Val Gly Leu Glu Asn Asp Asp Ser Pro Arg Thr Ser His His Leu
385                 390                 395                 400

Pro Leu Ala Gly Ser Lys Arg Ser Arg Ala Ala Val Gln Ala Ala Glu
                405                 410                 415

Glu Glu Lys Gly His Asp Met Glu Pro Gln Val Glu Val Arg Gln Val
            420                 425                 430

Glu Ala Asn Glu Phe Phe Leu Gln Met Leu Cys Glu Arg Lys Pro Gly
            435                 440                 445

Arg Phe Val Gln Ile Met Asp Ser Ile Ala Ala Leu Gly Leu Glu Val
450                 455                 460

Thr Asn Val Asn Val Thr Ser His Glu Ser Leu Val Leu Asn Val Phe
465                 470                 475                 480

Arg Ala Ala Arg Arg Asp Ser Glu Val Ala Val Gln Ala Asp Arg Val
                485                 490                 495

Arg Asp Ser Leu Leu Glu Val Thr Arg Glu Pro Tyr Gly Val Trp Ser
            500                 505                 510

Ser Ala Ala Pro Pro Val Gly Val Gly Met Ser Gly Gly Ile Val
            515                 520                 525

Asp Val Lys Leu Asp Gly Val Asp Lys Leu Asp Gly Ile Ile Asp
            530                 535                 540

Gly Gln Ala Ala Pro Gly Val Ala Val Gly Glu Asp Gln Tyr
545                 550                 555                 560

Gly Gly Tyr Asn His Leu Leu Gln Tyr Leu Ala
            565                 570

<210> SEQ ID NO 4
<211> LENGTH: 552
```

<212> TYPE: PRT
<213> ORGANISM: Oryza Sativa

<400> SEQUENCE: 4

```
Met Gly Arg Gly Asp His Leu Leu Met Lys Asn Ser Asn Ala Ala Ala
1               5                   10                  15

Ala Ala Ala Ala Val Asn Gly Gly Thr Ser Leu Asp Ala Ala Leu
            20                  25                  30

Arg Pro Leu Val Gly Ser Asp Gly Trp Asp Tyr Cys Ile Tyr Trp Arg
        35                  40                  45

Leu Ser Pro Asp Gln Arg Phe Leu Glu Met Thr Gly Phe Cys Cys Ser
    50                  55                  60

Ser Glu Leu Glu Ala Gln Val Ser Ala Leu Leu Asp Leu Pro Ser Ser
65                  70                  75                  80

Ile Pro Leu Asp Ser Ser Ile Gly Met His Ala Gln Ala Leu Leu
            85                  90                  95

Ser Asn Gln Pro Ile Trp Gln Ser Ser Ser Glu Glu Glu Ala Asp
            100                 105                 110

Gly Gly Gly Gly Ala Lys Thr Arg Leu Leu Val Pro Val Ala Gly Gly
            115                 120                 125

Leu Val Glu Leu Phe Ala Ser Arg Tyr Met Ala Glu Glu Gln Gln Met
    130                 135                 140

Ala Glu Leu Val Met Ala Gln Cys Gly Gly Gly Ala Gly Asp Asp
145                 150                 155                 160

Gly Gly Gly Gln Ala Trp Pro Pro Pro Glu Thr Pro Ser Phe Gln Trp
                165                 170                 175

Asp Gly Gly Ala Asp Ala Gln Arg Leu Met Tyr Gly Gly Ser Ser Leu
                180                 185                 190

Asn Leu Phe Asp Ala Ala Ala Asp Asp Pro Phe Leu Gly Gly
            195                 200                 205

Gly Gly Gly Asp Ala Val Gly Asp Glu Ala Ala Ala Gly Ala Trp
            210                 215                 220

Pro Tyr Ala Gly Met Ala Val Ser Glu Pro Ser Val Ala Val Ala Gln
225                 230                 235                 240

Glu Gln Met Gln His Ala Ala Gly Gly Val Ala Glu Ser Gly Ser
                245                 250                 255

Glu Gly Arg Lys Leu His Gly Gly Asp Pro Glu Asp Gly Asp Gly
            260                 265                 270

Glu Gly Arg Ser Gly Gly Ala Lys Arg Gln Gln Cys Lys Asn Leu Glu
            275                 280                 285

Ala Glu Arg Lys Arg Arg Lys Lys Leu Asn Gly His Leu Tyr Lys Leu
290                 295                 300

Arg Ser Leu Val Pro Asn Ile Thr Lys Met Asp Arg Ala Ser Ile Leu
305                 310                 315                 320

Gly Asp Ala Ile Asp Tyr Ile Val Gly Leu Gln Lys Gln Val Lys Glu
                325                 330                 335

Leu Gln Asp Glu Leu Glu Asp Asn His Val His His Lys Pro Pro Asp
                340                 345                 350

Val Leu Ile Asp His Pro Pro Ala Ser Leu Val Gly Leu Asp Asn
            355                 360                 365

Asp Asp Ala Ser Pro Pro Asn Ser His Gln Gln Gln Pro Pro Leu Ala
            370                 375                 380

Val Ser Gly Ser Ser Ser Arg Arg Ser Asn Lys Asp Pro Ala Met Thr
385                 390                 395                 400
```

Asp Asp Lys Val Gly Gly Gly Gly Gly Gly His Arg Met Glu Pro
            405                 410                 415

Gln Leu Glu Val Arg Gln Val Gln Gly Asn Glu Leu Phe Val Gln Val
            420                 425                 430

Leu Trp Glu His Lys Pro Gly Gly Phe Val Arg Leu Met Asp Ala Met
            435                 440                 445

Asn Ala Leu Gly Leu Glu Val Ile Asn Val Asn Val Thr Thr Tyr Lys
450                 455                 460

Thr Leu Val Leu Asn Val Phe Arg Val Met Val Arg Asp Ser Glu Val
465                 470                 475                 480

Ala Val Gln Ala Asp Arg Val Arg Asp Ser Leu Leu Glu Val Thr Arg
            485                 490                 495

Glu Thr Tyr Pro Gly Val Trp Pro Ser Pro Gln Glu Gly Asp Asp Ala
            500                 505                 510

Lys Phe Asp Gly Gly Asp Gly Gly Gln Ala Ala Ala Ala Ala Ala Ala
            515                 520                 525

Ala Gly Gly Glu His Tyr His Asp Glu Val Gly Gly Gly Tyr His Gln
            530                 535                 540

His Leu His Tyr Leu Ala Phe Asp
545                 550

<210> SEQ ID NO 5
<211> LENGTH: 1422
<212> TYPE: DNA
<213> ORGANISM: Sorghum bicolor

<400> SEQUENCE: 5

```
atgattgctg ggggaggcta ttttgatggt tctcatgatc atattctcat ggaaggatcg    60
atgatccatg attcttccca atcttccatc tatgacaata cagatgttga acagcagaac   120
ttcagacttg cgcccttat catagaagat cactccaatc cagccaacct tacctctgag    180
cctgcaaggg tgatcgacca aattcatcac cagcttggga ttgacatgga gcaggaccat   240
agtgatcaca tgatccaagg agttcctcca gcagaaactg caaatttagt tcctgttgtc   300
tatggtgtcc aagatcgtat cctcagccac cagatagaag gtccacataa cataactgtg   360
gaacaacagg tcctggacta cgaccctgca tcatatggaa atggcactta tgcagctgca   420
catgatcttc taaattctct acagatccaa aggtgcagtt tgattcctga atttccttcg   480
acagaacata tctttggtga tccagcacag aacatggtca atcctttgga cattaccaat   540
gaccttcaag gagtagcaac tcatgaaagt ggaatgatgt tcagcgattc aactctacca   600
ttaggttatc atgctactca atctcatatg ttgaaggatc tctatcattc actaccacaa   660
aactatggga tatttaccag tgatgatgag agagatggga tggtcggggt agcagggtc   720
tcaggaaata ttttccagga gatagatggg agacagttcg acagcccagt actggggact   780
agaagacaga aagtggatt tggcaagggc aaggaaaag ctaactttgc aactgaaaga    840
gagaggaggg agcagctaaa tgtgaagtat ggggctttaa gatcactgtt cccaaaccct   900
actaagaatg acagggcctc tatagttgga gatgccattg actacatcaa tgagcttaat   960
agaacagtga aagaactgaa gatcttactg gaaaagaaga ggaacagcac tgacaggagg  1020
aagatactga agttggatga tgaagcagct gatgatgggg aaagctcttc aatgcagcca  1080
gtaagtgatg accaaaacaa tcagatgaat gggctataa ggagctcctg ggttcaaaga   1140
aggtccaagg agtgcgatgt tgatgtccgc atagttgatg atgaaataaa tatcaagttc  1200
```

| acagagaaga agagagccaa ctctttgctt tgtgctgcaa aggttctaga ggagtttcgt | 1260 |
| cttgagctca tccatgttgt tgggggaatc ataggagatc accatatatt catgttcaat | 1320 |
| acaaagatac ctaagggctc ttcggtgtac gcgtgcgcgg tggctaagaa gctccttgaa | 1380 |
| gctgtggaga taaagaagca ggctcttaat atcttcaact ag | 1422 |

<210> SEQ ID NO 6
<211> LENGTH: 1422
<212> TYPE: DNA
<213> ORGANISM: Sorghum bicolor

<400> SEQUENCE: 6

| atgattgctg ggggaggcta ttttgatggt tctcatgatc atattctcat ggaaggatcg | 60 |
| atgatccatg attcttccca atcttccatc tatgacaata cagatgttga acagcagaac | 120 |
| ttcagacttg cgccctttat catagaagat cactccaatc cagccaacct tacctctgag | 180 |
| cctgcaaggg tgatcgacca aattcatcac cagcttggga ttgacatgga gcaggaccat | 240 |
| agtgatcaca tgatccaagg agttcctcca gcagaaactg caaatttagt tcctgttgtc | 300 |
| tatggtgtcc aagatcgtat cctcagccac cagatagaag gtccacataa cataactgtg | 360 |
| gaacaacagg tcctggacta cgaccctgca tcatatggaa atggcactta tgcagctgca | 420 |
| catgatcttc taaattctct acagatctaa aggtgcagtt tgattcctga atttccttcg | 480 |
| acagaacata tctttggtga tccagcacag aacatggtca atcctttgga cattaccaat | 540 |
| gaccttcaag gagtagcaac tcatgaaagt ggaatgatgt tcagcgattc aactctacca | 600 |
| ttaggttatc atgctactca atctcatatg ttgaaggatc tctatcattc actaccacaa | 660 |
| aactatggga tatttaccag tgatgatgag agagatggga tggtcggggt agcaggggtc | 720 |
| tcaggaaata ttttccagga gatagatggg agacagttcg acagcccagt actggggact | 780 |
| agaagacaga aaggtggatt tggcaagggc aagggaaaag ctaactttgc aactgaaaga | 840 |
| gagaggaggg agcagctaaa tgtgaagtat ggggctttaa gatcactgtt cccaaaccct | 900 |
| actaagaatg acagggcctc tatagttgga gatgccattg actacatcaa tgagcttaat | 960 |
| agaacagtga agaactgaa gatcttactg gaaaagaaga ggaacagcac tgacaggagg | 1020 |
| aagatactga agttggatga tgaagcagct gatgatgggg aaagctcttc aatgcagcca | 1080 |
| gtaagtgatg accaaaacaa tcagatgaat ggggctataa ggagctcctg ggttcaaaga | 1140 |
| aggtccaagg agtgcgatgt tgatgtccgc atagttgatg atgaaataaa tatcaagttc | 1200 |
| acagagaaga agagagccaa ctctttgctt tgtgctgcaa aggttctaga ggagtttcgt | 1260 |
| cttgagctca tccatgttgt tgggggaatc ataggagatc accatatatt catgttcaat | 1320 |
| acaaagatac ctaagggctc ttcggtgtac gcgtgcgcgg tggctaagaa gctccttgaa | 1380 |
| gctgtggaga taaagaagca ggctcttaat atcttcaact ag | 1422 |

<210> SEQ ID NO 7
<211> LENGTH: 1422
<212> TYPE: DNA
<213> ORGANISM: Sorghum bicolor

<400> SEQUENCE: 7

| atgattgctg ggggaggcta ttttgatggt tctcatgatc atattctcat ggaaggatcg | 60 |
| atgatccatg attcttccca atcttccatc tatgacaata cagatgttga acagcagaac | 120 |
| ttcagacttg cgccctttat catagaagat cactccaatc cagccaacct tacctctgag | 180 |
| cctgcaaggg tgatcgacca aattcatcac cagcttggga ttgacatgga gcaggaccat | 240 |

```
agtgatcaca tgatccaagg agttcctcca gcagaaactg caaatttagt tcctgttgtc    300
tatggtgtcc aagatcgtat cctcagccac cagatagaag gtccacataa cataactgtg    360
gaacaacagg tcctggacta cgaccctgca tcatatggaa atggcactta tgcagctgca    420
catgatcttc taaattctct atagatccaa aggtgcagtt tgattcctga atttccttcg    480
acagaacata tctttggtga tccagcacag aacatggtca atcctttgga cattaccaat    540
gaccttcaag gagtagcaac tcatgaaagt ggaatgatgt tcagcgattc aactctacca    600
ttaggttatc atgctactca atctcatatg ttgaaggatc tctatcattc actaccacaa    660
aactatggga tatttaccag tgatgatgag agagatggga tggtcggggt agcaggggtc    720
tcaggaaata ttttccagga gatagatggg agacagttcg acagcccagt actggggact    780
agaagacaga aaggtggatt tggcaagggc aagggaaaag ctaactttgc aactgaaaga    840
gagaggaggg agcagctaaa tgtgaagtat ggggctttaa gatcactgtt cccaaacccct   900 actaagaatg acagggcctc tatagttgga gatgccattg actacatcaa tgagcttaat    960
agaacagtga aagaactgaa gatcttactg gaaaagaaga ggaacagcac tgacaggagg   1020
aagatactga agttggatga tgaagcagct gatgatgggg aaagctcttc aatgcagcca   1080
gtaagtgatg accaaaacaa tcagatgaat ggggctataa ggagctcctg ggttcaaaga   1140
aggtccaagg agtgcgatgt tgatgtccgc atagttgatg atgaaataaa tatcaagttc   1200
acagagaaga agagagccaa ctctttgctt tgtgctgcaa aggttctaga ggagtttcgt   1260
cttgagctca tccatgttgt tgggggaatc ataggagatc accatatatt catgttcaat   1320
acaaagatac ctaagggctc ttcggtgtac gcgtgcgcgg tggctaagaa gctccttgaa   1380
gctgtggaga taaagaagca ggctcttaat atcttcaact ag                     1422
```

<210> SEQ ID NO 8
<211> LENGTH: 473
<212> TYPE: PRT
<213> ORGANISM: Sorghum bicolor

<400> SEQUENCE: 8

Met Ile Ala Gly Gly Gly Tyr Phe Asp Gly Ser His Asp His Ile Leu
1               5                   10                  15

Met Glu Gly Ser Met Ile His Asp Ser Ser Gln Ser Ser Ile Tyr Asp
            20                  25                  30

Asn Thr Asp Val Glu Gln Gln Asn Phe Arg Leu Ala Pro Phe Ile Ile
        35                  40                  45

Glu Asp His Ser Asn Pro Ala Asn Leu Thr Ser Glu Pro Ala Arg Val
    50                  55                  60

Ile Asp Gln Ile His His Gln Leu Gly Ile Asp Met Glu Gln Asp His
65                  70                  75                  80

Ser Asp His Met Ile Gln Gly Val Pro Pro Ala Glu Thr Ala Asn Leu
                85                  90                  95

Val Pro Val Val Tyr Gly Val Gln Asp Arg Ile Leu Ser His Gln Ile
            100                 105                 110

Glu Gly Pro His Asn Ile Thr Val Glu Gln Gln Val Leu Asp Tyr Asp
        115                 120                 125

Pro Ala Ser Tyr Gly Asn Gly Thr Tyr Ala Ala Ala His Asp Leu Leu
    130                 135                 140

Asn Ser Leu Gln Ile Gln Arg Cys Ser Leu Ile Pro Glu Phe Pro Ser
145                 150                 155                 160

```
Thr Glu His Ile Phe Gly Asp Pro Ala Gln Asn Met Val Asn Pro Leu
                165                 170                 175

Asp Ile Thr Asn Asp Leu Gln Gly Val Ala Thr His Glu Ser Gly Met
            180                 185                 190

Met Phe Ser Asp Ser Thr Leu Pro Leu Gly Tyr His Ala Thr Gln Ser
        195                 200                 205

His Met Leu Lys Asp Leu Tyr His Ser Leu Pro Gln Asn Tyr Gly Ile
    210                 215                 220

Phe Thr Ser Asp Asp Glu Arg Asp Gly Met Val Gly Val Ala Gly Val
225                 230                 235                 240

Ser Gly Asn Ile Phe Gln Glu Ile Asp Gly Arg Gln Phe Asp Ser Pro
                245                 250                 255

Val Leu Gly Thr Arg Arg Gln Lys Gly Gly Phe Gly Lys Gly Lys Gly
            260                 265                 270

Lys Ala Asn Phe Ala Thr Glu Arg Glu Arg Glu Gln Leu Asn Val
        275                 280                 285

Lys Tyr Gly Ala Leu Arg Ser Leu Phe Pro Asn Pro Thr Lys Asn Asp
    290                 295                 300

Arg Ala Ser Ile Val Gly Asp Ala Ile Asp Tyr Ile Asn Glu Leu Asn
305                 310                 315                 320

Arg Thr Val Lys Glu Leu Lys Ile Leu Leu Glu Lys Arg Asn Ser
                325                 330                 335

Thr Asp Arg Arg Lys Ile Leu Lys Leu Asp Asp Glu Ala Ala Asp Asp
            340                 345                 350

Gly Glu Ser Ser Ser Met Gln Pro Val Ser Asp Gln Asn Asn Gln
        355                 360                 365

Met Asn Gly Ala Ile Arg Ser Ser Trp Val Gln Arg Arg Ser Lys Glu
    370                 375                 380

Cys Asp Val Asp Val Arg Ile Val Asp Asp Glu Ile Asn Ile Lys Phe
385                 390                 395                 400

Thr Glu Lys Lys Arg Ala Asn Ser Leu Leu Cys Ala Ala Lys Val Leu
                405                 410                 415

Glu Glu Phe Arg Leu Glu Leu Ile His Val Val Gly Gly Ile Ile Gly
            420                 425                 430

Asp His His Ile Phe Met Phe Asn Thr Lys Ile Pro Lys Gly Ser Ser
        435                 440                 445

Val Tyr Ala Cys Ala Val Ala Lys Lys Leu Leu Glu Ala Val Glu Ile
    450                 455                 460

Lys Lys Gln Ala Leu Asn Ile Phe Asn
465                 470

<210> SEQ ID NO 9
<211> LENGTH: 472
<212> TYPE: PRT
<213> ORGANISM: Sorghum bicolor

<400> SEQUENCE: 9

Met Ile Ala Gly Gly Tyr Phe Asp Gly Ser His Asp His Ile Leu
1               5                   10                  15

Met Glu Gly Ser Met Ile His Asp Ser Ser Gln Ser Ser Ile Tyr Asp
            20                  25                  30

Asn Thr Asp Val Glu Gln Gln Asn Phe Arg Leu Ala Pro Phe Ile Ile
        35                  40                  45

Glu Asp His Ser Asn Pro Ala Asn Leu Thr Ser Glu Pro Ala Arg Val
    50                  55                  60
```

```
Ile Asp Gln Ile His His Gln Leu Gly Ile Asp Met Glu Gln Asp His
65                  70                  75                  80

Ser Asp His Met Ile Gln Gly Val Pro Pro Ala Glu Thr Ala Asn Leu
                85                  90                  95

Val Pro Val Val Tyr Gly Val Gln Asp Arg Ile Leu Ser His Gln Ile
            100                 105                 110

Glu Gly Pro His Asn Ile Thr Val Glu Gln Gln Val Leu Asp Tyr Asp
            115                 120                 125

Pro Ala Ser Tyr Gly Asn Gly Thr Tyr Ala Ala Ala His Asp Leu Leu
        130                 135                 140

Asn Ser Leu Gln Ile Arg Cys Ser Leu Ile Pro Glu Phe Pro Ser Thr
145                 150                 155                 160

Glu His Ile Phe Gly Asp Pro Ala Gln Asn Met Val Asn Pro Leu Asp
                165                 170                 175

Ile Thr Asn Asp Leu Gln Gly Val Ala Thr His Glu Ser Gly Met Met
            180                 185                 190

Phe Ser Asp Ser Thr Leu Pro Leu Gly Tyr His Ala Thr Gln Ser His
        195                 200                 205

Met Leu Lys Asp Leu Tyr His Ser Leu Pro Gln Asn Tyr Gly Ile Phe
210                 215                 220

Thr Ser Asp Asp Glu Arg Asp Gly Met Val Gly Val Ala Gly Val Ser
225                 230                 235                 240

Gly Asn Ile Phe Gln Glu Ile Asp Gly Arg Gln Phe Asp Ser Pro Val
                245                 250                 255

Leu Gly Thr Arg Arg Gln Lys Gly Gly Phe Gly Lys Gly Lys Gly Lys
            260                 265                 270

Ala Asn Phe Ala Thr Glu Arg Glu Arg Glu Gln Leu Asn Val Lys
        275                 280                 285

Tyr Gly Ala Leu Arg Ser Leu Phe Pro Asn Pro Thr Lys Asn Asp Arg
290                 295                 300

Ala Ser Ile Val Gly Asp Ala Ile Asp Tyr Ile Asn Glu Leu Asn Arg
305                 310                 315                 320

Thr Val Lys Glu Leu Lys Ile Leu Leu Glu Lys Arg Asn Ser Thr
                325                 330                 335

Asp Arg Arg Lys Ile Leu Lys Leu Asp Asp Glu Ala Ala Asp Asp Gly
            340                 345                 350

Glu Ser Ser Ser Met Gln Pro Val Ser Asp Gln Asn Asn Gln Met
        355                 360                 365

Asn Gly Ala Ile Arg Ser Ser Trp Val Gln Arg Ser Lys Glu Cys
        370                 375                 380

Asp Val Asp Val Arg Ile Val Asp Asp Glu Ile Asn Ile Lys Phe Thr
385                 390                 395                 400

Glu Lys Lys Arg Ala Asn Ser Leu Leu Cys Ala Ala Lys Val Leu Glu
                405                 410                 415

Glu Phe Arg Leu Glu Leu Ile His Val Val Gly Gly Ile Gly Asp
            420                 425                 430

His His Ile Phe Met Phe Asn Thr Lys Ile Pro Lys Gly Ser Ser Val
            435                 440                 445

Tyr Ala Cys Ala Val Ala Lys Lys Leu Leu Glu Ala Val Glu Ile Lys
        450                 455                 460

Lys Gln Ala Leu Asn Ile Phe Asn
465                 470
```

<210> SEQ ID NO 10
<211> LENGTH: 472
<212> TYPE: PRT
<213> ORGANISM: Sorghum bicolor

<400> SEQUENCE: 10

```
Met Ile Ala Gly Gly Tyr Phe Asp Gly Ser His Asp His Ile Leu
1               5                   10                  15

Met Glu Gly Ser Met Ile His Asp Ser Ser Gln Ser Ser Ile Tyr Asp
                20                  25                  30

Asn Thr Asp Val Glu Gln Gln Asn Phe Arg Leu Ala Pro Phe Ile Ile
                35                  40                  45

Glu Asp His Ser Asn Pro Ala Asn Leu Thr Ser Glu Pro Ala Arg Val
            50                  55                  60

Ile Asp Gln Ile His His Gln Leu Gly Ile Asp Met Glu Gln Asp His
65                  70                  75                  80

Ser Asp His Met Ile Gln Gly Val Pro Pro Ala Glu Thr Ala Asn Leu
                85                  90                  95

Val Pro Val Val Tyr Gly Val Gln Asp Arg Ile Leu Ser His Gln Ile
                100                 105                 110

Glu Gly Pro His Asn Ile Thr Val Glu Gln Gln Val Leu Asp Tyr Asp
                115                 120                 125

Pro Ala Ser Tyr Gly Asn Gly Thr Tyr Ala Ala Ala His Asp Leu Leu
            130                 135                 140

Asn Ser Leu Ile Gln Arg Cys Ser Leu Ile Pro Glu Phe Pro Ser Thr
145                 150                 155                 160

Glu His Ile Phe Gly Asp Pro Ala Gln Asn Met Val Asn Pro Leu Asp
                165                 170                 175

Ile Thr Asn Asp Leu Gln Gly Val Ala Thr His Glu Ser Gly Met Met
                180                 185                 190

Phe Ser Asp Ser Thr Leu Pro Leu Gly Tyr His Ala Thr Gln Ser His
                195                 200                 205

Met Leu Lys Asp Leu Tyr His Ser Leu Pro Gln Asn Tyr Gly Ile Phe
            210                 215                 220

Thr Ser Asp Asp Glu Arg Asp Gly Met Val Gly Val Ala Gly Val Ser
225                 230                 235                 240

Gly Asn Ile Phe Gln Glu Ile Asp Gly Arg Gln Phe Asp Ser Pro Val
                245                 250                 255

Leu Gly Thr Arg Arg Gln Lys Gly Gly Phe Gly Lys Gly Lys Gly Lys
                260                 265                 270

Ala Asn Phe Ala Thr Glu Arg Glu Arg Glu Gln Leu Asn Val Lys
            275                 280                 285

Tyr Gly Ala Leu Arg Ser Leu Phe Pro Asn Pro Thr Lys Asn Asp Arg
            290                 295                 300

Ala Ser Ile Val Gly Asp Ala Ile Asp Tyr Ile Asn Glu Leu Asn Arg
305                 310                 315                 320

Thr Val Lys Glu Leu Lys Ile Leu Leu Glu Lys Lys Arg Asn Ser Thr
                325                 330                 335

Asp Arg Arg Lys Ile Leu Lys Leu Asp Asp Glu Ala Ala Asp Asp Gly
            340                 345                 350

Glu Ser Ser Ser Met Gln Pro Val Ser Asp Asp Gln Asn Asn Gln Met
            355                 360                 365

Asn Gly Ala Ile Arg Ser Ser Trp Val Gln Arg Arg Ser Lys Glu Cys
370                 375                 380
```

```
Asp Val Asp Val Arg Ile Val Asp Asp Glu Ile Asn Ile Lys Phe Thr
385                 390                 395                 400

Glu Lys Lys Arg Ala Asn Ser Leu Leu Cys Ala Ala Lys Val Leu Glu
            405                 410                 415

Glu Phe Arg Leu Glu Leu Ile His Val Val Gly Gly Ile Ile Gly Asp
            420                 425                 430

His His Ile Phe Met Phe Asn Thr Lys Ile Pro Lys Gly Ser Ser Val
            435                 440                 445

Tyr Ala Cys Ala Val Ala Lys Lys Leu Leu Glu Ala Val Glu Ile Lys
    450                 455                 460

Lys Gln Ala Leu Asn Ile Phe Asn
465                 470

<210> SEQ ID NO 11
<211> LENGTH: 5465
<212> TYPE: DNA
<213> ORGANISM: Sorghum bicolor

<400> SEQUENCE: 11
```

| | | |
|---|---|---|
| ctacctcccg ttggaatcac ctccccaatt cgaagtttaa tactaaaact ttcgaatttc | 60 |
| actgtttttc aacttccagc tcaatttgcc tcctattgct aattgaattt gccactgtaa | 120 |
| tacagctctg caaaacgatc agaatgctag tttagtaaac caattgtagt tacgtattca | 180 |
| ttgccaagca tttacagctc cagaaaaaca tatgaacccc ataccacatg gttagaacag | 240 |
| gctgtcatga atgctgccat gaacaaattc aaggatggcc ataagatcca tcaccaaagt | 300 |
| cacaaagcta agcgcagacg agccttggca gttgagctcc atcactctgt tgttttctca | 360 |
| taggtgttcc ctccctcttg aagatggatt tgagatgggc tgcagggtgt ttctcttgac | 420 |
| ccttctgttg gatgaggtgt tcatttgcag tcaaaattga aaaaggacac ggtatgttcc | 480 |
| tgaaacatat attcagagag tcctcgttta gacagtctct gcctagcaca tatattgtat | 540 |
| gggaaataat aagaactcca gaaatgtcaa ccgcataact actgtatact ggatcgaagt | 600 |
| ttacaaagta caaagaaatg caagcatgac atgattatta ggttctatgc agtgatgcaa | 660 |
| ggttatgact cccttttgcaa ctgtccagtg tttcaggtag ttggacttgt cctttagtt | 720 |
| tctgaaagca cactacagca taatgtccgt aaaatacgga ggaacggaga aggcatgact | 780 |
| tgcatttccc aacttcctat ggcatgaata acagcaaaga tgccaagttc aaagagtgtg | 840 |
| agttttccat ctttctcatg gccattctta atgatgatga tgatctgaaa tctgatagcc | 900 |
| cttcactttg acctcttcta agaatgttca agagaaactt ttaggaaatg attggtgttg | 960 |
| atataaacat attctgttat ctgttcatca attttacgtg gcaaccaaat ttccgtacta | 1020 |
| ctgcggtact ggccacatgc caattacatt ttgccttta ccatgacgtt gtatatatat | 1080 |
| tactagcagc acactcaaac tacttcacaa ggatggtttt cagcaactag tttctgaaca | 1140 |
| gcgtgtttgc tatctggtct gtcaaaataa tcttggtact gttctcttct ctttactttc | 1200 |
| agttttttcgt actattggca ggatgcaaat gctagattga atctgccgac tttgtttata | 1260 |
| ccaacctgaa gaaacaatat gtatctaaag aatgaagttt tgcttatgtc tttgagattt | 1320 |
| aaacataccc ttttcaacta ttggacttgt agtgcattgt ttagaagatt tcaagaaggt | 1380 |
| aaagggcact ttggtcattg tcaatactta tactagtctg tgttctgctg attaattgtt | 1440 |
| gagcttggta gttgaagcac aaactagcaa gattaatatt tttaggtgta gggcgcaaat | 1500 |
| aaagacgcaa ggcagtttgt tgggtcctaa ggaagcaaaa aggcttcctg tctcatccat | 1560 |

```
gtgctaataa aactccacac ggaaaagata gagagaaaca gattgcctag cttaaacctt    1620
gagtattctc ttcctcctct caaacaatca aaccaactaa gccagctgca atcttctctg    1680
cttaatcaac tccatcgttg tttcatacag gtcgagacat cttttccctc aattcatggg    1740
caccagctaa tattttttgt ctatttcaga tcctctagca tgctacttct atgtttctta    1800
atcagttttg tctcctgcct ttgcttcttc ctaagtgttt tgctaaatag atacttatat    1860
ggtgcatata gttcctaaat gctgtatttt tttatcttga gtgaaggtaa ccagggccaa    1920
aatgattgct gggggaggct attttgatgg ttctcatgat catattctca tggaaggatc    1980
gatgatccat gattcttccc aatcttccat ctatgacaat acagatgttg aacagcagaa    2040
cttcagactt gcgcccttta tcatagaaga tcactccaat ccagccaacc ttacctctga    2100
gcctgcaagg gtgatcgacc aaattcatca ccagcttggg attgacatgg agcaggacca    2160
tagtgatcac atgatccaag gagttcctcc agcagaaact gcaaatttag ttcctgttgt    2220
ctatggtgtc caagatcgta tcctcagcca ccagatagaa ggtccacata acataactgt    2280
ggaacaacag gtcctggact acgaccctgc atcatatgga aatggcactt atgcagctgc    2340
acatgatctt ctaaattctc tacagatcca aaggtgcagt ttgattcctg aatttccttc    2400
gacagaacat atctttggtg atccagcaca gaacatggtt caatcctttg gacattacca    2460
atgaccttca aggagtagca actcatgaaa gtggaatgat gttcagcgat tcaactctac    2520
cattaggtta tcatgctact caatctcata tgttgaagga tctctatcat tcactaccac    2580
aaaactatgg gatatttacc agtgatgatg agagagatgg gatggtcggg gtagcagggg    2640
tctcaggaaa tattttccag gagatagatg ggagacagtt cgacagccca gtactgggga    2700
ctagaagaca gaaaggtgga tttggcaagg gcaagggaaa agctaacttt gcaactgaaa    2760
gagagaggag ggagcagcta aatgtgaagt atggggcttt aagatcactg ttcccaaacc    2820
ctactaaggt ttgtataact tatctctcca agcacaaatt ccttaattgc ttctctcatt    2880
acagaactca ttttccacag ttgcatggat ttgtagaaca tttagtaagt tctattcgta    2940
caggatgtat tggaacatgt attcagattg ttttccctag gaaaaataaa atttaaaaca    3000
aatgtgtgta tgataaaaaa aactttatta aagatggatt tgtcattagc aaactcttat    3060
aaagtgctat cagttcaagt atgtggagga atgcgatcat ggaattttg catgtatcag    3120 tggacagatg cacgtaaatt gatctttagt atcagcatcc aacaaaatag aatgaaatta    3180
taaaatatgc gggataagag aatttccatt ccagaaactc tagttatgcc cagcacaatg    3240
caatattgtt tttctttcct aaatctacat ttattgtact cttagtgaat aagaggctat    3300
gaattctgaa ttgctgtaaa actattctcc agaatgacag ggcctctata gttggagatg    3360
ccattgacta catcaatgag cttaatagaa cagtgaaaga actgaagatc ttactggaaa    3420
agaagaggaa cagcactgac aggaggaaga tactgaagtt ggatgatgaa gcagctgatg    3480
atggggaaag ctcttcaatg cagccagtaa gtgatgacca aaacaatcag atgaatgggg    3540
ctataaggag ctcctgggtt caagaaggt ccaaggagtg cgatgttgat gtccgcatag    3600
ttgatgatga aataaatatc aagttcacag agaagaagag agccaactct tgctttgtg    3660 ctgcaaaggt tctagaggag tttcgtcttg agctcatcca tgttgttggg ggaatcatag    3720
gagatcacca tatattcatg ttcaatacaa aggtaacaaa caaattttct taaacgaaag    3780
taggttcttg atccttttcc ctgtgtctgt agcacagaca ttagttataa tacttcatat    3840
cttgatactc agatacctta agggctcttc ggtgtacgcg tgcgcggtgg ctaagaagct    3900
ccttgaagct gtggagataa agaagcaggc tcttaatatc ttcaactagc catacccatc    3960
```

```
ataatgttta ttcagacaac ttagcatgct ggtctgctct ttagcatcta ataaggtgct    4020
tacttatcag cgaatgacca cattgacaaa acttctttga tgactgctgc aaactttctt    4080
gatagcttgt tcatgctgaa cttcttgtct tcttttctgt acactttaac agtcatgttg    4140
gaatatgtgg tgcttctgat ttcccggcat tgtcactcaa tactttatta tgtttaattc    4200
cttttctgaa cttatatggc agatcgactc cactacccaa cttacatatc tcaggctcag    4260
gtctagtgaa tgtgtttgtg ttcggaggaa atgctacatc acgattccat aaaaataaaa    4320
agctagtata tatctaacaa tatgatccat gttaaatttg tcttggagtt atgacacata    4380
attgtggtag aaattgttac tgcgtgatgg ctgggatgag atccttaccg ctatgcacag    4440
gacagtcggg gtgggtttct cctacagtca cagagtccat cacgctacga tgtctggaga    4500
tctaaactaa gtacctgaac tcctgggggg atcaatcaat agtaagcaaa actcaaaaag    4560
gatacaagga ttggaatcaa tttggccagc cgcacccgta gtcaagatct ccgtgtttgc    4620
cgaggctgac gaactggagc aggtctaccg caggtgcagt agctgatccg aacataaata    4680
atcattccac tccgctcttg tacctgatct cgcagatctc cagtgcagtg tgcagctgca    4740
gtttgctgcc ctagtcatct ggcatgctgc atggtcttta atgtggcgga gttgctgaat    4800
cctcacacat aaggccaacg tttaaactac ccacattagt cacatactta gcgccccttt    4860
ggaacgcagg attttcgtat aggtatgtag aaattttaca ggattcaatt caatttttata    4920 ggaaaaacac aggtctttag gaaattttcc tacgttccca agggacctta tagataataa    4980
aattaaagca taaatgcat aattcagatg atatttggta ttcatgttaa attgtacaac    5040
aaacttgatg aaaacataaa aatgattaga aaattaccta actgatggtg atttggttcg    5100
tccttgcctc ctgtatcttc atcagaatag tcactgaact tgaattaaca cacaaaagtt    5160
ggacacttac aagaaatcag agatgtattt ttcacaaaag acaactaaag tagtatttag    5220
gaatgattaa atgatgatcc catttaacca attcagtttg tgcaagtcta taaaaattcg    5280
gtacaaatat ataatcgtcg atttcaattt atgcaattga aatagagatg aagaagtatg    5340
atattccatg gactcatggg gatttgccac ttgccagatt gggagattga gacttcagaa    5400
ggcatcaaca aaaagtaaa tcgatacaag cagctgccgt gcgccaatcg cagaccctga    5460
tgtgc                                                                5465
```

<210> SEQ ID NO 12
<211> LENGTH: 1450
<212> TYPE: DNA
<213> ORGANISM: Sorghum bicolor

<400> SEQUENCE: 12

```
atcttgagtg aaggtaacca gggccaaaat gattgctggg ggaggctatt ttgatggttc      60
tcatgatcat attctcatgg aaggatcgat gatccatgat tcttcccaat cttccatcta     120
tgacaataca gatgttgaac agcagaactt cagacttgcg cccttatca tagaagatca      180 ctccaatcca gccaacctta cctctgagcc tgcaagggtg atcgaccaaa ttcatcacca     240
gcttgggatt gacatggagc aggaccatag tgatcacatg atccaaggag ttcctccagc     300
agaaactgca aatttagttc ctgttgtcta tggtgtccaa gatcgtatcc tcagccacca     360
gatagaaggt ccacataaca taactgtgga acaacaggtc ctggactacg accctgcatc     420
atatggaaat ggcacttatg cagctgcaca tgatcttcta aattctctac agatccaaag     480
gtgcagtttg attcctgaat ttccttcgac agaacatatc tttggtgatc cagcacagaa     540
```

| | |
|---|---|
| catggtcaat cctttggaca ttaccaatga ccttcaagga gtagcaactc atgaaagtgg | 600 |
| aatgatgttc agcgattcaa ctctaccatt aggttatcat gctactcaat ctcatatgtt | 660 |
| gaaggatctc tatcattcac taccacaaaa ctatgggata tttaccagtg atgatgagag | 720 |
| agatgggatg gtcggggtag caggggtctc aggaaatatt ttccaggaga tagatgggag | 780 |
| acagttcgac agcccagtac tggggactag aagacagaaa ggtggatttg gcaagggcaa | 840 |
| gggaaaagct aactttgcaa ctgaaagaga gaggagggag cagctaaatg tgaagtatgg | 900 |
| ggctttaaga tcactgttcc caaaccctac taagaatgac agggcctcta tagttggaga | 960 |
| tgccattgac tacatcaatg agcttaatag aacagtgaaa gaactgaaga tcttactgga | 1020 |
| aaagaagagg aacagcactg acaggaggaa gatactgaag ttggatgatg aagcagctga | 1080 |
| tgatggggaa agctcttcaa tgcagccagt aagtgatgac caaaacaatc agatgaatgg | 1140 |
| ggctataagg agctcctggg ttcaaagaag gtccaaggag tgcgatgttg atgtccgcat | 1200 |
| agttgatgat gaaataaata tcaagttcac agagaagaag agagccaact ctttgctttg | 1260 |
| tgctgcaaag gttctagagg agtttcgtct tgagctcatc catgttgttg ggggaatcat | 1320 |
| aggagatcac catatattca tgttcaatac aaagatacct aagggctctt cggtgtacgc | 1380 |
| gtgcgcggtg gctaagaagc tccttgaagc tgtggagata aagaagcagg ctcttaatat | 1440 |
| cttcaactag | 1450 |

<210> SEQ ID NO 13
<211> LENGTH: 1991
<212> TYPE: DNA
<213> ORGANISM: Oryza Sativa

<400> SEQUENCE: 13

| | |
|---|---|
| ggaactcacc ggctagccat cattggcgac cgttaaacgg agattaaata cagcgaatta | 60 |
| atgctaaact aaaggaaaaa aatcatgttg aaatgatgag agaggagtgg ggaatcgatt | 120 |
| tttgcaatca attggaggaa caaatgcacg gggaggcaga ttgacatggc agcggcgcta | 180 |
| gggtttggct cagcggtggc tggaggcaca cgctgcgcgt gtagcggatc agatgactta | 240 |
| cgaaaaataa ataagaatt cttgcttta ttaattaggt atagatatat aatattcact | 300 |
| ggtacgaaat cggtcatttg tgttgggtgc caccctatg tgtgttggtg gagaacctga | 360 |
| tcacagagaa gaggtcacta atgtgaaaaa ctcgtctgca tcggacgagc gaccgttagg | 420 |
| catacatttt aaacgggttt taaaaaaca accagtcacc gatatggttc acccagagca | 480 |
| aattagataa caagccatcc cggacgactc atcggtgata gggcccaatt acaactcaac | 540 |
| aatgatgttg ttcacttatg acggggttac gttgtaaccc attaccgatg aggttttacc | 600 |
| taaacagata atatcatttt attgttaacc tcaggcaatt gcgccatgcc cccactgcaa | 660 |
| attgacaaaa atatagaatt tgccactaat atcacgctga tacgtgggtg ttcctagtaa | 720 |
| caaattcata gatataggat aaattatgtt ggtggtatat aaacttatta gacgggtgca | 780 |
| atttagtaca tgaatttata aaacgttcgt tatagtgaat aaatttgtct aggatgtgta | 840 |
| aaccaagtcg aaaacaacgt attgactta ttattgttga gttaaatcat gattagtatg | 900 |
| tcaaacgcac acgcgagggg gtaagaaaca tgtcatattt gcaaacaacc tttatatata | 960 |
| cacacatggc acttatttt tccttccatt gttttttcc gttgcatctt cttttatgta | 1020 |
| tttatacatt tttatatgtg caatgagcat ggcttattct gcgtttaatt gagcacatgc | 1080 |
| atatgtatgt cgcatcgtct tgatatgcaa gcatacgtgg catcctaacc ggtgttcaac | 1140 |
| tcagtgagat tagctatgac gtgtttctta tgtcttggtt tgtgatcact tgttctaaat | 1200 |

```
tctggagata aggtcttcca tggatacccc cgaaacatcc cctcgatttt tttcatcatg    1260
aatgataaac tagatgtttt taaatggatg tagattgaag aaactgtgta actaagcccc    1320 ctcaatttt gtttctggat ccgcctctac gtacccgtca tcggctcgca tcgcatcggg    1380
cgctcggtgc aaagcattat cgacgataac aataattaaa aaaaaatata tcacgcaaaa    1440
agcaagctga aattgttttt gaaaataaaa aaacaggaaa gaaatgtgt ctgaaccttt     1500 ctcgctccct cccgcgcgtt tctctcctct tttctctctc cttccttgat ctcctctctc    1560
tctcctcctc ctcctccttc tccttctccc tctcccgccc gatccaccca agaactgccg    1620
atttcgccgg ctcgatcccc accccgaccc cgctgcctcg cgggagatcg atcgttcgat    1680
cgatcagaac aagctaattc tctcattcct ctctctgtct ctctcatcgg ttcttggttc    1740
gacccagctc ccagatgatt tcatcctgaa tcatcgtcgt cgtcgtcgtc gtcacaggca    1800
agaagaggag aaggaattac acctgggatt atcgattggt tgttcggatt ttcttttgga    1860
tctattcatg ctcgctctgt gcgccgggga ttcgatcgtt gggcagggca gtgatctctg    1920
cgtcgagggt ttcgacgaat tggactgcag attcgtcgcc atctcttcgc agagggatt    1980 ctgcctccgc c                                                        1991
```

<210> SEQ ID NO 14
<211> LENGTH: 1648
<212> TYPE: DNA
<213> ORGANISM: Oryza Sativa

<400> SEQUENCE: 14

```
atctgttctg cccatcgccg tcgctgatcc ccttttatcg ccccagcttc ctcctccagc      60
tcgctactct cgccggcgga cgccggtctc gccgcccct ccagctcgcc actctcgctg     120
gaagaggaga ggagagggga gaaagatgaa gagagggaga tggggagaga ggaggaagaa     180
gaggaagggt gagtttgact gacatgtggg gcccacgtgg gtcccacaat ttttttattat    240 cttctatgtg agactgacat gtgggtccct aggttttat tattttttccg ggtcgaattg     300 acacgtaaag cgccacgtca atgccacgtt ggacgaagac cgagtcaaat tagccaccta    360
ggcgccacgt cagccaaaac cgccctcaaa accaccgagg gacctgatct gcaccggttt    420
tgatagttga gggacccgtt gtgtctggtt ttccgatcga gggacgaaaa tcggattcgg    480
tgtaaagtta agggacctca gatgaactta ttccggagca tgattgggaa gggaggacat    540
aaggcccatg tcgcatgtgt ttggacggtc cagatctcca gatcactcag caggatcggc    600
cgcgttcgcg tagcacccgc ggtttgattc ggcttcccgc aaggcggcgg ccggtggccg    660
tgccgccgta gcttccgccg gaagcgagca cgccgccgcc gccgacccgg ctctgcgttt    720
gcaccgcctt gcacgcgata catcgggata gatagctact actctctccg tttcacaatg    780
taaatcattc tactattttc cacattcata ttgatgttaa tgaatataga catatatatc    840
tatttagatt cattaacatc aatatgaatg taggaaatgc tagaatgact acattgtga    900 attgtgaaat ggacgaagta cctacgatgg atggatgcag gatcatgaaa gaattaatgc    960
aagatcgtat ctgccgcatg caaaatctta ctaattgcgc tgcatatatg catgacagcc    1020
tgcatgcggg cgtgtaagcg tgttcatcca ttaggaagta accttgtcat tacttatacc    1080
agtactacat actatatagt attgatttca tgagcaaatc tacaaaactg gaaagcaata    1140
agaaatacgg gactggaaaa gactcaacat taatcaccaa atattcgcc ttctccagca     1200 gaatatatat ctctccatct tgatcactgt acacactgac agtgtacgca taaacgcagc    1260
```

| | |
|---|---|
| agccagctta actgtcgtct caccgtcgca cactggcctt ccatctcagg ctagctttct | 1320 |
| cagccaccca tcgtacatgt caactcggcg cgcgcacagg cacaaattac gtacaaaacg | 1380 |
| catgaccaaa tcaaaaccac cggagaagaa tcgctcccgc gcgcggcggc ggcgcgcacg | 1440 |
| tacgaacgca cgcacgcacg cccaacccca cgacacgatc gcgcgcgacg ccggcgacac | 1500 |
| cggccgtcca cccgcgccct cacctcgccg actataaata cgtaggcatc tgcttgatct | 1560 |
| tgtcatccat ctcaccacca aaaaaaaaag gaaaaaaaaa caaaacacac caagccaaat | 1620 |
| aaaagcgaca atgggatcgc tcaccacc | 1648 |

<210> SEQ ID NO 15
<211> LENGTH: 263
<212> TYPE: DNA
<213> ORGANISM: Oryza Sativa

<400> SEQUENCE: 15

| | |
|---|---|
| aaaaagggga tcgagaggaa gaggaagctt tgtgagtttg ggcctttatt tggtggaggc | 60 |
| ccattgattc ctacgtgggc tgggccgaac acgtccagg tagttggtcc acattccagg | 120 |
| ttgaacgatt ccagcggcgg cggcgagtgg tggcgcgcga tcatctccca ctcccaccgt | 180 |
| tgttcctcct caacacgcgc cactcctcac attcatttcc acctgctcat ctatatctat | 240 |
| ctatcatcaa gctgatcatc cat | 263 |

<210> SEQ ID NO 16
<211> LENGTH: 4049
<212> TYPE: DNA
<213> ORGANISM: Oryza Sativa

<400> SEQUENCE: 16

| | |
|---|---|
| acgtagttga atgtcctgtg ttcgttgagc tgattccagc agcggcagag gaggaggcca | 60 |
| ttgcagctgt ccaccagctg agatcatca cacttgggca ggaaggaaaa cgagggatcg | 120 |
| atgaggggag ggggatccag cgccgggacg atctggaaac ggtttagtac gcggtagtcg | 180 |
| gcgtagagga agccggcgag gggctggagg tgatgccgcg ggagctggcg gcggtggtcg | 240 |
| gggtggggaga tgacgcggcg ccaccgcatg gagacgcact tgaggcggca gagcgacttg | 300 |
| tagggcacgc gcgagaggat ctcgacgagg aggtcgtcgg tgagctcctc cgcaatggct | 360 |
| gcgcatagag agacggagaa gcgaagggat taggaaagag aggtgaaacc aaaaccaccg | 420 |
| gcggcggcat ggaggagggc gcgtaccgga ggtggtcccg ttggagacgg cggcggcgag | 480 |
| ggcttggggt tttgggcggc ggcggtggcg tacgcagaga cggcgaagga gaagcctcgg | 540 |
| catcgctcac cggagcagag atcggcggcg gcggcggcgg cggccgtgga gcagtcgagg | 600 |
| cttcgaggag gtgcgagggg aggaggccca gagagaaagc tagccgtagc ccattgggcc | 660 |
| tggacgaatc ctgaccgatc gatcaaacgg acggccacga ttctcccgg tttcaatttt | 720 |
| cgaatcgccc gagaaagcga gacgtgaggc gcggcgccac cctcgcctcc ccccatcacc | 780 |
| tcgctacgtg tccgcacggc aacgcaggct gccaagtggg ccccactcca accccccttc | 840 |
| tgccggaccc acatgtcagt cacacgctga agagtctcac accgactccc ttcttctcct | 900 |
| cctccctctt gagctcgcct cctctcgtcg atttgctcgc ctataaatgc cggcgtcacc | 960 |
| ggcggagagg agagagagag agagagccac gacgacccgc tcgccgccgt cccctccggc | 1020 |
| cgccgacgcc tagggtttcc ccgcccgccg gcgcgtcgct cgcggtggag gctgggtatt | 1080 |
| gtcgctgcgc gccgccgcgt cgatccaccg cccgcccgac tgcggacttc gcttgattgt | 1140 |
| ttgtgccttc cctcctcgtc ctagccgctc ctggtacgta cgcgcgctcc gattccggct | 1200 |

```
gcatttggtt attttgctca tgagcgtccg ccgccgcttc gctccatcga tcctggccat    1260
ccgtgcggct ctcgatcgtc agggattcgg agccctttga tgtgcggggg ggacgcgttt    1320
gggggaagat gcggcgcttg atttgcgtgt tgtgcatcat gattgctctt gtcaattcga    1380
tcgattgatc atcgatgcag gattttttcgt taagctgatt cgctgtgtgt ttgcagatac   1440
ggactagtta attggttaca gtttgtattg ttccgtagga tcggtacgtg atgatccatt    1500
gacgagcgca gttgcgttct tcccccactt caaaagcgtc ataaatcttg tactactact    1560
atgacatcta cacatccagt gcagctgttt ctcaaacagc gatataatgt ttttgaaagc    1620
aagtttgatc actgtttttc tgttactcct ttttgcacca tatttcaaaa gtttataact    1680
ggttcaaaaa cgtactagtg gtttttattc actcacaaat gagaaagata gtacgaagaa    1740
tgtaaattct tgatggaact ttctgcattc ccaacagttg gcagtccttt atttgtgtcg    1800
tgttcgaaac aagtagaaca ctttgatttg ttgctttatg cagaacatat ccagatcata    1860
tctcattttt tttccaaatg ggaccctcct gtacctattt cctcaagcac ctctgttctt    1920
gggtggttcc aagtaacaat cagtttatga gacactgcct atttgccaaa tttaacataa    1980
cagcctgttt gagccagact gctggtgatc cctattttgt ttcttgaagc cttctttctt    2040
aggccttgtt tagttcccaa aacaaaaact tttcacccat cacatcaaat gtttggacac    2100
atgcatgaag tattaaatat ggacggaaat aaaaaccaat tacacagttc tgacggaaat    2160
tgcgagacga atctttaaa cctaattgcg ccatgattta acaatgtggt gctacagtaa     2220
acatttgcta acgatggatt aattaggctt aataaattcg tctcgcagtt tcctggcaga    2280
atctgtaatt tgtttttgtta ttaaactacg tttaatactt caaatgtgtg tccatatatc   2340
cgatgtgaca ccccaaagca aaaattttg gaactaaac tgggccttag tatttgcagc      2400
tgtcaactta ttcatgaaaa ctatgctcct actatgcata gaaatgtaaa gctaaaaata    2460
gcatctggtt aggaaggga aaatgaaaga gccaaatgat ggcatgcaat ggttcatgtc     2520
caatttgcta cttatagcat aaaaaatagg caaacaccaa acagctggac cgtccttccc    2580
aagtttgaaa gttctgtttc attctttcat aaaccaagtc tgatgttgtg aaactaaaat    2640
ttatgtagta cccctgtctg atccattctt ttagcccaca gttggcttgt gaaatcctac    2700
atgcacttat tcgtaaaccc catgcatggg gcatgtcttt gtgagtacaa aatttatttt    2760 tattttttc gccgggccgg caaagataac cggccaagtt ttgcattaag aaggagagag     2820
ttttacagca gcccctaaac cagaaaaggc ttaggttaca gaaaaaactt cacaacaata    2880
aagacaacaa acaagcacag ctgctaaaac ctcagcaaat taaccgccag cgattgcgct    2940
cagtagcccg gcagccttcc atgtttccca ttcgtcgaca attgtggcac aaaggtgaac    3000
cgctgaagta gctcgtccat caaacacacg cgcattcctt tccttccaga ctatccatgt    3060
taccaagata accccagcat caaaggtccc ccgatccgtc ttgtgaactg atttgcgtgc    3120
ttcacaccac caatccaaca tgtcttccgt ggggaaaca caggagagtc ccaggcgact     3180
cctgattctc gtccaaactg ccctcgtgta ctcgcaagcg tggaagatat gggcacatga    3240
ttcagcatcc ttcccgcaaa ggtgacagta tggagccaag tgccatcctc gccgctggag    3300
gttgtccgcc atcaggcatg ctccacgcat ggcaaggaac atgaagaact tgcaatgggc    3360
cggcgcgcga gacttccaaa tcagcttccc aaccgccaag cgtgtcttcc cagcgcagag    3420
gagtgaatag gctgatttta ctgagaaacc accatctgcg gcaggcttcc aagaaaacaa    3480
atcaggctga gtcgggttca aggaaacggt ggcaacaagg tcccagattt ggaggtattc    3540
```

| | |
|---|---|
| aaacatcgct tgcagcgaga gacctcccct gatgtcgccg gtccaggcat catcctgcag | 3600 |
| cgccaaatga accgttctgc ctctgttttt aacaaaggaa cacaggattg gggctcagtt | 3660 |
| caggatcgac cccccatctg ggagccagtc atctgtccag aagaaggaac tcttcccgtc | 3720 |
| gcccagcact atcctgcatc cggccgctag acaatgttcg gctttcctat cttgcggcga | 3780 |
| cgtgaaggac acccagtggc gctccagctg ggcacgccgc agccaaagcc accgcgtccg | 3840 |
| aagggcaatg cccattctgc caagattgat gatgcccaac ccgccatttt cgatcggcag | 3900 |
| acagagctta tcccaagcaa ctaggctgca tccacccggt gcatcctcat cccccttttca | 3960 |
| caagaaaccg cggcatttct tttcaattgc tttaattgcc cacaccggca attccaacac | 4020 |
| cgagaaattt attttattta gctcagtta | 4049 |

<210> SEQ ID NO 17
<211> LENGTH: 446
<212> TYPE: DNA
<213> ORGANISM: Arabidopsis thaliana

<400> SEQUENCE: 17

| | |
|---|---|
| gaagaaatag ttggcattgc aagaagaaga catgatgagt cttgtcttgg taaatttgtt | 60 |
| gcataattgg atatatataa aagatttttct tgaaatgatg acatgacaac tatttctgaa | 120 |
| tttagccatt gtcaaaagct ctcttcgttt tgaagcggta gaaaattaga atgtttatg | 180 |
| tttagccaaa ttcaaaagta gaggagattc cttgaatttc tgttttctct cgctgtcttc | 240 |
| tcaatattca aaactcaaat tggtgtcttc tccaatttag aaaacgttaa aaacaagaga | 300 |
| aaataaaact aaacttttta gaaccaaaaa aaataaaaat aaaacgcatt tgggatttct | 360 |
| cattgtcatc ccaagttctt ggaacagcca aatacttttt cattattagt ttataatcgt | 420 |
| ctcataaagg caaaaaggtt tatttc | 446 |

<210> SEQ ID NO 18
<211> LENGTH: 612
<212> TYPE: DNA
<213> ORGANISM: Arabidopsis thaliana

<400> SEQUENCE: 18

| | |
|---|---|
| atgatggtgt ttgggtcata taccttcttg ttcttatttt actagtttga gatccttagg | 60 |
| cttgcatcca tatacagtac atgaaatacc atatgtttaa aattgttgtt tgtcttacca | 120 |
| ttagaaaata aaataaacac acaaaagaaa tggatatcat ggttgcttta gtaaatcttt | 180 |
| attcctcaag ttaaacaatg tttgccattt atggtgctca caaggtgttc acacaaagtc | 240 |
| ttgtgtaaga atatgatatc atggttgctt tagtaaatct taattagggt tctataactt | 300 |
| ttgtaaaaag tttaataaaa aaattctaat gaactaactt agaggaatat gcggtttgga | 360 |
| tcagtctaat ccagattttc tatagaatat agaaaaaatg tgacaaacat acagaaattg | 420 |
| gtacttatac atttactgat taacgttatt agtatattct cttttgtata atatctctgt | 480 |
| ttctccggag aaacagggga aaactagagg aagagaaacc gttatgctct gcctctctaa | 540 |
| ttcgcttaag ttttattacc atctctcttt tctctgtttt ctctttcttg cgttcctaag | 600 |
| aaacttggga aa | 612 |

<210> SEQ ID NO 19
<211> LENGTH: 1717
<212> TYPE: DNA
<213> ORGANISM: Oryza Sativa

<400> SEQUENCE: 19

```
gctttgggtg tactcactgt tcacaccaat aaataaatat cacaagaatt ctataaattc    60
ctacataatt tttttaacat agtgtacata taattttata aaattatgta cttttaacat   120
aacatgcacg tacatataaa gttttcactt cagatacatt atacatattg tacaaagtag   180
gggaaaaatg attagtaccc ccatctgtca aaaagatct attcctagat ccccgaggca    240
agtttagtat taacgtgaaa ttaccaaagt accatcctta actgcattca tccatcaaca   300
ctgccattct ctgcacacac attaaaattg agttgcattt gcccaagaaa agattacatt   360
tgccgttaga aagggaacaa cctacaagaa ctacaccaag aacaaagaac agagaagaac   420
caagaataga ggggaaaaaa tggaatcaag ttcttgaatc agatctgcca catataggct   480
tgcaaacttt caccttcacc tcctgcatca caacaatatg ccctaccat cgccgccgca    540
tccatccgcc accgcatcca tctcccattg ttgccgctgc atcgatctgc accgtcgtc   600
accgcggcat cgatctgcca ccgtcgtcac cacggcattg atctgccacc gccttcaccg   660
ccaccatcat cgccgcatcc atctcctgtc gtcgccgcca tccctgcaga gaggagtgga   720
aagaggggca aatttgaagg gagagattga gttgaacaac tgaggaggca gagggagaga   780
gaagccaaat gagagggagg ggaaaagatt gccgtgtgaa ccggagaaaa gaaaagttga   840
ggccctctga ctccttctcg agcacccatg cggtattgaa tgtgtatctt ttttttacag   900
gaattagttt tttgggacaa ccacacccca ccccaggaat cgatttttt gcggacagag    960
agagtagtat actagtatgg gaagtaattg tacaattttt aaaataattt ttaatagttg  1020
attgtatagc gagatcatcc aaaactttat atgtataagt tgtgttttg ttgtcggccc   1080
tagttttctg aaagttgcaa agagttctaa taacttattc attgatattt ccttaacatc  1140
aacttttcat actagaatgc taacgatctt catcccccaa tttgaattcc agcacatctt  1200
caaggtccgg aggccacaag agatctacac cctacaacac atttattaat agtgcgaaat  1260
tgaaccgagt cttttttct ctaaaactaa aatcaggtat aaattgaaat agcatgctat   1320
aaatacaatc tttaaatacc aatttgcata aattgatgag ccacaccttt tgagtggact  1380
gaaactaaga ttaggcaaca tggggacgcc aacagacgaa attcctctga agtaaagtaa  1440
aaaaaaacgt ggatccctga taggtggacc tcaccttcat gaacgtcagt ggctcatatc  1500
cctctaacgt atgtaagagg agcctcttcc gatatgggga accatagcaa tgctcaaccg  1560
ccagccaacc aagccatggc ctgaaaatag caaaaggcca acacatgcct gcatgccaca  1620
gacatagcaa aatcttgttg tcgccaccac cactatatat atgtgcatgc cggccggcgt  1680
tcaagttcgc cggagagaga agcaccggcg gtcaata                            1717
```

<210> SEQ ID NO 20
<211> LENGTH: 2022
<212> TYPE: DNA
<213> ORGANISM: Oryza Sativa

<400> SEQUENCE: 20

```
gacaagctgc aagcgacctg gatacttcgt agctgaaatc cacatgccca ggagtatcaa    60
tcaagttaag caaatagctt ggagcatctg gctgatcaga tgcaggaagt tggttgttag   120
catgtctgta gaacatagtt gctgtttgtg ctttgactgt gattcccctc tctctctcta   180
cctgtagaga acagatacaa tcatacaaat gttatgacaa atgcacacag tataaatatt   240
tcttttcaat ttcagtaaga aaatatccac tgaaaatgaa cactatctgt tatgctagtg   300
```

```
ctgtcatcat ctcaaatgaa atgagatgcc aattaaggaa atagtcactt aagatccagt      360
atgctcaaaa gtcaacacag tgagtacaag gattatcttt gctattacta ccggtcacca      420
aacataacga agttcaactc aactaaattc tggagtaact tccaattgat taattccggt      480
atgtgcattt atccaataag cttatggaat acggaccaca aatcaaagct accaatttct      540
cactcaacgc gtccccattt ttttcaaaac ggcaagtttg ttctcacacc tgtaacttgt      600
cgaggtactg aggttggcca tggcccttct tgatggtgcc ggtgagctcc agcaaccggt      660
cggcgagcgt ggacttgccg tggtcgacgt gcgcgatgat ggagaagttc ctgaccctct      720 ccggggata cagcccaagc tccgaaccca gcaccccgcc gcggtccggc gaagcctggg       780
aggagaggag gcgctcaggg tgctgtagcg cccgggacaa ggcgtaggcg cctggcagga      840
cgacacggcg cgcggatcgc cggagcgcgc cggcgccggc catcccggaa cagcgcggcg      900
gcggcggcgg cgggagctag ggttctggtt ggggtttggc gcaaaaggtc cacatagact      960
agagaggaac acgctgtgca actgtaagat gggcccccact gatacgatga cctatgggct     1020
taatgggcct ggagaaaatg aaggggcacc tatcagccca acaaaaatg gtttcgtatg       1080 aaacatttcg gcccataata ctactacgct gagaaatact aggaattccg aaatactacc      1140
tccgtccagg attgtcatga aattgctaat taacgactag ttgtgtaccg cgtgcgattg      1200
tctattattt taaatatac atacaaactg tataaatata aatataaagt ctgtgtgcat       1260
attttttacg tcctaaatgc atacaaatat gtataaaata tacgaagatt tttatacatt      1320
ttatgttaat gcatgtagta taattagatt tgtattttaa aatattttta tataatgtta     1380
aattcgtagt tgataataat gtattaatta atggtcaaag taaagtattg gagaccgcgt      1440
aaaatgctac tgttttaac cgagaataac aaacattttc acaatgaaca attttcatag       1500
ttaaagtttg taatttgaga taaaaaaaag tttcttatat cgactgtgtt tgcccacata      1560
ggaatgaata ctaacaagat atgcccgatt aataccttc catatatata attcttatcc       1620
ctccatcaat ggcaaagatc aatgctggct gcaaataatc acatcatttc cttaccaaca      1680
gccgacgcac gatgatcatg tgttggtgtt ggcatgcaat gcaacagacg aacggaacgc      1740
tcaccaccac caagccgacg agcggtcatc acgccgcgac acgcgacggc gacacgctat      1800
atagaaaccc ccgccgcacg cacgcgcgcc tcggcggccg gctcacctct ctccgccgcc      1860
cggcccgctc gctgatgctg ccgccgccgg cttcacgcgg gaagaggtct cagaaaccct      1920
aggcgaaagc cgccacacat ttcctgagtc ctctttcccg cggtgcggcg gccggccggg      1980
gcggcgctcc atacacccat cggatcgttc tgaaccagca gc                         2022
```

<210> SEQ ID NO 21
<211> LENGTH: 2008
<212> TYPE: DNA
<213> ORGANISM: Oryza Sativa

<400> SEQUENCE: 21

```
cctggcaaca gagcgacacg ataacatgtc aaaacttgtg cactctataa aatggtgaag       60
atatagacac gaagcataag atgtatagta agtagctagc aagaggatcg aaatgtaaga      120
gctaacccca gctagtgttt tcttttctt tttctttttt ggaacccttg ctcaatcact       180
gttaattagt ggacatctac caaaaagccc aaacttaaat tccgggttac caagttaacc      240
aaaattcttg tgacggccta taaagtttgc attctctgga tgtggatggc attgacttga      300
gcaatggagt ttgctctgga tatatgtgtg acgtctcagc ttgaaagctg aattactgta      360
ataaactttg gtcggaagct cttgagctaa aggctgggaa acaagttgat cccacaaaac      420
```

```
acgatatcat gtggctcttt taatcttctg tacgtgtagc aactaacaat aaccaccatt      480
ataatataca gatgcttgtg caacccctcc gcggactgcg gctgttccgc agatcgttgc      540
aagattcttc ctctgacttt ggtatctcgc gtcatctcct cggcttttg ctgctaccaa       600 aagtctctgc atagttaaat gtgagataca tttggggtac ttatatattt agagcacatc      660
cggatccatg gtttgtacgg aacacagacg atgcaaggga ttttctgaaa tttgaaaacc      720
tgacaattag atcattcatg aagatgaagg acatggatgt caggggcgat cgattcaata      780
tccgggccag tatatgcatc ttgtactagt agactactag tttcaacatt tcacgctgat      840
atgattagga tttgtgcaag aattgcagat aagacggata tcccttcagt tacgtttcgt      900
gactagtata cattggactg aaattattgg ttccggccgg acatttcctg cagctcgtat      960
gaacttgcta agcaagatgc caacttgcta tcccccaaat tgtcaacctc gccgtaggtt     1020
ggcatccaat tggcagttac tttattgacc tgatagggat ggccgtgtcc ttcaactcca     1080
gcttagcggt gacccccagca ggtgaatgtg gcaactcgga tatcccagcc gcagctagag    1140
ctcctctcac caatcactag ctctctgttg catcatcatt aagtcatggt gattagttaa     1200
gataaaaatg acgtattgtg attagtttag cctgcgatct catgctgtcc cagcttgctc     1260
tgaccaacaa agattcaaga taccgtttct gcactattga actaccagcc atcggttgag    1320
acgacttaga tttgatatta ttgattcatg gcttggcttg agtttacttg ggtatccaat    1380
gggcgcctct ggcttgctgg ttcctgtaac ttcgatatct taaatatata taggtggctg    1440
tttacttact taagtagcac atgtacgcct gtaatctcct catcaaactt tgaatgcgca     1500
gtgatagtca ggatcaattt tgagctaaac aaaagtttgc attgccttgg ttaaattggt    1560
cgatggttaa ttggattgag tttggatgta gtggggacat acttctcgca aatgtctgcg    1620
ctacagtgct acctgttcat tctccggtag ccatttgtcc gtagcacata aataaacaag    1680
ataataccga aattaattag ggacataact tttttaggag aaaactgtaa tgcttagcac    1740
accactaaac acgccgaggc catttttaagg ccgtagagat ccctacgatc atggctagcc    1800
atccacgacc aaaccgcaaa aatttacgcc atttttggat cgacggccgt caagtcccgt    1860
acgtcttctt ttaccaccac catttgatct gtttccttct cagacaccaa aggaacttgt    1920
tttttgtatt tttcttttcg gtagctactt tctacatctc tcttatttgg atcacgtatt    1980 atccttttc attccacgac cgacgacc                                         2008
```

<210> SEQ ID NO 22
<211> LENGTH: 2774
<212> TYPE: DNA
<213> ORGANISM: Zea mays

<400> SEQUENCE: 22

```
gagaaacccg aagtggcgag tttggagttg tacggtcctg gtgcaccgga cactgtctgg       60
tggcatacca gacagtccgg tgtgccagat cagggcaccc ttcggttcct ttgctccttt      120
gcttttgaac cctaactttg atcgtttatt ggtttgtgtt gaacctttat gcacctgtgg      180
aatatataat ctagaacaaa ctagttagtc caatcatttg tgttgggcat tcaaccacca      240
aaattattta taggaaaagg ttaaacctta tttccctttc aatctccccc ttttggtga      300 ttgatgccaa cacaaaccaa agaaaatata taagtgcaga attgaactag tttgcataag     360
gtaagtgcat aggttactta gaattaaatc aatttatact tttacttgat atgcatggtt     420
gctttctttt atttaacat tttggaccac atttgcacca cttgttttgt tttttgcaaa       480
```

```
tcttttttgga aattctttttt caaagtctttt tgcaaatagt caaaggtata tgaataagat    540
tgtaagaagc atttttcaaga tttgaaattt ctccccctgt ttcaaatgct tttcctttga     600
ctaaacaaaa ctcccccctga ataaaattct cctcttagct ttcaagaggg ttttaaatag    660
atatcaattg gaaatatatt tagatgctaa ttttgaaaat ataccaattg aaaatcaaca     720
taccaatttg aaattaaaca taccaatttta aaaaatttca aaaagtggtg gtgcggtcct    780
tttgctttgg gcttaatatt tctccccctt tggcattaac ggccaaaaaa cggagacttt    840
gtgagccatt tatactttct ccccattggt aaatgaaata tgagtgaaag attataccaa    900
atttggacag tgatgcggag tgacggcgaa ggataaacga taccgttaga gtggagtgga    960
agccttgtct tcgccgaaga ctccatttcc ctttcaatct acgacttagc atagaaatac   1020
acttgaaaac acattagtcg tagccacgaa agagatatga tcaaaggtat acaaatgagc   1080
tatgtgtgta atgtttcaat caaagtttcg agaatcaaga atatttagct cattcctaag   1140
tttgctaaag gttttatcat ctaatggttt ggtaaagata tcgactaatt gttctttggt   1200
gctaacataa gcaatctcga tatcacccct ttgttggtga tccctcaaaa agtgataccg   1260
aatgtctatg tgcttagtgc ggctgtgttc aacgggatta tccgccatgc agatagcact   1320
ctctcattgt cacataggag agggactttg ctcaatttgt agccatagtc cctaaggttt   1380
tgcctcatcc aaagtaattg cacacaacaa tgtcctgcgg caatatactt ggcttcggcg   1440
gtagaaagag ctattgagtt ttgtttctttt gaagtccaag acaccaggga tctccctaga   1500
aactgacaag tccctgatgt gctcttccta tcaattttac accctgccca atcggcatct   1560
gaatatccta ttaaatcaaa ggtggatccc ttggggtacc aaatttaagg agtgtaaact   1620
aaatatctca tgattctttt cacggcccta aggtgaactt ccttaggatc ggcttggaat   1680
cttgcacaca tgcatataga aagcatacta tctggtcgag atgcacataa atagagtaaa   1740
gatcctatca tcgaccggta tacctttttgg tctacggatt tacctcccgt gtcgaggtcg   1800
agatgcccat tagttcccat gggtgtcctg atgggcttgg catccttcat tccaaacttg   1860
ttgagtatgt cttgaatgta ctttgtttgg ctgatgaagg tgccatcttg gagttgcttg   1920
acttgaaatc ctagaaaata tttcaacttc cccatcatag acatctcgaa tttcggaatc   1980
atgatcctac taaactcttc acaagtagat ttgttagtag acccaaatat aatatcatca   2040
acataaattt ggcatacaaa caaaactttt gaaatggttt tagtaaagag agtaggatcg   2100
gctttactga ctctgaagcc attagtgata agaaaatctc ttaggcattc ataccatgct   2160
gttggggctt gcttgagccc ataaagcgcc tttgagagtt tataaacatg ttagggtac   2220
tcactatctt caaagccgag aggttgctca acatagacct attcacccca tttgatcact   2280
ttttttggtcc ttcaggatct aatagttatg tataatttag agtctcttgt ttaatggcca   2340
gatatttcta attaatctaa gaatttatga tatttttttaa ttttttatca tgtctgatga   2400
gaattaacat aaaggctcaa ttgggtcctg aattaataat agagtgaaaa ttaatccaga   2460
ggctctatta gaaccttcaa ttagtaatac caagatatat ataagatagt agagtatagt   2520
ttaaatgttg gcattgttca ttctttcttt tgttatttaa tttatgcttt ccacggtggt   2580
tagtggttac ttctgaaggg tccaaataat gcatgaagag tttgaggaca agaagtctgc   2640
cctaaaaata gcgatgcaaa ggcatggtgt ccaagccata catatagcgc actaattttta   2700
tcagcagaac aatggtattt ataggtccta gtgcccaggc aacaagagac acgaataaag   2760
catcgatcac gaca                                                      2774
```

<210> SEQ ID NO 23
<211> LENGTH: 1560
<212> TYPE: DNA
<213> ORGANISM: Oryza Sativa

<400> SEQUENCE: 23

```
atggctcgcg gcgacggcga gctggagctg tcggtggggg tccgcggcgc cggcggcggg      60
gccgcggcgg cggaccacgt ggcgccgatc agcctcggca ggctcatcct cgccggcatg     120
gtcgccggcg gcgtgcagta cggctgggcg ctgcagctct ccctcctgac gccctacgtg     180
cagactctgg ggctttcaca tgccctcact tcattcatgt ggctatgcgg tcctattgct     240
ggcttagtgg ttcaaccgtt ggttggcctg tacagtgata ggtgtacagc aagatgggga     300
agacggaggc cattcattct gacaggatgt gtgctcatct gcattgctgt cattgttgtt     360
ggcttttcgt cagacatcgg agctgcgcta ggggacacaa aggaacattg cagtctctat     420
catggtcctc gctggcatgc tgcaattgta tatgttctgg ggttttggct ccttgacttc     480
tccaacaata ctgtgcaagg tccagcacgt gctatgatgg ctgatttgtg cggtcatcat     540
gggcctagtg cagctaattc aatcttctgt tcttggatgg cgctgggaaa catcctaggt     600
tattcctctg gttccacaaa caattggcac aagtggtttc ccttcctcaa acaaatgcc      660
tgttgtgaag cctgtgcaaa cctgaaaggt gcatttctgg tggctgtggt gttcctagtc     720
atatgcttgg ctataaccct cgtcttcgcc aaggaagtac atacagagg aaacgagaac      780
ctcccaacaa aagcaaacgg cgaggttgaa gctgaaccta ccgggccact tgctgtgctc     840
aagggcttca gaacttgcc ccgcgggatg ccatccgttc ttctcgtaac tggcctcacc      900
tggctctcgt ggttcccgtt catcctctac gacaccgact ggatgggccg tgagatctac     960
cacggcgacc caaagggcac caatgctcag atctcggcat caacgaagg tgtcagaata     1020
ggcgcattcg ggctgcttct caactcgatt gttctaggat tcagctcgtt cctgatcgag    1080
cccatgtgcc ggaaggtcgg gccgagggtt gtgtgggtga cgagcaactt catggtgtgc    1140
atcgccatgg cggccaccgc gctgatcagc ttctggtcgc tcaaggacta ccacggatac    1200
gtgcagaacg ccatcaccgc cagcacgagc atcaaggccg tctgcctcgt cctcttcgcc    1260
ttcctgggtg tccctctcgc catcctgtac agcgtcccgt tcgcggtgac ggcgcagcta    1320
gcggccagca tgggcggcgg gcaggggctg tgcaccggcg tcctcaacat ctccatcgtt    1380
atccccagg tgatcatcgc ggtgggcgca ggcccgtggg acgcgctgtt cggcaagggc    1440
aacatcccgg cgttcggcgt ggcgtcgggg ttcgccctca tcggcggcgt cgtgggcatg    1500
ttcctgctgc ccaggatctc caagcgccag ttcagggccg tcagcgcggg cggccactga    1560
```

<210> SEQ ID NO 24
<211> LENGTH: 1899
<212> TYPE: DNA
<213> ORGANISM: Oryza Sativa

<400> SEQUENCE: 24

```
atggcgagtc ggggccggcc tcggccgggc tcgctccagg acctcgccgc cgccgccatc      60
gccatcctcc tcctgtccgc cgcgtccggg gccgccgctg gatccccga tcggcccgcg     120
ccggggccgc cgctgttcct cccgctcacg cgctcgtacc caacgccag ccggctcgcc      180
gcctcgtcga ggcgcggcct cggcgacggg gcgcacccca cgcgcgcat cgcctccac      240
gacgatctcc tcaccaacgg gtactacacg acgaggctgt acatcgggac gccccgcag      300
gagttcgcgt tgatcgttga ctccgggagc accgtcacct acgtgccctg cgcctcctgc     360
```

```
gagcagtgcg gcaaccacca ggatccacga tttcaacctg atctctccag ttcatattca    420
cctgtgaaat gcaacgtcga ttgtacttgt gacagtgaca aaaaacagtg cacttatgag    480
aggcagtatg ctgaaatgag ctccagcagt ggggtgcttg gtgaggacat tgtgtctttt    540
ggcagagaga gtgaacttaa gccacagcgt gctgttttg gctgtgaaaa ttctgaaact     600
ggagatttgt tcagtcagca tgctgatggt ataatgggcc tgggtcgtgg tcaacttagc    660
ataatggatc agcttgttga aaagggtgtc taagcgatt cattctcatt gtgctatggc     720
ggtatggata ttggtggtgg tgctatggtg cttggtggag tgcctgctcc ttctgacatg    780
gttttttcac attctgaccc tctccgcagt ccatattaca acattgagtt aaaggaaata    840
catgttgctg gaaaggcact gcgggtagat tcaagggtct ttaacagcaa acatgggact    900
gttttggata gtgggaccac atatgcctat ttgccagagc aagctttcgt ggcttttaaa    960
gatgctgtga caagtaaagt gcattctctc aagaaaattc gtggccctga tccaaattat   1020
aaggatatct gctttgcagg tgctggaagg aacgtctcaa agctacatga ggtatttcca   1080
gatgttgaca tggtatttgg aaatggacag aagctgtctc ttacacctga aaattattta   1140
ttccggcact ccaaagttga tggggcttat tgcttgggtg tattccaaaa tggtaaagat   1200
ccaacaacac tattaggagg catcattgtt cgtaatacac ttgtgaccta tgaccgtcac   1260
aatgaaaaga ttggcttttg gaaaactaac tgttcagagt tgtgggagag ctacatatc    1320 agtgacgctc catcaccagc cccttcaagt gatacaaatt cagaaactga tatgtcacct   1380
gctcctgccc ctagtagctt gccagagttt gatgttggtc tcattaccgt tgatatgtcc   1440
ataaatgtta cttacccgaa tctgaaacct catctgcatg agttggccga gctgatagct   1500
aaagaactgg agattgactc tagtcaggtt cgagttatga atatcacgag ccaaggaaat   1560
tctactctga ttagatgggg tattttccca gcagaatctg ataatgctat gtccaacgca   1620
acagcaatgg gtatcatcta tcggttaact cagcatcatg ttcagttgcc tgaaaatctt   1680
ggcagttatc aattgctcga gtggaatgtg cagcctttac cgagaaggtc atggtttcaa   1740
gaacatgtag tctctatact gcttgggatt ttactagttg ttttggtcac tttgtcagcc   1800
cttttagtag tacttgtttg gagaaagaaa tttagtggtc aaactgccta cagacctgtt   1860
gattcagtgg ctcccgagca agaactacag ccactataa                          1899
```

<210> SEQ ID NO 25
<211> LENGTH: 3246
<212> TYPE: DNA
<213> ORGANISM: Oryza Sativa

<400> SEQUENCE: 25

```
atggcgggga cgagtggat caatgggtac ctggaggcga tcctcgacag ccgcaccacg     60
gctgggggag ggggaggagg aggcggcggc ggcggcggcg gggaccccag gtcgccggtg    120 gcggggggcgt cgccgacgaa ggcggcgagc ccccgcggcc cgcacatgaa cttcaacccc   180
tcgcactact tcgtcgagga ggtggtcaag ggcgtcgacg agagcgacct ccaccggaca    240
tggatcaagg tcgtcgccac acgcaacgcc cgcgagcgca gcaccaggct cgagaacatg    300
tgctggcgga tctggcatct cgcgcgtaag aagaaacagc tggagctgga gggcatgcag   360
agaatctcgg cacgcaggaa ggaacaggag caggtgcgcc gtgaggcgac ggaggacctg    420
gctgaggatc tggatgaagg cgagaaagcg gacacccctcg gcgagcttgc gccggttgag   480
acagccaaga gaagttcca gaggaacttc tctgacctga ccgtcggtc tgacgacaat     540 aaggagaaga agcttacat tgtgctcatc agtgtgcatg gtcttgttcg tggcgaaaac   600
```

```
atggaactag gtcgtgattc tgacaccggt ggccaggtga atatgttgt cgaacttgca    660 agggcaatgt caatgatgcc tggagtgtac agggtggacc tcttcactcg tcaagtgtca   720
tctcctgacg tggactggag ctatggtgag ccaacggaga tgttatgctc cggttccaat   780
gatggagagg ggggcgagag tgccggagcc tacattgtgc gcataccgtg tgggccacgc   840
gataaatacc tcaagaagga agcgctgtgg ccttacctcc aagaatttgt cgatggagct   900
cttgcgcata tcctgaacat gtccaaggct ctgggagagc aggttggaaa tgggaagcca   960
gtactgcctt acgtgataca tggacactat gccgatgctg agatgttgc tgctctcctc   1020 tccggtgcgc tgaatgtgcc catggtgctc actggtcact cacttgggag gaacaagctg   1080
gagcaactgc tgaagcaagg gcgcatgtct aaagcggaga tagattcaac ctacaagatc   1140
atgaggcgta tcgagggtga ggagctgtcc ctggatgcgt cagagcttgt catcacgagc   1200
acaaggcagg agattgatga acagtgggga ttatacgatg gatttgacgt caagcttgag   1260
aaagtgttga gagcccgggc gaggcgtggg gttagctgcc atggtcgttt catgcctagg   1320
atggtggtga ttcctccagg aatggacttc agcaatgtta ttcctgaaga cattgatggg   1380
gatggtgaca gcaaagatga tatcgttggt ttggaggttg cctcacccaa gtcaatgcct   1440
ccaatttggg ctgaggtgat gcggttccta accaaccctc acaagccgat gatcctcgct   1500
ttgtcaaggc cagacccgaa gaagaacatc actaccctcg tcaaagcgtt tggagagtgc   1560
cgcccactca gggaacttgc aaaccttact ctgatcatgg gaacagaga tgacatcgac   1620 gaaatgtctg ctgggaatgc cagtgtcctc accacagttc tgaagctgat tgacaagtat   1680
gatctgtatg aagtgtggc cttccctaag catcacaatc aggctgatgt cccagagatc   1740
taccgcctcg cggccaaaat gaagggcgtc ttcatcaacc ctgctctcgt tgagccgttc   1800
ggtctcaccc tgatcgaggc tgcggcacac ggacttccaa tagtcgctac caagaatggt   1860
ggtccagtcg acattacaac tgcactgaac aatggactgc tcgttgaccc acacgaccag   1920
aacgccatcg ctgatgcact gctgaagctt gtggcggata gaacctgtg caggagtgc    1980 cggagaaacg ggctgcgcaa catccacctc tactcatggc cggagcactg ccgcacttac   2040
ctcaccaggg tggctgggtg ccggttaagg aacccgaggt ggctgaagga cacaccggca   2100
gatgctggag ctgatgatga ggagttcctg gaggattcca tggacgctca ggacctgtca   2160
ctccgtctgt ccatcgatgg tgagaagagc tccctgaaca ctaacgaccc actgtcgtcg   2220
gacccgcagg atcaggtgca gaagatcatg aacaagatca gcagtcatc agcgcttccg   2280 ccgtcgatgt cctcgggcgg tgacggtgcc aagaatgcag ccgaggccac aggcggcacc   2340
atgaacaagt acccactcct gcgccggcgc cggcgcctgt tcgtcatagc tgtggactgc   2400
tacgaagacg atggccgtgc tagcaagaag atgctgcagg tgatccaaga agttttcaga   2460
gcagtccggt cggactccca gatgtccaag atctcagggt tcgcgctgtc aactgcgatg   2520
ccgttgtccg agacactcca gcttctgaag ctcggcaaga tcccagcgac cgacttcgac   2580
gccctcatct gtggcagtgg cagcgaggtg tactatcctg gcacggtgaa ctgcatcgac   2640
gctgaaggaa agctgcgccc agaccaggac tatctgatgc acatcagcca ccgctggtcc   2700
catgacggcg cgaggcagac catagcaaag ctcatggcca gtcaggacgg ttcagacgat   2760
gctgtcgagc tggacgtggc gtccagcaat gcacactgct tcgcgttcct catcaaagat   2820
cccaaaaagg tgaaaacggt cgatgagatg agagagaggc tgaggatgcg tggtctccgg   2880
tgccacatca tgtactgcag gaacgcgaca agacttcagg ttgtcccct gctagcatca   2940
```

| | |
|---|---|
| aggtcacagg cactcaggta cctttcgtg cgctggggcc tatctgtggg gaacatgtat | 3000 |
| ctgatcactg gggaacatgg cgataccgat ctagaggaga tgctatctgg gttacacaag | 3060 |
| actgtcatcg tccggggtgt caccgagaag ggttcggaag cgctgctgag gagctcggga | 3120 |
| agttacaaga gggacgacgt cgtcccgact gagacccct tggctgcgta cacgactggt | 3180 |
| gagctgaagg ccgatgagat catgcgggct ctgaagcagg tctctaagac ttccagcggc | 3240 |
| atgtga | 3246 |

<210> SEQ ID NO 26
<211> LENGTH: 5668
<212> TYPE: DNA
<213> ORGANISM: Arabidopsis thaliana

<400> SEQUENCE: 26

| | |
|---|---|
| atactgcgtt cccacatccc caccctactt agatcaacac ataaaagtta gtaagtgaag | 60 |
| aaccacaaca acaacactag attcatcttc aagtgtatgt aggtatagta acatgaacaa | 120 |
| gaacagactc aagtacaaga tcgcatacga aaatggaaat ggcaatgtca cttccacata | 180 |
| atcaaacacg aatcctcata tcaacaaggc ctgagattct aactagctca taacaactta | 240 |
| gccaatagtt acttgagact accaaatgta tgtagaacta aagactaagg gacagagagt | 300 |
| tcgtctaaac aggtgaatct agtcgttgtt atctaataaa caattcagcc ccaaatgcag | 360 |
| aacacacata gagctctcta ttgattcaaa ttacgatctg atactgataa cgtctagatt | 420 |
| tttagggtta aagcaatcaa tcacctgacg attcaaggtg gttggatcat gacgattcca | 480 |
| gaaaacatca agcaagctct caaagctaca ctctttggga tcatactgaa ctctaacaac | 540 |
| ctcgttatgt cccgtagtgc cagtacagac atcctcgtaa ctcggattgt gcacgatgcc | 600 |
| atggctatac ccaacctcgg tcttggtcac accaggaact ctctggtaag ctagctccac | 660 |
| tccccagaaa caaccggcgc caaattgcgc gaattgctga cctgaagacg gaacatcatc | 720 |
| gtcgggtcct tgggcgattg cggcggaaga tgggtcagct tgggcttgag gacgagaccc | 780 |
| gaatccgagt ctgttgaaaa ggttgttcat tggggatttg tatacggaga ttggtcgtcg | 840 |
| agaggtttga gggaaaggac aaatgggttt ggctctggag aaagagagtg cggctttaga | 900 |
| gagagaattg agaggtttag agagagatgc ggcggcgatg agcggaggag agacgacgag | 960 |
| gacctgcatt atcaaagcag tgacgtggtg aaatttggaa ctttaagag gcagatagat | 1020 |
| ttattatttg tatccatttt cttcattgtt ctagaatgtc gcggaacaaa ttttaaaact | 1080 |
| aaatcctaaa ttttttctaat tttgttgcca atagtggata tgtgggccgt atagaaggaa | 1140 |
| tctattgaag gcccaaaccc atactgacga gcccaaaggt tcgttttgcg ttttatgttt | 1200 |
| cggttcgatg ccaacgccac attctgagct aggcaaaaaa caaacgtgtc tttgaataga | 1260 |
| ctcctctcgt taacacatgc agcggctgca tggtgacgcc attaacacgt ggcctacaat | 1320 |
| tgcatgatgt ctccattgac acgtgacttc tcgtctcctt tcttaatata tctaacaaac | 1380 |
| actcctacct cttccaaaat atatacacat cttttgatc aatctctcat tcaaaatctc | 1440 |
| attctctcta gtaaacaaga acaaaaaaat ggcggataca gctagaggaa cccatcacga | 1500 |
| tatcatcggc agagaccagt acccgatgat gggccgagac cgagaccagt accagatgtc | 1560 |
| cggacgagga tctgactact ccaagtctag gcagattgct aaagctgcaa ctgctgtcac | 1620 |
| agctggtggt tccctccttg ttctctccag ccttacccttt gttggaactg tcatagcttt | 1680 |
| gactgttgca acacctctgc tcgttatctt cagcccaatc cttgtcccgg ctctcatcac | 1740 |
| agttgcactc ctcatcaccg gttttcttc ctctggaggg tttggcattg ccgctataac | 1800 |

```
cgttttctct tggatttaca agtaagcaca catttatcat cttacttcat aattttgtgc   1860
aatatgtgca tgcatgtgtt gagccagtag ctttggatca attttttggg tcgaataaca   1920
aatgtaacaa taagaaattg caaattctag ggaacatttg gttaactaaa tacgaaattt   1980
gacctagcta gcttgaatgt gtctgtgtat atcatctata taggtaaaat gcttggtatg   2040
atacctattg attgtgaata ggtacgcaac gggagagcac ccacagggat cagacaagtt   2100
ggacagtgca aggatgaagt tgggaagcaa agctcaggat ctgaaagaca gagctcagta   2160
ctacggacag caacatactg gtggggaaca tgaccgtgac cgtactcgtg gtggccagca   2220
cactactgcg gtaccctga tggcctcctc cgaggacgtc atcaaggagt tcatgcgctt   2280
caaggtgcgc atggagggct ccgtgaacgg ccacgagttc gagatcgagg gcgagggcga   2340
gggccgcccc tacgagggca cccagaccgc caagctgaag gtgaccaagg gcggcccct   2400 gcccttcgcc tgggacatcc tgtcccctca gttccagtac ggctccaagg cctacgtgaa   2460
gcacccccgc gacatccccg actacttgaa gctgtccttc cccgagggct tcaagtggga   2520
gcgcgtgatg aacttcgagg acggcggcgt ggtgaccgtg acccaggact cctccctgca   2580
ggacggcgag ttcatctaca aggtgaagct gcgcggcacc aacttcccct ccgacggccc   2640
cgtaatgcag aagaagacca tgggctggga ggcctccacc gagcggatgt accccgagga   2700
cggcgccctg aagggcgaga tcaagatgag gctgaagctg aaggacggcg ccactacga   2760 cgccgaggtc aagaccacct acatggccaa gaagcccgtg cagctgcccg gcgcctacaa   2820
gaccgacatc aagctggaca tcacctccca caacgaggac tacaccatcg tggaacagta   2880
cgagcgcgcc gagggccgcc actccaccgg cgcctaatct agagtccgca aaaatcacca   2940
gtctctctct acaaatctat ctctctctat ttttctccag aataatgtgt gagtagttcc   3000
cagataaggg aattagggtt cttatagggt ttcgctcatg tgttgagcat ataagaaacc   3060
cttagtatgt atttgtattt gtaaaatact tctatcaata aaatttctaa ttcctaaaac   3120
caaaatccag tgaccatggc tatacccaac ctcggtcttg gtcacaccag gaactctctg   3180
gtaagctagc tccactcccc agaaacaacc ggcgccaaat tgcgcgaatt gctgacctga   3240
agacggaaca tcatcgtcgg gtccttgggc gattgcggcg gaagatgggt cagcttgggc   3300
ttgaggacga gacccgaatc cgagtctgtt gaaaaggttg ttcattgggg atttgtatac   3360
ggagattggt cgtcgagagg tttgagggaa aggacaaatg ggtttggctc tggagaagaa   3420
gagtgcggct ttagagagag aattgagagg tttagagaga gatgcggcgg cgatgagcgg   3480
aggagagacg acgaggacct gcattatcaa agcagtgacg tggtgaaatt tggaactttt   3540
aagaggcaga tagatttatt atttgtatcc attttcttca ttgttctaga atgtcgcgga   3600
acaaatttta aaactaaatc ctaaatttt ctaatttgt tgccaatagt ggatatgtgg   3660
gccgtataga aggaatctat tgaaggccca aacccatact gacgagccca aaggttcgtt   3720
ttgcgtttta tgtttcggtt cgatgccaac gccacattct gagctaggca aaaacaaac   3780 gtgtctttga atagactcct ctcgttaaca catgcagcgg ctgcatggtg acgccattaa   3840
cacgtggcct acaattgcat gatgtctcca ttgacacgtg acttctcgtc tcctttctta   3900
atatatctaa caaacactcc tacctcttcc aaaatatata cacatctttt tgatcaatct   3960
ctcattcaaa atctcattct ctctagtaaa caagaacaaa aaaatggcgg atacagctag   4020
aggaacccat cacgatatca tcggcagaga ccagtacccg atgatgggcc gagaccgaga   4080
ccagtaccag atgtccggac gaggatctga ctactccaag tctaggcaga ttgctaaagc   4140
```

```
tgcaactgct gtcacagctg gtggttccct ccttgttctc tccagcctta cccttgttgg    4200
aactgtcata gctttgactg ttgcaacacc tctgctcgtt atcttcagcc caatccttgt    4260
cccggctctc atcacagttg cactcctcat caccggtttt ctttcctctg gagggtttgg    4320
cattgccgct ataaccgttt tctcttggat ttacaagtaa gcacacattt atcatcttac    4380
ttcataattt tgtgcaatat gtgcatgcat gtgttgagcc agtagctttg gatcaatttt    4440
tttggtcgaa taacaaatgt aacaataaga aattgcaaat tctagggaac atttggttaa    4500
ctaaatacga aatttgacct agctagcttg aatgtgtctg tgtatatcat ctatataggt    4560
aaaatgcttg gtatgatacc tattgattgt gaataggtac gcaacgggag agcacccaca    4620
gggatcagac aagttggaca gtgcaaggat gaagttggga agcaaagctc aggatctgaa    4680
agacagagct cagtactacg acagcaaca tactggtggg gaacatgacc gtgaccgtac    4740
tcgtggtggc cagcacacta ctgcggtacc cctgatggcc tcctccgagg acgtcatcaa    4800
ggagttcatg cgcttcaagg tgcgcatgga gggctccgtg aacggccacg agttcgagat    4860
cgagggcgag ggcgagggcc gcccctacga gggcacccag accgccaagc tgaaggtgac    4920
caagggcggc cccctgccct cgcctggga catcctgtcc cctcagttcc agtacggctc    4980
caaggcctac gtgaagcacc ccgccgacat ccccgactac ttgaagctgt ccttccccga    5040
gggcttcaag tgggagcgcg tgatgaactt cgaggacggc ggcgtggtga ccgtgaccca    5100
ggactcctcc ctgcaggacg gcgagttcat ctacaaggtg aagctgcgcg gcaccaactt    5160
cccctccgac ggccccgtaa tgcagaagaa gaccatgggc tgggaggcct ccaccgagcg    5220
gatgtacccc gaggacggcg ccctgaaggg cgagatcaag atgaggctga agctgaagga    5280
cggcggccac tacgacgccg aggtcaagac cacctacatg gccaagaagc ccgtgcagct    5340
gcccggcgcc tacaagaccg acatcaagct ggacatcacc tcccacaacg aggactacac    5400
catcgtggaa cagtacgagc gcgccgaggg ccgccactcc accggcgcct aatctagagt    5460
ccgcaaaaat caccagtctc tctctacaaa tctatctctc tctatttttc tccagaataa    5520
tgtgtgagta gttcccagat aagggaatta gggttcttat agggtttcgc tcatgtgttg    5580
agcatataag aaacccttag tatgtatttg tatttgtaaa atacttctat caataaaatt    5640
tctaattcct aaaaccaaaa tccagtga                                        5668
```

<210> SEQ ID NO 27
<211> LENGTH: 3359
<212> TYPE: DNA
<213> ORGANISM: Sorghum bicolor

<400> SEQUENCE: 27

```
acgggccgag ggagtagtat atatgagatg tttatttttc ttttctttt tccaacttgt      60 tgggtattct ggttctgggt ggaaaggggg gcatcaaaat tcaaaagag aaaaaggtgt     120 atatgatccg cctacttgcc ggtcgatcag tatggcacct gactgagtac aggtcatggg    180
ggcaaaagca ggccactgtt tcatgaatag tggagtgggt catgaactca taatgtgttt    240
ttattagcat gatgaaatga aaaaggtacg gaaaggagaa gagagctagc gatacaaagg    300
cacgcttagt ttggcatttt ggagtggaaa gggctgtact tcgatttttt tttccttgca    360
aaaaggcgta tttggtttag gccttgttta gttccccaaa aattttgcaa aatttttcac    420
attctccgtc acatcgaatc tttagacgta tgcattgagt attaaatata aataaaaata    480
aaaactaatt gcagagtttg gtcgaaattg acgagacgaa tcttttgagc ctagttagtc    540
tataattgga caatatttgt caaatacaaa cgaaagtgat actattccta ttttgcaaaa    600
```

| | |
|---|---|
| aaaattggaa gtaaacaagc ccttaattgg agcggaactg ttcccatcga agtactacgg | 660 |
| tatagcacca agcaaatgca gctgtgcaca gggcaagctg ccaaaggagt ggcagggcac | 720 |
| cagccacata ggtttgacgt ggaaggcatt gtcctacgca atgagaattt taggtcccga | 780 |
| ttagcaaagc tcccaagctt attgtggact aaatccaata agaactctgc taaacagagt | 840 |
| ttttttttaga gagaattgat tttctgtgtt gaataatttt ttgaaatgaa ctaagaggct | 900 |
| gtaaaaagta gtttctattg attctgtgta gtcattctct actgtgattt taagagttta | 960 |
| tattaaagaa tcgaagagaa tcactgtaag tcacataatc acttttcacc aagaatcaga | 1020 |
| attagataga gcttcaccaa acatgccctt taccacgaac acacttgaag cgaagcaaat | 1080 |
| ttgcagccaa aatctggaag atcgattttg accggtagaa gaaactgatc ttatgtgtca | 1140 |
| ccgctccacc tagtccaata agaacgggga gggacacaat aatgtcgaaa ttaggtgccc | 1200 |
| agcttgatgc tagtagtagc ttagcttcag tggttcatct cgaaaagcaa ggcatgctag | 1260 |
| ctgctagcag cggtttgaac ggctccaaaa cgttgattcc tgtctccctt tcgcctagta | 1320 |
| tcctcgtcag agcttttcag tttccaaggc ctcctgactt tacacgccag catcggaatc | 1380 |
| aggcgaagtc catactgtac caaacacttc ttttttttaat taataaaaaa aagaagaaaa | 1440 |
| atggagcata tggtgtgagg tgaacgaatg ggccaacggg cacacaaatt attgcatgga | 1500 |
| cccagactat tgcaagcctg ctaatagcga gacacggaac tggacttcag agacacgcaa | 1560 |
| ggcaagagag aaaaaaagcc cagactacgg cccacatgag attcggcccc gtcaccttca | 1620 |
| cctccgtcct ccggcaacca gcggccgatc caagtgagcg tccgtccaca acctcgtacg | 1680 |
| tatcgccgcg cggaagcggc gcgatcgcgc aacgcacgcc ttgtcgtctc gtcgacaccc | 1740 |
| cccctacaca ggtgtcgcgc ggctccggac acgagtctcg catgcgtccc acgcggcggc | 1800 |
| gccaggtccc gcctccgcgc atccccacgc cctctataaa cgccccgctc tccctggccc | 1860 |
| tcgtccacct cactcgtagc cgtagcatca gctgcagcag gcgctctggg cagtgtgcgc | 1920 |
| acgtggtggt actacctagc tcgctctgct aagctaagct aagcagcttg ccatggcgga | 1980 |
| tcaccaccgg ggcgggacgg gaggtggcgc gggtggctac ggcgactaca accgtgggg | 2040 |
| cggcgccggc atgtacggcg agtcgcagca gcagcagcag aagcagggcg ccatgatgac | 2100 |
| ggcgatcaag gcggcgacgg ccgcgacctt cggcgggtcg atgctggtgc tgtccgggct | 2160 |
| gatcctggcg ggcaccgtga tcgcgctcac ggtcgccacc ccggtgctgg tgatcttcag | 2220 |
| cccggtgctg gtgccggccg ccatcgcgct ggcgctcatg gccgccgggt tcgtcacctc | 2280 |
| cggcggcctc ggcgtcgccg cgctgtccgt cttctcctgg atgtacaagt acctgacggg | 2340 |
| caagcacccg ccgggcgccg accagctgga ccacgccaag gcgaggctgg cgtccaaggc | 2400 |
| ccgcgacatc aaggacgcag cgcagcaccg catcgaccag gcgcagggt ctgcggtacc | 2460 |
| cctgatggcc tcctccgagg acgtcatcaa ggagttcatg cgcttcaagg tgcgcatgga | 2520 |
| gggctccgtg aacggccacg agttcgagat cgagggcgag ggcgagggcc gccctacga | 2580 |
| gggcacccag accgccaagc tgaaggtgac caagggcggc cccctgccct cgcctggga | 2640 |
| catcctgtcc cctcagttcc agtacggctc caaggcctac gtgaagcacc ccgccgacat | 2700 |
| ccccgactac ttgaagctgt ccttccccga gggcttcaag tgggagcgcg tgatgaactt | 2760 |
| cgaggacggc ggcgtggtga ccgtgaccca ggactcctcc ctgcaggacg gcgagttcat | 2820 |
| ctacaaggtg aagctgcgcg gcaccaactt cccctccgac ggccccgtaa tgcagaagaa | 2880 |
| gaccatgggc tgggaggcct ccaccgagcg gatgtacccc gaggacggcg ccctgaaggg | 2940 |

```
cgagatcaag atgaggctga agctgaagga cggcggccac tacgacgccg aggtcaagac   3000
cacctacatg gccaagaagc ccgtgcagct gcccggcgcc tacaagaccg acatcaagct   3060
ggacatcacc tcccacaacg aggactacac catcgtggaa cagtacgagc gcgccgaggg   3120
ccgccactcc accggcgcct aatctagagt ccgcaaaaat caccagtctc tctctacaaa   3180
tctatctctc tctatttttc tccagaataa tgtgtgagta gttcccagat aagggaatta   3240
gggttcttat agggtttcgc tcatgtgttg agcatataag aaacccttag tatgtatttg   3300
tatttgtaaa atacttctat caataaaatt tctaattcct aaaaccaaaa tccagtgac     3359
```

<210> SEQ ID NO 28
<211> LENGTH: 2941
<212> TYPE: DNA
<213> ORGANISM: Sorghum bicolor

<400> SEQUENCE: 28

```
ctacctgccg ttggctctag gattggaggg cgcgagtaag gcgaagcaca gataaaaagg     60
gattgattca ttctaggaag cttccactat gtcataaaag cccggtagct ttgtccagta    120
actctcaaaa tggaagccat gcttgatatg aataccatct ttgagaccga gcaccaaggg    180
gcaatgatca gagatatcaa aagcttggct ccgcaagata cactttggaa agagtggttc    240
ccaatatgta ttgtagtaca aaggacccaa tcaagtttga ccaaagtggg tgcttccctc    300
tttttcgacc agggtttctt gtgctttgat cgatgtgaag atattgtttc ctatttagaa    360
acaaaaggaa acaatttgta tgttttgct cttctctcct ctcttctctc tattccttgc     420
tatattagca aaatacttat gtagcacagt tagtgcacat agaaactatg atagtttcta    480
tactatgagt acctaagaa aattgacatt tgtttagatg gtttgcttgc taatttggat     540
ttcatacttc tacgaggcca gtctcaatgt gacttacaaa agaatttcat tctcatttca    600
tgatatgaca catcaacaaa tttgttagtt agcaagttat tatgatgtga aatagagagc    660
atgggtgatg accgatctaa tttatctcac caactgaaat gagaaaaaag ctccctactg    720
ctggcaaggc tgaccttgac cttgcttagc aaaccctatc aaatctttgg caagagctga    780
aatcaaagat agtgactcat ggcccgacat cgctcggccc actgctatag aacaagagca    840
tacacaacaa accctcactc gttgtggttt atgataccttt aatgacaagt gggcctgtac    900
ctttctggcc ccatgtctct gacagaggta taggtgtat gctatgggtg agaagcagga     960
tggccgagga gaggctggca tgggcggtgg agtgctccct agtccgatag tccctagtcc   1020
tagtctcttc ggttccctcc tatatatggc caaatgggcc ggacacgatc ggcatgggct   1080
tggcacaaaa aaaaagcaca agcatgatgt aaggctgtgc ctaggccgtt ggttcggccc   1140
gcaatgccga catggggcat gacatggtta atgggccggc acgacagcga ccctattatt   1200
ttgcgccatt ggatagccat aggagacacc agcaccgttg gatcagccga gactgtcaca   1260
tataaggaaa gatgtgcctg aaaccctacc tctccacctc tcctacgcag gcgccgctgc   1320 gctctcccctc tccccactcc cttttcccac ataggcgcac tatcgctctc tccgactccc   1380
actcttcctc tctccgatcc cttcacttcg cataggcgcg tgcgtggcct cgccactctc   1440
gaagcttgtg gcgcggccc catccccggt agtgcggtgg cagccttcct acggtggtgg    1500
gctagcctaa cctgtgatgt gtggttttat atgagacaaa catttgttga tctgtatttt   1560
tgatatgttt ttctttgatt catcgatcta tttctcttct cgatctatga ttcttaagtt   1620
tcttttttca atctgtgatg tagtcactat gaatttgaag atctcagcag gtgtcatggc   1680
ataggtaaaa ggccatagta ctgtgcctag gtcaagacgg tgacttggtg gcactatcag   1740
```

```
gcaggcaagc taccgtgctg cgcagtgccg tgtctagccg tgcccgtgct gccgtttggc    1800
ctcgtatacc tagtccctct tcgtccccgg ttccccctcc acctcttgct tgtccagttc    1860
gtctcctcaa taaccacacc cgcacaccta caccgagagg cggcgacaga gggaagacac    1920
atacaccgtc tctttccttc ctttgtcgtc aactcgtcgt gtctctctgc ggtacccctg    1980
atggcctcct ccgaggacgt catcaaggag ttcatgcgct tcaaggtgcg catggagggc    2040
tccgtgaacg gccacgagtt cgagatcgag ggcgagggcg agggccgccc ctacgagggc    2100
acccagaccg ccaagctgaa ggtgaccaag ggcggccccc tgcccttcgc ctgggacatc    2160
ctgtcccctc agttccagta cggctccaag gcctacgtga agcaccccgc cgacatcccc    2220
gactacttga agctgtcctt ccccgagggc ttcaagtggg agcgcgtgat gaacttcgag    2280
gacggcggcg tggtgaccgt gacccaggac tcctccctgc aggacggcga gttcatctac    2340
aaggtgaagc tgcgcggcac caacttcccc tccgacggcc ccgtaatgca agaagaagacc   2400 atgggctggg aggcctccac cgagcggatg taccccgagg acggcgccct gaagggcgag    2460
atcaagatga ggctgaagct gaaggacggc ggccactacg acgccgaggt caagaccacc    2520
tacatggcca agaagcccgt gcagctgccc ggcgcctaca agaccgacat caagctggac    2580
atcacctccc acaacgagga ctacaccatc gtggaacagt acgagcgcgc cgagggccgc    2640
cactccaccg gcgcctaatc tagagtccgc aaaaatcacc agtctctctc tacaaatcta    2700
tctctctcta ttttttctcca gaataatgtg tgagtagttc ccagataagg gaattagggt    2760
tcttataggg tttcgctcat gtgttgagca tataagaaac ccttagtatg tatttgtatt    2820
tgtaaaatac ttctatcaat aaaatttcta attcctaaaa ccaaaatcca gtgacgcggc    2880
cgcacccata atacccataa tagctgtttg ccagtaatca tggtcatagc tgtttcctgt    2940
g                                                                   2941

<210> SEQ ID NO 29
<211> LENGTH: 1851
<212> TYPE: DNA
<213> ORGANISM: Hordeum vulgare

<400> SEQUENCE: 29
gatctcgatg tgtagtctac gagaagggtt aaccgtctct tcgtgagaat aaccgtggcc     60
taaaaataag ccgatgagga taaataaaat gtggtggtac agtacttcaa gaggtttact    120
catcaagagg atgcttttcc gatgagctct agtagtacat cggacctcac atacctccat    180
tgtggtgaaa tattttgtgc tcatttagtg atgggtaaat tttgtttatg tcactctagg    240
ttttgacatt tcagttttgc cactcttagg ttttgacaaa taatttccat tccgcggcaa    300
aagcaaaaca attttatttt acttttacca ctcttagctt tcacaatgta tcacaaatgc    360
cactctagaa attctgttta tgccacagaa tgtgaaaaaa aacactcact tatttgaagc    420
caaggtgttc atggcatgga aatgtgacat aaagtaacgt tcgtgtataa gaaaaaattg    480
tactcctcgt aacaagagac ggaaacatca tgagacaatc gcgtttggaa ggctttgcat    540 caccctttgga tgatgcgcat gaatggagtc gtctgcttgc tagccttcgc ctaccgccca    600
ctgagtccgg gcggcaacta ccatcggcga accacccaga tgacctctac cgatcgaccg    660
gacatgaatg cgctaccttc gtcggcgacg atggccgcgt acgctggcga cgtgcccccg    720
catgcatggc ggcacatggc gagctaggaa cctaggaccg tcgtggccg ccggctataa    780 atatcccatg gtcgtgagac cactagaagg aagcagcacc tggcactgcg agagcgagcg    840
```

```
tgcagtgagt agatagacta gaccaacgac gacggcaggc ggtacccctg atggcctcct    900
ccgaggacgt catcaaggag ttcatgcgct tcaaggtgcg catggagggc tccgtgaacg    960
gccacgagtt cgagatcgag ggcgagggcg agggccgccc ctacgagggc acccagaccg   1020
ccaagctgaa ggtgaccaag gcggccccc  tgcccttcgc ctgggacatc ctgtcccctc   1080
agttccagta cggctccaag gcctacgtga agcaccccgc cgacatcccc gactacttga   1140
agctgtcctt ccccgagggc ttcaagtggg agcgcgtgat gaacttcgag gacggcggcg   1200
tggtgaccgt gacccaggac tcctccctgc aggacggcga gttcatctac aaggtgaagc   1260
tgcgcggcac caacttcccc tccgacggcc ccgtaatgca agaagacc   atgggctggg   1320 aggcctccac cgagcggatg taccccgagg acggcgccct gaagggcgag atcaagatga   1380
ggctgaagct gaaggacggc ggccactacg acgccgaggt caagaccacc tacatggcca   1440
agaagcccgt gcagctgccc ggcgcctaca agaccgacat caagctggac atcacctccc   1500
acaacgagga ctacaccatc gtggaacagt acgagcgcgc cgaggccgc  cactccaccg   1560 gcgcctaatc tagagtccgc aaaaatcacc agtctctctc tacaaatcta tctctctcta   1620
tttttctcca gaataatgtg tgagtagttc ccagataagg gaattagggt tcttataggg   1680
tttcgctcat gtgttgagca tataagaaac ccttagtatg tatttgtatt tgtaaaatac   1740
ttctatcaat aaaatttcta attcctaaaa ccaaaatcca gtgacgcggc cgcacccata   1800
atacccataa tagctgtttg ccagtaatca tggtcatagc tgtttcctgt g            1851
```

<210> SEQ ID NO 30
<211> LENGTH: 753
<212> TYPE: DNA
<213> ORGANISM: Eutrema salsugineum

<400> SEQUENCE: 30

```
atggagggct cgtccaaagg gttgagaaaa ggtgcttgga ctgctgaaga agatagtctc     60
ttgaggcaat gcattgataa gtatggagaa ggcaaatggc atcaagttcc tttaagagct    120
gggctaaatc ggtgcaggaa gagttgtaga ttaagatggt tgaactacct gaagccaagt    180
atcaaaagag gaaaacttag ctctgatgag gttgatcttc ttcttcgcct tcataagctt    240
ctaggaaaca ggtggtcctt aattgctggt agattacccg gtcgtactgc taatgatgtc    300
aagaattact ggaacaccca tttgagtaag aagcatgaac catgttgtaa gacaaagatg    360
aaaaatagaa acattccttg ctcttctacc gcaccagcca aaaaaatcga cgttttcaaa    420
cctcgacctc gatccttcac tgttaacaac ggctgcagtc gtcatccgca tggcctgcca    480
gaagctgacg ttagtcctcc atgccttgga cccaaaagca tcagtaattt tgtgaaaat    540 attatcacat gtgaaaaaga tgaggagaaa tatgagcttg ttagtaattt aatggttaat    600
ggagagaagt ggtgggagaa tttgttagat gagagccaag agccagattc gctcgttcca    660
gaagccacgg tagcagaaaa gggggcaact tccgcttttg acgttgagga actttggagt    720
ttgttggatg gggacactgt ggaacttgat tag                                 753
```

<210> SEQ ID NO 31
<211> LENGTH: 21
<212> TYPE: DNA
<213> ORGANISM: Sorghum bicolor

<400> SEQUENCE: 31

```
tctctacaga tccaaaggtg c                                               21
```

```
<210> SEQ ID NO 32
<211> LENGTH: 7
<212> TYPE: PRT
<213> ORGANISM: Sorghum bicolor

<400> SEQUENCE: 32

Ser Leu Gln Ile Gln Arg Cys
1               5

<210> SEQ ID NO 33
<211> LENGTH: 21
<212> TYPE: DNA
<213> ORGANISM: Sorghum bicolor

<400> SEQUENCE: 33
tctctacaga tctaaaggtg c                                                 21

<210> SEQ ID NO 34
<211> LENGTH: 4
<212> TYPE: PRT
<213> ORGANISM: Sorghum bicolor

<400> SEQUENCE: 34

Ser Leu Gln Ile
1

<210> SEQ ID NO 35
<211> LENGTH: 21
<212> TYPE: DNA
<213> ORGANISM: Sorghum bicolor

<400> SEQUENCE: 35
tctctataga tccaaaggtg c                                                 21
```

STERILE MUTANT AND TWO LINE BREEDING SYSTEM

CROSS REFERENCE TO RELATED APPLICATIONS

This patent application is the U.S. national stage entry, under 35 U.S.C. § 371, of International Application Number PCT/US2019/012217, filed Jan. 3, 2019, which claims priority to U.S. Provisional Application No. 62/813,305, filed Jan. 3, 2018, the entire contents of each of which are hereby incorporated herein by reference.

GOVERNMENT FUNDING

This invention was made with government support under IOS-0721192 and IOS-1322796 awarded by the National Science Foundation. The government has certain rights in the invention.

SEQUENCE LISTING

The present specification makes reference to a Sequence Listing (submitted electronically as a .txt file named "020871-9140-WO01_As_Filed_Sequence_Listing.txt." The .txt file was generated on Jan. 3, 2019 and is 98,730 bytes in size. The entire contents of the Sequence Listing are hereby incorporated by reference.

TECHNICAL FIELD

The present invention relates to nuclear male sterile mutant plants, such as sorghum mutants, three-component genetic constructs, and methods of using said mutants and genetic constructs, such as in a two-line male sterility system for hybrid breeding.

BACKGROUND

Sorghum (*Sorghum bicolor* L. Moench) is the fifth most important grain crop in the world. Moreover, sorghum is becoming increasingly important as a promising bioenergy crop for sugar, biomass, and biofuel production. At present, genetic crosses between two sorghum lines, which is required for breeding and many genetic studies, is primarily carried out by hand emasculation to remove anthers or using plastic bag to prevent pollen shedding from the maternal parent. The hand emasculation method is inefficient and painstaking. The plastic bag method is to tightly wrap a plastic bag around the panicle during anthesis. The resulting high moisture around the panicle prevents anthers from dehiscence. Two or three days after anthesis when pollen grains are dead, the anthers are shaken off. After the plastic bag is removed, the panicle is manually pollinated. This method is widely used for making crosses between two lines that are phenotypically different, so that the F1 plants can be visibly separated from the self-pollinated plants because the plastic bag covering cannot kill all pollen grains and the probability to produce self-pollinated seeds is pretty high. The high temperature and high moisture within the plastic bag also kill ovaries, leading to low or no seed set. In addition, the plastic bag method is not feasible for making crosses between two lines that have similar appearance or between mutants isolated from the same genetic background unless molecular markers are available to distinguish the F1 plants from the self-pollinated plants.

The cytoplasmic male sterility (CMS)-based three-line system and the nuclear male sterility (NMS)-based two-line system are employed for plant hybrid breeding. CMS, which is caused by incompatibility of the cytoplasmic genome with the nuclear genome, is predominantly used for hybrid production in crops. The CMS breeding system requires three lines for hybrid seed production and is complicated and expensive, and limits the use of diverse germplasm resources for exploring strong heterosis. The completely male sterile (A line) serves as the female parent. The maintainer line (B line) is needed to pollinate the A line for maintaining the A line. The F1 hybrid seeds are produced by pollination between the male parent (R line) and the A line. The commercial production of hybrid sorghum mainly uses the A1 cytoplasm, although several types of CMS lines are available. Similar to T-cytoplasmic maize hybrids, the A-cytoplasmic sorghum hybrids are predisposed to devastating diseases.

Nuclear male sterile (NMS) can be manipulated to develop into the two-line breeding system, but requires the conditional male sterility to produce pure male sterile parent. In the NMS two-line breeding system, the conditional male sterile line, such as photoperiod/thermosensitive genic male sterile lines (PTGMS), is used as the male sterile line. The male fertility PTGMS is reversible, which allows hybrid seed production under the restrictive condition and maintaining PTGMS under the permissive condition. The production of pure PTGMS and hybrid seeds rely on the strict environmental conditions, but which are not reliable. Furthermore, unavailability of conditional male sterile mutants, such as PTGMS, restricts the wide application of the NMS two-line breeding system to other crops. No NMS breeding system has been used to produce hybrid seeds in sorghum. Therefore, compared with maize and rice, the lack of widely applicable hybrid breeding system cannot meet rapidly increasing demands for sorghum production.

Eight different NMS lines were previously reported in sorghum; however, only five of them, i.e., ms1, ms2, ms3, ms7 and msaI, have been preserved and introduced into different genetic backgrounds. Because the lack of conditional NMS, no NMS hybrid breeding system is used in sorghum. Due to the difficulty to produce a large amount of pure male sterile lines, the NMS and NMS genes are not exploited for hybrid breeding. There is a need to generate and develop a new breeding system, such as an NMS two-line breeding system, for producing sorghum hybrid varieties.

SUMMARY

The present disclosure is directed to a three-component genetic construct for use in a two-line nuclear male sterility system, the three-component system comprising: (a) a first component comprising a nuclear male sterile gene operably linked to a first promoter, wherein the nuclear male sterile gene comprises a MALE STERILE8 (MS8) gene encoding a protein having at least about 80% identity to the polypeptide sequence of SEQ ID NO: 1 or a TAPETUM DEGENERATION RETARDATION (TDR) gene encoding a protein having at least about 80% identity to the polypeptide sequence of SEQ ID NO: 3; (b) a second component comprising a pollen killing nucleotide sequence operably linked to a second promoter, wherein the second promoter is a pollen specific promoter; and (c) a third component comprising a seed specific selectable marker gene operably linked to a third promoter.

The present disclosure is directed to a method of generating a bridge plant for use in a two-line nuclear male sterility breeding system, the method comprising: (a) introducing a transgene construct into an ms8:ms8 mutant plant thereby generating a transformed mutant plant, wherein the transgene construct comprises said three-component genetic construct; (b) collecting seed from the transformed mutant plant; and (c) growing the collected seed thereby generating the bridge plant, wherein the bridge plant comprises the ms8:ms8 mutant background and one copy of said three-component genetic construct.

The present disclosure is directed to a bridge plant generated by said method, wherein the bridge plant is used to produce transgene-free male sterile plants.

The present disclosure is directed to a method for generating a male sterile plant and/or a maintained bridge plant, the method comprising: (a) growing seed collected from said bridge plant, wherein the seed comprises maintained bridge plant seed and male sterile plant seed, wherein the maintained bridge plant seed is suspected as being homozygous for the ms8 mutation and hemizygous for the transgene construct, and wherein the male sterile plant seed is suspected as being homozygous for the ms8 mutation and does not comprise the transgene construct; (b) determining the presence or absence of the detectable marker in the seed; (c) identifying the maintained bridge plant seed based on the presence of the detectable marker in the seed and identifying the male sterile plant seed based on absence of the detectable marker in the seed; and d) isolating and growing the male sterile plant seed thereby generating the male sterile plant and/or isolating and growing the maintained bridge plant seed thereby generating the maintained bridge plant.

The present disclosure is directed to a male sterile plant generated by said method.

The present disclosure is directed to a bridge plant generated by said method.

The present disclosure is directed to a two-line nuclear male sterility system for plant breeding, the system comprising: said male sterile plant and said bridge plant.

The present disclosure is directed to a method of generating a hybrid seed, the method comprising: (a) planting seed of said male sterile plant adjacent to seed of a male fertile plant variety; (b) allowing the male fertile plant to cross-pollinate with the male sterile plant; and (c) harvesting and sorting F1 hybrid seed.

The present disclosure is directed to an isolated polynucleotide sequence encoding a modified MALE STERILE 8 (MS8) polypeptide, the isolated polynucleotide sequence comprising a nucleotide sequence having at least 80% identity to SEQ ID NO: 5 and a nucleotide substitution at a position corresponding to position 442 or 448 of SEQ ID NO: 5, wherein the modified MS8 polypeptide is functionally abnormal in pollen production.

The present disclosure is directed to a vector comprising said isolated polynucleotide sequence.

The present disclosure is directed to a sorghum plant comprising a recessive nuclear male sterile gene, wherein the sorghum plant is male sterile and the recessive nuclear male sterile gene is a modified basic HELIX-LOOP-HELIX (bHLH) transcription factor gene encoding an inactivated bHLH transcription factor, wherein the inactivated bHLH transcription factor causes early degeneration of tapetal cells in the anther of the sorghum plant.

The present disclosure is directed to a *Sorghum bicolor* seed designated as MS8, wherein a sample of said seed has been deposited as ATCC Patent Deposit No. PTA-127606.

The present disclosure is directed to a plant, or a part thereof, produced by growing said seed.

The present disclosure is directed to a pollen from said plant.

The present disclosure is directed to an ovule from said plant.

The present disclosure is directed to a *Sorghum bicolor* plant having all the physiological and morphological characteristics of said plant.

The present disclosure is directed to a tissue culture of regenerable cells from said plant, or said part thereof.

The present disclosure is directed to a protoplast produced from said tissue culture.

The present disclosure is directed to a *Sorghum bicolor* plant regenerated from said tissue culture, wherein the plant has all of the physiological and morphological characteristics of a plant produced by growing a seed designated MS8 and deposited under ATCC Patent Deposit No.

The present disclosure is directed to a tissue culture of regenerable cells from said plant, or said part thereof.

The present disclosure is directed to a protoplast produced from said tissue culture.

The present disclosure is directed to a *Sorghum bicolor* plant regenerated from said tissue culture, wherein the plant has all of the physiological and morphological characteristics of a plant produced by growing a seed designated MS8 and deposited under ATCC Patent Deposit No. PTA-127606.

The present disclosure is directed to a method for producing a *Sorghum bicolor* mutant MS8-derived *Sorghum bicolor* L. Moench plant, comprising: (a) crossing MS8 plants grown from MS8 seed, representative seed of which has been deposited under ATCC Patent Deposit No. PTA-127606, with a second *Sorghum bicolor* plant to yield progeny *Sorghum bicolor* seed; and (b) growing the progeny seed to yield an *Sorghum bicolor* mutant MS8-derived *Sorghum bicolor* plant.

The present disclosure is directed to a method of introducing a desired trait into *Sorghum bicolor* MS8 comprising: (a) crossing MS8 plants grown from MS8 seed, representative seed of which has been deposited under ATCC Patent Deposit No. PTA-127606, with plants of a second *Sorghum bicolor* mutant that comprise a desired trait to produce F1 progeny plants, wherein the desired trait is selected from the group consisting of male sterility, site-specific recombination, increased transformability, abiotic stress tolerance, herbicide resistance, insect resistance, disease resistance, altered phosphorus, altered antioxidants, altered fatty acids, altered essential amino acids and altered carbohydrates; (b) selecting F1 progeny plants that have the desired trait to produce selected F1 progeny plants; (c) crossing the selected progeny plants with the MS8 plants to produce backcross progeny plants; (d) selecting for backcross progeny plants that have the desired trait and physiological and morphological characteristics of *Sorghum bicolor* mutant MS8 to produce selected backcross progeny plants; and (e) repeating steps (c) and (d) three or more times in succession to produce selected fourth or higher backcross progeny plants that comprise the desired trait and all the physiological and morphological characteristics of *Sorghum bicolor* mutant MS8.

The present disclosure is directed to a plant produced by said method, wherein the plant has the desired trait and all of the physiological and all morphological characteristics of said *Sorghum bicolor* mutant MS8.

The present disclosure is directed to a method for producing a *Sorghum bicolor* mutant plant having an altered agronomic trait comprising introducing a polynucleotide into a MS8 plant grown from MS8 seed, representative seed of which has been deposited under ATCC Patent Deposit No. PTA-127606, wherein the polynucleotide confers an altered agronomic trait to the plant selected from the group consisting of insect resistance, disease resistance, herbicide resistance, abiotic stress resistance, fatty acid metabolism, starch metabolism, carbohydrate metabolism, amino acid metabolism, phosphorus metabolism, antioxidant metabolism, male sterility, site specific DNA integration, plant growth, forage yield and flowering, and wherein the polynucleotide is expressed in the plant.

The present disclosure is directed to a *Sorghum bicolor* mutant plant produced by said method, wherein the plant has the altered agronomic trait and all of the physiological and all morphological characteristics of said *Sorghum bicolor* mutant MS8.

BRIEF DESCRIPTION OF THE DRAWINGS

FIG. 1A shows fresh yellow anthers were extruded from sessile spikelets of the BTx623 wild-type panicle at the anthesis stage. FIG. 1B shows anthers were small and white in ms8 spikelets at the anthesis stage; thus they were nearly invisible in the panicle.

FIG. 1C shows yellow anthers in BTx623 spikelets at the anthesis stage. FIG. 1D shows white small anthers and hairy stigmas observed at the anthesis stage.

FIG. 1E shows an ms8 panicle bagged before anthesis showing no developing seeds. FIG. 1F shows seeds were normally developed in a manually pollinated ms8 panicle.

FIG. 2A shows a wild-type (BTx623) panicle during anthesis. FIG. 2B shows an ms8 mutant panicle during anthesis. FIG. 2C shows a mature self-pollinated wild-type panicle. FIG. 2D shows a mature ms8 panicle bagged before anthesis. FIG. 2E shows a mature ms8 panicle manually pollinated with wild-type pollen.

FIGS. 3A-3B show ms8 is defective in pollen production. FIG. 3A shows a wild-type (BTx623) spikelet showing three mature anthers (top) and pollen grains released from anthers and stacked on hairy stigmas (bottom). FIG. 3B shows an ms8 spikelet showing three pale and flattened anthers (top) and no pollen grains on the ms8 stigma (bottom).

FIG. 4A shows the BTx623 wild-type ovary (left) was the same as that of the ms8 mutant (right) without manual pollination. FIG. 4B shows there was no difference of ovary development between BTx623 and the ms8 mutant after manual pollination. dap: days after pollination. Bars=1 mm in A and B.

FIG. 4C shows a part of wild-type anther displaying round pollen grains inside anther lobes. FIG. 4D shows a part of ms8 mutant anther exhibiting no pollen grains inside the anther lobe.

FIGS. 5A-5C show wild-type (BTx623) semi-thin sections showing anthers at stage 5 (FIG. 5A), 9 (FIG. 5B), and 12 (FIG. 5C). FIGS. 5D-5F show ms8 semi-thin sections exhibiting anthers at stage 5 (FIG. 5D), 9 (FIG. 5E), and 12 (FIG. 5F). Tapetal cells in FIG. 5E were prematurely degenerated. E: epidermis, En: endothecium, ML: middle layer, T: tapetum, M: microsporocyte, Ms: microspores, and DT: prematurely degenerating tapetum.

FIG. 7 shows the alignment between the protein sequences of MS8 (SEQ ID NO: 1) and its rice ortholog OsEAT1 (SEQ ID NO: 2). Alignment was analyzed by Clustal Omega.

FIG. 8 shows the alignment between the protein sequences of SbTDR (SEQ ID NO: 3) and its rice ortholog p (SEQ ID NO: 4). Alignment was analyzed by Clustal Omega.

FIGS. 9A and 9B show the ms8 mutation. FIG. 9A shows the wild-type nucleotide sequence (SEQ ID NO: 5) and mutated nucleotide locations bolded and underlined (position 448 for ms8-1 (SEQ ID NO: 6) and position 442 for ms8-2 (SEQ ID NO: 7). FIG. 9B shows the wild-type protein sequence (SEQ ID NO: 8) with * in the MS8 protein sequence indicating where the translation stops due to the ms8 nonsense mutation (position 150 for ms8-1 (SEQ ID NO: 9) and position 148 for md8-2 (SEQ ID NO: 10)).

FIG. 12A shows pollen staining from the wild-type plant showing viable pollen grains in red color. FIG. 12B shows pollen staining from the transgenic plant showing viable (red color) and inviable (blue color) pollen grains. FIG. 12C shows statistical analysis showing the transgenic plant produced nearly 50% of inviable and viable pollen grains, respectively.

FIG. 13A shows *Arabidopsis* wild-type seeds under the fluorescence microscope. FIG. 13B shows *Arabidopsis* AtOLE1:RFP transgenic seeds showing strong red color under the fluorescence microscope. FIG. 13C shows *Arabidopsis* wild-type seeds. FIG. 13D shows *Arabidopsis* 35S: EsMYB41 transgenic seeds showing black color. The OLE1 gene encodes the OLEOSIN1 protein in *Arabidopsis*. The MYB41 gene which encodes a MYB transcription factor is cloned from *Eutrema salsugineum*.

DETAILED DESCRIPTION

Figures 1A, 1B:
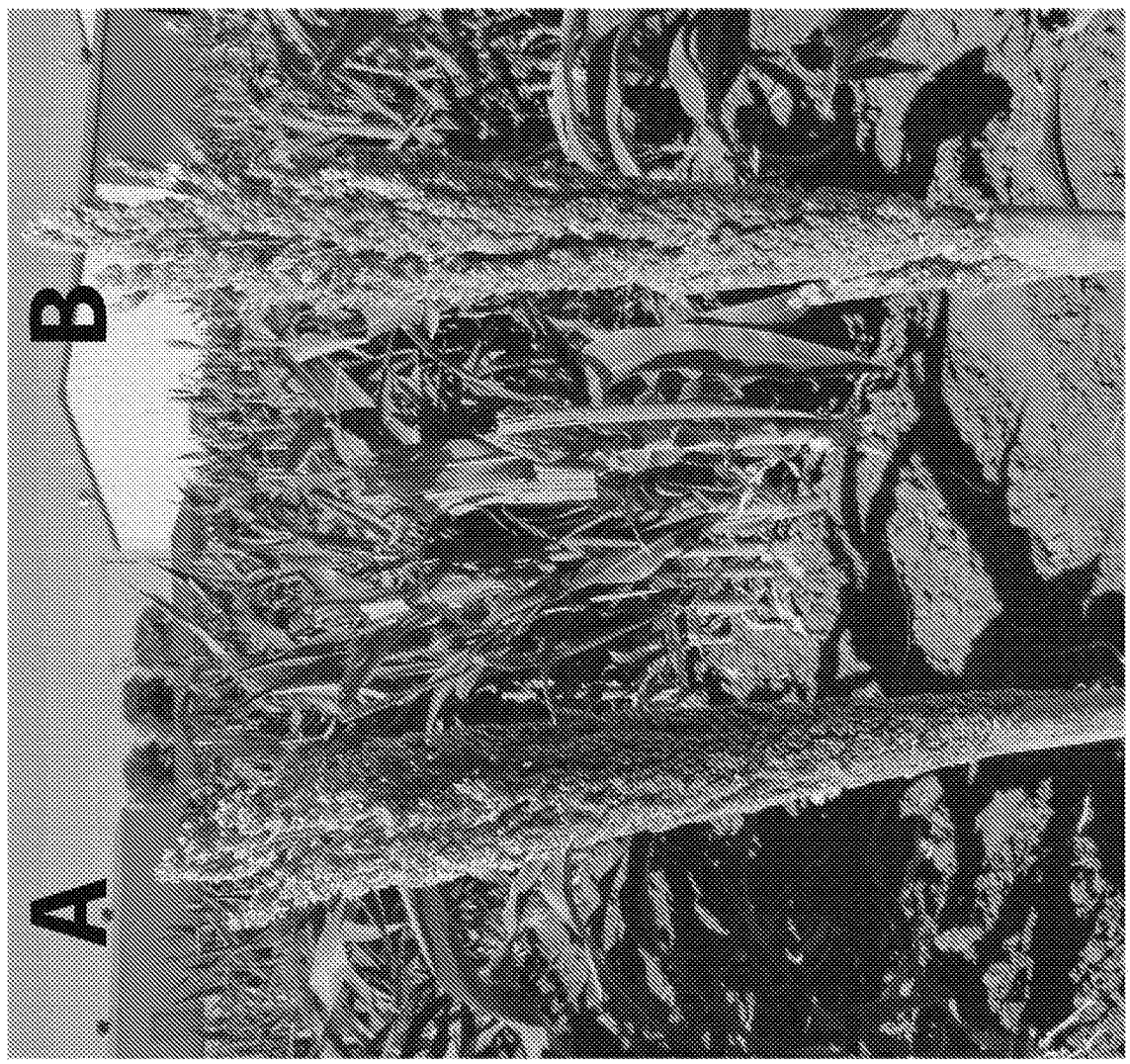
FIGS. 1A-1B show a comparison of BTx623 wild-type panicle and spikelets with that of the ms8 mutant.

The present disclosure provides compositions and methods for producing sterile mutants and two-line breeding systems. The inventors have discovered nuclear male sterile mutants of sorghum that were created by ethyl methane sulfonate (EMS) mutagenesis. The mutant genes responsible for the sterility were identified in these sorghum plants and sequenced. One such mutant is an easily recognizable NMS sorghum mutant male sterile 8 (ms8) isolated from an elite inbred BTx623 mutagenized by EMS. The ms8 mutant phenotype was caused by mutations on a single recessive nuclear gene that is different from all available NMS loci reported in sorghum. These sterile mutants can be used to create a new breeding system for Sorghum using a two-line breeding system versus the current systems that use three lines in combination with a three-component (3C) genetic construct. For example, the 3C genetic construct can include (1) the wild-type version of the mutant gene, such as the MS8 gene driven by its native promoter, (2) a barnase gene driven by a pollen-specific promoter or RNAi sequences driven by pollen specific promoters to silence genes essential for pollen development, and (3) red fluorescence protein or transcription factor protein that changes seed and leaf color for elimination of the transgenes by seed sorting.

Also disclosed is a bridge plant that is homozygous for the ms8 mutation but hemizygous for a transgene construct, which includes the 3C genetic construct. Due to the expression of the wild-type MS8 gene from the 3C genetic construct, the bridge plant should be fertile and produce two types of pollens: the mutant ms8 pollen, and the wild-type MS8 pollen coupled with a pollen-killing gene. The wild-type pollen will be subsequently killed during pollen maturation, leaving only the mutant ms8 pollen, which can be used to pollinate homozygous ms8 mutant plants. The progenies from such cross will be 100% ms8 mutants that are free of any transgene from the 3C genetic construct and can serve as a female (male sterile) parent in hybrid breeding.

The self-pollinated bridge plants will produce 50% hemizygous plants and 50% homozygous ms8 mutants and can be used as a maintainer line for male sterility. The transgene and the ms8 mutation can be bred into a panel of diverse lines through marker-assisted selection to generate a foundation of female lines that can be pollinated with any other lines, opening up unlimited possibilities to exploit hybrid vigor in sorghum. To completely eliminate transgenic pollen, a third component is added to the 3C genetic construct to allow for selection, such as the RFP marker gene or *Eutrema salsugineum* MYB41 (EsMYB41) gene driven by a strong seed promoter. For example, any escaped wild-type pollen will produce seeds expressing the RFP marker gene, which can be selected with a seed sorter machine. This component is a safeguard to ensure no transgenic seeds will be planted.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of," and "consisting essentially of," the embodiments or elements presented herein, whether explicitly set forth or not.

All ranges disclosed herein are inclusive of the endpoints, and the endpoints are independently combinable with each other. Each range disclosed herein constitutes a disclosure of any point or sub-range lying within the disclosed range. For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The use of the terms "a" and "an" and "the" and words of a similar nature in the context of describing the improvements disclosed herein (especially in the context of the following claims) are to be construed to cover both the singular and the plural, unless otherwise indicated herein or clearly contradicted by context. Further, it should further be noted that the terms "first," "second," and the like herein do not denote any order, quantity, or relative importance, but rather are used to distinguish one element from another.

The modifier "about" used in connection with a quantity is inclusive of the stated value and has the meaning dictated by the context (e.g., it includes, at a minimum the degree of error associated with measurement of the particular quantity). The term "about" as used herein as applied to one or more values of interest, refers to a value that is similar to a stated reference value. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed.

"Backcrossing" as used herein refers to a process in which a breeder repeatedly crosses hybrid progeny back to one of the parents (recurrent parent), for example, a first generation hybrid $F_1$ with one of the parental genotypes of the $F_1$ hybrid.

"Bridge plant" or "Bridge seed" as used herein refers to a male fertile plant that contains a three-component (3C) genetic construct and is crossed onto the same or similar plant having the male sterile gene. This cross produces male sterile seed.

"Cell" or "plant cell" as used interchangeably herein includes a plant cell, whether isolated, in tissue culture, or incorporated in a plant or plant part.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual plant or animal cell to which the nucleic acid is administered. The coding sequence may be codon optimize.

"Complement" or "complementary" as used herein means a nucleic acid can mean Watson-Crick (e.g., A-T/U and C-G) or Hoogsteen base pairing between nucleotides or nucleotide analogs of nucleic acid molecules. "Complementarity" refers to a property shared between two nucleic acid sequences, such that when they are aligned antiparallel to each other, the nucleotide bases at each position will be complementary.

As used herein, a "control plant" is a plant that is substantially equivalent to a test plant or modified plant in all parameters with the exception of the test parameters. For example, when referring to a plant into which a polynucleotide according to the present invention has been introduced, in certain embodiments, a control plant is an equivalent plant into which no such polynucleotide has been introduced. In certain embodiments, a control plant is an equivalent plant into which a control polynucleotide has been introduced. In such instances, the control polynucleotide is one that is expected to result in little or no phenotypic effect on the plant.

"Cross-pollination" as used herein refers to the fertilization by the union of two gametes from different plants.

"Female line" as used herein refers to the female parent of a hybrid.

A "functional homolog," "functional equivalent," or "functional fragment" of a polypeptide of the present invention is a polypeptide that is homologous to the specified polypeptide but has one or more amino acid differences from the specified polypeptide. A functional fragment or equivalent of a polypeptide retains at least some, if not all, of the activity of the specified polypeptide.

A "fusion protein" as used herein refers to an artificially made or recombinant molecule that comprises two or more protein sequences that are not naturally found within the same protein. The fusion protein may include non-proteinaceous elements as well as proteinaceous elements.

"Gene" as used herein refers to a segment of nucleic acid. A gene can be introduced into a genome of a species, whether from a different species or from the same species, using transformation or various breeding methods.

"Genetic construct" as used herein refers to the DNA or RNA molecules that comprise a nucleotide sequence that encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Genetically modified" or "GM" as used interchangeably herein refers to an organism or crop containing genetic material that has been artificially altered so as to produce a desired characteristic.

"Genotype" as used herein refers to the genetic constitution of a cell or organism.

"Haploid" as used herein is a cell nucleus containing only one representative of each chromosome of the chromosome complement, denoted by the symbol n. The haploid number (n) is the number of chromosomes in a haploid cell nucleus. Gametes are haploid cells.

"Heterosis" as used herein is the tendency of a crossbred plant to show qualities superior to those of both parents. Heterosis is also called hybrid vigor.

"Identical" or "identity" as used herein in the context of two or more nucleic acids or polypeptide sequences means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

Optimal alignment of sequences for comparison may be conducted by methods commonly known in the art, for example by the search for similarity method described by Pearson and Lipman 1988, Proc. Natl. Acad. Sci. USA 85: 2444-2448, by computerized implementations of algorithms such as GAP, BESTFIT, BLAST, FASTA, and TFASTA in the Wisconsin Genetics Software Package, Genetics Computer Group (GCG), Madison, Wis., or by inspection. In a preferred embodiment, protein and nucleic acid sequence identities are evaluated using the Basic Local Alignment Search Tool ("BLAST"), which is well known in the art (Karlin and Altschul, *Proc. Natl. Acad. Sci.* USA 87: 2267-2268 (1990); Altschul et al., *Nucl. Acids Res.* 25: 3389-3402 (1997)), the disclosures of which are incorporated by reference in their entireties. The BLAST programs identify homologous sequences by identifying similar segments, which are referred to herein as "high-scoring segment pairs," between a query amino or nucleic acid sequence and a test sequence which is preferably obtained from a protein or nucleic acid sequence database. Preferably, the statistical significance of a high-scoring segment pair is evaluated using the statistical significance formula (Karlin and Altschul, 1990). The BLAST programs can be used with the default parameters or with modified parameters provided by the user.

The terms "isolated," "purified" or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated nucleic acid of the present invention is separated from open reading frames that flank the desired gene and encode proteins other than the desired protein. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Locus" as used herein confers one or more traits such as, for example, herbicide tolerance, insect resistance, disease resistance, flower color, flower shape, plant height, etc. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

"Male line" as used herein refers to the male parent of a hybrid.

"Male sterile gene" as used herein refers to any nuclear or cytoplasmic gene which confers the male sterile (MS) characteristic to the plant.

"Mutations" as used herein are changes in the DNA sequence of a cell's genome and are caused by mutagens, like radiation or chemicals, as well as by errors that occur spontaneously during DNA replication.

"Nuclear male sterile gene" as used herein refers to a male sterile allele or alleles which are contained within the nucleus of the cell.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

The specificity of single-stranded DNA to hybridize complementary fragments is determined by the "stringency" of the reaction conditions (Sambrook et al., *Molecular Cloning and Laboratory Manual*, Second Ed., Cold Spring Harbor (1989)). Hybridization stringency increases as the propensity to form DNA duplexes decreases. In nucleic acid hybridization reactions, the stringency can be chosen to favor specific hybridizations (high stringency), which can be used to identify, for example, full-length clones from a library. Less-specific hybridizations (low stringency) can be used to identify related, but not exact (homologous, but not identical), DNA molecules or segments.

DNA duplexes are stabilized by: (1) the number of complementary base pairs; (2) the type of base pairs; (3) salt concentration (ionic strength) of the reaction mixture; (4) the temperature of the reaction; and (5) the presence of certain organic solvents, such as formamide, which decrease DNA duplex stability. In general, the longer the probe, the higher the temperature required for proper annealing. A common approach is to vary the temperature; higher relative temperatures result in more stringent reaction conditions.

To hybridize under "stringent conditions" describes hybridization protocols in which nucleotide sequences at least 60% homologous to each other remain hybridized. Generally, stringent conditions are selected to be about 5° C. lower than the thermal melting point ($T_m$) for the specific sequence at a defined ionic strength and pH. The Tm is the temperature (under defined ionic strength, pH, and nucleic acid concentration) at which 50% of the probes complementary to the target sequence hybridize to the target sequence at equilibrium. Since the target sequences are generally present at excess, at $T_m$, 50% of the probes are occupied at equilibrium.

"Operably linked" as used herein means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

"Orthologous" or as used herein refers to homologous sequences that are descended from the same ancestral sequence separated by a speciation event. When a species diverges into two separate species, the copies of a single gene in the two resulting species are said to be orthologous. Orthologs, or orthologous genes, are genes in different species that originated by vertical descent from a single gene of the last common ancestor.

"Outbreeding" or "outcrossing" as used interchangeably herein is the practice of introducing unrelated genetic material into a breeding line by crossing between unrelated or distantly related individuals. Outbreeding is the opposite of inbreeding.

"Percent identity" as used herein refers to the comparison of the homozygous alleles of two plants. Percent identity is determined by comparing a statistically significant number of the homozygous alleles of two developed plants.

"Percent similarity" as used herein refers to the comparison of the homozygous alleles of one plant with another plant, and if the homozygous allele of both plants matches at least one of the alleles from the other plant then they are scored as similar. Percent similarity is determined by comparing a statistically significant number of loci and recording the number of loci with similar alleles as a percentage.

"Phenotype" as used herein refers to any observable characteristic or trait of a plant, such as flower color, plant size, etc.

As used herein, the term "plant" includes reference to whole plants, plant organs (e.g., leaves, stems, roots, etc.), seeds, plant cells, and progeny of same. Parts of transgenic plants comprise, for example, plant cells, protoplasts, tissues, callus, embryos as well as flowers, ovules, stems, fruits, leaves, roots originating in transgenic plants or their progeny previously transformed with a DNA. As used herein, the term "plant cell" includes, without limitation, protoplasts and cells of seeds, suspension cultures, embryos, meristematic regions, callus tissue, leaves, roots, shoots, gametophytes, sporophytes, pollen, and microspores.

"Plant part" as used herein includes protoplasts, leaves, stems, roots, root tips, anthers, pistils, seed, embryo, pollen, ovules, cotyledon, hypocotyl, cyathium, bract, shoot, tissue, petiole, cells and meristematic cells, and the like.

A "plant variety" as used herein means a plant grouping within a single botanical taxon of the lowest known rank which can be defined by the expression of the characteristics resulting from a given genotype or combination of phenotypes, distinguished from any other plant grouping by the expression of at least one of the said characteristics and considered as a unit with regard to its suitability for being propagated unchanged (International convention for the protection of new varieties of plants).

"Pollination" as used herein is the process by which pollen is transferred in plants, thereby enabling fertilization and sexual reproduction.

"Progeny" as used herein includes an $F_1$ plant produced from the cross of two plants. Progeny further includes, but is not limited to, subsequent $F_2$, $F_3$, $F_4$, $F_5$, $F_6$, $F_7$, $F_5$, $F_9$, and $F_{10}$ generational crosses with the parents and between the progeny.

"Promoter" as used herein means a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents.

"Regeneration" as used herein refers to the development of a plant from tissue culture.

The term "substantial identity" of polynucleotide sequences means that a polynucleotide comprises a sequence that has at least 25% sequence identity compared to a reference sequence as determined using the programs described herein; preferably BLAST using standard parameters, as described. Alternatively, percent identity can be any integer from 25% to 100%. More preferred embodiments include polynucleotide sequences that have at least about: 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98% or 99% sequence identity compared to a reference sequence. These values can be appropriately adjusted to determine corresponding identity of proteins encoded by two nucleotide sequences by taking into account codon degeneracy, amino acid similarity, reading frame positioning, and the like. Accordingly, polynucleotides of the present invention encoding a protein of the present invention include nucleic acid sequences that have substantial identity to the nucleic acid sequences that encode the polypeptides of the present invention. Polynucleotides encoding a polypeptide comprising an amino acid sequence that has at least about: 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity compared to a reference polypeptide sequence are also preferred.

The term "substantial identity" of amino acid sequences (and of polypeptides having these amino acid sequences) normally means sequence identity of at least 40% compared to a reference sequence as determined using the programs described herein; preferably BLAST using standard parameters, as described. Preferred percent identity of amino acids can be any integer from 40% to 100%. More preferred embodiments include amino acid sequences that have at least about: 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity compared to a reference sequence. Polypeptides that are "substantially identical" share amino acid sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine. Accordingly, polypeptides or proteins, encoded by the polynucleotides of the present invention, include amino acid sequences that have substantial identity to the amino acid sequences of the polypeptides, encoded by the polynucleotides of the present invention, which include the three-component genetic construct.

"Target plant" as used herein refers to a plant or tree that will be transformed with recombinant genetic material not normally found in plants or trees of this type and which will be introduced into the plant in question (or into progenitors of the plant) by human manipulation.

"Transgene" as used herein refers to a gene or genetic material containing a gene sequence that has been isolated from one organism, such as one plant or plant cell, and is introduced into a different organism, such as a different plant or plant cell. This non-native segment of DNA may retain the ability to produce RNA or protein in the transgenic organism, such as the transgenic plant, or it may alter the normal function of the transgenic organism's genetic code. The introduction of a transgene has the potential to change the phenotype of an organism, such as a plant.

"Transgenic plant" as used herein refers to a plant or tree that contains recombinant genetic material not normally found in plants or trees of this type and which has been introduced into the plant in question (or into progenitors of the plant) by human manipulation. Thus, a plant that is grown from a plant cell into which recombinant DNA is introduced by transformation is a transgenic plant, as are all offspring of that plant that contain the introduced transgene (whether produced sexually or asexually). It is understood that the term transgenic plant encompasses the entire plant or tree and parts of the plant or tree, for instance grains, seeds, flowers, leaves, roots, fruit, pollen, stems etc.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequence substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes may be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes may be substituted and still retain protein function. In one aspect, amino acids having hydropathic indexes of ±2 are substituted. The hydrophilicity of amino acids may also be used to reveal substitutions that would result in proteins retaining biological function. A consideration of the hydrophilicity of amino acids in the context of a peptide permits calculation of the greatest local average hydrophilicity of that peptide. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Vector" as used herein means a nucleic acid sequence containing an origin of replication. A vector may be a viral vector, bacteriophage, bacterial artificial chromosome, or yeast artificial chromosome. A vector may be a DNA or RNA vector. A vector may be a self-replicating extrachromosomal vector, and preferably, is a DNA plasmid. For example, the vector may encode a three-component genetic construct, as disclosed herein Alternatively, the vector may comprise a polynucleotide sequence encoding a three-component genetic construct as disclosed herein.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

Nuclear Male Sterile Sorghum Mutants

The present disclosure relates to nuclear male sterile sorghum mutants. In one embodiment, this disclosure describes a novel plant species of Sorghum (*Sorghum bicolor* L. Moench) comprised of a genetic mutation leading to a nuclear encoded male sterile mutant. An easily recognizable and stable sorghum NMS mutant, male sterile 8 (ms8), was identified from a sorghum mutant library, which was generated by the ethyl methane sulfonate (EMS) mutagenesis of the elite inbred line BTx623 seeds. The ms8 mutant has no defects in growth and development except for the male sterility. The phenotypic analyses show that the defects in tapetum development result in male sterility in the ms8 mutant. The MS8 gene encodes a basic helix-loop-helix (bHLH) protein regulating tapetum development. ms8 is a nuclear male sterile mutant defective in tapetum development in sorghum.

In fertile sorghum plants, yellow anthers appeared first during anthesis, while in the ms8 mutant, white hairy stigma emerged first and only small white anthers were observed, making ms8 plants easily recognizable when flowering. The ovary development and seed production after manual pollination are normal in the ms8 mutant, indicating it is female fertile and male sterile only. ms8 anthers did not produce pollen grains. Further analysis revealed that ms8 anthers were defective in tapetum development, which led to the arrest of pollen formation. As a stable male sterile mutant across different environments, greenhouses, and fields in different locations, the ms8 can greatly facilitate breeding and genetic crosses in sorghum and can be a useful breeding tool. Because of the ease of recognition at early stage of anthesis, the ms8 mutant can be used as a convenient tool to backcross other mutants isolated from our sorghum mutant library. The ms8 mutant may also serve as a valuable tool as an accurate test of heterosis potential during development of new inbred lines in sorghum. Examining heterosis between inbred lines in A/B and R system is complex, time consuming, and expensive. It is often necessary to make crosses with several combinations of A/B and R pairs to determine the value of new inbred lines. The ms8 mutation can be introduced into a core collection of diverse sorghum accessions that serve as potential B lines, because the ms8 mutant is derived from the BTx623 B line. The modified B lines with the ms8 mutation can be used to cross with many diverse R lines to identify desirable levels of heterosis. Once such pairs of lines are identified, large effort can be focused on developing corresponding A/B pair and R lines. ms8 can be used to elucidate male gametophyte development in sorghum and other plants.

Sorghum is an essentially self-pollinated species with an outcross rate from 0 to 5%. The ms8 mutant may aid the development of long-term random mating population for sorghum improvement and genomic selection. Recently, sorghum scientists have empaneled three diversity populations for genome wide association studies on key important agronomic, bioenergy, and nutrition traits in sorghum. These diversity panels captured the majority of genomic variations of sorghum and can serve as a powerful initial resource for sorghum improvement through long-term random mating. For example, ms8 mutant plants can be planted within the field of sorghum diversity panels. Plants homozygous at ms8 locus can be tagged at anthesis.

Because homozygous ms8 mutants cannot produce any pollen, all seeds on ms8 plants have to be derived from random mating with pollens from the diversity panel. Only tagged panicles will be harvested and then F2 seeds are produced through self-fertilization. The F2 seeds can be planted into the diversity panel. Again, only the tagged open-pollinated panicles from the F2 plants homozygous at the ms8 locus will be harvested. This cycle can continue for many generations with or without selection pressure at early stages. Genomic selection or simply breeding selection can be applied at advanced generations to develop sorghum inbred lines that are superior in biotic/abiotic stress resilience, yield, and quality.

The present disclosure relates to *Sorghum bicolor* seed designated as MS8, wherein a sample of said seed has been deposited as ATCC Patent Deposit No. PTA-127606. The present disclosure relates to a plant, or a part thereof, produced by growing said seed. The present disclosure relates to a pollen from said plant. The present disclosure relates to an ovule from said plant. The present disclosure relates to a *Sorghum bicolor* plant having all the physiological and morphological characteristics of said plant.

The present disclosure relates to a tissue culture of regenerable cells from said plant, or the part thereof. In some embodiments, the regenerable cells are selected from the group consisting of protoplasts and calli, and wherein the regenerable cells are from a leaf, pollen, ovule, cotyledon, hypocotyl, embryo, root, pod, flower, shoot or stalk. The present disclosure relates to a protoplast produced from said tissue culture.

The present disclosure relates to a *Sorghum bicolor* plant regenerated from said tissue culture, wherein the plant has all of the physiological and morphological characteristics of a plant produced by growing a seed designated MS8 and deposited under ATCC Patent Deposit No. PTA-127606. The present disclosure relates to a tissue culture of regenerable cells from said plant, or the part thereof. In some embodiments, the regenerable cells are selected from the group consisting of protoplasts and calli, and wherein the regenerable cells are from a leaf, pollen, ovule, cotyledon, hypocotyl, embryo, root, pod, flower, shoot or stalk. The present disclosure relates to a protoplast produced from said tissue culture. The present disclosure relates to a *Sorghum bicolor* plant regenerated from the tissue culture of regenerable cells from said plant, or the part thereof, wherein the plant has all of the physiological and morphological characteristics of a plant produced by growing a seed designated MS8 and deposited under ATCC Patent Deposit No. PTA-127606.

The present disclosure relates to method for producing a *Sorghum bicolor* mutant MS8-derived *Sorghum bicolor* L. Moench plant. The method includes: (a) crossing MS8 plants grown from MS8 seed, representative seed of which has been deposited under ATCC Patent Deposit No. PTA-127606, with a second *Sorghum bicolor* plant to yield progeny *Sorghum bicolor* seed; and (b) growing the progeny seed to yield a *Sorghum bicolor* mutant MS8-derived *Sorghum bicolor* plant. In some embodiments, the method further comprises: (c) crossing the *Sorghum bicolor* mutant MS8-derived *Sorghum bicolor* plant of (b) with itself or a third *Sorghum bicolor* plant to yield a second *Sorghum bicolor* MS8-derived *Sorghum bicolor* progeny seed; and (d) growing the second *Sorghum bicolor* progeny seed of (c) to yield a second *Sorghum bicolor* mutant MS8-derived *Sorghum bicolor* plant. In some embodiments, steps (c) and (d) are repeated at least one time to generate an additional *Sorghum bicolor* mutant MS8-derived *Sorghum bicolor* plant.

The present disclosure relates to a method of introducing a desired trait into *Sorghum bicolor* "MS8." The method includes: (a) crossing MS8 plants grown from MS8 seed, representative seed of which has been deposited under ATCC Patent Deposit No. PTA-127606, with plants of a second *Sorghum bicolor* mutant that comprise a desired trait to produce F1 progeny plants, wherein the desired trait is selected from the group consisting of male sterility, site-specific recombination, increased transformability, abiotic stress tolerance, herbicide resistance, insect resistance, disease resistance, altered phosphorus, altered antioxidants, altered fatty acids, altered essential amino acids and altered carbohydrates; (b) selecting F1 progeny plants that have the desired trait to produce selected F1 progeny plants; (c) crossing the selected progeny plants with the MS8 plants to produce backcross progeny plants; (d) selecting for backcross progeny plants that have the desired trait and physiological and morphological characteristics of *Sorghum bicolor* mutant MS8 to produce selected backcross progeny plants; and (e) repeating steps (c) and (d) three or more times in succession to produce selected fourth or higher backcross progeny plants that comprise the desired trait and all the physiological and morphological characteristics of *Sorghum bicolor* mutant MS8. The present disclosure relates to a plant produced by the method described herein, wherein the plant has the desired trait and all of the physiological and all morphological characteristics of said *Sorghum bicolor* mutant MS8.

The present disclosure relates to a method for producing a *Sorghum bicolor* mutant plant having an altered agronomic trait comprising introducing a polynucleotide into a MS8 plant grown from MS8 seed, representative seed of which has been deposited under ATCC Patent Deposit No. PTA-127606, wherein the polynucleotide confers an altered agronomic trait to the plant selected from the group consisting of insect resistance, disease resistance, herbicide resistance, abiotic stress resistance, fatty acid metabolism, starch metabolism, carbohydrate metabolism, amino acid metabolism, phosphorus metabolism, antioxidant metabolism, male sterility, site specific DNA integration, plant growth, forage yield and flowering, and wherein the polynucleotide is expressed in the plant. The present disclosure relates to a *Sorghum bicolor* mutant plant produced by the method described herein, wherein the plant has the altered agronomic trait and all of the physiological and all morphological characteristics of said *Sorghum bicolor* mutant MS8.

Modified MALE STERILE 8 (MS8) Gene

The ms8 recessive mutation occurred in a single nuclear gene causes the male sterile phenotype. Identification of the ms8 mutant and its causal gene, the Sb04g030850 gene, which encodes a basic Helix-Loop-Helix (bHLH) transcription factor, makes it possible for us to develop a new two-line NMS hybrid breeding system for hybrid sorghum breeding. The MS8 gene functions at early stages of microsporogenesis before pollen formation. In rice, the MS8 orthologous gene is EAT1/DTD. The eat1/dtd mutant is characterized as the delayed programmed cell death of tapetal cells and produces abnormal anthers that do not form viable pollen. In the dtd mutant, the anther cells can undergo meiosis to form microspores but the microspores degrade and no mature pollen is produced.

Transcription factors in the bHLH family, which contains 158 members, play important roles in tapetal cell differentiation. Loss-of-functions of DYT1 and bHLH010/bHLH089/bHLH091 in *Arabidopsis* and their rice orthologous genes UNDEVELOPED TAPETUM1 (UDT1)/bHLH164, TAPETUM DEGENERATION RETARDATION (TDR)/bHLH5, TDR INTERACTING PROTEIN2 (TIP2)/bHLH142, and ETERNAL TAPETUM1 (EAT1)/DELAYED TAPETUM DEGENERATION (DTD)/bHLH141 results in aberrant degeneration of tapetal cells. In rice, complex interactions among UDT1, TDR, TIP2, EAT1/DTD are required for normal tapetum development. EAT1 can dimerize with TDR, which competes the activity of TIP2-TDR heterodimer. EAT1 directly activates expression of two aspartic protease genes AP25 and AP37, which are important for tapetal programmed cell death. EAT1, via the possible interaction with TIP2 and UDT1, promotes biogenesis of 24-nt phasiRNAs (24-nucleotides phased secondary small interfering RNA). In maize, bHLH122 (the EAT1 orthologue), MS23 (MALE STERILE23, the TIP2 orthologue), MS32 (the UDT1 orthologue), and bHLH51 (the TDR orthologue) also control tapetal cell differentiation and function using a similar regulation mechanism as described above.

The present disclosure relates to an isolated polynucleotide sequence encoding a modified MALE STERILE 8 (MS8) polypeptide. The isolated polynucleotide sequence includes a nucleotide sequence having at least 80% identity to SEQ ID NO: 5 and a nucleotide substitution at a position corresponding to position 442 or 448 of SEQ ID NO: 5. The modified MS8 polypeptide is functionally abnormal in pollen production. In some embodiments, the nucleotide substitution generates a premature stop codon. In some embodiments, the isolated polynucleotide sequence comprises a C-T mutation at the position corresponding to position 442 or 448 of SEQ ID NO: 5. In some embodiments, the isolated polynucleotide sequence comprises a nucleotide sequence of SEQ ID NO: 6, SEQ ID NO: 7, or a variant thereof. In some embodiments, the modified MS8 polypeptide has a premature stop codon at a position corresponding to position 148 or 150 of SEQ ID NO: 1. In some embodiments, the modified MS8 polypeptide comprises an amino acid sequence corresponding to positions 1-149 of SEQ ID NO: 9, positions 1-147 of SEQ ID NO: 10, or a variant thereof.

The present disclosure relates to vector comprising the isolated polynucleotide sequence described above. In some embodiments, the isolated polynucleotide is operably linked to a promoter. In some embodiments, the promoter is the native MS8 promoter.

The present disclosure relates to sorghum plant comprising a recessive nuclear male sterile gene, wherein the sorghum plant is male sterile and the recessive nuclear male sterile gene is a modified basic HELIX-LOOP-HELIX (bHLH) transcription factor gene encoding an inactivated bHLH transcription factor. The inactivated bHLH transcription factor causes early degeneration of tapetal cells in the anther of the sorghum plant. In some embodiments, the nuclear male sterile gene is a mutant MS8 gene or a mutant TDR gene. In some embodiments, the recessive nuclear male sterile gene comprising an isolated nucleotide sequence having at least 80% identity to SEQ ID NO: 5 and a nucleotide substitution at a position corresponding to position 442 or 448 of SEQ ID NO: 5. In some embodiments, the nucleotide substitution generates a premature stop codon. In some embodiments, the isolated polynucleotide sequence comprises a C-T mutation at the position corresponding to position 442 or 448 of SEQ ID NO: 5. In some embodiments, the isolated polynucleotide sequence comprises a nucleotide sequence of SEQ ID NO: 6, SEQ ID NO: 7, or a variant thereof. In some embodiments, the modified MS8 polypeptide has a premature stop codon at a position corresponding to position 148 or 150 of SEQ ID NO: 1. In some embodiments, the modified MS8 polypeptide comprises an amino acid sequence corresponding to positions 1-149 of SEQ ID NO: 9, positions 1-147 of SEQ ID NO: 10, or a variant thereof. In some embodiments, the sorghum plant is an ms8 mutant plant. In some embodiments, the sorghum plant is a *Sorghum bicolor*.

Three-Component Genetic Construct

The present disclosure relates to a three-component genetic construct for use in a two-line nuclear male sterility system, as described below. In an embodiment, this disclosure describes three-component genetic constructs comprising the capacity to produce pure male sterile plants, rescue the male fertility, ablate transgenic pollen, sort the transgenic seeds from non-transgenic seeds, and allow propagation of pure male sterile sorghum plants for hybrid breeding and maintenance of a maintainer line.

The three-component system includes: (a) a first component comprising a nuclear male sterile gene operably linked to a first promoter; (b) a second component comprising a pollen killing nucleotide sequence operably linked to a second promoter, wherein the second promoter is a pollen specific promoter; and (c) a third component comprising a seed specific selectable marker gene operably linked to a third promoter.

In an embodiment, this disclosure describes one three-component gene construct comprised of the wild-type MS8 gene driven by the native promoter, a Barnase gene driven by a pollen-specific promoter, and red fluorescence protein for elimination of the transgenes by seed florescence color. In an embodiment, this disclosure describes another three-component gene construct comprised of the wild-type MS8 gene driven by the native promoter, RNAi components to silence the sorghum ASPARTIC PROTEASE 65 (SbAP65) gene and the sorghum SUCROSE TRANSPORTER1 (SbSUT1) gene via a pollen-specific promoter, and red fluorescence protein for elimination of the transgenes by seed florescence color. In an embodiment, this disclosure describes two genetic constructs for the creation of transgene free male sterile sorghum plants. In an embodiment, this disclosure describes a three-component transgene system for sorghum comprising a red fluorescence protein gene to enable sorting of transgenic and non-transgenic seeds.

First Component

The first component provides a means to rescue the mutant phenotype. The nuclear male sterile gene comprises a MALE STERILE8 (MS8) gene encoding a protein having at least about 80% identity to the polypeptide sequence of SEQ ID NO: 1 or a TAPETUM DEGENERATION RETARDATION (TDR) gene encoding a protein having at least about 80% identity to the polypeptide sequence of SEQ ID NO: 3. In some embodiments, the nuclear male sterile gene includes a MS8 gene from *Sorghum bicolor* (SEQ ID NO:5), or an orthologue thererof, such as EAT1 from rice. In some embodiments, the nuclear male sterile gene includes a TDR gene from *Sorghum bicolor*, or an orthologue thereof, such as TDR from rice. In some embodiments, the first promoter is a native promoter associated with the nuclear male sterile gene. In some embodiments, the first promoter is a non-native promoter that is not associated with the nuclear male sterile gene. In some embodiments, the nuclear male sterile gene is MS8 from *Sorghum bicolor* and the first promoter is the native MS8 promoter.

Second Component

The second component provides a means for inhibiting pollen production. In some embodiments, the pollen killing nucleotide sequence is a polynucleotide sequence that encodes a sequence that will cause the pollen to not form properly, thereby leading to a non-viable pollen. In some embodiments, the pollen killing nucleotide sequence is a Barnase gene or an RNAi species for targeting a gene involved in pollen development. In some embodiments, the pollen killing nucleotide sequence comprises an RNAi species for targeting an ASPARTIC PROTEASE 65 gene, an RNAi species for targeting a SUCROSE TRANSPORTER1 gene, or a combination thereof. In some embodiments, the ASPARTIC PROTEASE 65 gene is a *Sorghum bicolor* ASPARTIC PROTEASE 65 (SbAP65) gene, or an ortholog thereof, and the SUCROSE TRANSPORTER1 gene is a *Sorghum bicolor* SUCROSE TRANSPORTER1 (SbSUT1) gene, or an ortholog thereof.

Barnase Gene

The Barnase protein (also referred to as "Barnase") is an RNase that has 110 amino acid residues and hydrolyzes RNA. Barnase originates from *Bacillus amyloliquefaciens*. When expressed in cells, this enzyme inhibits the functions of the cells as a result of its potent RNase activity and thus causes cell death in many cases. By using this characteristic, it is therefore expected that the function of the specific site can be selectively controlled by expressing the barnase gene in a specific site of a plant.

In some embodiments, the pollen specific promoter is a promoter for a late-stage pollen-specific gene. In some embodiments, the pollen specific promoter is an *Oryza sativa* POLLEN LATE-STAGE PROMOTER2 (OsPLP2), an *Oryza sativa* BORON EFFLUX TRANSPORTER4 (OsBOR4) promoter, an *Oryza sativa* LATE POLLEN SPECIFIC PROMOTER1 (OsLPS1), an *Oryza sativa* Indica POLLEN ALLERGEN (OsIPA) promoter, or an orthologous sorghum promoter thereof.

Third Component

The third component provides a means to select for the transgene construct. In some embodiments, the seed specific selectable marker gene is a detectable marker. The detectable marker can allow the detection of the transgene construct in the seed or the leaves of the plant containing the transgene. In some embodiments, the detectable marker comprises a red fluorescent protein (RFP), black seed coat color and/or purple leaf color caused by expressing the *Eutrema salsugineum* MYB41 (EsMYB41) transcription factor gene, or a combination thereof. In some embodiments, the detectable marker comprises red fluorescent protein (RFP). In some embodiments, the third promoter is a promoter active in seed. In some embodiments, the third promoter is a *Sorghum bicolor* ABA INSENSITIVE3 (SbABI3) promoter, an *Arabidopsis thaliana* OLEOSIN1 (AtOLE1) promoter, a *Sorghum bicolor* OLEOSIN1 (SbOLE1) promoter, or a *Hordeum vulgare* LIPID TRANSFER PROTEIN 2 (HvLTP2) promoter. In some embodiments, the third component further comprises a polynucleotide sequence encoding an AtOLE1 or SbOLE1 polypeptide sequence, wherein a fusion protein is generated when the third component is expressed. In some embodiments, the third component comprises AtOLE1 promoter: AtOLE1 coding sequence-RFP coding sequence (AtOLE1: AtOLE1-RFP) and SbOLE1 promoter:SbOLE1 coding sequence-RFP coding sequence (SbOLE1:SbOLE1-RFP). In some embodiments, the fusion protein is AtOLE1-RFP and SbOLE1-RFP. In some embodiments, the detectable marker further comprises black seed coat color and/or purple leaf color caused by expressing the EsMYB41 transcription factor gene.

In some embodiments, the detectable marker is black seed coat color and/or purple leaf color caused by expressing the EsMYB41 transcription factor gene. In some embodiments, the third promoter is a constitutive promoter. In some embodiments, the constitutive promoter is cauliflower mosaic virus 35S promoter.

Figures 10A, 10B, 10C, 10D:
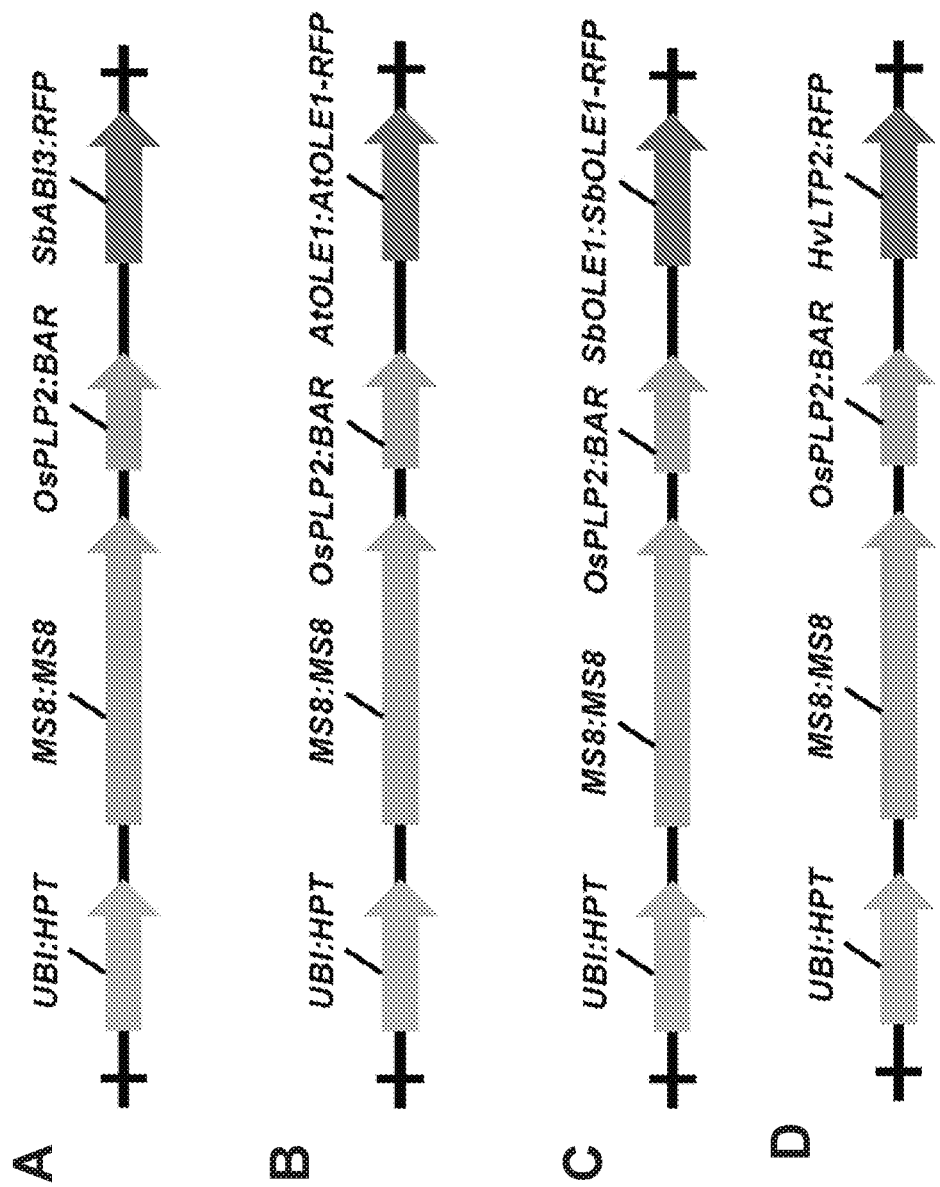
FIGS. 10A-10P show various constructs.
Figures 10E, 10F, 10G, 10H:
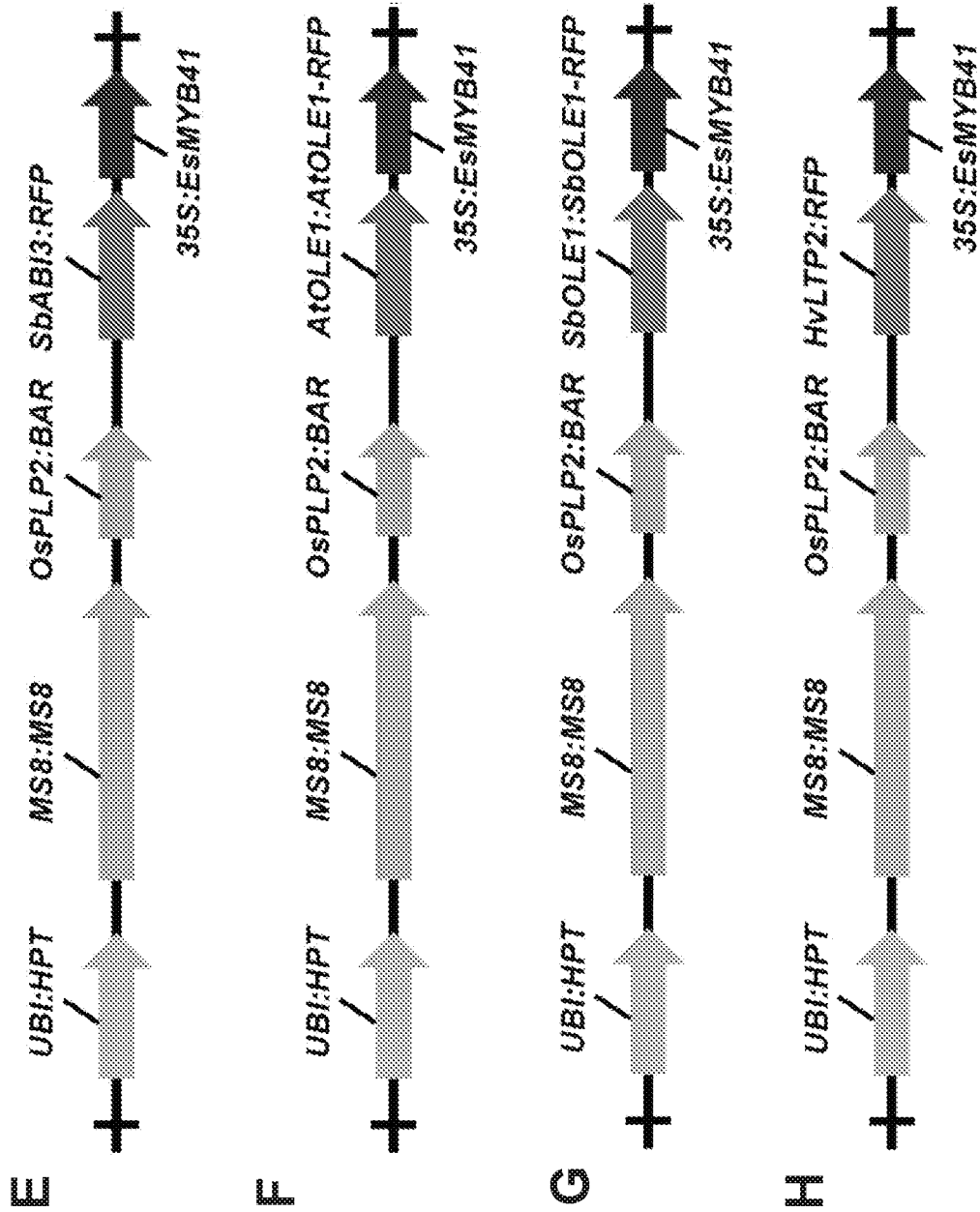
Figures 10I, 10J, 10K, 10L:
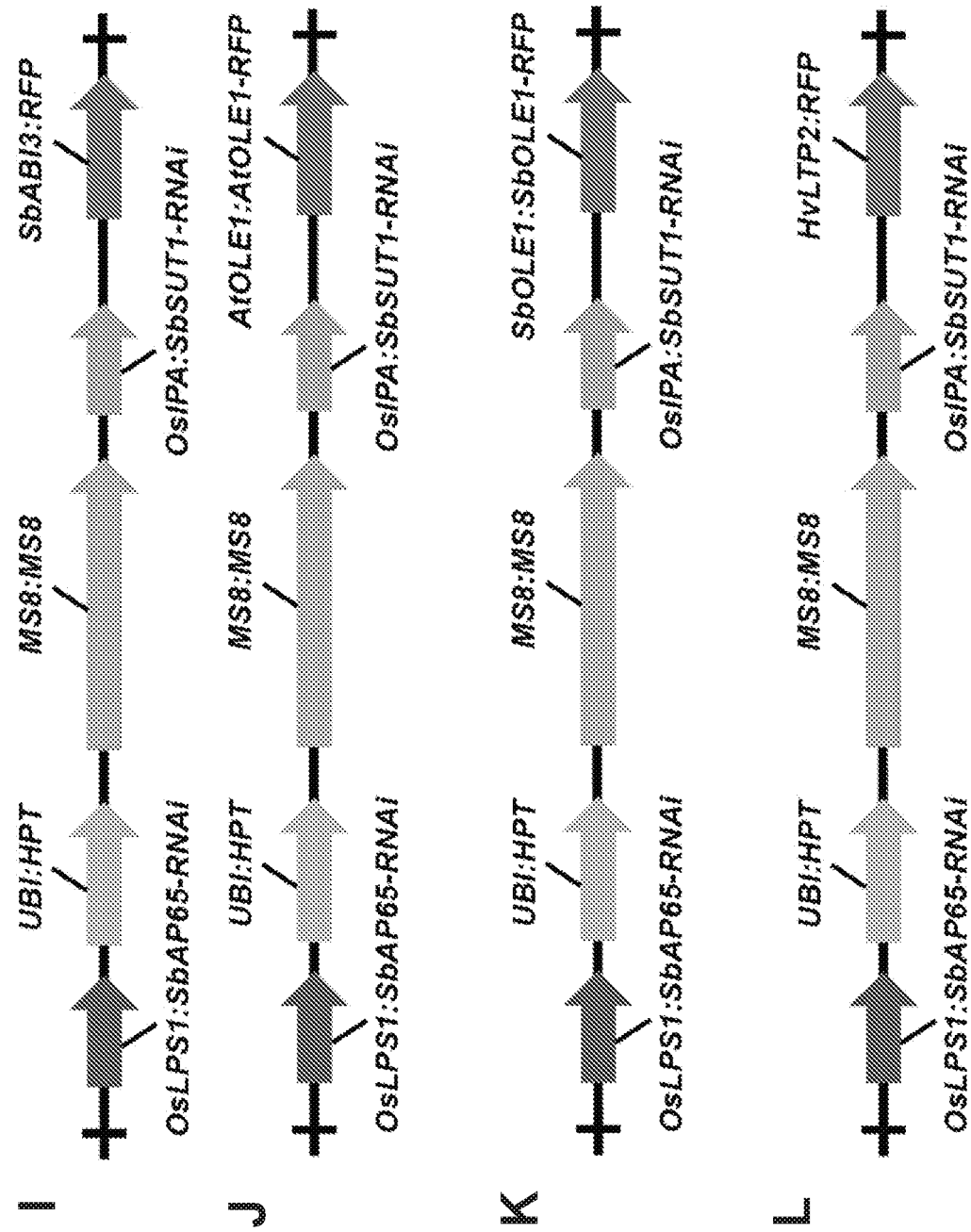
Figures 10M, 10N, 10O, 10P:
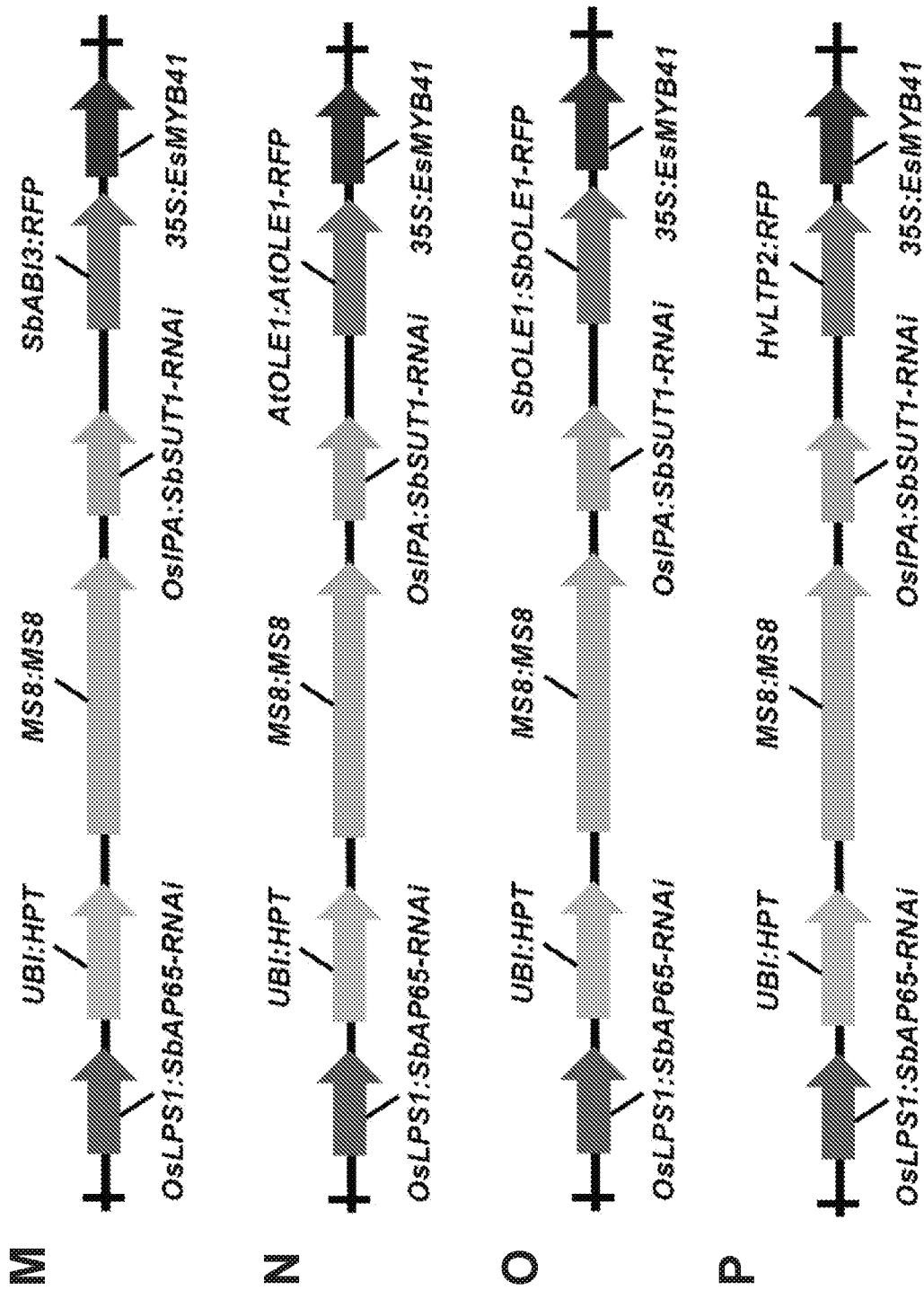

In some embodiments, the three-component genetic construct is used to rescue male sterility in an ms8 mutant plant, ablate transgenic pollen, sort the transgenic and non-transgenic seeds, or a combination thereof. In some embodiments, the ms8 mutant plant is sorghum, *Arabidopsis*, rice, maize, wheat, soybean, or rapeseed. In some embodiments, the plant is a sorghum variety selected from BTx623, BTx399, BOK11, RTx430, ARG1, M35, P898012, Sugardrip (sweet sorghum), and Greenleaf (forage sorghum). Exemplary embodiments of the three-component genetic construct are shown in FIGS. 10A-10P.

Bridge Plant and Methods of Generating the Bridge Plant and Male Sterile Plants

The present disclosure relates to method of generating a bridge plant for use in a two-line nuclear male sterility breeding system. The method includes: (a) introducing a transgene construct into a ms8:ms8 mutant plant thereby generating a transformed mutant plant; (b) collecting seed from the transformed mutant plant; and (c) growing the collected seed thereby generating the bridge plant. The transgene construct comprises the three-component genetic construct, described above. The bridge plant comprises the ms8:ms8 mutant background and at least one copy of the three-component genetic construct, described above. In some embodiments, the bridge plant is a self-maintained plant. In some embodiments, the bridge plant is sorghum, *Arabidopsis*, rice, maize, wheat, soybean, or rapeseed. In some embodiments, the bridge plant is a sorghum variety selected from BTx623, BTx399, BOK11, RTx430, ARG1, M35, P898012, Sugardrip (sweet sorghum), and Greenleaf (forage sorghum).

The present disclosure relates to bridge plant generated by said method. The bridge plant can be used to produce transgene-free male sterile plants. In some embodiments, the bridge plant is sorghum, *Arabidopsis*, rice, maize, wheat, soybean, or rapeseed. In some embodiments, the bridge plant is a sorghum variety selected from BTx623, BTx399, BOK11, RTx430, ARG1, M35, P898012, Sugardrip (sweet sorghum), and Greenleaf (forage sorghum).

The present disclosure relates to a method for generating a male sterile plant and/or a maintained bridge plant. The method includes: (a) growing seed collected from the bridge plant, described above, wherein the seed includes maintained bridge plant seed and male sterile plant seed; (b) determining the presence or absence of the detectable marker in the seed; (c) identifying the maintained bridge plant seed based on the presence of the detectable marker in the seed and identifying the male sterile plant seed based on absence of the detectable marker in the seed; and (d) isolating and growing the male sterile plant seed thereby generating the male sterile plant and/or isolating and growing the maintained bridge plant seed thereby generating the maintained bridge plant. The maintained bridge plant seed is suspected as being homozygous for the ms8 mutation and hemizygous for the transgene construct. The male sterile plant seed is suspected as being homozygous for the ms8 mutation and does not comprise the transgene construct.

In some embodiments, the detectable marker is black seed coat color and/or purple leaf color caused by expressing EsMYB41 which encodes a transcription factor, and wherein the maintained bridge plant is identified based on the presence of the detectable marker of black seed coat color and/or purple leaf color and the fertile plants are identified and separated from the male sterile plants based on the presence of the detectable marker in the leaf. In some embodiments, the bridge plant is sorghum, *Arabidopsis*, rice, maize, wheat, soybean, or rapeseed. In some embodiments, the bridge plant is a sorghum variety selected from BTx623, BTx399, BOK11, RTx430, ARG1, M35, P898012, Sugardrip (sweet sorghum), and Greenleaf (forage sorghum).

The present disclosure also relates to male sterile plants generated by said method for generating a male sterile plant and/or a maintained bridge plant. In an embodiment, this disclosure describes a method for the creation of transgene free male sterile sorghum plants. The present disclosure also relates to bridge plant generated by said method for generating a male sterile plant and/or a maintained bridge plant.

In an embodiment, this disclosure describes a method for the creation of male sterile sorghum plants comprising a three-component genetic construct that can rescue the male fertility, ablate transgenic pollen, sort the transgenic seeds from non-transgenic seeds, and allow propagation of pure male sterile sorghum plants for hybrid breeding and maintenance of a maintainer line. In one embodiment, this disclosure describes a three-component construct can be introduced into sorghum accessions with diverse genetic backgrounds, which can be widely used to make various sorghum hybrids. In another embodiment, this disclosure describes bridge plants that are homozygous for the ms8 mutation, but hemizygous for a transgene construct.

Two-Line Nuclear Male Sterility Breeding System

The present disclosure relates to a two-line nuclear male sterility (NMS) hybrid breeding system based on the MS8 gene and the ms8 mutant plant. In an embodiment, this disclosure describes a two-line NMS hybrid sorghum breeding system. In an embodiment, this disclosure describes a two-line NMS hybrid sorghum breeding system comprising a male sterile mutant. In some embodiments, the ms8 mutation and the three-component genetic construct can be introduced into sorghum accessions with diverse genetic backgrounds, which can be widely used to make various sorghum hybrids. This is particularly important for bioenergy sorghum breeding, because most of accessions suitable for bioenergy cannot serve as the B or R line and it is difficult to use the three-line system for breeding bioenergy sorghum hybrids. Furthermore, the disclosed two-line NMS hybrid breeding system can be extended to other crops by genetically editing the MS8 homologs, which have been shown to regulate male sterility in both monocot and dicot plants. Therefore, application of our technology will greatly improve hybrid breeding and production not only in sorghum but also in other crops. In one embodiment, this disclosure describes a method for the creation of transgene free male sterile sorghum plants in diverse genetic backgrounds.

In some embodiments, the two-line NMS hybrid breeding system can be used with a diverse panel of foundation lines, which will greatly enhance the breeding efficiency and increase the number of hybrids for achieving the ideal hybrid vigor. This two-line NMS hybrid breeding system can be useful for breeding for all types of sorghum hybrids, including grain, forage, sweet, feed, and especially bioenergy sorghum, will substantially simplify sorghum breeding, and make it possible to breed all types of sorghum hybrids.

In some embodiments, the two-line NMS hybrid breeding system includes the disclosed three-component genetic construct to rescue the male fertility of ms8 plants, ablate the transgenic pollen and sort the transgenic and non-transgenic seeds. The resulting self-maintained bridge plants will produce 100% of transgene-free male sterile plants, which can be pollinated by any other fertile lines for hybrid production. This approach is different from previous studies. For example, a pollen-specific promoter can be used to drive a pollen killing polynucleotide sequence, such as the BARNASE gene with a mild toxicity, to devitalize pollen carrying the MS8 gene. Alternatively, to prevent pollen development, pollen-specific promoters can be used to silence genes essential for pollen formation. The RFP (Red Fluorescent Protein) marker expressed in seeds can be used as a safeguard to sort out transgenic seeds from non-transgenic seeds to ensure obtaining 100% of transgene-free male sterile plants and transgenic plants for self-maintenance. In the alternative or in addition to the RFP, the EsMYB41 gene can be used to change the seed coat color and/or leaf color by increasing the synthesis of anthocyanin.

In another embodiment, an expression cassette of the wild-type MS8 gene driven by a dexamethasone (DEX)-inducible promoter can be used to transform the ms8 mutant. Homozygous ms8 plants can be maintained via treating male sterile plants with DEX. During hybrid production, plants homozygous for the ms8 mutation will be male sterile in the absence of chemical inducer. The transgene together with the ms8 mutation can be easily introduced into other sorghum accessions through marker-assisted selection as needed. The advantage of the inducible male fertile system is that we can breed sorghum hybrid under the same condition without the need to produce hybrid seeds and maintain the male sterile line under different conditions.

The present disclosure relates to two-line nuclear male sterility system for plant breeding. The system includes: the male sterile plant generated by the disclosed methods for generating a male sterile plant and/or a maintained bridge plant, and the bridge plant generated by the disclosed methods of generating a bridge plant or generating a male sterile plant and/or a maintained bridge plant.

The present disclosure relates to method of generating a hybrid seed. The method includes: a) planting seed of a male sterile plant, described above, adjacent to seed of a male fertile plant variety; b) allowing the male fertile plant to cross-pollinate with the male sterile plant; and c) harvesting and sorting F1 hybrid seed. The three-component genetic construct can be used to prevent transgene flow via pollen dispersal in transgenic sorghum, rice, maize, wheat, soybean, or rapeseed. For example, if the herbicide resistance gene (e.g., Roundup) is introduced into a bridge plant, the viable pollen produced in the bridge plant will not have the herbicide resistance gene. Therefore, the bridge plant can be used for grain production and completely male sterile plants derived from the bridge plant can be used for sugar production (e.g., sweet sorghum) and green feed (e.g., forage sorghum). In some embodiments, the male sterile plant is generated from a bridge plant having a transgene and the method prevents the transgene flow via pollen dispersal in transgenic sorghum, rice, maize, wheat, soybean, or rapeseed.

Constructs and Plasmids

The genetic constructs may comprise a nucleic acid sequence that encodes the three-component genetic construct, disclosed herein. The genetic construct, such as a plasmid, may comprise a nucleic acid that encodes the three-component genetic construct. The genetic construct may be present in the cell as a functioning extrachromosomal molecule. The genetic construct may be a linear minichromosome including centromere, telomeres, or plasmids or cosmids.

The genetic construct may also be part of a genome of a recombinant viral vector, including recombinant cauliflower mosaic virus, recombinant tobacco mosaic virus, and recombinant potato virus X-based vectors. The genetic construct may be part of the genetic material in attenuated live microorganisms or recombinant microbial vectors which live in cells. The genetic constructs may comprise regulatory elements for gene expression of the coding sequences of the nucleic acid. The regulatory elements may be a promoter, an enhancer an initiation codon, a stop codon, or a polyadenylation signal.

In certain embodiments, the polynucleotides to be introduced into the plant are operably linked to a promoter sequence and may be provided as a construct. As used herein, a polynucleotide is "operably linked" when it is placed into a functional relationship with a second polynucleotide sequence. For instance, a promoter is operably linked to a coding sequence if the promoter is connected to the coding sequence such that it may effect transcription of the coding sequence. In various embodiments, the polynucleotides may be operably linked to at least one, at least two, at least three, at least four, at least five, or at least ten promoters.

The nucleic acid sequences may make up a genetic construct that may be a vector. The vector may be capable of expressing the three-component genetic construct in the cell of a plant. The vector may be recombinant. The vector may comprise heterologous nucleic acid encoding the three-component genetic construct. The vector may be a plasmid. The vector may be useful for transfecting cells with nucleic acid encoding the three-component genetic construct, after which the transformed host cell is cultured and maintained under conditions wherein expression of the three-component genetic construct takes or can take place.

Coding sequences may be optimized for stability and high levels of expression. In some instances, codons are selected to reduce secondary structure formation of the RNA such as that formed due to intramolecular bonding.

The vector may comprise heterologous nucleic acid encoding the three-component genetic construct and may further comprise an initiation codon, which may be upstream of the three-component genetic construct coding sequence and a stop codon, which may be downstream of the three-component genetic construct coding sequence. The initiation and termination codon may be in frame with the three-component genetic construct coding sequence. The vector may also comprise a promoter that is operably linked to the three-component genetic construct coding sequence. The promoter that is operably linked to the three-component genetic construct and/or three-component genetic construct coding sequence may be not natively associated with the polynucleotide encoding the three-component genetic construct. Promoters useful in the practice of the present invention include, but are not limited to, constitutive, inducible, temporally-regulated, developmentally regulated, chemically regulated, tissue-preferred and tissue-specific promoters. Suitably, the promoter causes sufficient expression in the plant to produce the phenotypes described herein. Suitable promoters include, without limitation, the 35S promoter of the cauliflower mosaic virus, ubiquitin, tCUP cryptic constitutive promoter, the Rsyn7 promoter, pathogen-inducible promoters, the maize In2-2 promoter, the tobacco PR-1a promoter, glucocorticoid-inducible promoters, and tetracycline-inducible and tetracycline-repressible promoters.

The vector may also comprise a polyadenylation signal, which may be downstream of the three-component genetic construct and/or three-component genetic construct coding sequence. The vector may also comprise an enhancer upstream of the three-component genetic construct and/or three-component genetic construct coding sequence. The enhancer may be necessary for DNA expression. The vector may also comprise a plant origin of replication in order to maintain the vector extrachromosomally and produce multiple copies of the vector in a cell. The vector may also comprise a regulatory sequence, which may be well suited for gene expression in a plant cell into which the vector is administered. The vector may also comprise a reporter gene, such as green fluorescent protein ("GFP") and/or a selectable marker, such as hygromycin ("Hygro").

The vector may be expression vectors or systems to produce protein by routine techniques and readily available starting materials including Sambrook et al., 1989, which is incorporated fully by reference. In some embodiments the vector may comprise the nucleic acid sequence encoding the three-component genetic construct.

Plant Transformation

The three-component genetic construct of the present disclosure may be introduced into a plant cell to produce a transgenic plant. As used herein, "introduced into a plant" with respect to polynucleotides encompasses the delivery of a polynucleotide into a plant, plant tissue, or plant cell using any suitable polynucleotide delivery method. Methods suitable for introducing polynucleotides into a plant useful in the practice of the present invention include, but are not limited to, freeze-thaw method, microparticle bombardment, direct DNA uptake, whisker-mediated transformation, electroporation, sonication, microinjection, plant virus-mediated, and *Agrobacterium*-mediated transfer to the plant. Any suitable *Agrobacterium* strain, vector, or vector system for transforming the plant may be employed according to the present disclosure. In certain embodiments, the polynucleotide is introduced using at least one of stable transformation methods, transient transformation methods, or virus-mediated methods.

By "stable transformation" is intended that the nucleotide construct introduced into a plant integrates into the genome of the plant and is capable of being inherited by progeny thereof. By "transient transformation" is intended that a nucleotide construct introduced into a plant does not integrate into the genome of the plant.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al., *Biotechniques* 4:320-334 (1986)), electroporation (Riggs et al., *Proc. Natl. Acad. Sci. USA* 83:5602-5606 (1986)), *Agrobacterium*-mediated transformation (U.S. Pat. Nos. 5,981,840 and 5,563,055), direct gene transfer (Paszkowski et al., *EMBO J.* 3:2717-2722 (1984)), and ballistic particle acceleration (see, for example, U.S. Pat. Nos. 4,945,050; 5,879,918; 5,886,244; 5,932,782; Tomes et al., in *Plant Cell, Tissue, and Organ Culture: Fundamental Methods*, ed. Gamborg and Phillips (Springer-Verlag, Berlin) (1995); and McCabe et al., *Biotechnology* 6:923-926 (1988)). Also see Weissinger et al., *Ann. Rev. Genet.* 22:421-477 (1988); Sanford et al., *Particulate Science and Technology* 5:27-37 (1987) (onion); Christou et al., *Plant Physiol.* 87:671-674 (1988) (soybean); McCabe et al., *Bio/Technology* 6:923-926 (1988) (soybean); Finer and McMullen, *In Vitro Cell Dev. Biol.* 27P:175-182 (1991) (soybean); Singh et al., *Theor. Appl. Genet.* 96:319-324 (1998) (soybean); Datta et al., *Biotechnology* 8:736-740(1990) (rice); Klein et al., *Proc. Natl. Acad. Sci. USA* 85:4305-4309 (1988) (maize); Klein et al., *Biotechnology* 6:559-563 (1988) (maize); U.S. Pat. Nos. 5,240,855; 5,322,783 and 5,324,646; Klein et al., *Plant Physiol.* 91:440-444 (1988) (maize); Fromm et al., *Biotechnology* 8:833-839 (1990) (maize); Hooykaas-Van Slogteren et al., Nature (London) 311:763-764(1984); U.S. Pat. No. 5,736,369 (cereals); Bytebier et al., *Proc. Natl. Acad. Sci. USA* 84:5345-5349 (1987) (Liliaceae); De Wet et al., in *The Experimental Manipulation of Ovule Tissues*, ed. Chapman et al., (Longman, N.Y.), pp. 197-209 (1985) (pollen); Kaeppler et al., *Plant Cell Reports* 9:415-418 (1990) and Kaeppler et al., *Theor. Appl. Genet.* 84:560-566 (1992) (whisker-mediated transformation); D'Halluin et al., *Plant Cell* 4:1495-1505 (1992) (electroporation); Li et al., *Plant Cell Reports* 12:250-255 (1993) and Christou and Ford, *Annals of Botany* 75:407-413 (1995) (rice); Osjoda et al., *Nature Biotechnology* 14:745-750 (1996) (maize via *Agrobacterium tumefaciens*); all of which are herein incorporated by reference in their entireties.

In some embodiments, a plant may be regenerated or grown from the plant, plant tissue or plant cell. Any suitable methods for regenerating or growing a plant from a plant cell or plant tissue may be used, such as, without limitation, tissue culture or regeneration from protoplasts. Suitably, plants may be regenerated by growing transformed plant cells on callus induction media, shoot induction media and/or root induction media. See, for example, McCormick et al., *Plant Cell Reports* 5:81-84 (1986). These plants may then be grown, and either pollinated with the same transformed strain or different strains, and the resulting hybrid having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. Thus as used herein, "transformed seeds" refers to seeds that contain the nucleotide construct stably integrated into the plant genome.

BIOLOGICAL DEPOSITS

A representative sample of seeds of *Sorghum bicolor* seed designated as MS8, was deposited with the American Type Culture Collection (ATCC), 10801 University Blvd., Manassas, Virginia, 20110, United States of America on Jun. 14, 2023 under the terms of the Budapest Treaty on the International Recognition of the Deposit of Microorganisms for the Purposes of Patent Procedure ("Budapest Treaty"); the sample was accepted on Nov. 10, 2023, and was assigned ATCC Patent Deposit No. PTA-127606. ATCC performed viability testing under the Budapest Treaty on Jun. 20, 2023, and issued a Viability Statement (BP/9) on Nov. 10, 2023 that indicated the sample was viable. The deposit will be maintained at the ATCC depository under the terms of the Budapest Treaty for a term of at least thirty years and at least five years after the most recent request for the furnishing of a sample of the deposit was received by the depository. Additional deposits will be made at the ATCC as needed to ensure availability. Access to ATCC Patent Deposit No. PTA-127606 will be available during pendency of the patent application to one determined by the Director to be entitled thereto under 37 C.F.R. § 1.14 and 35 U.S.C. § 122. All restrictions imposed by the depositor on the availability to the public of the deposited material will be irrevocably removed upon the granting of a patent. Applicant has no authority to wave any restrictions imposed by law on the transfer of biological material or its transportation in worldwide commerce. Applicant does not waive any of its rights granted under any patents issuing from this application in any country or under the U.S. Plant Variety Protection Act (7 U.S.C. § 2321 et seq.) or other international or foreign plant variety protection systems. Applicant has satisfied all the requirements of 37 C.F.R. §§ 1.801-1.809.

The present invention has multiple aspects, illustrated by the following non-limiting examples.

EXAMPLES

The foregoing may be better understood by reference to the following examples, which are presented for purposes of illustration and are not intended to limit the scope of the invention.

Example 1

Ms8 is an Easily Recognizable, Novel, and Stable Sorghum NMS Mutant

An NMS mutant named male sterile 8 (ms8) was isolated from a sorghum mutant library, which was generated by the ethyl methane sulfonate (EMS) mutagenesis of the elite inbred line BTx623 seeds.

Generation of Sorghum Mutant Library. Sorghum [*Sorghum bicolor* (L.) Moench] inbred line BTx623 seeds were obtained from the National Germplasm Resources Information Network of USDA-ARS. After six generations of purification through single seed descent, the BTx623 seeds were mutagenized through treatment with EMS at concentrations ranging from 0.1 to 0.3% (v/v). The treated seeds were thoroughly washed in about 400 ml of tap water for five hours at ambient temperature, with changing of the wash water every 30 min. Then the mutagenized seeds were air-dried and prepared for planting.

Field Planting and Management. The sorghum mutant library was planted annually on the Research Farm of the Plant Stress and Germplasm Development Research Unit, USDA-ARS, Lubbock, Texas, USA (latitude 33° 35' N, longitude 101° 53' W, and altitude 958 m). The soil type is an Amarillo fine sandy loam (fine-loamy, mixed, superactive thermic Aridic Paleustalfs). Before planting, a mixture of bulk ammonium sulfate and mono ammonium phosphate was applied to the field, calculated to achieve levels of 65 kg nitrogen and 27 kg phosphorous per hectare. The plot size is 4.67-m long with 1.02-m row spacing. Sorghum seeds were planted at 80 per row at a depth of 3 cm using a John Deere MaxEmerge Planter. The plots were watered from underground drip lines as needed to maintain sufficient soil moisture.

Screening of the NMS Mutant. A panicle with no extruded anther was observed from a plant in plot 3049, in which the mutant line 25M2-1075 was planted. The main shoot of the plant that bore the sterile panicle was cut to stimulate tiller growing. Four tillers were developed later. One tiller was left open. Three tillers were bagged before heading. One of the three bagged tillers was pollinated with BTx623 wild-type pollen when the stigma had extruded from approximately 50% of the sessile spikelets. The other two panicles were continually bagged until harvesting. Neither of the two continually bagged tillers set any seed. However, both the open pollinated panicle and the manually pollinated panicle set seeds. The F1 plants from both open-pollinated and manually pollinated panicles were completely fertile, suggesting the male sterility mutation was recessive. The F2 plants derived from the manually-pollinated F1 progeny segregated 9 male sterile to 31 fertile, a ratio of approximately 1 to 3. Because of the easiness to identify the male sterility phenotype, we continued to backcross ms8 to BTx623 to develop a near isogenic line to serve as a convenient tool for backcrossing other mutants isolated from the mutant library.

Examination of Female Fertility. After panicles were emerged, the ms8 mutant plants were determined by the anther phenotype. The top parts of BTx623 and ms8 panicles were cut and bagged. One day later, the cut panicles were manually pollinated by the BTx623 pollen. Ovaries were dissected out from panicles before as well as 2 and 3 days after pollination. Ovaries were observed and imaged with the Olympus SZX7 dissection microscope equipped with an Olympus DP 70 digital camera (Olympus, Center Valley, PA, USA).

Pollen Staining and Anther Sectioning. Alexander staining was used to determine pollen viability. Briefly, anthers just before anther dehiscence were dissected out and fixed 24 hr in the fixative (methanol, 60 mL; chloroform, 3 0 mL; distilled water, 20 mL; picric acid, 1 g; and $HgCl_2$, 1 g). Anthers were transferred through 70%, 50%, and 30% ethanol followed by distilled water (1 hr in each change) and incubated in the staining buffer (ethanol 95%, 10 mL; malachite green, 10 mg; acid fuchsin, 50 mg; orange G, 5 mg; phenol, 5 g; glacial acetic acid, 2 mL; glycerol, 25 mL; and distilled water 50 mL) at 50° C. for 48 h. Anthers were mounted on the glass slide for observation.

Semi-thin sectioning was carried out. Sorghum spikelets were fixed in the fixative (2.5% glutaraldehyde, 0.1 M HEPES, 0.02% Triton X-100, pH 7.2) overnight at room temperature. Samples were washed three times (30 min each) in the wash buffer (0.1M HEPES, 0.02% Triton X-100, pH 7.2) and then post fixed in 1% $OsO_4$ overnight at room temperature. Samples were dehydrated through an acetone series (10% increments, 1 hr each change) and infiltrated in 20%, 40%, 60%, and 80% of low viscosity Spurr's resin (3 hr each change). Samples were then transferred into 100% Spurr's resin three times (24 hr each change) and embedded in 100% Spurr's resin. Samples were finally polymerized at 60° C. overnight. Semi-thin (0.5 µm) sections were performed using an Ultracut E ultramicrotome (Reichert-Jung) and were stained with 0.05% of Toluidine Blue O. Images of pollen staining and anther semi-thin sections were photographed with an Olympus BX51 microscope equipped with an Olympus DP 70 digital camera (Olympus, Center Valley, PA, USA).

Figures 2A, 2B, 2C, 2D, 2E:
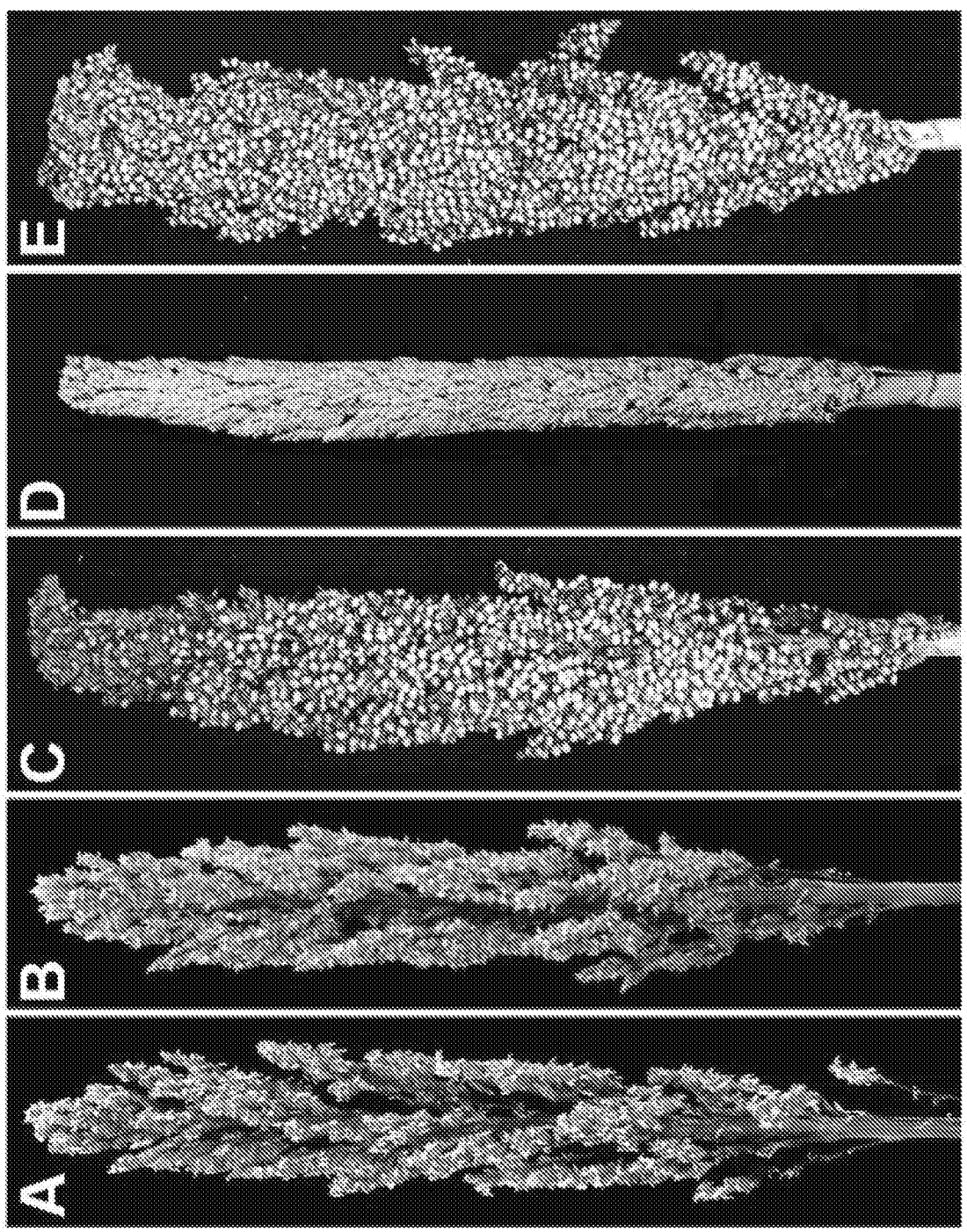
FIGS. 2A-2E show ms8 is an easily recognizable male sterile mutant.

The ms8 mutant had no defects in growth and development except for the male sterility. In the wild-type BTx623 plant, yellow anthers appear in the panicle during anthesis (FIG. 2A). The ms8 mutant was easily recognized, because its panicle was full of white anthers (FIG. 2B). Compared with the wild-type (FIG. 2A), no seeds were produced in the ms8 panicle (FIG. 2B). The seed production of ms8 mutant plants was fully recovered when pollinated with BTx623 pollen grains (FIG. 2E), indicating that ms8 is a male sterile mutant. All available male sterile mutants (ms1, ms2, ms3, ms7, and msaI) were pollinated using pollen from the heterozygous ms8 plants. All resulting $F_1$ plants were male fertile, suggesting that ms8 was a new sorghum male sterile mutant. The male sterility of ms8 was absolute and stable, since the ms8 plants never produced any seeds in the absence of a pollen source over several field seasons in Lubbock, TX, USA, Puerto Rico, and under different greenhouse conditions. In summary, ms8 was an easily recognizable, novel, and stable NMS mutant in sorghum.

Figures 1C, 1D:
FIGS. 1C-1D show a comparison of BTx623 wild-type panicle and spikelets with that of the ms8 mutant.

In the wild-type BTx623, yellow anthers appeared earlier than stigmas in all sessile spikelets during anthesis (FIGS. 1A and 1C). Conversely, anthers in the ms8 mutant were small and white (FIGS. 1B and 1D). Furthermore, white hairy stigmas emerged before anthers in the ms8 mutant. Thus, the ms8 mutant can be easily recognized via observing clearly visible white anthers and stigmas in all sessile florets at the beginning of anthesis.

To eliminate the effects of other unlinked mutations, ms8 was backcrossed to the wild-type BTx623 for six generations. The ms8 mutant plants were never observed to produce any seeds in the absence of a pollen source over the last several field seasons in Lubbock, TX, USA (FIG. 2B) and Puerto Rico (FIG. 2C), as well as under greenhouse conditions (FIG. 2D). The results demonstrated that the ms8 male sterility phenotype was easily recognized and stable. The backcrossed ms8 can be routinely used as a near isogenic line of BTx623 to backcross other plants to avoid hand emasculation or plastic-bag crosses.

Figure 1F:
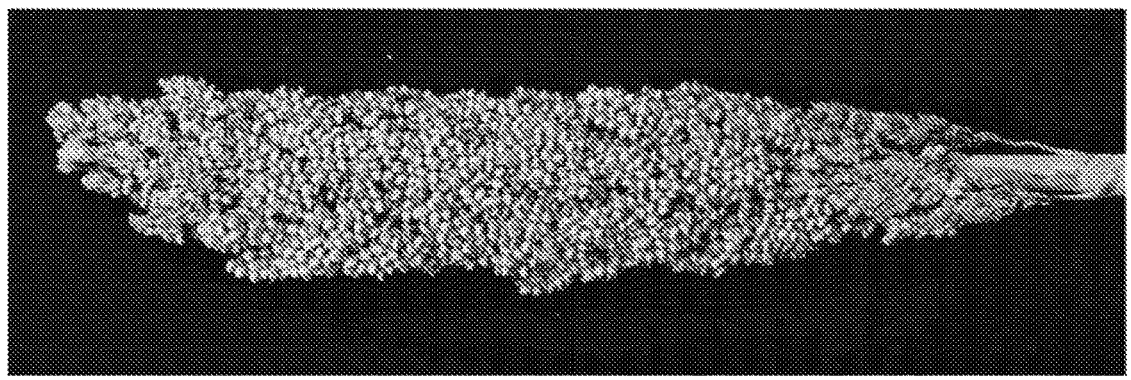
FIGS. 1E-1F show the female fertility is normal in the ms8 mutant.
Figure 1E:
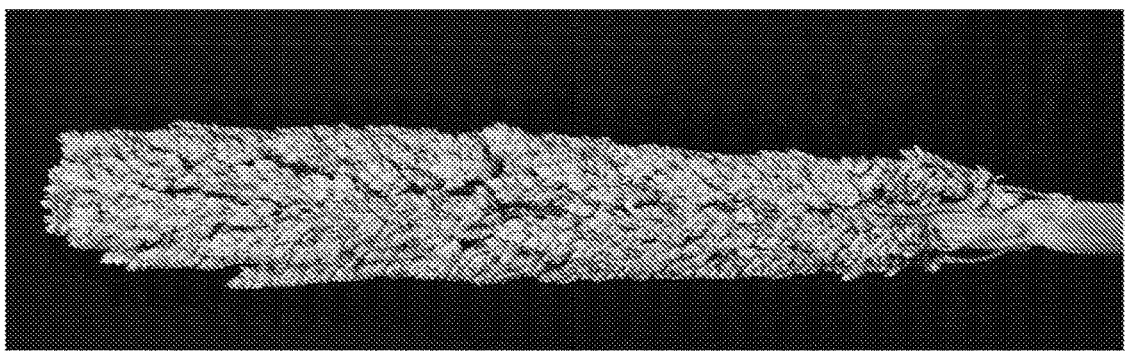
Figures 4A, 4B:
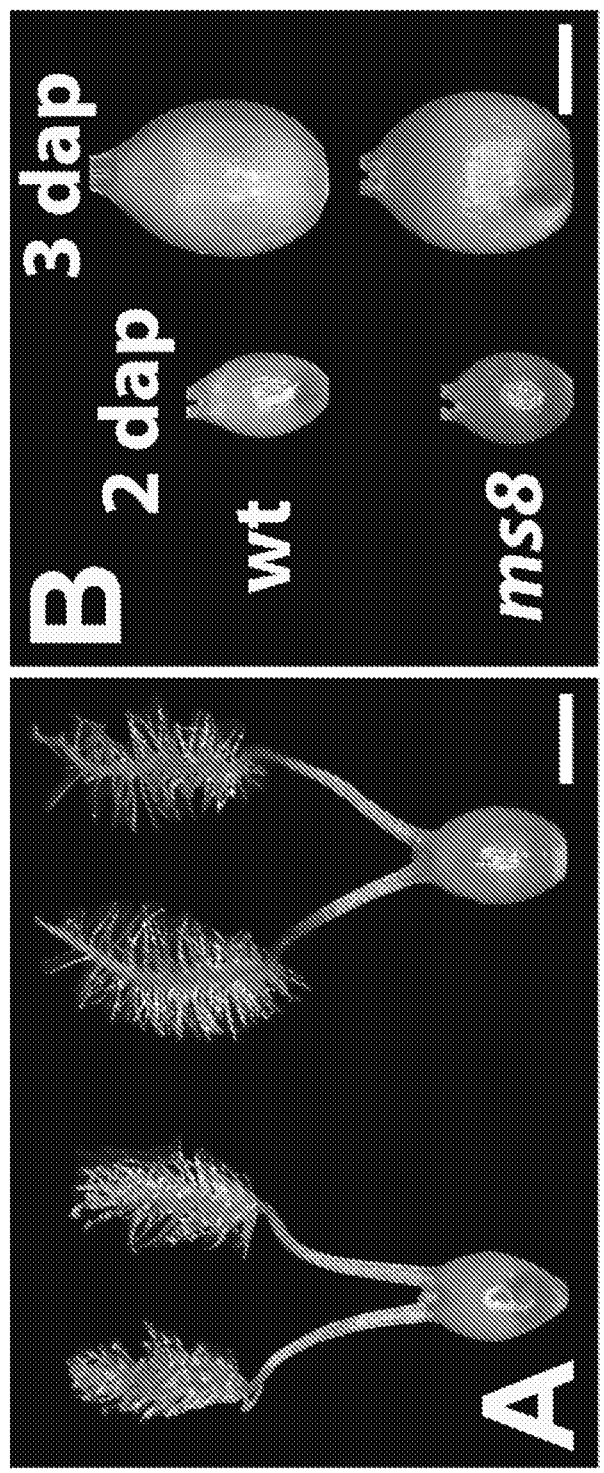
FIGS. 4A-4B show the female fertility is normal in the ms8 mutant.

To examine whether female organs are affected by the ms8 mutation, the ovaries were examined before and after manual pollination in ms8 plants. There was no difference in ovary size and appearance before pollination (FIG. 4A). After manual pollination, ovaries in both wild-type and ms8 mutant plants developed similarly (FIG. 4B). Without pollination, the ms8 panicle had no developing seeds (FIG. 1E). However, after the manual pollination, a full set of normally developing seeds were observed (FIG. 1F). The results suggested that the ms8 mutation only affected the male sterility but had no effect on the female fertility.

Example 2 ms8 is Defective in Tapetum Development

Figures 4C, 4D:
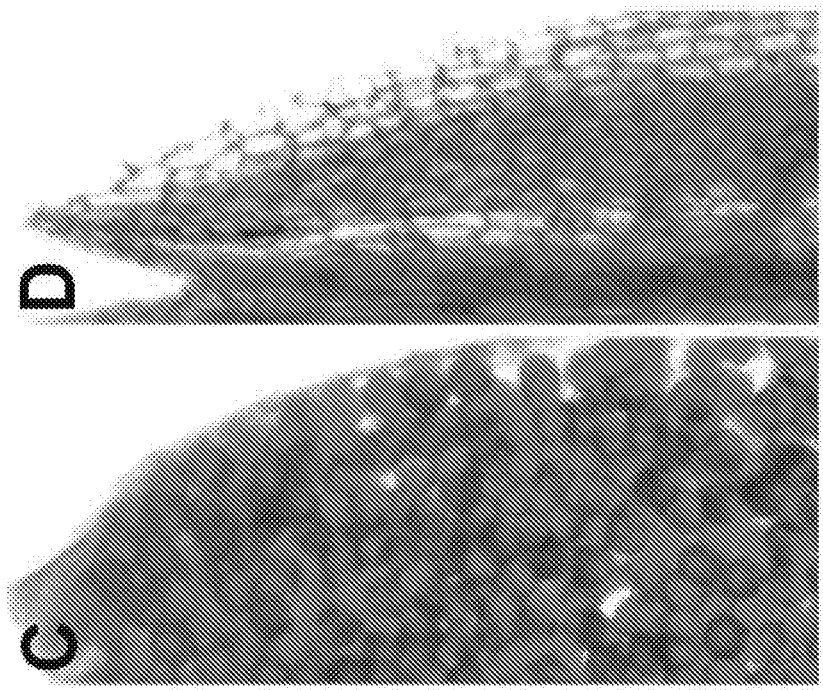
FIGS. 4C-4D show ms8 fails to produce pollen grains.

To investigate what caused the male sterility in the ms8 mutant, pollen viability and anther development was examined. In the BTx623 wild-type mature spikelet (sessile spikelet), there were three extruding yellow anthers and two stigmas with pollen grains (FIG. 3A). However, in the ms8 mutant spikelet (sessile spikelet), three extruding anthers were pale colored and flattened (FIG. 3B). In addition, pollen grains were not observed on the ms8 stigmas (FIG. 3B). To evaluate pollen production and viability of ms8 mutant anthers, Alexander staining of pollen grains was performed prior to anthesis. In BTx623 anthers, round red pollen grains were evenly distributed in anther lobes (FIG. 4C). Conversely, no pollen grains were found in ms8 mutant anthers (FIG. 4D), indicating that the ms8 mutant failed to produce pollen.

Figures 5A, 5B, 5C, 5D, 5E, 5F:
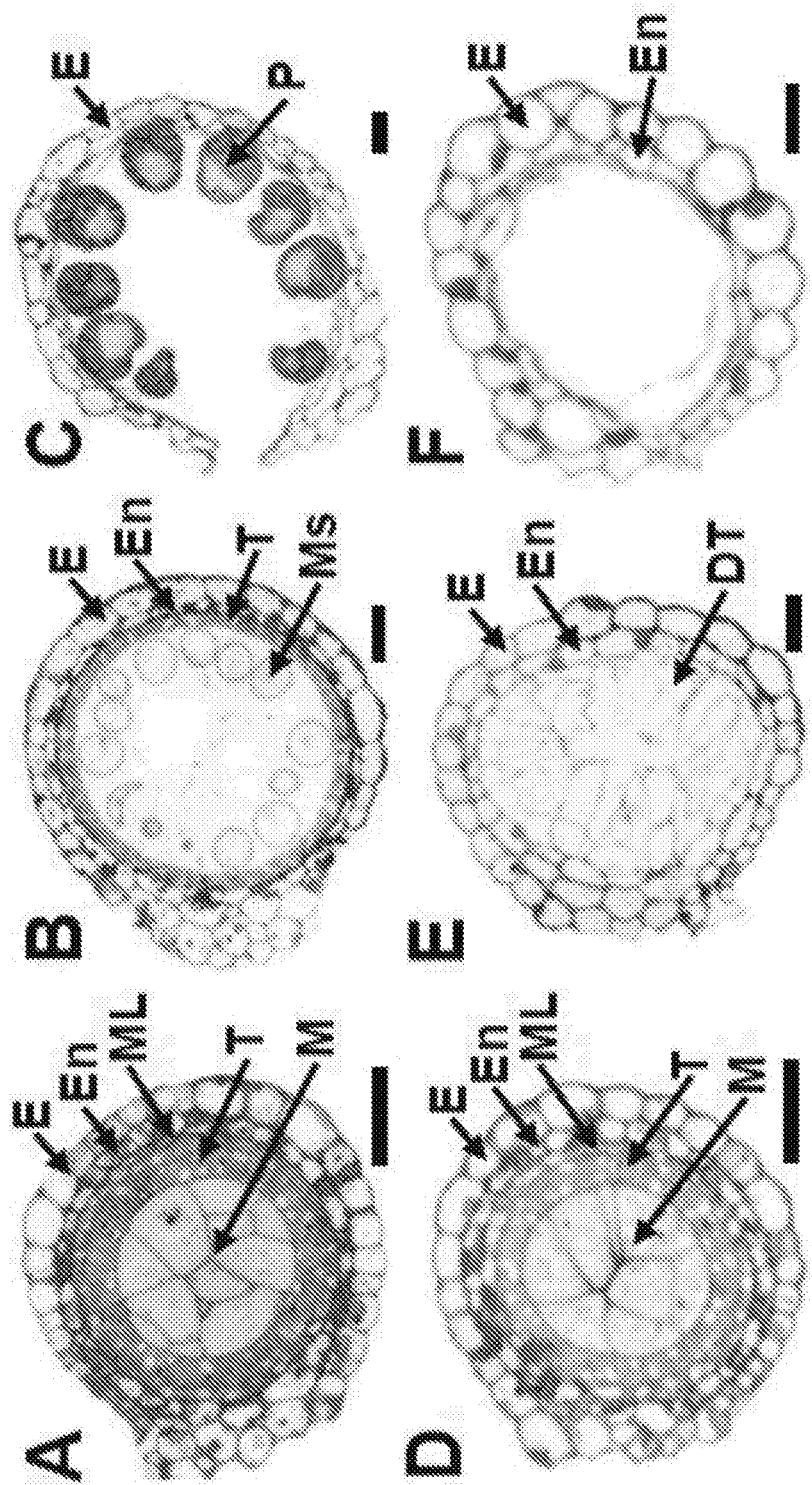
FIGS. 5A-5F show ms8 is abnormal in tapetum development.

To further examine what results in the failure of pollen production in ms8 mutant, semi-thin sectioning of wild-type and ms8 anthers was performed. Analysis of semi-thin sections showed that, similar to BTx623 anthers (FIG. 5A), ms8 anthers produced normal microsporocytes and concentrically organized anther wall cells, i.e., epidermis, endothecium, middle layer, and tapetum at stage 6 (FIG. 5D). In BTx623 anthers at stage 9, microspores were vacuolated and the middle layer was invisible (FIG. 5B). Conversely, in ms8 anthers, the tapetum was degenerated prematurely, no microspores were observed (FIG. 5E). At stage 12, pollen grains were formed in BTx623 anthers (FIG. 5C), but the ms8 anther lobe was empty (FIG. 5F). The results suggested that the precocious degeneration of tapetum caused abnormal development of microspores, and consequently the failure of pollen production.

Example 3

The MS8 Gene Encodes a Basic Helix-Loop-Helix (bHLH) Protein

To eliminate the effects of other unlinked mutations, ms8 was backcrossed to the wild-type BTx623 for six generations. The results provided several lines of evidence to support that ms8 was a recessive mutation in a nuclear encoded gene. The ms8×BTx623 F1 plants (the F1 plants between a cross of the ms8 mutant and the wild-type BTx623) were completely fertile (Table 1), suggesting that ms8 was a recessive mutation. The male sterility was segregated as a single recessive nuclear gene mutation during the subsequent backcrosses to the wild-type BTx623. The segregation ratio of male sterile plants to fertile plants in the F2 population yielded from the MS8/ms8 heterozygous plants was 1:3 (108 male sterile to 320 fertile). The F2 plants after six backcrosses segregated as 108 male sterile and 320 fertile (Table 1). Statistical analysis indicated that the 1:3 (mutant:wild-type) segregation ratio can be accepted according to the X2 test (Table 1), suggesting that the ms8 recessive mutation occurred in a single nuclear gene.

Furthermore, to increase the frequency of male sterile plants that could be used for backcrossing, the ms8 heterozygous plants (fertile) was crossed with the ms8 homozygous mutant plants (male sterile). Fifty plots (4.5 m×1 m) of resulting F1 seeds were planted in the winter nursery in Puerto Rico. Three plots were examined for male sterile and fertile plants. The segregation ratio was 59 male sterile to 63 fertile plants, which agreed with the expected ratio of 50% male sterile (homozygous at ms8 locus) to 50% fertile (heterozygous) plants.

To test if the ms8 mutant was allelic to other NMS mutants reported previously in sorghum, other NMS mutants were obtained, including ms1, ms2, ms3, ms7, and msaI. Pollen collected from the heterozygous ms8 plants were used to pollinate male sterile plants from the previously reported ms mutants. If ms8 was allelic to those male sterile lines, the progeny would segregate for 50% male sterile and 50% fertile plants. If ms8 belonged to a different locus from the examined NMS line, all F1 plants would be male fertile. As shown in Table 1, all F1 plants were male fertile for all crosses. Thus, ms8 represents a new male sterile mutant. Whether ms8 was allelic to ms4, ms5, or ms6 was not determined, because these lines were not available.

Collectively, the results support that ms8 was a novel male sterile locus distinct from all NMS lines currently available.

TABLE 1

Genetic analysis of the sorghum nuclear male sterile mutant ms8.

| Cross | Number of Plants | F1 Phenotype | Fertile F2 | Sterile F2 | X2 (p-value) |
|---|---|---|---|---|---|
| BTX623* ms8 | 8 | All Fertile | 320 | 108 | 0.91 |
| ms8*msx F1 | 16 | 9 ms, 7 fertile | | | 0.61 |
| ms1* ms8 F1 | 16 | All Fertile | | | |
| ms2* ms8 F1 | 16 | All Fertile | | | |
| ms3* ms8 F1 | 16 | All Fertile | | | |
| ms7* ms8 F1 | 15 | All Fertile | | | |
| msa1* ms8 F1 | 13 | All Fertile | | | |

Figure 6:
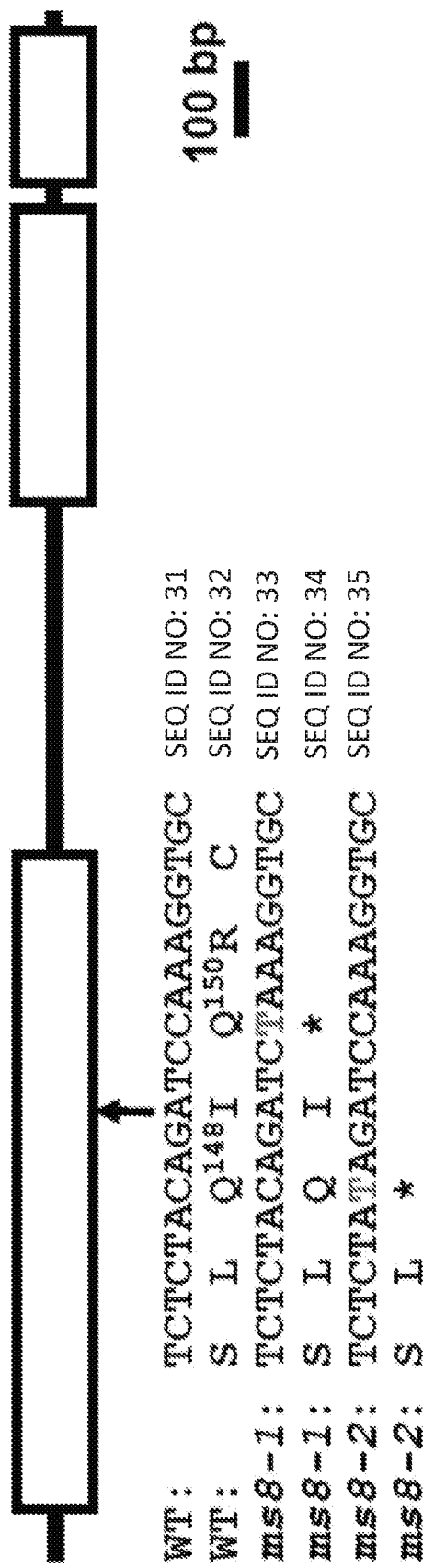
FIG. 6 shows the MS8 gene and the ms8 mutations. The MS8 gene (Sb04g030850) contains 3 exons (open boxes) and 2 introns. C to T mutations in ms8-1 and ms8-2 generate early stop codons at positions of Q150 and Q148, respectively.

To clone the MS8 gene, the whole genome sequence of the ms8 mutant was performed via next-generation sequencing (NGS). A C-T non-synonymous mutation (ms8-1) was identified in the loci Sb04g030850 locus which converts the codon for a glutamine (CAA: Q) at the position 150 to a stop codon (TAA, FIG. 6). From an independent MS8 allele ms8-2, another C-T mutation was identified resulting in a stop codon at Q148 (CAG to TAG) in the same gene (FIG. 6). The results show that the ms8 mutant phenotype was caused by mutations in the Sb04g030850 gene, which encodes a basic Helix-Loop-Helix (bHLH) transcription factor. The MS8 gene was the first NMS gene identified in sorghum. The nucleotide sequence of the wild-type MS8 with the mutations in ms8-1 and ms8-2 indicated is shown in FIG. 9A while the corresponding polypeptide sequence is shown in FIG. 9B. The MS8 gene was similar to the rice EAT1 gene (OsEAT1) (FIG. 7). Another nuclear male sterile sorghum mutant was sequenced and the mutant gene was found to be similar to rice TDR gene (FIG. 8).

Example 4

Three-Component Construct for Producing Pure Male Sterile Plants

Two three-component constructs were generated (FIGS. 10A and 10J) and one construct (FIG. 10A) was transformed into the wild-type sorghum. Component 1 contained the MS8 gene under its native promoter to rescue the ms8 mutant male fertility. Component 2 contained the mild cytotoxic gene BARNASE driven by the pollen-specific promoter OsPLP2 to impair the viability of pollen grains carrying the MS8 transgene (FIG. 10A). Alternatively, the pollen specific promoter OsLPS1 is used to silence the sorghum ASPARTIC PROTEASE 65 (SbAP65) gene and OsIPA is used to silence the sorghum SUCROSE TRANSPORTER1 (SbSUT1) gene, which will arrest the pollen development (FIG. 10J). In some embodiments, the construct shown in FIG. 10A can be used without the SbABl3:RFP reporter gene. Component 3 contained the RFP (Red Fluorescent Protein) gene driven by the SbABl3 promoter or the hybrid gene AtOLE1:AtOLE1-RFP. The RFP marker was used to sort out transgenic and non-transgenic seeds. Those three genes were cloned into the pEarleyGate vector to generate the three-component construct, which was then transformed into the BTx623 wild-type and ms8 heterozygous plants by the Plant Transformation Core Facility at the University of Missouri-Columbia.

Figures 12A, 12B, 12C:
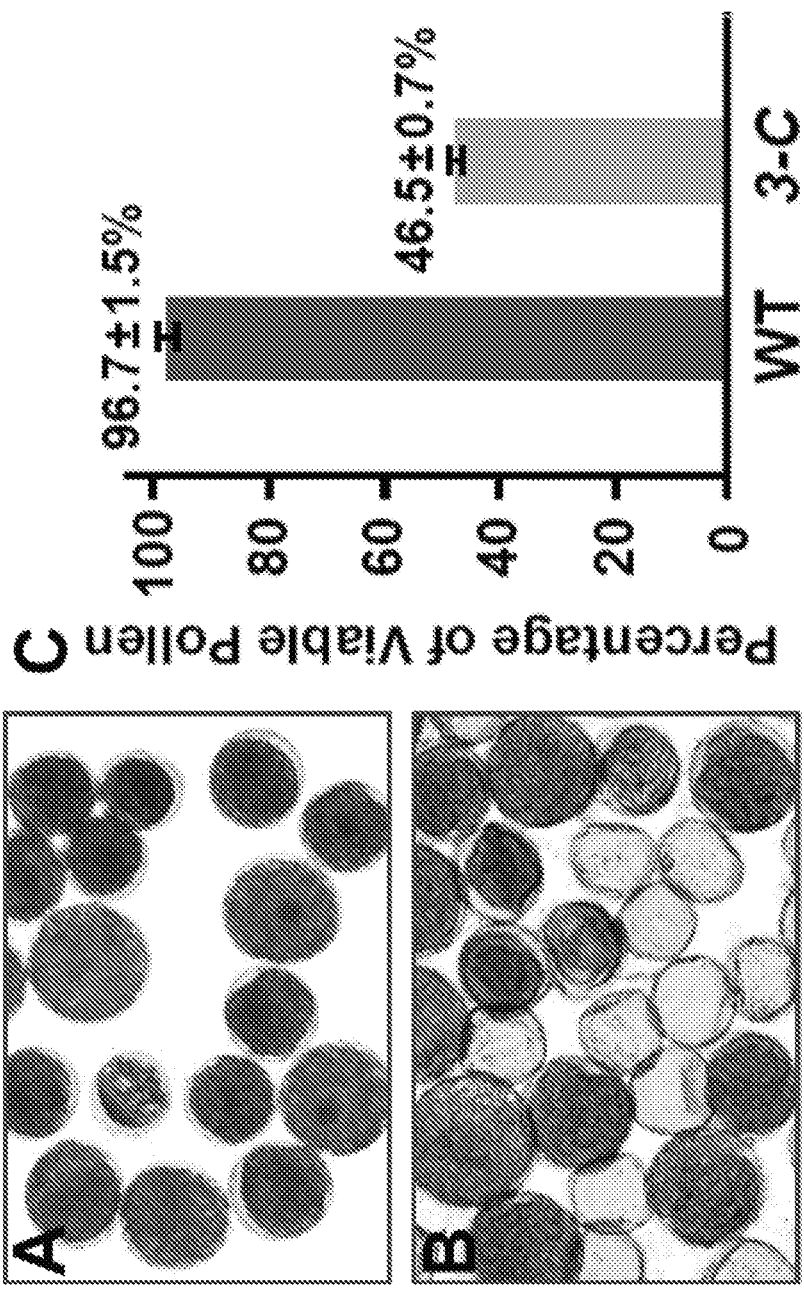
FIGS. 12A-12C show the transgenic sorghum plant harboring the three-component transgene shown in FIG. 10A produced nearly 50% of inviable and viable pollen grains, respectively.
Figure 13A:
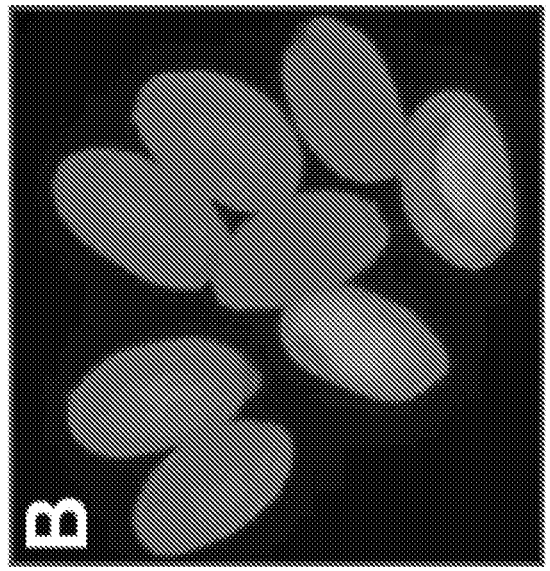
FIGS. 13A-13D show the markers used for seed sorting.
Figure 13B:
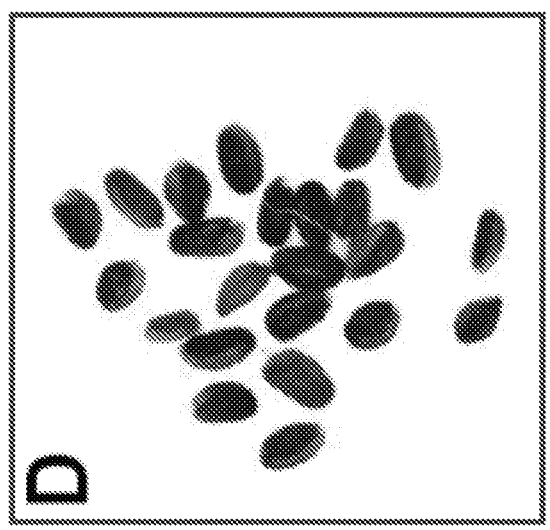
Figure 13C:
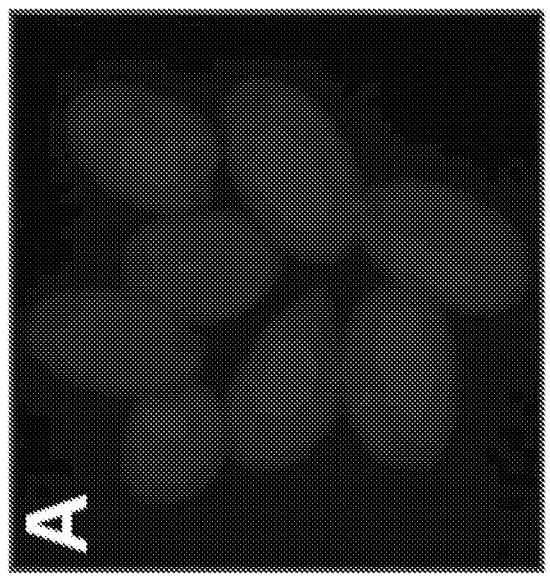
Figure 13D:
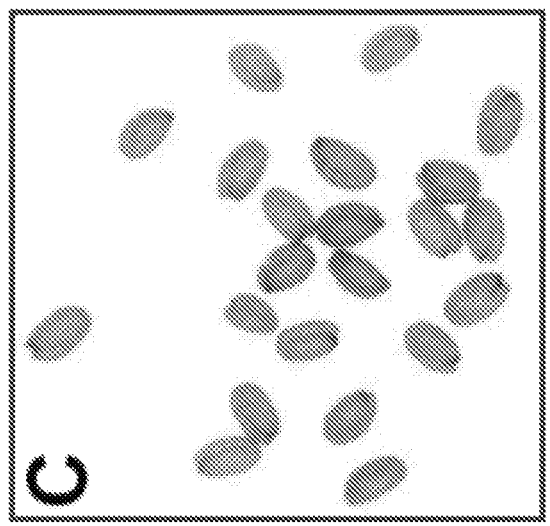

FIGS. 12A-12C show transformed wild-type sorghum plant harboring the three-component transgene shown in FIG. 10A produced nearly 50% of inviable and viable pollen grains, respectively. FIG. 12A shows pollen staining from the wild-type plant showing viable pollen grains in red color. FIG. 12B shows pollen staining from the transgenic plant showing viable (red color) and inviable (blue color) pollen grains. The haploid pollen that are clear (blue color) are dead because they carry the 3-C transgenes. FIG. 12C shows statistical analysis showing the transgenic plant produced nearly 50% of inviable and viable pollen grains, respectively.

Other possible three-component constructs are shown in FIGS. 10A-10P. Other possible reporter genes are shown in FIGS. 13A-13D, which demonstrate that AtOLE1:AtOLE1-RFP and 35S:EsMYB41 work for seed sorting in *Arabidopsis*.

Example 5

Test the Two-Line Male Sterility System (NMS) for Sorghum Hybrid Breeding

Figure 11A:
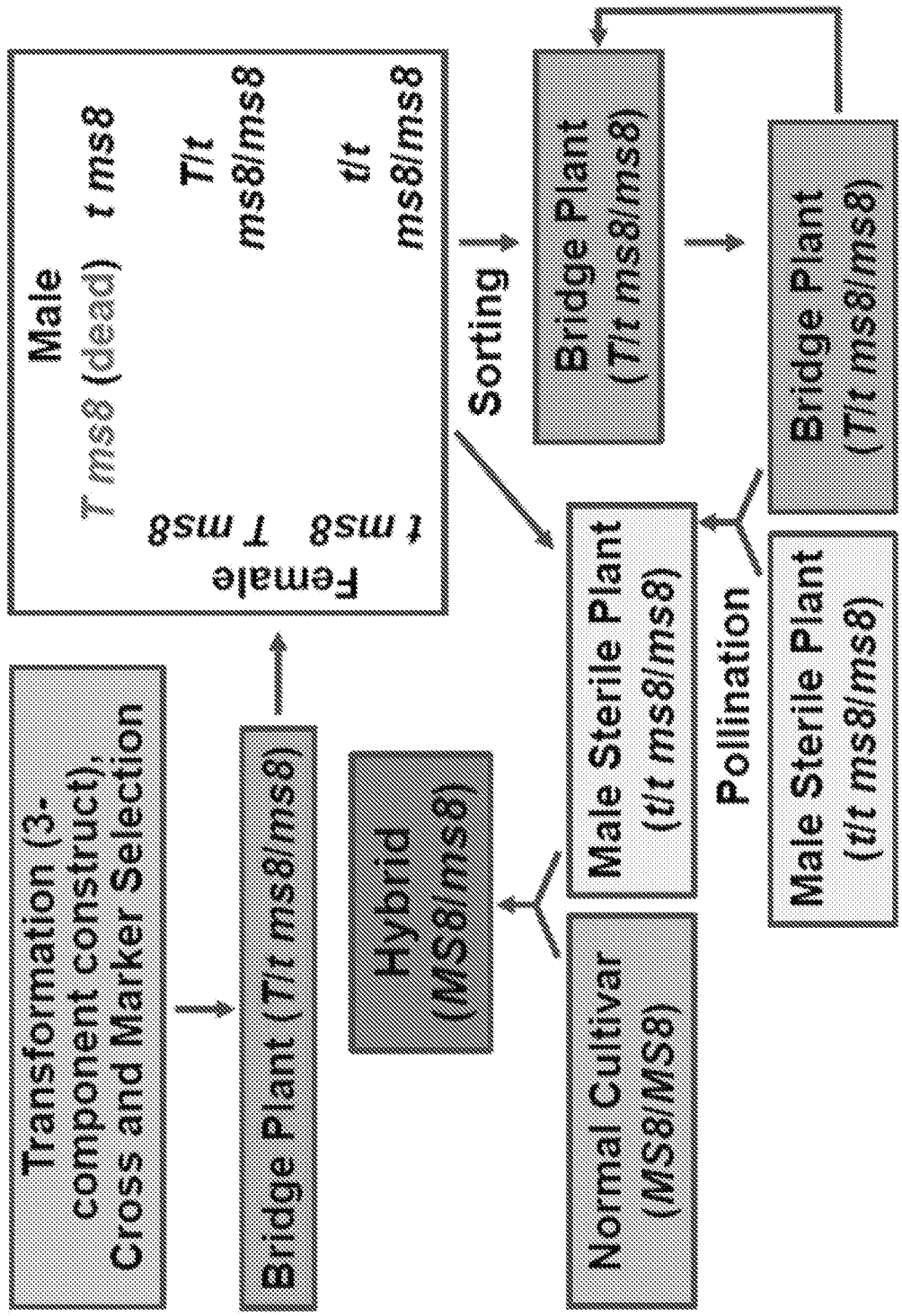
FIG. 11A shows a schematic diagram showing how the two-line Nuclear Male Sterility (NMS) hybrid breeding system works for hybrid breeding in sorghum.
Figure 11B:
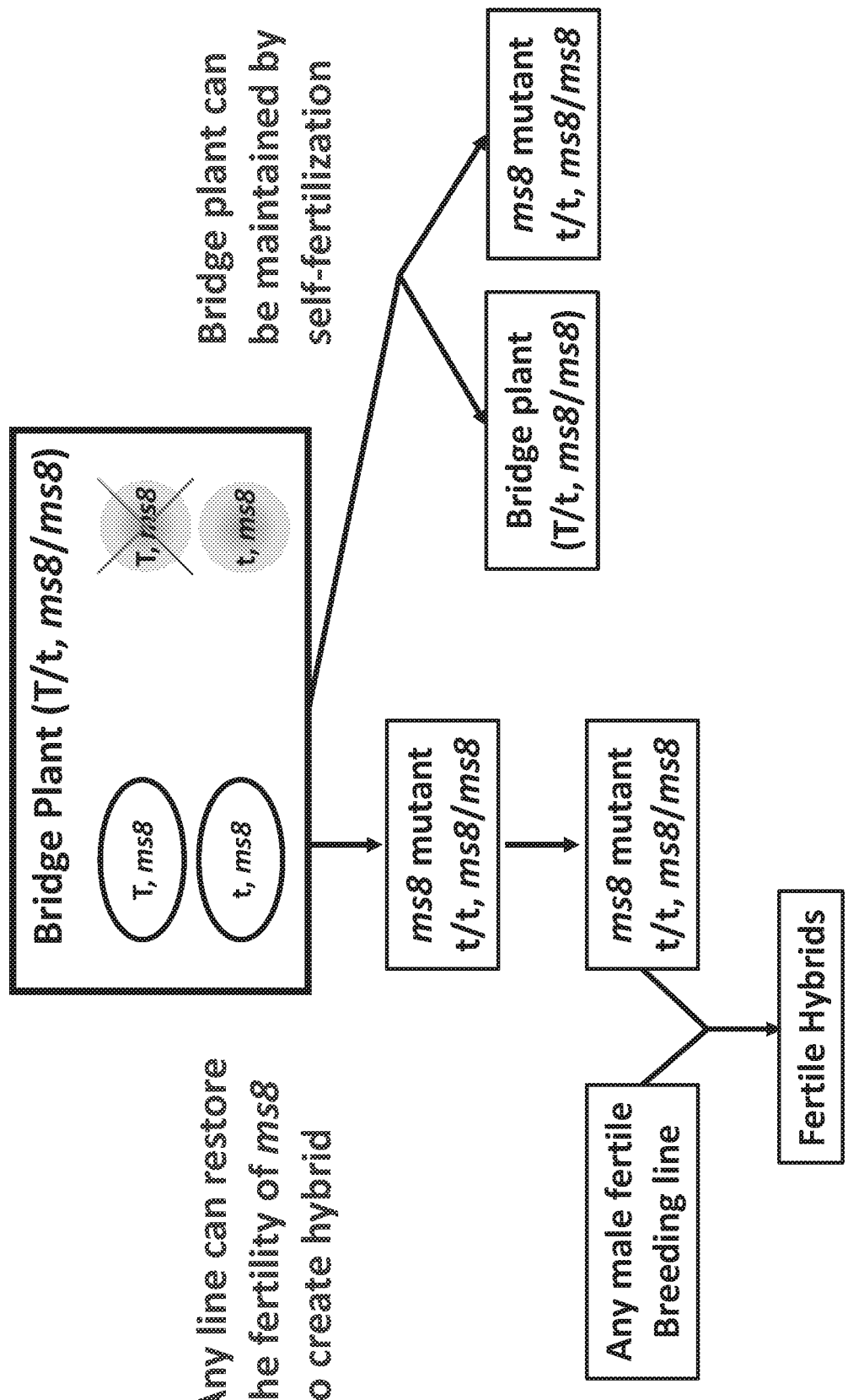
FIG. 11B shows the breeding procedure.

Plants homozygous for the male sterility (ms8/ms8) but hemizygous for the 3-C transgenes (T/t) will be screened from the F2 population. Via genetic cross and marker selection, a bridge plant is generated that is homozygous for the male sterility (ms8/ms8) but hemizygous for the three-component transgenes (T/t three-component transgenes are named T, t means no three-component transgenes; FIGS. 11A and 11B). The ms8/ms8 T/t plants will be expected to produce ms8/T and ms8/t two types of eggs in embryo sac and only the ms8/t type of sperm in pollen, because the ms8/T type of pollen will be killed by the BARNASE or by impairing SbAP65 and SbSUT1. Therefore, two kinds of progeny, ms8/ms8 T/t (maintaining bridge plants) and ms8/ms8 t/t (male sterile), will be obtained from self-pollinated ms8/ms8 T/t plants, which will be sorted by the RFP marker expressed in seeds. The ms8/ms8 T/t plants will be used to maintain the two-line NMS hybrid breeding system, while the pure ms8/ms8 t/t male sterile plants will be used for making hybrid seeds. Alternatively, the ms8/ms8 T/t plants can be used as the bridge plants. The pollen (ms8/ms8 t/t) from the bridge plant will be used to pollinate the ms8 mutant (ms8/ms8), which will produce 100% of male sterile plants. The self-pollinated fertile bridge plants can be maintained as the ms8/ms8 pollen donor. The RFP marker will be employed as a safeguard to sort out T/t ms8/ms8 seeds and ensure obtaining 100% of transgene-free ms8/ms8 seeds via seed sorting. An ms8/ms8 T/t line is expected to be obtained and will be used as a new two-line NMS hybrid breeding system to produce pure nuclear male sterile plants for sorghum hybrid breeding. The produced hybrids are transgene free.

The ms8 mutation and the three-component construct can be introduced into sorghum accessions with diverse genetic backgrounds, which can be widely used to make various sorghum hybrids, including those important for bioenergy production. The ms8 mutation and the three-component transgene construct will be introduced to a panel of diverse elite lines, with recommendations from the United Sorghum Checkoff Program (USCP) and breeding companies, by molecular marker assisted backcross for six generations. This panel of diverse lines is expected to produce male sterile lines with many different genetic backgrounds. The panel can be fertilized with any sorghum elite lines, natural accessions, and mutant lines to generate unlimited numbers of hybrids quickly. With this improved breeding efficiency, novel combinations of hybrids will be identified that support the continued yield gains in sorghum. The new technology can provide immediate support for breeding sweet and bioenergy sorghum hybrids, because any accessions that are suitable for the bioenergy traits can be used for breeding directly without knowing if they are B or R lines.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clauses:

Clause 1. A three-component genetic construct for use in a two-line nuclear male sterility system, the three-component system comprising: (a) a first component comprising a nuclear male sterile gene operably linked to a first promoter, wherein the nuclear male sterile gene comprises a MALE STERILE8 (MS8) gene encoding a protein having at least about 80% identity to the polypeptide sequence of SEQ ID NO: 1 or a TAPETUM DEGENERATION RETARDATION (TDR) gene encoding a protein having at least about 80% identity to the polypeptide sequence of SEQ ID NO: 3; (b) a second component comprising a pollen killing nucleotide sequence operably linked to a second promoter, wherein the second promoter is a pollen specific promoter; and (c) a third component comprising a seed specific selectable marker gene operably linked to a third promoter.

Clause 2. The three-component genetic construct of clause 1, wherein the pollen killing nucleotide sequence is a Barnase gene or an RNAi species for targeting a gene involved in pollen development.

Clause 3. The three-component genetic construct of clause 1, wherein the pollen killing nucleotide sequence comprises an RNAi species for targeting an ASPARTIC PROTEASE 65 gene, an RNAi species for targeting a SUCROSE TRANSPORTER1 gene, or a combination thereof.

Clause 4. The three-component genetic construct of clause 3, wherein the ASPARTIC PROTEASE 65 gene is a *Sorghum bicolor* ASPARTIC PROTEASE 65 (SbAP65) gene, or an ortholog thereof, and the SUCROSE TRANSPORTER1 gene is a *Sorghum bicolor* SUCROSE TRANSPORTER1 (SbSUT1) gene, or an ortholog thereof.

Clause 5. The three-component genetic construct of any one of clauses 1-4, wherein the pollen specific promoter is a promoter for a late-stage pollen-specific gene.

Clause 6. The three-component genetic construct of any one of clauses 1-5, wherein the pollen specific promoter is an *Oryza sativa* POLLEN LATE-STAGE PROMOTER2 (OsPLP2), an *Oryza sativa* BORON EFFLUX TRANSPORTER4 (OsBOR4) promoter, an *Oryza sativa* LATE POLLEN SPECIFIC PROMOTER1 (OsLPS1), an *Oryza sativa* Indica POLLEN ALLERGEN (OsIPA) promoter, or an orthologous sorghum promoter thereof.

Clause 7. The three-component genetic construct of any one of clauses 1-6, wherein the first promoter is a native promoter associated with the nuclear male sterile gene.

Clause 8. The three-component genetic construct of any one of clauses 1-6, wherein the first promoter is a non-native promoter that is not associated with the nuclear male sterile gene.

Clause 9. The three-component genetic construct of any one of clauses 1-6, wherein the nuclear male sterile gene is MS8 from *Sorghum bicolor* and the first promoter is the native MS8 promoter.

Clause 10. The three-component genetic construct of any one of clauses 1-9, wherein the seed specific selectable marker gene is a detectable marker.

Clause 11. The three-component genetic construct of clause 10, wherein the detectable marker comprises a red fluorescent protein (RFP), black seed coat color and/or purple leaf color caused by expressing a *Eutrema salsugineum* MYB41 (EsMYB41) transcription factor gene, or a combination thereof.

Clause 12. The three-component genetic construct of clause 11, wherein the detectable marker comprises red fluorescent protein (RFP).

Clause 13. The three-component genetic construct of any one of clauses 1-12, wherein the third promoter is a promoter active in seed.

Clause 14. The three-component genetic construct of clause 13, wherein the third promoter is a *Sorghum bicolor* ABA INSENSITIVE3 (SbABI3) promoter, an *Arabidopsis thaliana* OLEOSIN1 (AtOLE1) promoter, a *Sorghum bicolor* OLEOSIN1 (SbOLE1) promoter, or a *Hordeum vulgare* LIPID TRANSFER PROTEIN 2 (HvLTP2) promoter.

Clause 15. The three-component genetic construct of clause 14, wherein the third component further comprises a polynucleotide sequence encoding a AtOLE1 or SbOLE1 polypeptide sequence, wherein a fusion protein is generated when the third component is expressed.

Clause 16. The three-component genetic construct of clause 15, wherein the third component comprises AtOLE1 promoter:AtOLE1 coding sequence-RFP coding sequence (AtOLE1:AtOLE1-RFP) and SbOLE1 promoter:SbOLE1 coding sequence-RFP coding sequence (SbOLE1:SbOLE1-RFP).

Clause 17. The three-component genetic construct of clause 15 or 16, wherein the fusion protein is AtOLE1-RFP and SbOLE1-RFP.

Clause 18. The three-component genetic construct of any one of clauses 12-17, wherein the detectable marker further comprises black seed coat color and/or purple leaf color caused by expressing an EsMYB41 transcription factor gene.

Clause 19. The three-component genetic construct of clause 11, wherein the detectable marker is black seed coat color and/or purple leaf color caused by expressing an EsMYB41 transcription factor gene.

Clause 20. The three-component genetic construct of clause 18 or 19, wherein the third promoter is a constitutive promoter.

Clause 21. The three-component genetic construct of clause 20, wherein the constitutive promoter is cauliflower mosaic virus 35S promoter.

Clause 22. The three-component genetic construct of any one of clauses 1-21, wherein the three-component genetic construct is used to rescue male sterility in an ms8 mutant plant, ablate transgenic pollen, sort the transgenic and non-transgenic seeds, or a combination thereof.

Clause 23. The three-component genetic construct of clause 22, wherein the plant is sorghum, *Arabidopsis*, rice, maize, wheat, soybean, or rapeseed.

Clause 24. The three-component genetic construct of clause 22 or 23, wherein the plant is a sorghum variety selected from BTx623, BTx399, BOK11, RTx430, ARG1, M35, P898012, Sugardrip (sweet sorghum), and Greenleaf (forage sorghum).

Clause 25. A method of generating a bridge plant for use in a two-line nuclear male sterility breeding system, the method comprising: (a) introducing a transgene construct into an ms8:ms8 mutant plant thereby generating a transformed mutant plant, wherein the transgene construct comprises the three-component genetic construct of any one of clauses 1-24; (b) collecting seed from the transformed mutant plant; and (c) growing the collected seed thereby generating the bridge plant, wherein the bridge plant comprises the ms8:ms8 mutant background and one copy of the three-component genetic construct of any one of clauses 1-24.

Clause 26. The method of clause 25, wherein the bridge plant is a self-maintained plant.

Clause 27. The method of clause 25 or 26, wherein the bridge plant is sorghum, *Arabidopsis*, rice, maize, wheat, soybean, or rapeseed.

Clause 28. The method of any one of clauses 25-27, wherein the bridge plant is a sorghum variety selected from BTx623, BTx399, BOK11, RTx430, ARG1, M35, P898012, Sugardrip (sweet sorghum), and Greenleaf (forage sorghum).

Clause 29. A bridge plant generated by the method of any one of clauses 25-28, wherein the bridge plant is used to produce transgene-free male sterile plants.

Clause 30. The bridge plant of clause 29, wherein the bridge plant is sorghum, *Arabidopsis*, rice, maize, wheat, soybean, or rapeseed.

Clause 31. The bridge plant of clause 29 or 30, wherein the bridge plant is a sorghum variety selected from BTx623, BTx399, BOK11, RTx430, ARG1, M35, P898012, Sugardrip (sweet sorghum), and Greenleaf (forage sorghum).

Clause 32. A method for generating a male sterile plant and/or a maintained bridge plant, the method comprising: (a) growing seed collected from the bridge plant of any one of clauses 29-31, wherein the seed comprises maintained bridge plant seed and male sterile plant seed, wherein the maintained bridge plant seed is suspected as being homozygous for the ms8 mutation and hemizygous for the transgene construct, and wherein the male sterile plant seed is suspected as being homozygous for the ms8 mutation and does not comprise the transgene construct; (b) determining the presence or absence of the detectable marker in the seed; (c) identifying the maintained bridge plant seed based on the presence of the detectable marker in the seed and identifying the male sterile plant seed based on absence of the detectable marker in the seed; and (d) isolating and growing the male sterile plant seed thereby generating the male sterile plant and/or isolating and growing the maintained bridge plant seed thereby generating the maintained bridge plant.

Clause 33. The method of clause 32, wherein the detectable marker is black seed coat color and/or purple leaf color caused by expressing the EsMYB41 transcription factor gene, and wherein the maintained bridge plant is identified based on the presence of the detectable marker of black seed coat color and/or purple leaf color and the fertile plants are identified and separated from the male sterile plants based on the presence of the detectable marker in the leaf.

Clause 34. The method of clause 32 or 33, wherein the bridge plant is sorghum, *Arabidopsis*, rice, maize, wheat, soybean, or rapeseed.

Clause 35. The method of any one of clauses 32-34, wherein the bridge plant is a sorghum variety selected from BTx623, BTx399, BOK11, RTx430, ARG1, M35, P898012, Sugardrip (sweet sorghum), and Greenleaf (forage sorghum).

Clause 36. A male sterile plant generated by the method of any one of clauses 32-35.

Clause 37. A bridge plant generated by the method of any one of clause 32-35.

Clause 38. A two-line nuclear male sterility system for plant breeding, the system comprising: the male sterile plant of clause 36 and the bridge plant of any one of clauses 29-31 or 37.

Clause 39. A method of generating a hybrid seed, the method comprising: (a) planting seed of a male sterile plant of clause 36 adjacent to seed of a male fertile plant variety; (b) allowing the male fertile plant to cross-pollinate with the male sterile plant; and (c) harvesting and sorting F1 hybrid seed.

Clause 40. The method of clause 39, wherein the male sterile plant is generated from a bridge plant having a transgene and the method prevents the transgene flow via pollen dispersal in transgenic sorghum, rice, maize, wheat, soybean, or rapeseed.

Clause 41. An isolated polynucleotide sequence encoding a modified MALE STERILE 8 (MS8) polypeptide, the isolated polynucleotide sequence comprising a nucleotide sequence having at least 80% identity to SEQ ID NO: 5 and a nucleotide substitution at a position corresponding to position 442 or 448 of SEQ ID NO: 5, wherein the modified MS8 polypeptide is functionally abnormal in pollen production.

Clause 42. The isolated polynucleotide sequence of clause 41, wherein the nucleotide substitution generates a premature stop codon.

Clause 43. The isolated polynucleotide sequence of clause 41 or 42, wherein the isolated polynucleotide sequence comprises a C-T mutation at the position corresponding to position 442 or 448 of SEQ ID NO: 5.

Clause 44. The isolated polynucleotide sequence of any one of clauses 41-43, wherein the isolated polynucleotide sequence comprises a nucleotide sequence of SEQ ID NO: 6, SEQ ID NO: 7, or a variant thereof.

Clause 45. The isolated polynucleotide sequence of any one of clauses 41-44, wherein the modified MS8 polypeptide has a premature stop codon at a position corresponding to position 148 or 150 of SEQ ID NO: 1.

Clause 46. The isolated polynucleotide sequence of any one of clauses 41-45, wherein the modified MS8 polypeptide comprises an amino acid sequence corresponding to positions 1-149 of SEQ ID NO: 9, positions 1-147 of SEQ ID NO: 10, or a variant thereof.

Clause 47. A vector comprising the isolated polynucleotide sequence of any one of clauses 41-46.

Clause 48. The vector of clause 47, wherein the isolated polynucleotide is operably linked to a promoter.

Clause 49. The vector of clause 48, wherein the promoter is the native MS8 promoter.

Clause 50. A sorghum plant comprising a recessive nuclear male sterile gene, wherein the sorghum plant is male sterile and the recessive nuclear male sterile gene is a modified basic HELIX-LOOP-HELIX (bHLH) transcription factor gene encoding an inactivated bHLH transcription factor, wherein the inactivated bHLH transcription factor causes early degeneration of tapetal cells in the anther of the sorghum plant.

Clause 51. The sorghum plant of clause 50, wherein the nuclear male sterile gene is a mutant MS8 gene or a mutant TDR gene.

Clause 52. The sorghum plant of clause 50 or 51, wherein the recessive nuclear male sterile gene comprising an isolated nucleotide sequence having at least 80% identity to SEQ ID NO: 5 and a nucleotide substitution at a position corresponding to position 442 or 448 of SEQ ID NO: 5.

Clause 53. The sorghum plant of clause 52, wherein the nucleotide substitution generates a premature stop codon.

Clause 54. The sorghum plant of clause 52 or 53, wherein the isolated polynucleotide sequence comprises a C-T mutation at the position corresponding to position 442 or 448 of SEQ ID NO: 5.

Clause 55. The sorghum plant of any one of clauses 50-54, wherein the isolated polynucleotide sequence comprises a nucleotide sequence of SEQ ID NO: 6, SEQ ID NO: 7, or a variant thereof.

Clause 56. The sorghum plant of any one of clauses 52-55, wherein the modified MS8 polypeptide has a premature stop codon at a position corresponding to position 148 or 150 of SEQ ID NO: 1.

Clause 57. The sorghum plant of any one of clauses 52-56, wherein the modified MS8 polypeptide comprises an amino acid sequence corresponding to positions 1-149 of SEQ ID NO: 9, positions 1-147 of SEQ ID NO: 10, or a variant thereof.

Clause 58. The sorghum plant of any one of clauses 50-57, wherein the sorghum plant is an ms8 mutant plant.

Clause 59. The sorghum plant of any one of clauses 52-58, wherein the sorghum plant is a *Sorghum bicolor*.

Clause 60. A *Sorghum bicolor* seed designated as MS8, wherein a sample of said seed has been deposited as ATCC Patent Deposit No. PTA-127606.

Clause 61. A plant, or a part thereof, produced by growing the seed of clause 60.

Clause 62. A pollen from the plant of clause 60.

Clause 63. An ovule from the plant of clause 60.

Clause 64. A *Sorghum bicolor* plant having all the physiological and morphological characteristics of the plant of clause 60.

Clause 65. A tissue culture of regenerable cells from the plant, or the part thereof, of clause 60.

Clause 66. The tissue culture of regenerable cells of clause 65, wherein the regenerable cells are selected from the group consisting of protoplasts and calli, and wherein the regenerable cells are from a leaf, pollen, ovule, cotyledon, hypocotyl, embryo, root, pod, flower, shoot or stalk.

Clause 67. A protoplast produced from the tissue culture of clause 65 or 66.

Clause 68. A *Sorghum bicolor* plant regenerated from the tissue culture of clause 65 or 66, wherein the plant has all of the physiological and morphological characteristics of a plant produced by growing a seed designated MS8 and deposited under ATCC Patent Deposit No. PTA-127606.

Clause 69. A tissue culture of regenerable cells from the plant, or the part thereof, of clause 68.

Clause 70. The tissue culture of clause 69, wherein said regenerable cells are selected from the group consisting of protoplasts and calli, and wherein the regenerable cells are from a leaf, pollen, ovule, cotyledon, hypocotyl, embryo, root, pod, flower, shoot or stalk.

Clause 71. A protoplast produced from the tissue culture of clause 70.

Clause 72. A *Sorghum bicolor* plant regenerated from the tissue culture of clause 70 or 71, wherein the plant has all of the physiological and morphological characteristics of a plant produced by growing a seed designated MS8 and deposited under ATCC Accession No. PTA-127606.

Clause 73. A method for producing a *Sorghum bicolor* mutant MS8-derived *Sorghum bicolor* L. Moench plant, comprising: (a) crossing MS8 plants grown from MS8 seed, representative seed of which has been deposited under ATCC Patent Deposit No. PTA-127606, with a second *Sorghum bicolor* plant to yield progeny *Sorghum bicolor* seed; and (b) growing the progeny seed to yield an *Sorghum bicolor* mutant MS8-derived *Sorghum bicolor* plant.

Clause 74. The method of clause 73, further comprising: (c) crossing the *Sorghum bicolor* mutant MS8-derived *Sorghum bicolor* plant of (b) with itself or a third *Sorghum bicolor* plant to yield a second *Sorghum bicolor* MS8-derived *Sorghum bicolor* progeny seed; and (d) growing the second *Sorghum bicolor* progeny seed of (c) to yield a second *Sorghum bicolor* mutant MS8-derived *Sorghum bicolor* plant.

Clause 75. The method of clause 73, wherein (c) and (d) are repeated at least one time to generate an additional *Sorghum bicolor* mutant MS8-derived *Sorghum bicolor* plant.

Clause 76. A method of introducing a desired trait into *Sorghum bicolor* MS8 comprising: (a) crossing MS8 plants grown from MS8 seed, representative seed of which has been deposited under ATCC Patent Deposit No. PTA-127606, with plants of a second *Sorghum bicolor* mutant that comprise a desired trait to produce F1 progeny plants, wherein the desired trait is selected from the group consisting of male sterility, site-specific recombination, increased transformability, abiotic stress tolerance, herbicide resistance, insect resistance, disease resistance, altered phosphorus, altered antioxidants, altered fatty acids, altered essential amino acids and altered carbohydrates; (b) selecting F1 progeny plants that have the desired trait to produce selected F1 progeny plants; (c) crossing the selected progeny plants with the MS8 plants to produce backcross progeny plants; (d) selecting for backcross progeny plants that have the desired trait and physiological and morphological characteristics of *Sorghum bicolor* mutant MS8 to produce selected backcross progeny plants; and (e) repeating steps (c) and (d) three or more times in succession to produce selected fourth or higher backcross progeny plants that comprise the desired trait and all the physiological and morphological characteristics of *Sorghum bicolor* mutant MS8.

Clause 77. A plant produced by the method of clause 76, wherein the plant has the desired trait and all of the physiological and all morphological characteristics of said *Sorghum bicolor* mutant MS8.

Clause 78. A method for producing a *Sorghum bicolor* mutant plant having an altered agronomic trait comprising introducing a polynucleotide into a MS8 plant grown from MS8 seed, representative seed of which has been deposited under ATCC Patent Deposit No. PTA-127606, wherein the polynucleotide confers an altered agronomic trait to the plant selected from the group consisting of insect resistance, disease resistance, herbicide resistance, abiotic stress resistance, fatty acid metabolism, starch metabolism, carbohydrate metabolism, amino acid metabolism, phosphorus metabolism, antioxidant metabolism, male sterility, site specific DNA integration, plant growth, forage yield and flowering, and wherein the polynucleotide is expressed in the plant.

Clause 79. A *Sorghum bicolor* mutant plant produced by the method of clause 78, wherein the plant has the altered agronomic trait and all of the physiological and all morphological characteristics of said *Sorghum bicolor* mutant MS8.

APPENDIX

MS8/*Sorghum bicolor* transcription factor EAT1 (SbEAT1) (SEQ ID NO: 1)
MIAGGGYFDGSHDHILMEGSMIHDSSQSSIYDNTDVEQQNFRLAPFIIEDHSNPANLTSEPARVIDQIHH

QLGIDMEQDHSDHMIQGVPPAETANLVPVVYGVQDRILSHQIEGPHNITVEQQVLDYDPASYGNGTYAAA

HDLLNSLQIQRCSLIPEFPSTEHIFGDPAQNMVNPLDITNDLQGVATHESGMMFSDSTLPLGYHATQSHM

LKDLYHSLPQNYGIFTSDDERDGMVGVAGVSGNIFQEIDGRQFDSPVLGTRRQKGGFGKGKGKANFATER

ERREQLNVKYGALRSLFPNPTKNDRASIVGDAIDYINELNRTVKELKILLEKKRNSTDRRKILKLDDEAA

DDGESSSMQPVSDDQNNQMNGAIRSSWVQRRSKECDVDVRIVDDEINIKFTEKKRANSLLCAAKVLEEFR

LELIHVVGGIIGDHHIFMFNTKIPKGSSVYACAVAKKLLEAVEIKKQALNIFN*

OsEAT1 (SEQ ID NO: 2)
MIVGAGYFEDSHDQSLMAGSLIHDSNQAPASSENTSIDLQKFKVHPYSTEALSNTANLAEAARAINHLQH

QLEIDLEQEVPPVETANWDPAICTIPDHIINHQFSEDPQNILVEQQIQQYDSALYPNGVYTPAPDLLNLM

QCTMAPAFPATTSVFGDTTLNGTNYLDLNGELTGVAAVPDSGSGLMFASDSALQLGYHGTQSHLIKDICH

SLPQNYGLFPSEDERDVIIGVGSGDLFQEIDDRQFDSVLECRRGKGEFGKGKGKANFATERERREQLNVK

FRTLRMLFPNPTKNDRASIVGDAIEYIDELNRTVKELKILVEQKRHGNNRRKVLKLDQEAAADGESSSMR

PVRDDQDNQLHGAIRSSWVQRRSKECHVDVRIVDDEVNIKLTEKKKANSLLHAAKVLDEFQLELIHVVGG

IIGDHHIFMFNTKVSEGSAVYACAVAKKLLQAVDVQHQALDIFN*

SbTDR (SEQ ID NO: 3)
MGGGGHSCVAAAGDGAGASMEAALRTLVGVDAWDYCIYWRLSPDQRFLEMTGFCCSSEFEAQLSALGDLP

PSIQLDSSSAGMHAEAMVSNQPIWQSSRVSELQTSYSSEPIGSGGGPRTRLLVPVAGGLVELFAARYMAE

EEQMAELVMAQCGVPGGAEAGEGGGGVHAWQPGFAWDGAADASRGMMYGGAAVPPSLGLFDAAGSVAADP

FQAVVVQQAPGAGGGGGVDDAGWQYAAAAAAAGSELAAVQQEPQPPQPQPRGADSGSEGSDMQVDPEDDG

DGDGDVDAQGRGGGGGGGKGGGKRQQCKNLVAERRRRKKLNDRLYKLRSLVPNISKMDRASILGDAIDYI

VGLQNQVKALQDELEDPADGGAPDVLLDHPPPASLVGLENDDSPRTSHHLPLAGSKRSRAAVQAAEEEKG

HDMEPQVEVRQVEANEFFLQMLCERKPGRFVQIMDSIAALGLEVTNVNVTSHESLVLNVFRAARRDSEVA

VQADRVRDSLLEVTREPYGVWSSAAPPVGVGMSGGGIVDVKLDGVDVKLDGIIDGQAAPGVAVAVGEDQY

GGYNHLLQYLA*

OsTDR (SEQ ID NO: 4)
MGRGDHLLMKNSNAAAAAAAVNGGGTSLDAALRPLVGSDGWDYCIYWRLSPDQRFLEMTGFCCSSELEAQ

VSALLDLPSSIPLDSSSIGMHAQALLSNQPIWQSSSEEEEADGGGGAKTRLLVPVAGGLVELFASRYMAE

EQQMAELVMAQCGGGGAGDDGGGQAWPPPETPSFQWDGGADAQRLMYGGSSLNLFDAAAADDDPFLGGGG

GDAVGDEAAAAGAWPYAGMAVSEPSVAVAQEQMQHAAGGGVAESGSEGRKLHGGDPEDDGDGEGRSGGAK

RQQCKNLEAERKRRKKLNGHLYKLRSLVPNITKMDRASILGDAIDYIVGLQKQVKELQDELEDNHVHHKP

PDVLIDHPPPASLVGLNDDASPPNSHQQQPPLAVSGSSSRRSNKDPAMTDDKVGGGGGGGHRMEPQLEV

RQVQGNELFVQVLWEHKPGGFVRLMDAMNALGLEVINVNVTTYKTLVLNVFRVMVRDSEVAVQADRVRDS

LLEVTRETYPGVWPSPQEEDDAKFDGGDGGQAAAAAAAAGGEHYHDEVGGGYHQHLHYLAFD*

APPENDIX -continued

Sb04G030850 cDNA:KNOWN_protein_coding region (SEQ ID NO: 5)
ATGATTGCTGGGGAGGCTATTTTGATGGTTCTCATGATCATATTCTCATGGAAGGATCGATGATCCATG

ATTCTTCCCAATCTTCCATCTATGACAATACAGATGTTGAACAGCAGAACTTCAGACTTGCGCCCTTTAT

CATAGAAGATCACTCCAATCCAGCCAACCTTACCTCTGAGCCTGCAAGGGTGATCGACCAAATTCATCAC

CAGCTTGGGATTGACATGGAGCAGGACCATAGTGATCACATGATCCAAGGAGTTCCTCCAGCAGAAACTG

CAAATTTAGTTCCTGTTGTCTATGGTGTCCAAGATCGTATCCTCAGCCACCAGATAGAAGGTCCACATAA

CATAACTGTGGAACAACAGGTCCTGGACTACGACCCTGCATCATATGGAAATGGCACTTATGCAGCTGCA

CATGATCTTCTAAATTCTCTACAGATCCAAAGGTGCAGTTTGATTCCTGAATTTCCTTCGACAGAACATA

TCTTTGGTGATCCAGCACAGAACATGGTCAATCCTTTGGACATTACCAATGACCTTCAAGGAGTAGCAAC

TCATGAAAGTGGAATGATGTTCAGCGATTCAACTCTACCATTAGGTTATCATGCTACTCAATCTCATATG

TTGAAGGATCTCTATCATTCACTACCACAAAACTATGGGATATTTACCAGTGATGATGAGAGAGATGGGA

TGGTCGGGGTAGCAGGGGTCTCAGGAAATATTTTCCAGGAGATAGATGGGAGACAGTTCGACAGCCCAGT

ACTGGGGACTAGAAGACAGAAAGGTGGATTTGGCAAGGGCAAGGGAAAAGCTAACTTTGCAACTGAAAGA

GAGAGGAGGGAGCAGCTAAATGTGAAGTATGGGGCTTTAAGATCACTGTTCCCAAACCCTACTAAGAATG

ACAGGGCCTCTATAGTTGGAGATGCCATTGACTACATCAATGAGCTTAATAGAACAGTGAAAGAACTGAA

GATCTTACTGGAAAAGAAGAGGAACAGCACTGACAGGAGGAAGATACTGAAGTTGGATGATGAAGCAGCT

GATGATGGGGAAAGCTCTTCAATGCAGCCAGTAAGTGATGACCAAAACAATCAGATGAATGGGGCTATAA

GGAGCTCCTGGGTTCAAAGAAGGTCCAAGGAGTGCGATGTTGATGTCCGCATAGTTGATGATGAAATAAA

TATCAAGTTCACAGAGAAGAAGAGAGCCAACTCTTTGCTTTGTGCTGCAAAGGTTCTAGAGGAGTTTCGT

CTTGAGCTCATCCATGTTGTTGGGGGAATCATAGGAGATCACCATATATTCATGTTCAATACAAAGATAC

CTAAGGGCTCTTCGGTGTACGCGTGCGCGGTGGCTAAGAAGCTCCTTGAAGCTGTGGAGATAAAGAAGCA

GGCTCTTAATATCTTCAACTAG

Sb04G030850 cDNA:KNOWN_protein_coding mutant (ms8-1) (SEQ ID NO: 6)
ATGATTGCTGGGGAGGCTATTTTGATGGTTCTCATGATCATATTCTCATGGAAGGATCGATGATCCATG

ATTCTTCCCAATCTTCCATCTATGACAATACAGATGTTGAACAGCAGAACTTCAGACTTGCGCCCTTTAT

CATAGAAGATCACTCCAATCCAGCCAACCTTACCTCTGAGCCTGCAAGGGTGATCGACCAAATTCATCAC

CAGCTTGGGATTGACATGGAGCAGGACCATAGTGATCACATGATCCAAGGAGTTCCTCCAGCAGAAACTG

CAAATTTAGTTCCTGTTGTCTATGGTGTCCAAGATCGTATCCTCAGCCACCAGATAGAAGGTCCACATAA

CATAACTGTGGAACAACAGGTCCTGGACTACGACCCTGCATCATATGGAAATGGCACTTATGCAGCTGCA

CATGATCTTCTAAATTCTCTACAGATCTAAAGGTGCAGTTTGATTCCTGAATTTCCTTCGACAGAACATA

TCTTTGGTGATCCAGCACAGAACATGGTCAATCCTTTGGACATTACCAATGACCTTCAAGGAGTAGCAAC

TCATGAAAGTGGAATGATGTTCAGCGATTCAACTCTACCATTAGGTTATCATGCTACTCAATCTCATATG

TTGAAGGATCTCTATCATTCACTACCACAAAACTATGGGATATTTACCAGTGATGATGAGAGAGATGGGA

TGGTCGGGGTAGCAGGGGTCTCAGGAAATATTTTCCAGGAGATAGATGGGAGACAGTTCGACAGCCCAGT

ACTGGGGACTAGAAGACAGAAAGGTGGATTTGGCAAGGGCAAGGGAAAAGCTAACTTTGCAACTGAAAGA

GAGAGGAGGGAGCAGCTAAATGTGAAGTATGGGGCTTTAAGATCACTGTTCCCAAACCCTACTAAGAATG

ACAGGGCCTCTATAGTTGGAGATGCCATTGACTACATCAATGAGCTTAATAGAACAGTGAAAGAACTGAA

GATCTTACTGGAAAAGAAGAGGAACAGCACTGACAGGAGGAAGATACTGAAGTTGGATGATGAAGCAGCT

GATGATGGGGAAAGCTCTTCAATGCAGCCAGTAAGTGATGACCAAAACAATCAGATGAATGGGGCTATAA

GGAGCTCCTGGGTTCAAAGAAGGTCCAAGGAGTGCGATGTTGATGTCCGCATAGTTGATGATGAAATAAA

TATCAAGTTCACAGAGAAGAAGAGAGCCAACTCTTTGCTTTGTGCTGCAAAGGTTCTAGAGGAGTTTCGT

APPENDIX -continued

CTTGAGCTCATCCATGTTGTTGGGGGAATCATAGGAGATCACCATATATTCATGTTCAATACAAAGATAC

CTAAGGGCTCTTCGGTGTACGCGTGCGCGGTGGCTAAGAAGCTCCTTGAAGCTGTGGAGATAAAGAAGCA

GGCTCTTAATATCTTCAACTAG

Sb04G030850 cDNA:KNOWN_protein_coding mutant (ms8-2) (SEQ ID NO: 7)
ATGATTGCTGGGGGAGGCTATTTTGATGGTTCTCATGATCATATTCTCATGGAAGGATCGATGATCCATG

ATTCTTCCCAATCTTCCATCTATGACAATACAGATGTTGAACAGCAGAACTTCAGACTTGCGCCCTTTAT

CATAGAAGATCACTCCAATCCAGCCAACCTTACCTCTGAGCCTGCAAGGGTGATCGACCAAATTCATCAC

CAGCTTGGGATTGACATGGAGCAGGACCATAGTGATCACATGATCCAAGGAGTTCCTCCAGCAGAAACTG

CAAATTTAGTTCCTGTTGTCTATGGTGTCCAAGATCGTATCCTCAGCCACCAGATAGAAGGTCCACATAA

CATAACTGTGGAACAACAGGTCCTGGACTACGACCCTGCATCATATGGAAATGGCACTTATGCAGCTGCA

CATGATCTTCTAAATTCTCTATAGATCCAAAGGTGCAGTTTGATTCCTGAATTTCCTTCGACAGAACATA

TCTTTGGTGATCCAGCACAGAACATGGTCAATCCTTTGGACATTACCAATGACCTTCAAGGAGTAGCAAC

TCATGAAAGTGGAATGATGTTCAGCGATTCAACTCTACCATTAGGTTATCATGCTACTCAATCTCATATG

TTGAAGGATCTCTATCATTCACTACCACAAAACTATGGGATATTTACCAGTGATGATGAGAGAGATGGGA

TGGTCGGGGTAGCAGGGGTCTCAGGAAATATTTTCCAGGAGATAGATGGGAGACAGTTCGACAGCCCAGT

ACTGGGGACTAGAAGACAGAAAGGTGGATTTGGCAAGGGCAAGGGAAAAGCTAACTTTGCAACTGAAAGA

GAGAGGAGGGAGCAGCTAAATGTGAAGTATGGGGCTTTAAGATCACTGTTCCCAAACCCTACTAAGAATG

ACAGGGCCTCTATAGTTGGAGATGCCATTGACTACATCAATGAGCTTAATAGAACAGTGAAAGAACTGAA

GATCTTACTGGAAAAGAAGAGGAACAGCACTGACAGGAGGAAGATACTGAAGTTGGATGATGAAGCAGCT

GATGATGGGAAAGCTCTTCAATGCAGCCAGTAAGTGATGACCAAAACAATCAGATGAATGGGGCTATAA

GGAGCTCCTGGGTTCAAAGAAGGTCCAAGGAGTGCGATGTTGATGTCCGCATAGTTGATGATGAAATAAA

TATCAAGTTCACAGAGAAGAAGAGAGCCAACTCTTTGCTTTGTGCTGCAAAGGTTCTAGAGGAGTTTCGT

CTTGAGCTCATCCATGTTGTTGGGGGAATCATAGGAGATCACCATATATTCATGTTCAATACAAAGATAC

CTAAGGGCTCTTCGGTGTACGCGTGCGCGGTGGCTAAGAAGCTCCTTGAAGCTGTGGAGATAAAGAAGCA

GGCTCTTAATATCTTCAACTAG

Sb04G030850 peptide: Sb04g030850.1
pep:KNOWN_protein_coding (SEQ ID NO: 8)
MIAGGGYFDGSHDHILMEGSMIHDSSQSSIYDNTDVEQQNFRLAPFIIEDHSNPANLTSEPARVIDQIHH

QLGIDMEQDHSDHMIQGVPPAETANLVPVVYGVQDRILSHQIEGPHNITVEQQVLDYDPASYGNGTYAAA

HDLLNSLQIQRCSLIPEFPSTEHIFGDPAQNMVNPLDITNDLQGVATHESGMMFSDSTLPLGYHATQSHM

LKDLYHSLPQNYGIFTSDDERDGMVGVAGVSGNIFQEIDGRQFDSPVLGTRRQKGGFGKGKGKANFATER

ERREQLNVKYGALRSLFPNPTKNDRASIVGDAIDYINELNRTVKELKILLEKKRNSTDRRKILKLDDEAA

DDGESSSMQPVSDDQNNQMNGAIRSSWVQRRSKECDVDVRIVDDEINIKFTEKKRANSLLCAAKVLEEFR

LELIHVVGGIIGDHHIFMFNTKIPKGSSVYACAVAKKLLEAVEIKKQALNIFN

Sb04G030850 peptide: Sb04g030850.1 pep:KNOWN_protein_coding-mutant
(ms8-1)(*indicates stop codon)(SEQ ID NO: 9)
MIAGGGYFDGSHDHILMEGSMIHDSSQSSIYDNTDVEQQNFRLAPFIIEDHSNPANLTSEPARVIDQIHH

QLGIDMEQDHSDHMIQGVPPAETANLVPVVYGVQDRILSHQIEGPHNITVEQQVLDYDPASYGNGTYAAA

HDLLNSLQI*RCSLIPEFPSTEHIFGDPAQNMVNPLDITNDLQGVATHESGMMFSDSTLPLGYHATQSHM

LKDLYHSLPQNYGIFTSDDERDGMVGVAGVSGNIFQEIDGRQFDSPVLGTRRQKGGFGKGKGKANFATER

ERREQLNVKYGALRSLFPNPTKNDRASIVGDAIDYINELNRTVKELKILLEKKRNSTDRRKILKLDDEAA

APPENDIX -continued

DDGESSSMQPVSDDQNNQMNGAIRSSWVQRRSKECDVDVRIVDDEINIKFTEKKRANSLLCAAKVLEEFR

LELIHVVGGIIGDHHIFMFNTKIPKGSSVYACAVAKKLLEAVEIKKQALNIFN

Sb04G030850 peptide: Sb04g030850.1 pep:KNOWN_protein_coding-mutant
(ms8-2)(*indicates stop codon)(SEQ ID NO: 10)
MIAGGGYFDGSHDHILMEGSMIHDSSQSSIYDNTDVEQQNFRLAPFIIEDHSNPANLTSEPARVIDQIHH

QLGIDMEQDHSDHMIQGVPPAETANLVPVVYGVQDRILSHQIEGPHNITVEQQVLDYDPASYGNGTYAAA

HDLLNSL*IQRCSLIPEFPSTEHIFGDPAQNMVNPLDITNDLQGVATHESGMMFSDSTLPLGYHATQSHM

LKDLYHSLPQNYGIFTSDDERDGMVGVAGVSGNIFQEIDGRQFDSPVLGTRRQKGGFGKGKGKANFATER

ERREQLNVKYGALRSLFPNPTKNDRASIVGDAIDYINELNRTVKELKILLEKKRNSTDRRKILKLDDEAA

DDGESSSMQPVSDDQNNQMNGAIRSSWVQRRSKECDVDVRIVDDEINIKFTEKKRANSLLCAAKVLEEFR

LELIHVVGGIIGDHHIFMFNTKIPKGSSVYACAVAKKLLEAVEIKKQALNIFN

1. The MS8 gene (Sb04g03085 from Sorghum bicolor)(SEQ ID NO: 11)—
The genomic sequence of MS8 gene Legend (showing example sequences):
*CTACCTCC* The promoter region is italicized.
ATGATTGC Exons are bolded.
<u>GTTTGTAT</u> Introns are underlined.
<u>*CCATACCC*</u> 3'region is italicized and underlined.

*CTACCTCCCGTTGGAATCACCTCCCCAATTCGAAGTTTAATACTAAAACTTTCGAATTTCACTGTTTTTC*

*AACTTCCAGCTCAATTTGCCTCCTATTGCTAATTGAATTTGCCACTGTAATACAGCTCTGCAAAACGATC*

*AGAATGCTAGTTTAGTAAACCAATTGTAGTTACGTATTCATTGCCAAGCATTTACAGCTCCAGAAAAACA*

*TATGAACCCCATACCACATGGTTAGAACAGGCTGTCATGAATGCTGCCATGAACAAATTCAAGGATGGCC*

*ATAAGATCCATCACCAAAGTCACAAAGCTAAGCGCAGACGAGCCTTGGCAGTTGAGCTCCATCACTCTGT*

*TGTTTTCTCATAGGTGTTCCCTCCCTCTTGAAGATGGATTTGAGATGGGCTGCAGGGTGTTTCTCTTGAC*

*CCTTCTGTTGGATGAGGTGTTCATTTGCAGTCAAAATTGAAAAAGGACACGGTATGTTCCTGAAACATAT*

*ATTCAGAGAGTCCTCGTTTAGACAGTCTCTGCCTAGCACATATATTGTATGGGAAATAATAAGAACTCCA*

*GAAATGTCAACCGCATAACTACTGTATACTGGATCGAAGTTTACAAAGTACAAAGAAATGCAAGCATGAC*

ATGATTATTAGGTTCTATGCAGTGATGCAAGGTTATGACTCCCTTTGCAACTGTCCAGTGTTTCAGGTAG

*TTGGACTTGTCCTTTTAGTTTCTGAAAGCACACTACAGCATAATGTCCGTAAAATACGGAGGAACGGAGA*

*AGGCATGACTTGCATTTCCCAACTTCCTATGGCATGAATAACAGCAAAGATGCCAAGTTCAAAGAGTGTG*

*AGTTTTCCATCTTTCTCATGGCCATTCTTAATGATGATGATGATCTGAAATCTGATAGCCCTTCACTTTG*

*ACCTCTTCTAAGAATGTTCAAGAGAAACTTTTAGGAAATGATTGGTGTTGATATAAACATATTCTGTTAT*

*CTGTTCATCAATTTTACGTGGCAACCAAATTTCCGTACTACTGCGGTACTGGCCACATGCCAATTACATT*

*TTGCCTTTTACCATGACGTTGTATATATATTACTAGCAGCACACTCAAACTACTTCACAAGGATGGTTTT*

*CAGCAACTAGTTTCTGAACAGCGTGTTTGCTATCTGGTCTGTCAAAATAATCTTGGTACTGTTCTCTTCT*

*CTTTACTTTCAGTTTTTCGTACTATTGGCAGGATGCAAATGCTAGATTGAATCTGCCGACTTTGTTTATA*

*CCAACCTGAAGAAACAATATGTATCTAAAGAATGAAGTTTTGCTTATGTCTTTGAGATTTAAACATACCC*

*TTTTCAACTATTGGACTTGTAGTGCATTGTTTAGAAGATTTCAAGAAGGTAAAGGGCACTTTGGTCATTG*

*TCAATACTTATACTAGTCTGTGTTCTGCTGATTAATTGTTGAGCTTGGTAGTTGAAGCACAAACTAGCAA*

*GATTAATATTTTAGGTGTAGGGCGCAAATAAAGACGCAAGGCAGTTTGTTGGGTCCTAAGGAAGCAAAA*

*AGGCTTCCTGTCTCATCCATGTGCTAATAAAACTCCACACGGAAAAGATAGAGAGAAACAGATTGCCTAG*

*CTTAAACCTTGAGTATTCTCTTCCTCCTCTCAAACAATCAAACCAACTAAGCCAGCTGCAATCTTCTCTG*

*CTTAATCAACTCCATCGTTGTTTCATACAGGTCGAGACATCTTTTCCCTCAATTCATGGGCACCAGCTAA*

APPENDIX -continued

```
TATTTTTTGTCTATTTCAGATCCTCTAGCATGCTACTTCTATGTTTCTTAATCAGTTTTGTCTCCTGCCT

TTGCTTCTTCCTAAGTGTTTTGCTAAATAGATACTTATATGGTGCATATAGTTCCTAAATGCTGTATTTT

TTTATCTTGAGTGAAGGTAACCAGGGCCAAAATGATTGCTGGGGGAGGCTATTTTGATGGTTCTCATGAT

CATATTCTCATGGAAGGATCGATGATCCATGATTCTTCCCAATCTTCCATCTATGACAATACAGATGTTG

AACAGCAGAACTTCAGACTTGCGCCCTTTATCATAGAAGATCACTCCAATCCAGCCAACCTTACCTCTGA

GCCTGCAAGGGTGATCGACCAAATTCATCACCAGCTTGGGATTGACATGGAGCAGGACCATAGTGATCAC

ATGATCCAAGGAGTTCCTCCAGCAGAAACTGCAAATTTAGTTCCTGTTGTCTATGGTGTCCAAGATCGTA

TCCTCAGCCACCAGATAGAAGGTCCACATAACATAACTGTGGAACAACAGGTCCTGGACTACGACCCTGC

ATCATATGGAAATGGCACTTATGCAGCTGCACATGATCTTCTAAATTCTCTACAGATCCAAAGGTGCAGT
                                                     ms8-2 mut. T      T ms8-1 mut.
TTGATTCCTGAATTTCCTTCGACAGAACATATCTTTGGTGATCCAGCACAGAACATGGTTCAATCCTTTG

GACATTACCAATGACCTTCAAGGAGTAGCAACTCATGAAAGTGGAATGATGTTCAGCGATTCAACTCTAC

CATTAGGTTATCATGCTACTCAATCTCATATGTTGAAGGATCTCTATCATTCACTACCACAAAACTATGG

GATATTTACCAGTGATGATGAGAGAGATGGGATGGTCGGGGTAGCAGGGGTCTCAGGAAATATTTTCCAG

GAGATAGATGGGAGACAGTTCGACAGCCCAGTACTGGGGACTAGAAGACAGAAAGGTGGATTTGGCAAGG

GCAAGGGAAAAGCTAACTTTGCAACTGAAAGAGAGAGGAGGGAGCAGCTAAATGTGAAGTATGGGGCTTT

AAGATCACTGTTCCCAAACCCTACTAAGGTTTGTATAACTTATCTCTCCAAGCACAAATTCCTTAATTGC

TTCTCTCATTACAGAACTCATTTTCCACAGTTGCATGGATTTGTAGAACATTTAGTAAGTTCTATTCGTA

CAGGATGTATTGGAACATGTATTCAGATTGTTTTCCCTAGGAAAAATAAAATTTAAAACAAATGTGTGTA

TGATAAAAAAAACTTTATTAAAGATGGATTTGTCATTAGCAAACTCTTATAAAGTGCTATCAGTTCAAGT

ATGTGGAGGAATGCGATCATGGAATTTTTGCATGTATCAGTGGACAGATGCACGTAAATTGATCTTTAGT

ATCAGCATCCAACAAAATAGAATGAAATTATAAAATATGCGGGATAAGAGAATTTCCATTCCAGAAACTC

TAGTTATGCCCAGCACAATGCAATATTGTTTTCTTTCCTAAATCTACATTTATTGTACTCTTAGTGAAT

AAGAGGCTATGAATTCTGAATTGCTGTAAAACTATTCTCCAGAATGACAGGGCCTCTATAGTTGGAGATG

CCATTGACTACATCAATGAGCTTAATAGAACAGTGAAAGAACTGAAGATCTTACTGGAAAAGAAGAGGAA

CAGCACTGACAGGAGGAAGATACTGAAGTTGGATGATGAAGCAGCTGATGATGGGGAAAGCTCTTCAATG

CAGCCAGTAAGTGATGACCAAAACAATCAGATGAATGGGGCTATAAGGAGCTCCTGGGTTCAAAGAAGGT

CCAAGGAGTGCGATGTTGATGTCCGCATAGTTGATGATGAAATAAATATCAAGTTCACAGAGAAGAAGAG

AGCCAACTCTTTGCTTTGTGCTGCAAAGGTTCTAGAGGAGTTTCGTCTTGAGCTCATCCATGTTGTTGGG

GGAATCATAGGAGATCACCATATATTCATGTTCAATACAAAGGTAACAAACAAATTTTCTTAAACGAAAG

TAGGTTCTTGATCCTTTTCCCTGTGTCTGTAGCACAGACATTAGTTATAATACTTCATATCTTGATACTG

CAGATACCTAAGGGCTCTTCGGTGTACGCGTGCGCGGTGGCTAAGAAGCTCCTTGAAGCTGTGGAGATAA

AGAAGCAGGCTCTTAATATCTTCAACTAGCCATACCCATCATAATGTTTATTCAGACAACTTAGCATGCT

GGTCTGCTCTTTAGCATCTAATAAGGTGCTTACTTATCAGCGAATGACCACATTGACAAAACTTCTTTGA

TGACTGCTGCAAACTTTCTTGATAGCTTGTTCATGCTGAACTTCTTGTCTTCTTTTCTGTACACTTTAAC

AGTCATGTTGGAATATGTGGTGCTTCTGATTTCCCGGCATTGTCACTCAATACTTTATTATGTTTAATTC

CTTTTCTGAACTTATATGGCAGATCGACTCCACTACCCAACTTACATATCTCAGGCTCAGGTCTAGTGAA

TGTGTTTGTGTTCGGAGGAAATGCTACATCACGATTCCATAAAAATAAAAAGCTAGTATATATCTAACAA

TATGATCCATGTTAAATTTGTCTTGGAGTTATGACACATAATTGTGGTAGAAATTGTTACTGCGTGATGG

CTGGGATGAGATCCTTACCGCTATGCACAGGACAGTCGGGGTGGGTTTCTCCTACAGTCACAGAGTCCAT
```

APPENDIX -continued

*CACGCTACGATGTCTGGAGATCTAAACTAAGTACCTGAACTCCTGGGGGATCAATCAATAGTAAGCAAA*

*ACTACAAAAGGATACAAGGATTGGAATCAATTTGGCCAGCCGCACCCGTAGTCAAGATCTCCGTGTTTGC*

*CGAGGCTGACGAACTGGAGCAGGTCTACCGCAGGTGCAGTAGCTGATCCGAACATAAATAATCATTCCAC*

*TCCGCTCTTGTACCTGATCTCGCAGATCTCCAGTGCAGTGTGCAGCTGCAGTTTGCTGCCCTAGTCATCT*

*GGCATGCTGCATGGTCTTTAATGTGGCGGAGTTGCTGAATCCTCACACATAAGGCCAACGTTTAAACTAC*

*CCACATTAGTCACATACTTAGCGCCCCTTTGGAACGCAGGATTTTCGTATAGGTATGTAGAAATTTTACA*

*GGATTCAATTCAATTTTATAGGAAAAACACAGGTCTTTAGGAAATTTTCCTACGTTCCCAAGGGACCTTA*

*TAGATAATAAAATTAAAGCATAAAATGCATAATTCAGATGATATTTGGTATTCATGTTAAATTGTACAAC*

*AAACTTGATGAAAACATAAAAATGATTAGAAAATTACCTAACTGATGGTGATTTGGTTCGTCCTTGCCTC*

*CTGTATCTTCATCAGAATAGTCACTGAACTTGAATTAACACACAAAAGTTGGACACTTACAAGAAATCAG*

*AGATGTATTTTCACAAAAGACAACTAAAGTAGTATTTAGGAATGATTAAATGATGATCCCATTTAACCA*

*ATTCAGTTTGTGCAAGTCTATAAAAATTCGGTACAAATATATAATCGTCGATTTCAATTTATGCAATTGA*

*AATAGAGATGAAGAAGTATGATATTCCATGGACTCATGGGGATTTGCCACTTGCCAGATTGGGAGATTGA*

*GACTTCAGAAGGCATCAACAAAAAAGTAAATCGATACAAGCAGCTGCCGTGCGCCAATCGCAGACCCTGA*

*TGTGC*

1.2 The cDNA sequence of MS8 gene (SEQ ID NO: 12)—"ATG" start codon and "TAG" stop codon underlined ATCTTGAGTGAAGGTAACCAGGGCCAAA<u>ATG</u>ATTGCTGGGGGAGGCTATTTTGATGGTTCTCATGATCAT

ATTCTCATGGAAGGATCGATGATCCATGATTCTTCCCAATCTTCCATCTATGACAATACAGATGTTGAAC

AGCAGAACTTCAGACTTGCGCCCTTTATCATAGAAGATCACTCCAATCCAGCCAACCTTACCTCTGAGCC

TGCAAGGGTGATCGACCAAATTCATCACCAGCTTGGGATTGACATGGAGCAGGACCATAGTGATCACATG

ATCCAAGGAGTTCCTCCAGCAGAAACTGCAAATTTAGTTCCTGTTGTCTATGGTGTCCAAGATCGTATCC

TCAGCCACCAGATAGAAGGTCCACATAACATAACTGTGGAACAACAGGTCCTGGACTACGACCCTGCATC

ATATGGAAATGGCACTTATGCAGCTGCACATGATCTTCTAAATTCTCTACAGATCCAAAGGTGCAGTTTG

ATTCCTGAATTTCCTTCGACAGAACATATCTTTGGTGATCCAGCACAGAACATGGTCAATCCTTTGGACA

TTACCAATGACCTTCAAGGAGTAGCAACTCATGAAAGTGGAATGATGTTCAGCGATTCAACTCTACCATT

AGGTTATCATGCTACTCAATCTCATATGTTGAAGGATCTCTATCATTCACTACCACAAAACTATGGGATA

TTTACCAGTGATGATGAGAGAGATGGATGGTCGGGGTAGCAGGGGTCTCAGGAAATATTTTCCAGGAGA

TAGATGGGAGACAGTTCGACAGCCCAGTACTGGGGACTAGAAGACAGAAAGGTGGATTTGGCAAGGGCAA

GGGAAAAGCTAACTTTGCAACTGAAAGAGAGGAGGGAGCAGCTAAATGTGAAGTATGGGCTTTAAGA

TCACTGTTCCCAAACCCTACTAAGAATGACAGGGCCTCTATAGTTGGAGATGCCATTGACTACATCAATG

AGCTTAATAGAACAGTGAAAGAACTGAAGATCTTACTGGAAAAGAAGAGGAACAGCACTGACAGGAGGAA

GATACTGAAGTTGGATGATGAAGCAGCTGATGATGGGAAAGCTCTTCAATGCAGCCAGTAAGTGATGAC

CAAAACAATCAGATGAATGGGCTATAAGGAGCTCCTGGGTTCAAAGAAGGTCCAAGGAGTGCGATGTTG

ATGTCCGCATAGTTGATGATGAAATAAATATCAAGTTCACAGAGAAGAAGAGAGCCAACTCTTTGCTTTG

TGCTGCAAAGGTTCTAGAGGAGTTTCGTCTTGAGCTCATCCATGTTGTTGGGGGAATCATAGGAGATCAC

CATATATTCATGTTCAATACAAAGATACCTAAGGGCTCTTCGGTGTACGCGTGCGCGGTGGCTAAGAAGC

TCCTTGAAGCTGTGGAGATAAAGAAGCAGGCTCTTAATATCTTCAAC<u>TAG</u>

APPENDIX -continued

2. MS8s and sequences of pollen specific promoters 2.1 Pollen specific promoter used for the BARNASE gene >OsMADS68, pollen late-stage promoter 2(OsPLP2)(LOC_Os11g43740)
(SEQ ID NO: 13); Liu et al. (2013). The Plant Cell 25, 1288-1303:
Yan et al. (2015). Plant Molecular Biology 88, 415-428.
GGAACTCACCGGCTAGCCATCATTGGCGACCGTTAAACGGAGATTAAATACAGCGAATTAATGCTAAACT

AAAGGAAAAAAATCATGTTGAAATGATGAGAGAGGAGTGGGGAATCGATTTTTGCAATCAATTGGAGGAA

CAAATGCACGGGGAGGCAGATTGACATGGCAGCGGCGCTAGGGTTTGGCTCAGCGGTGGCTGGAGGCACA

CGCTGCGCGTGTAGCGGATCAGATGACTTACGAAAAATAAATAAAGAATTCTTGCTTTTATTAATTAGGT

ATAGATATATAATATTCACTGGTACGAAATCGGTCATTTGTGTTGGGTGCCACCCTTATGTGTGTTGGTG

GAGAACCTGATCACAGAGAAGAGGTCACTAATGTGAAAAACTCGTCTGCATCGGACGAGCGACCGTTAGG

CATACATTTTAAACGGGTTTTAAAAAAACAACCAGTCACCGATATGGTTCACCCAGAGCAAATTAGATAA

CAAGCCATCCCGGACGACTCATCGGTGATAGGGCCCAATTACAACTCAACAATGATGTTGTTCACTTATG

ACGGGGTTACGTTGTAACCCATTACCGATGAGGTTTTACCTAAACAGATAATATCATTTTATTGTTAACC

TCAGGCAATTGCGCCATGCCCCCACTGCAAATTGACAAAAATATAGAATTTGCCACTAATATCACGCTGA

TACGTGGGTGTTCCTAGTAACAAATTCATAGATATAGGATAAATTATGTTGGTGGTATATAAACTTATTA

GACGGGTGCAATTTAGTACATGAATTTATAAAACGTTCGTTATAGTGAATAAATTTGTCTAGGATGTGTA

AACCAAGTCGAAAACAACGTATTATGACTAATTATGTTGAGTTAAATCATGATTAGTATGTCAAACGCAC

ACGCGAGGGGGTAAGAAACATGTCATATTTGCAAACAACCTTTATATATACACACATGGCACTTATTTTT

TCCTTCCATTGTTTTTTTCCGTTGCATCTTCTTTTATGTATTTATACATTTTTATATGTGCAATGAGCAT

GGCTTATTCTGCGTTTAATTGAGCACATGCATATGTATGTCGCATCGTCTTGATATGCAAGCATACGTGG

CATCCTAACCGGTGTTCAACTCAGTGAGATTAGCTATGACGTGTTTCTTATGTCTTGGTTTGTGATCACT

TGTTCTAAATTCTGGAGATAAGGTCTTCCATGGATACCCCCGAAACATCCCCTCGATTTTTTCATCATG

AATGATAAACTAGATGTTTTTAAATGGATGTAGATTGAAGAAACTGTGTAACTAAGCCCCCTCAATTTTT

GTTTCTGGATCCGCCTCTACGTACCCGTCATCGGCTCGCATCGCATCGGGCGCTCGGTGCAAAGCATTAT

CGACGATAACAATAATTAAAAAAAAATATATCACGCAAAAAGCAAGCTGAAATTGTTTTGAAAATAAAA

AAACAGGAAAGAAAATGTGTCTGAACCTTTCTCGCTCCCTCCCGCGCGTTTCTCTCCTCTTTTCTCTCTC

CTTCCTTGATCTCCTCTCTCTCTCCTCCTCCTCCTCCTTCTCCTTCTCCCTCTCCCGCCCGATCCACCCA

AGAACTGCCGATTTCGCCGGCTCGATCCCCACCCCGACCCCGCTGCCTCGCGGGAGATCGATCGTTCGAT

CGATCAGAACAAGCTAATTCTCTCATTCCTCTCTCTGTCTCTCTCATCGGTTCTTGGTTCGACCCAGCTC

CCAGATGATTTCATCCTGAATCATCGTCGTCGTCGTCGTCACAGGCAAGAAGAGGAGAAGGAATTAC

ACCTGGGATTATCGATTGGTTGTTCGGATTTTCTTTTGGATCTATTCATGCTCGCTCTGTGCGCCGGGGA

TTCGATCGTTGGGCAGGGCAGTGATCTCTGCGTCGAGGGTTTCGACGAATTGGACTGCAGATTCGTCGCC

ATCTCTTCGCAGAGGGGATTCTGCCTCCGCC 2.2 Pollen specific promoters used for RNAi

>LOC_Os10g40090, The Oryza Sativa Indica Pollen Allergen Gene (OsIPA)
Promoter (SEQ ID NO: 14); Swapna et al. (2011). Molecular
biotechnology 48, 49-59.
ATCTGTTCTGCCCATCGCCGTCGCTGATCCCCTTTTATCGCCCCAGCTTCCTCCTCCAGCTCGCTACTCT

CGCCGGCGGACGCCGGTCTCGCCGCCCCCTCCAGCTCGCCACTCTCGCTGGAAGAGGAGAGGAGAGGGGA

GAAAGATGAAGAGAGGGAGATGGGGAGAGAGGAGGAAGAAGAGGAAGGGTGAGTTTGACTGACATGTGGG

GCCCACGTGGGTCCCACAATTTTTTATTATCTTCTATGTGAGACTGACATGTGGGTCCCTAGGTTTTTAT

TATTTTTCCGGGTCGAATTGACACGTAAAGCGCCACGTCAATGCCACGTTGGACGAAGACCGAGTCAAAT

APPENDIX -continued

```
TAGCCACCTAGGCGCCACGTCAGCCAAAACCGCCCTCAAAACCACCGAGGGACCTGATCTGCACCGGTTT

TGATAGTTGAGGGACCCGTTGTGTCTGGTTTTCCGATCGAGGGACGAAAATCGGATTCGGTGTAAAGTTA

AGGGACCTCAGATGAACTTATTCCGGAGCATGATTGGGAAGGGAGGACATAAGGCCCATGTCGCATGTGT

TTGGACGGTCCAGATCTCCAGATCACTCAGCAGGATCGGCCGCGTTCGCGTAGCACCCGCGGTTTGATTC

GGCTTCCCGCAAGGCGGCGGCCGGTGGCCGTGCCGCCGTAGCTTCCGCCGGAAGCGAGCACGCCGCCGCC

GCCGACCCGGCTCTGCGTTTGCACCGCCTTGCACGCGATACATCGGGATAGATAGCTACTACTCTCTCCG

TTTCACAATGTAAATCATTCTACTATTTTCCACATTCATATTGATGTTAATGAATATAGACATATATATC

TATTTAGATTCATTAACATCAATATGAATGTAGGAAATGCTAGAATGACTTACATTGTGAATTGTGAAAT

GGACGAAGTACCTACGATGGATGGATGCAGGATCATGAAAGAATTAATGCAAGATCGTATCTGCCGCATG

CAAAATCTTACTAATTGCGCTGCATATATGCATGACAGCCTGCATGCGGGCGTGTAAGCGTGTTCATCCA

TTAGGAAGTAACCTTGTCATTACTTATACCAGTACTACATACTATATAGTATTGATTTCATGAGCAAATC

TACAAAACTGGAAAGCAATAAGAAATACGGGACTGGAAAAGACTCAACATTAATCACCAAATATTTCGCC

TTCTCCAGCAGAATATATATCTCTCCATCTTGATCACTGTACACACTGACAGTGTACGCATAAACGCAGC

AGCCAGCTTAACTGTCGTCTCACCGTCGCACACTGGCCTTCCATCTCAGGCTAGCTTTCTCAGCCACCCA

TCGTACATGTCAACTCGGCGCGCGCACAGGCACAAATTACGTACAAAACGCATGACCAAATCAAAACCAC

CGGAGAAGAATCGCTCCCGCGCGCGGCGGCGGCGCGCACGTACGAACGCACGACGCACGCCCAACCCCA

CGACACGATCGCGCGCGACGCCGGCGACACCGGCCGTCCACCCGCGCCCTCACCTCGCCGACTATAAATA

CGTAGGCATCTGCTTGATCTTGTCATCCATCTCACCACCAAAAAAAAAAGGAAAAAAAAACAAAACACAC

CAAGCCAAATAAAAGCGACAATGGGATCGCTCACCACC
```

>LOC_Os08g44660, *Oryza sativa* LATE POLLEN SPECIFIC PROMOTER1 (OsLPS1),
Similar to Polcalcin Phl p 7 (Calcium-binding pollen allergen Phl p7)
(SEQ ID NO: 15); Oo et al. (2014). Plant Reproduction 27, 47-58.
```
AAAAAGGGGATCGAGAGGAAGAGGAAGCTTTGTGAGTTTGGGCCTTTATTTGGTGGAGGCCCATTGATTC

CTACGTGGGCTGGGCCGAACACGGTCCAGGTAGTTGGTCCACATTCCAGGTTGAACGATTCCAGCGGCGG

CGGCGAGTGGTGGCGCGCGATCATCTCCCACTCCCACCGTTGTTCCTCCTCAACACGCGCCACTCCTCAC

ATTCATTTCCACCTGCTCATCTATATCTATCTATCATCAAGCTGATCATCCAT
```

2.3 Other pollen specific promoters

>OsBOR4, boron efflux transporter 4, LOC_Os05g08430 (SEQ ID NO: 16);
Tanaka et al. (2013). Plant & Cell Physiology 54, 2011-2019.
```
ACGTAGTTGAATGTCCTGTGTTCGTTGAGCTGATTCCAGCAGCGGCAGAGGAGGAGGCCATTGCAGCTGT

CCACCAGCTGGAGATCATCACACTTGGGCAGGAAGGAAAACGAGGGATCGATGAGGGGAGGGGGATCCAG

CGCCGGGACGATCTGGAAACGGTTTAGTACGCGGTAGTCGGCGTAGAGGAAGCCGGCGAGGGGCTGGAGG

TGATGCCGCGGGAGCTGGCGGCGGTGGTCGGGGTGGGAGATGACGCGGCGCCACCGCATGGAGACGCACT

TGAGGCGGCAGAGCGACTTGTAGGGCACGCGCGAGAGGATCTCGACGAGGAGGTCGTCGGTGAGCTCCTC

CGCAATGGCTGCGCATAGAGAGACGGAGAAGCGAAGGGATTAGGAAAGAGAGGTGAAACCAAAACCACCG

GCGGCGGCATGGAGGAGGGCGCGTACCGGAGGTGGTCCCGTTGGAGACGGCGGCGGCGAGGGCTTGGGGT

TTTGGGCGGCGGCGGTGGCGTACGCAGAGACGGCGAAGGAGAAGCCTCGGCATCGCTCACCGGAGCAGAG

ATCGGCGGCGGCGGCGGCGGCCGTGGAGCAGTCGAGGCTTCGAGGAGGTGCGAGGGGAGGAGGCCCA

GAGAGAAAGCTAGCCGTAGCCCATTGGGCCTGGACGAATCCTGACCGATCGATCAAACGGACGGCCACGA

TTCTCCCCGGTTTCAATTTTCGAATCGCCCGAGAAAGCGAGACGTGAGGCGCGGCGCCACCCTCGCCTCC

CCCCATCACCTCGCTACGTGTCCGCACGGCAACGCAGGCTGCCAAGTGGGCCCCACTCCAACCCCCCTTC

TGCCGGACCCACATGTCAGTCACACGCTGAAGAGTCTCACACCGACTCCCTTCTTCTCCTCCTCCCTCTT
```

APPENDIX -continued

```
GAGCTCGCCTCCTCTCGTCGATTTGCTCGCCTATAAATGCCGGCGTCACCGGCGGAGAGGAGAGAGAGAG
AGAGAGCCACGACGACCCGCTCGCCGCCGTCCCCTCCGGCCGCCGACGCCTAGGGTTTCCCCGCCCGCCG
GCGCGTCGCTCGCGGTGGAGGCTGGGTATTGTCGCTGCGCGCCGCCGCGTCGATCCACCGCCCGCCCGAC
TGCGGACTTCGCTTGATTGTTTGTGCCTTCCCTCCTCGTCCTAGCCGCTCCTGGTACGTACGCGCGCTCC
GATTCCGGCTGCATTTGGTTATTTTGCTCATGAGCGTCCGCCGCCGCTTCGCTCCATCGATCCTGGCCAT
CCGTGCGGCTCTCGATCGTCAGGGATTCGGAGCCCTTTGATGTGCGGGGGGGACGCGTTTGGGGGAAGAT
GCGGCGCTTGATTTGCGTGTTGTGCATCATGATTGCTCTTGTCAATTCGATCGATTGATCATCGATGCAG
GATTTTTCGTTAAGCTGATTCGCTGTGTGTTTGCAGATACGGACTAGTTAATTGGTTACAGTTTGTATTG
TTCCGTAGGATCGGTACGTGATGATCCATTGACGAGCGCAGTTGCGTTCTTCCCCCACTTCAAAAGCGTC
ATAAATCTTGTACTACTACTATGACATCTACACATCCAGTGCAGCTGTTTCTCAAACAGCGATATAATGT
TTTTGAAAGCAAGTTTGATCACTGTTTTTCTGTTACTCCTTTTTGCACCATATTTCAAAAGTTTATAACT
GGTTCAAAAACGTACTAGTGGTTTTTATTCACTCACAAATGAGAAAGATAGTACGAAGAATGTAAATTCT
TGATGGAACTTTCTGCATTCCCAACAGTTGGCAGTCCTTTATTTGTGTCGTGTTCGAAACAAGTAGAACA
CTTTGATTTGTTGCTTTATGCAGAACATATCCAGATCATATCTCATTTTTTTTCCAAATGGGACCCTCCT
GTACCTATTTCCTCAAGCACCTCTGTTCTTGGGTGGTTCCAAGTAACAATCAGTTTATGAGACACTGCCT
ATTTGCCAAATTTAACATAACAGCCTGTTTGAGCCAGACTGCTGGTGATCCCTATTTTGTTTCTTGAAGC
CTTCTTTCTTAGGCCTTGTTTAGTTCCCAAAACAAAAACTTTTCACCCATCACATCAAATGTTTGGACAC
ATGCATGAAGTATTAAATATGGACGGAAATAAAAACCAATTACACAGTTCTGACGGAAATTGCGAGACGA
ATCTTTTAAACCTAATTGCGCCATGATTTAACAATGTGGTGCTACAGTAAACATTTGCTAACGATGGATT
AATTAGGCTTAATAAATTCGTCTCGCAGTTTCCTGGCAGAATCTGTAATTTGTTTTGTTATTAAACTACG
TTTAATACTTCAAATGTGTGTCCATATATCCGATGTGACACCCCAAAGCAAAAATTTTTGGGAACTAAAC
TGGGCCTTAGTATTTGCAGCTGTCAACTTATTCATGAAAACTATGCTCCTACTATGCATAGAAATGTAAA
GCTAAAAATAGCATCTGGTTAGGAAGGGGAAAATGAAAGAGCCAAATGATGGCATGCAATGGTTCATGTC
CAATTTGCTACTTATAGCATAAAAAATAGGCAAACACCCAAACAGCTGGACCGTCCTTCCCAAGTTTGAAA
GTTCTGTTTCATTCTTTCATAAACCAAGTCTGATGTTGTGAAACTAAAATTTATGTAGTACCCCTGTCTG
ATCCATTCTTTTAGCCCACAGTTGGCTTGTGAAATCCTACATGCACTTATTCGTAAACCCCATGCATGGG
GCATGTCTTTGTGAGTACAAAATTTATTTTTATTTTTTTCGCCGGGCCGGCAAAGATAACCGGCCAAGTT
TTGCATTAAGAAGGAGAGAGTTTTACAGCAGCCCCTAAACCAGAAAAGGCTTAGGTTACAGAAAAAACTT
CACAACAATAAAGACAACAAACAAGCACAGCTGCTAAAACCTCAGCAAATTAACCGCCAGCGATTGCGCT
CAGTAGCCCGGCAGCCTTCCATGTTTCCCATTCGTCGACAATTGTGGCACAAAGGTGAACCGCTGAAGTA
GCTCGTCCATCAAACACACGCGCATTCCTTTCCTTCCAGACTATCCATGTTACCAAGATAACCCCAGCAT
CAAAGGTCCCCCGATCCGTCTTGTGAACTGATTTGCGTGCTTCACACCACCAATCCAACATGTCTTCCGT
GGGGGAAACACAGGAGAGTCCCAGGCGACTCCTGATTCTCGTCCAAACTGCCCTCGTGTACTCGCAAGCG
TGGAAGATATGGGCACATGATTCAGCATCCTTCCCGCAAAGGTGACAGTATGGAGCCAAGTGCCATCCTC
GCCGCTGGAGGTTGTCCGCCATCAGGCATGCTCCACGCATGGCAAGGAACATGAAGAACTTGCAATGGGC
CGGCGCGCGAGACTTCCAAATCAGCTTCCCAACCGCCAAGCGTGTCTTCCCAGCGCAGAGGAGTGAATAG
GCTGATTTTACTGAGAAACCACCATCTGCGGCAGGCTTCCAAGAAAACAAATCAGGCTGAGTCGGGTTCA
AGGAAACGGTGGCAACAAGGTCCCAGATTTGGAGGTATTCAAACATCGCTTGCAGCGAGAGACCTCCCCT
GATGTCGCCGGTCCAGGCATCATCCTGCAGCGCCAAATGAACCGTTCTGCCTCTGTTTTTAACAAAGGAA
CACAGGATTGGGGCTCAGTTCAGGATCGACCCCCCATCTGGGAGCCAGTCATCTGTCCAGAAGAAGGAAC
```

APPENDIX -continued

```
TCTTCCCGTCGCCCAGCACTATCCTGCATCCGGCCGCTAGACAATGTTCGGCTTTCCTATCTTGCGGCGA

CGTGAAGGACACCCAGTGGCGCTCCAGCTGGGCACGCCGCAGCCAAAGCCACCGCGTCCGAAGGGCAATG

CCCATTCTGCCAAGATTGATGATGCCCAACCCGCCATTTTCGATCGGCAGACAGAGCTTATCCCAAGCAA

CTAGGCTGCATCCACCCGGTGCATCCTCATCCCCCTTTCACAAGAAACCGCGGCATTTCTTTTCAATTGC

TTTAATTGCCCACACCGGCAATTCCAACACCGAGAAATTTATTTTTATTAGCTCAGTTA

> AtPSG2 (At1g28550, annotated as a RAB GTPase homolog A1I)
(SEQ ID NO: 17); Munoz-Strale et al. (2014)
Plant Physiology and Biochemistry 83, 292-299.
GAAGAAATAGTTGGCATTGCAAGAAGAAGACATGATGAGTCTTGTCTTGGTAAATTTGTTGCATAATTGG

ATATATATAAAAGATTTTCTTGAAATGATGACATGACAACTATTTCTGAATTTAGCCATTGTCAAAAGCT

CTCTTCGTTTTGAAGCGGTAGAAAATTAGAAATGTTTATGTTTAGCCAAATTCAAAAGTAGAGGAGATTC

CTTGAATTTCTGTTTTCTCTCGCTGTCTTCTCAATATTCAAAACTCAAATTGGTGTCTTCTCCAATTTAG

AAAACGTTAAAAACAAGAGAAAATAAAACTAAACTTTTTAGAACCAAAAAAAATAAAAATAAAACGCATT

TGGGATTTCTCATTGTCATCCCAAGTTCTTGGAACAGCCAAATACTTTTTCATTATTAGTTTATAATCGT

CTCATAAAGGCAAAAAGGTTTATTTC

> AtPSG4 (At4g27110, annotated as a COBRA-like protein 11 precursor)
(SEQ ID NO: 18); Munoz-Strale et al. (2014). Plant Physiology and
Biochemistry 83, 292-299.
ATGATGGTGTTTGGGTCATATACCTTCTTGTTCTTATTTTACTAGTTTGAGATCCTTAGGCTTGCATCCA

TATACAGTACATGAAATACCATATGTTTAAAATTGTTGTTTGTCTTACCATTAGAAAATAAAATAAACAC

ACAAAAGAAATGGATATCATGGTTGCTTTAGTAAATCTTTATTCCTCAAGTTAAACAATGTTTGCCATTT

ATGGTGCTCACAAGGTGTTCACACAAAGTCTTGTGTAAGAATATGATATCATGGTTGCTTTAGTAAATCT

TAATTAGGGTTCTATAACTTTTGTAAAAAGTTTAATAAAAAAATTCTAATGAACTAACTTAGAGGAATAT

GCGGTTTGGATCAGTCTAATCCAGATTTTCTATAGAATATAGAAAAAATGTGACAAACATACAGAAATTG

GTACTTATACATTTACTGATTAACGTTATTAGTATATTCTCTTTTGTATAATATCTCTGTTTCTCCGGAG

AAACAGGGGAAAACTAGAGGAAGAGAAACCGTTATGCTCTGCCTCTCTAATTCGCTTAAGTTTTATTACC

ATCTCTCTTTTCTCTGTTTTCTCTTTCTTGCGTTCCTAAGAAACTTGGGAAA

>LOC_Os06g40890, ortholog of PSG4 (At4g27110, annotated as a
COBRA-like protein 11 precursor) in the rice (SEQ ID NO: 19);
Munoz-Strale et al. (2014). Plant Physiology and Biochemistry
83, 292-299.
GCTTTGGGTGTACTCACTGTTCACACCAATAAATAAATATCACAAGAATTCTATAAATTCCTACATAATT

TTTTTAACATAGTGTACATATAATTTTATAAAATTATGTACTTTTAACATAACATGCACGTACATATAAA

GTTTTCACTTCAGATACATTATACATATTGTACAAAGTAGGGGAAAAATGATTAGTACCCCCATCTGTCA

AAAAGATCTATTCCTAGATCCCCGAGGCAAGTTTAGTATTAACGTGAAATTACCAAAGTACCATCCTTA

ACTGCATTCATCCATCAACACTGCCATTCTCTGCACACACATTAAAATTGAGTTGCATTTGCCCAAGAAA

AGATTACATTTGCCGTTAGAAAGGGAACAACCTACAAGAACTACACCAAGAACAAAGAACAGAGAAGAAC

CAAGAATAGAGGGGAAAAAATGGAATCAAGTTCTTGAATCAGATCTGCCACATATAGGCTTGCAAACTTT

CACCTTCACCTCCTGCATCACAACAATATGCCCCTACCATCGCCGCCGCATCCATCCGCCACCGCATCCA

TCTCCCATTGTTGCCGCTGCATCGATCTGCCACCGTCGTCACCGCGGCATCGATCTGCCACCGTCGTCAC

CACGGCATTGATCTGCCACCGCCTTCACCGCCACCATCATCGCCGCATCCATCTCCTGTCGTCGCCGCCA

TCCCTGCAGAGAGGAGTGGAAAGAGGGGCAAATTTGAAGGGAGAGATTGAGTTGAACAACTGAGGAGGCA

GAGGGAGAGAGAAGCCAAATGAGAGGGAGGGAAAAGATTGCCGTGTGAACCGGAGAAAGAAAAGTTGA

GGCCCTCTGACTCCTTCTCGAGCACCCATGCGGTATTGAATGTGTATCTTTTTTTACAGGAATTAGTTT

TTTGGGACAACCACACCCCACCCCAGGAATCGATTTTTTTGCGGACAGAGAGAGTAGTATACTAGTATGG
```

APPENDIX -continued

```
GAAGTAATTGTACAATTTTTAAAATAATTTTTAATAGTTGATTGTATAGCGAGATCATCCAAAACTTTAT

ATGTATAAGTTGTGTTTTTGTTGTCGGCCCTAGTTTTCTGAAAGTTGCAAAGAGTTCTAATAACTTATTC

ATTGATATTTCCTTAACATCAACTTTTCATACTAGAATGCTAACGATCTTCATCCCCCAATTTGAATTCC

AGCACATCTTCAAGGTCCGGAGGCCACAAGAGATCTACACCCTACAACACATTTATTAATAGTGCGAAAT

TGAACCGAGTCTTTTTTTCTCTAAAACTAAAATCAGGTATAAATTGAAATAGCATGCTATAAATACAATC

TTTAAATACCAATTTGCATAAATTGATGAGCCACACCTTTTGAGTGGACTGAAACTAAGATTAGGCAACA

TGGGGACGCCAACAGACGAAATTCCTCTGAAGTAAAGTAAAAAAAAACGTGGATCCCTGATAGGTGGACC

TCACCTTCATGAACGTCAGTGGCTCATATCCCTCAACGTATGTAAGAGGAGCCTCTTCCGATATGGGGA

ACCATAGCAATGCTCAACCGCCAGCCAACCAAGCCATGGCCTGAAAATAGCAAAAGGCCAACACATGCCT

GCATGCCACAGACATAGCAAAATCTTGTTGTCGCCACCACCACTATATATATGTGCATGCCGGCCGGCGT

TCAAGTTCGCCGGAGAGAGAAGCACCGGCGGTCAATA

>LOC_Os06g05260 pectate lyase precursor, putative (SEQ ID NO: 20);
Fujita et al. (2010). Plant & Cell Physiology 51, 2060-2081.
GACAAGCTGCAAGCGACCTGGATACTTCGTAGCTGAAATCCACATGCCCAGGAGTATCAATCAAGTTAAG

CAAATAGCTTGGAGCATCTGGCTGATCAGATGCAGGAAGTTGGTTGTTAGCATGTCTGTAGAACATAGTT

GCTGTTTGTGCTTTGACTGTGATTCCCCTCTCTCTCTACCTGTAGAGAACAGATACAATCATACAAAT

GTTATGACAAATGCACACAGTATAAATATTTCTTTTCAATTTCAGTAAGAAAATATCCACTGAAAATGAA

CACTATCTGTTATGCTAGTGCTGTCATCATCTCAAATGAAATGAGATGCCAATTAAGGAAATAGTCACTT

AAGATCCAGTATGCTCAAAAGTCAACACAGTGAGTACAAGGATTATCTTTGCTATTACTACCGGTCACCA

AACATAACGAAGTTCAACTCAACTAAAATTCTGGAGTAACTTCCAATTGATTAATTCCGGTATGTGCATTT

ATCCAATAAGCTTATGGAATACGGACCACAAATCAAAGCTACCAATTTCTCACTCAACGCGTCCCCATTT

TTTTCAAAACGGCAAGTTTGTTCTCACACCTGTAACTTGTCGAGGTACTGAGGTTGGCCATGGCCCTTCT

TGATGGTGCCGGTGAGCTCCAGCAACCGGTCGGCGAGCGTGGACTTGCCGTGGTCGACGTGCGCGATGAT

GGAGAAGTTCCTGACCCTCTCCGGGGGATACAGCCCAAGCTCCGAACCCAGCACCCCGCCGCGGTCCGGC

GAAGCCTGGGAGGAGAGGAGGCGCTCAGGGTGCTGTAGCGCCCGGGACAAGGCGTAGGCGCCTGGCAGGA

CGACACGGCGCGCGGATCGCCGGAGCGCGGCGGCGCCGGCCATCCCGGAACAGCGCGGCGGCGGCGGCGG

CGGGAGCTAGGGTTCTGGTTGGGGTTTGGCGCAAAAGGTCCACATAGACTAGAGAGGAACACGCTGTGCA

ACTGTAAGATGGGCCCCACTGATACGATGACCTATGGGCTTAATGGGCCTGGAGAAAATGAAGGGGCACC

TATCAGCCCAAACAAAAATGGTTTCGTATGAAACATTTCGGCCCATAATACTACTACGCTGAGAAATACT

AGGAATTCCGAAATACTACCTCCGTCCAGGATTGTCATGAAATTGCTAATTAACGACTAGTTGTGTACCG

CGTGCGATTGTCTATTATTTTAAAATATACATACAAACTGTATAAATATAAATATAAAGTCTGTGTGCAT

ATTTTTTACGTCCTAAATGCATACAAATATGTATAAAATATACGAAGATTTTTATACATTTTATGTTAAT

GCATGTAGTATAATTAGATTTGTATTTTAAAATATTTTTATATAATGTTAAATTCGTAGTTGATAATAAT

GTATTAATTAATGGTCAAAGTAAAGTATTGGAGACCGCGTAAAATGCTACTGTTTTTAACCGAGAATAAC

AAACATTTTCACAATGAACAATTTTCATAGTTAAAGTTTGTAATTTGAGATAAAAAAAAGTTTCTTATAT

CGACTGTGTTTGCCCACATAGGAATGAATACTAACAAGATATGCCCGATTAATACCCTTCCATATATATA

ATTCTTATCCCTCCATCAATGGCAAAGATCAATGCTGGCTGCAAATAATCACATCATTTCCTTACCAACA

GCCGACGCACGATGATCATGTGTTGGTGTTGGCATGCAATGCAACAGACGAACGGAACGCTCACCACCAC

CAAGCCGACGAGCGGTCATCACGCCGCGACACGCGACGGCGACACGCTATATAGAAACCCCCGCCGCACG

CACGCGCGCCTCGGCGGCCGGCTCACCTCTCTCCGCCGCCCGGCCCGCTCGCTGATGCTGCCGCCGCCGG
```

APPENDIX -continued

CTTCACGCGGGAAGAGGTCTCAGAAACCCTAGGCGAAAGCCGCCACACATTTCCTGAGTCCTCTTTCCCG

CGGTGCGGCGGCCGGCCGGGGCGGCGCTCCATACACCCATCGGATCGTTCTGAACCAGCAGC

>LOC_Os01g50810, invertase/pectin methylesterase inhibitor family
protein, putative, (SEQ ID NO: 21); Fujita et al. (2010).
Plant & Cell Physiology 51, 2060-2081.
CCTGGCAACAGAGCGACACGATAACATGTCAAAACTTGTGCACTCTATAAAATGGTGAAGATATAGACAC

GAAGCATAAGATGTATAGTAAGTAGCTAGCAAGAGGATCGAAATGTAAGAGCTAACCCCAGCTAGTGTTT

TCTTTTTCTTTTTCTTTTTTGGAACCCTTGCTCAATCACTGTTAATTAGTGGACATCTACCAAAAAGCCC

AAACTTAAATTCCGGGTTACCAAGTTAACCAAAATTCTTGTGACGGCCTATAAAGTTTGCATTCTCTGGA

TGTGGATGGCATTGACTTGAGCAATGGAGTTTGCTCTGGATATATGTGTGACGTCTCAGCTTGAAAGCTG

AATTACTGTAATAAACTTTGGTCGGAAGCTCTTGAGCTAAAGGCTGGGAAACAAGTTGATCCCACAAAAC

ACGATATCATGTGGCTCTTTTAATCTTCTGTACGTGTAGCAACTAACAATAACCACCATTATAATATACA

GATGCTTGTGCAACCCCTCCGCGGACTGCGGCTGTTCCGCAGATCGTTGCAAGATTCTTCCTCTGACTTT

GGTATCTCGCGTCATCTCCTCGGCTTTTTGCTGCTACCAAAAGTCTCTGCATAGTTAAATGTGAGATACA

TTTGGGGTACTTATATATTTAGAGCACATCCGGATCCATGGTTTGTACGGAACACAGACGATGCAAGGGA

TTTTCTGAAATTTGAAAACCTGACAATTAGATCATTCATGAAGATGAAGGACATGGATGTCAGGGGCGAT

CGATTCAATATCCGGGCCAGTATATGCATCTTGTACTAGTAGACTACTAGTTTCAACATTTCACGCTGAT

ATGATTAGGATTTGTGCAAGAATTGCAGATAAGACGGATATCCCTTCAGTTACGTTTCGTGACTAGTATA

CATTGGACTGAAATTATTGGTTCCGGCCGGACATTTCCTGCAGCTCGTATGAACTTGCTAAGCAAGATGC

CAACTTGCTATCCCCCAAATTGTCAACCTCGCCGTAGGTTGGCATCCAATTGGCAGTTACTTTATTGACC

TGATAGGGATGGCCGTGTCCTTCAACTCCAGCTTAGCGGTGACCCCAGCAGGTGAATGTGGCAACTCGGA

TATCCCAGCCGCAGCTAGAGCTCCTCTCACCAATCACTAGCTCTCTGTTGCATCATCATTAAGTCATGGT

GATTAGTTAAGATAAAAATGACGTATTGTGATTAGTTTAGCCTGCGATCTCATGCTGTCCCAGCTTGCTC

TGACCAACAAAGATTCAAGATACCGTTTCTGCACTATTGAACTACCAGCCATCGGTTGAGACGACTTAGA

TTTGATATTATTGATTCATGGCTTGGCTTGAGTTTACTTGGGTATCCAATGGGCGCCTCTGGCTTGCTGG

TTCCTGTAACTTCGATATCTTAAATATATATAGGTGGCTGTTTACTTACTTAAGTAGCACATGTACGCCT

GTAATCTCCTCATCAAACTTTGAATGCGCAGTGATAGTCAGGATCAATTTTGAGCTAAACAAAAGTTTGC

ATTGCCTTGGTTAAATTGGTCGATGGTTAATTGGATTGAGTTTGGATGTAGTGGGACATACTTCTCGCA

AATGTCTGCGCTACAGTGCTACCTGTTCATTCTCCGGTAGCCATTTGTCCGTAGCACATAAATAAACAAG

ATAATACCGAAATTAATTAGGGACATAACTTTTTTAGGAGAAAACTGTAATGCTTAGCACACCACTAAAC

ACGCCGAGGCCATTTTAAGGCCGTAGAGATCCCTACGATCATGGCTAGCCATCCACGACCAAACCGCAAA

AATTTACGCCATTTTTGGATCGACGGCCGTCAAGTCCCGTACGTCTTCTTTTACCACCACCATTTGATCT

GTTTCCTTCTCAGACACCAAAGGAACTTGTTTTTTGTATTTTTCTTTTCGGTAGCTACTTTCTACATCTC

TCTTATTTGGATCACGTATTATCCTTTTTCATTCCACGACCGACGACC

>GRMZM2G317406, PG47 (SEQ ID NO: 22); Chang et al. (2016). Proceedings
of the National Academy of Sciences of the United States of America
113, 14145-14150; Lonsdale, R.L.A.a.D.M. (1993). The Plant Journal
3(2): 261-271.
GAGAAACCCGAAGTGGCGAGTTTGGAGTTGTACGGTCCTGGTGCACCGGACACTGTCTGGTGGCATACCA

GACAGTCCGGTGTGCCAGATCAGGGCACCCTTCGGTTCCTTTGCTCCTTTGCTTTTGAACCCTAACTTTG

ATCGTTTATTGGTTTGTGTTGAACCTTTATGCACCTGTGGAATATATAATCTAGAACAAACTAGTTAGTC

CAATCATTTGTGTTGGGCATTCAACCACCAAAATTATTTATAGGAAAAGGTTAAACCTTATTTCCCTTTC

AATCTCCCCCTTTTTGGTGATTGATGCCAACACAAACCAAAGAAAATATATAAGTGCAGAATTGAACTAG

APPENDIX -continued

```
TTTGCATAAGGTAAGTGCATAGGTTACTTAGAATTAAATCAATTTATACTTTTACTTGATATGCATGGTT

GCTTTCTTTTATTTTAACATTTTGGACCACATTTGCACCACTTGTTTTGTTTTTTGCAAATCTTTTTGGA

AATTCTTTTTCAAAGTCTTTTGCAAATAGTCAAAGGTATATGAATAAGATTGTAAGAAGCATTTTCAAGA

TTTGAAATTTCTCCCCCTGTTTCAAATGCTTTTCCTTTGACTAAACAAAACTCCCCCTGAATAAAATTCT

CCTCTTAGCTTTCAAGAGGGTTTTAAATAGATATCAATTGGAAATATATTTAGATGCTAATTTTGAAAAT

ATACCAATTGAAAATCAACATACCAATTTGAAATTAAACATACCAATTTAAAAAATTTCAAAAAGTGGTG

GTGCGGTCCTTTTGCTTTGGGCTTAATATTTCTCCCCCTTTGGCATTAACGGCCAAAAAACGGAGACTTT

GTGAGCCATTTATACTTTCTCCCCATTGGTAAATGAAATATGAGTGAAAGATTATACCAAATTTGGACAG

TGATGCGGAGTGACGGCGAAGGATAAACGATACCGTTAGAGTGGAGTGGAAGCCTTGTCTTCGCCGAAGA

CTCCATTTCCCTTTCAATCTACGACTTAGCATAGAAATACACTTGAAAACACATTAGTCGTAGCCACGAA

AGAGATATGATCAAAGGTATACAAATGAGCTATGTGTGTAATGTTTCAATCAAAGTTTCGAGAATCAAGA

ATATTTAGCTCATTCCTAAGTTTGCTAAAGGTTTTATCATCTAATGGTTTGGTAAAGATATCGACTAATT

GTTCTTTGGTGCTAACATAAGCAATCTCGATATCACCCCTTTGTTGGTGATCCCTCAAAAAGTGATACCG

AATGTCTATGTGCTTAGTGCGGCTGTGTTCAACGGGATTATCCGCCATGCAGATAGCACTCTCTCATTGT

CACATAGGAGAGGGACTTTGCTCAATTTGTAGCCATAGTCCCTAAGGTTTTGCCTCATCCAAAGTAATTG

CACACAACAATGTCCTGCGGCAATATACTTGGCTTCGGCGGTAGAAAGAGCTATTGAGTTTTGTTTCTTT

GAAGTCCAAGACACCAGGGATCTCCCTAGAAACTGACAAGTCCCTGATGTGCTCTTCCTATCAATTTTAC

ACCCTGCCCAATCGGCATCTGAATATCCTATTAAATCAAAGGTGGATCCCTTGGGGTACCAAATTTAAGG

AGTGTAAACTAAATATCTCATGATTCTTTTCACGGCCCTAAGGTGAACTTCCTTAGGATCGGCTTGGAAT

CTTGCACACATGCATATAGAAAGCATACTATCTGGTCGAGATGCACATAAATAGAGTAAAGATCCTATCA

TCGACCGGTATACCTTTTGGTCTACGGATTTACCTCCCGTGTCGAGGTCGAGATGCCCATTAGTTCCCAT

GGGTGTCCTGATGGGCTTGGCATCCTTCATTCCAAACTTGTTGAGTATGTCTTGAATGTACTTTGTTTGG

CTGATGAAGGTGCCATCTTGGAGTTGCTTGACTTGAAATCCTAGAAAATATTTCAACTTCCCCATCATAG

ACATCTCGAATTTCGGAATCATGATCCTACTAAACTCTTCACAAGTAGATTTGTTAGTAGACCCAAATAT

AATATCATCAACATAAATTTGGCATACAAACAAAACTTTTGAAATGGTTTTAGTAAAGAGAGTAGGATCG

GCTTTACTGACTCTGAAGCCATTAGTGATAAGAAAATCTCTTAGGCATTCATACCATGCTGTTGGGGCTT

GCTTGAGCCCATAAAGCGCCTTTGAGAGTTTATAAACATGGTTAGGGTACTCACTATCTTCAAAGCCGAG

AGGTTGCTCAACATAGACCTATTCACCCCATTTGATCACTTTTTTGGTCCTTCAGGATCTAATAGTTATG

TATAATTTAGAGTCTCTTGTTTAATGGCCAGATATTTCTAATTAATCTAAGAATTTATGATATTTTTAA

TTTTTTATCATGTCTGATGAGAATTAACATAAAGGCTCAATTGGGTCCTGAATTAATAATAGAGTGAAAA

TTAATCCAGAGGCTCTATTAGAACCTTCAATTAGTAATACCAAGATATATATAAGATAGTAGAGTATAGT

TTAAATGTTGGCATTGTTCATTCTTTCTTTTGTTATTTAATTTATGCTTTCCACGGTGGTTAGTGGTTAC

TTCTGAAGGGTCCAAATAATGCATGAAGAGTTTGAGGACAAGAAGTCTGCCCTAAAAATAGCGATGCAAA

GGCATGGTGTCCAAGCCATACATATAGCGCACTAATTTTATCAGCAGAACAATGGTATTTATAGGTCCTA

GTGCCCAGGCAACAAGAGACACGAATAAAGCATCGATCACGACA
```

3. Genes and their sequences for RNAi
> Sobic.001G488700 (SbSUT1) ortholog of OsSUT1 in rice (SEQ ID NO: 23)-
rice sucrose transporter 1 (OsSUT1), LOC_Os03g07480; Hirose et al.
(2010). Journal of Experimental Botany 61, 3639-3646; Ishimaru et al.
(2001). Plant & Cell Physiology 42(10): 1181-1185.

```
ATGGCTCGCGGCGACGGCGAGCTGGAGCTGTCGGTGGGGGTCCGCGGCGCCGGCGGCGGGGCCGCGGCGG

CGGACCACGTGGCGCCGATCAGCCTCGGCAGGCTCATCCTCGCCGGCATGGTCGCCGGCGGCGTGCAGTA

CGGCTGGGCGCTGCAGCTCTCCCTCCTGACGCCCTACGTGCAGACTCTGGGGCTTTCACATGCCCTCACT
```

APPENDIX -continued

TCATTCATGTGGCTATGCGGTCCTATTGCTGGCTTAGTGGTTCAACCGTTGGTTGGCCTGTACAGTGATA

GGTGTACAGCAAGATGGGGAAGACGGAGGCCATTCATTCTGACAGGATGTGTGCTCATCTGCATTGCTGT

CATTGTTGTTGGCTTTTCGTCAGACATCGGAGCTGCGCTAGGGGACACAAAGGAACATTGCAGTCTCTAT

CATGGTCCTCGCTGGCATGCTGCAATTGTATATGTTCTGGGGTTTTGGCTCCTTGACTTCTCCAACAATA

CTGTGCAAGGTCCAGCACGTGCTATGATGGCTGATTTGTGCGGTCATCATGGGCCTAGTGCAGCTAATTC

AATCTTCTGTTCTTGGATGGCGCTGGGAAACATCCTAGGTTATTCCTCTGGTTCCACAAACAATTGGCAC

AAGTGGTTTCCCTTCCTCAAAACAAATGCCTGTTGTGAAGCCTGTGCAAACCTGAAAGGTGCATTTCTGG

TGGCTGTGGTGTTCCTAGTCATATGCTTGGCTATAACCCTCGTCTTCGCCAAGGAAGTACCATACAGAGG

AAACGAGAACCTCCCAACAAAAGCAAACGGCGAGGTTGAAGCTGAACCTACCGGGCCACTTGCTGTGCTC

AAGGGCTTCAAGAACTTGCCCCGCGGGATGCCATCCGTTCTTCTCGTAACTGGCCTCACCTGGCTCTCGT

GGTTCCCGTTCATCCTCTACGACACCGACTGGATGGGCCGTGAGATCTACCACGGCGACCCAAAGGGCAC

CAATGCTCAGATCTCGGCATTCAACGAAGGTGTCAGAATAGGCGCATTCGGGCTGCTTCTCAACTCGATT

GTTCTAGGATTCAGCTCGTTCCTGATCGAGCCCATGTGCCGGAAGGTCGGGCCGAGGGTTGTGTGGGTGA

CGAGCAACTTCATGGTGTGCATCGCCATGGCGGCCACCGCGCTGATCAGCTTCTGGTCGCTCAAGGACTA

CCACGGATACGTGCAGAACGCCATCACCGCCAGCACGAGCATCAAGGCCGTCTGCCTCGTCCTCTTCGCC

TTCCTGGGTGTCCCTCTCGCCATCCTGTACAGCGTCCCGTTCGCGGTGACGGCGCAGCTAGCGGCCAGCA

TGGGCGGCGGGCAGGGGCTGTGCACCGGCGTCCTCAACATCTCCATCGTTATCCCCCAGGTGATCATCGC

GGTGGGCGCAGGCCCGTGGGACGCGCTGTTCGGCAAGGGCAACATCCCGGCGTTCGGCGTGGCGTCGGGG

TTCGCCCTCATCGGCGGCGTCGTGGGCATGTTCCTGCTGCCCAGGATCTCCAAGCGCCAGTTCAGGGCCG

TCAGCGCGGGCGGCCACTGA

> Sobic.002G361300 (SbAP65) ortholog of OsSUT1 in rice (SEQ ID NO: 24)-
rice aspartic protease 65, LOC_Os07g40260; Huang et al. (2013).
Journal of Experimental Botany 64, 3351-3360.
ATGGCGAGTCGGGCCGGCCTCGGCCGGGCTCGCTCCAGGACCTCGCCGCCGCCGCCATCGCCATCCTCC

TCCTGTCCGCCGCGTCCGGGGCCGCCGCTGGATCCCCCGATCGGCCCGCGCCGGGGCCGCCGCTGTTCCT

CCCGCTCACGCGCTCGTACCCCAACGCCAGCCGGCTCGCCGCCTCGTCGAGGCGCGGCCTCGGCGACGGG

GCGCACCCCAACGCGCGCATGCGCCTCCACGACGATCTCCTCACCAACGGGTACTACACGACGAGGCTGT

ACATCGGGACGCCCCCGCAGGAGTTCGCGTTGATCGTTGACTCCGGGAGCACCGTCACCTACGTGCCCTG

CGCCTCCTGCGAGCAGTGCGGCAACCACCAGGATCCACGATTTCAACCTGATCTCTCCAGTTCATATTCA

CCTGTGAAATGCAACGTCGATTGTACTTGTGACAGTGACAAAAAACAGTGCACTTATGAGAGGCAGTATG

CTGAAATGAGCTCCAGCAGTGGGGTGCTTGGTGAGGACATTGTGTCTTTTGGCAGAGAGAGTGAACTTAA

GCCACAGCGTGCTGTTTTTGGCTGTGAAAATTCTGAAACTGGAGATTTGTTCAGTCAGCATGCTGATGGT

ATAATGGGCCTGGGTCGTGGTCAACTTAGCATAATGGATCAGCTTGTTGAAAAGGGTGTCATAAGCGATT

CATTCTCATTGTGCTATGGCGGTATGGATATTGGTGGTGGTGCTATGGTGCTTGGTGGAGTGCCTGCTCC

TTCTGACATGGTTTTTTCACATTCTGACCCTCTCCGCAGTCCATATTACAACATTGAGTTAAAGGAAATA

CATGTTGCTGGAAAGGCACTGCGGGTAGATTCAAGGGTCTTTAACAGCAAACATGGGACTGTTTTGGATA

GTGGGACCACATATGCCTATTTGCCAGAGCAAGCTTTCGTGGCTTTTAAAGATGCTGTGACAAGTAAAGT

GCATTCTCTCAAGAAAATTCGTGGCCCTGATCCAAATTATAAGGATATCTGCTTTGCAGGTGCTGGAAGG

AACGTCTCAAAGCTACATGAGGTATTTCCAGATGTTGACATGGTATTTGGAAATGGACAGAAGCTGTCTC

TTACACCTGAAAATTATTTATTCCGGCACTCCAAAGTTGATGGGCTTATTGCTTGGGTGTATTCCAAAA

TGGTAAAGATCCAACAACACTATTAGGAGGCATCATTGTTCGTAATACACTTGTGACCTATGACCGTCAC

APPENDIX -continued

```
AATGAAAAGATTGGCTTTTGGAAAACTAACTGTTCAGAGTTGTGGGAGAGGCTACATATCAGTGACGCTC

CATCACCAGCCCCTTCAAGTGATACAAATTCAGAAACTGATATGTCACCTGCTCCTGCCCCTAGTAGCTT

GCCAGAGTTTGATGTTGGTCTCATTACCGTTGATATGTCCATAAATGTTACTTACCCGAATCTGAAACCT

CATCTGCATGAGTTGGCCGAGCTGATAGCTAAAGAACTGGAGATTGACTCTAGTCAGGTTCGAGTTATGA

ATATCACGAGCCAAGGAAATTCTACTCTGATTAGATGGGGTATTTTCCCAGCAGAATCTGATAATGCTAT

GTCCAACGCAACAGCAATGGGTATCATCTATCGGTTAACTCAGCATCATGTTCAGTTGCCTGAAAATCTT

GGCAGTTATCAATTGCTCGAGTGGAATGTGCAGCCTTTACCGAGAAGGTCATGGTTTCAAGAACATGTAG

TCTCTATACTGCTTGGGATTTTACTAGTTGTTTTGGTCACTTTGTCAGCCCTTTTAGTAGTACTTGTTTG

GAGAAAGAAATTTAGTGGTCAAACTGCCTACAGACCTGTTGATTCAGTGGCTCCCGAGCAAGAACTACAG

CCACTATAA
```

>Sobic.003G403300.1 CDS ortholog of OsSPS1 in rice sucrose-phosphate
synthase, putative, LOC_Os01g69030 (SEQ ID NO: 25); Hirose et al.
(2014). Plant Science 225, 102-106.

```
ATGGCGGGGAACGAGTGGATCAATGGGTACCTGGAGGCGATCCTCGACAGCCGCACCACGGCTGGGGGAG

GGGGAGGAGGAGGCGGCGGCGGCGGCGGGGACCCCAGGTCGCCGGTGGCGGGGCGTCGCCGACGAA

GGCGGCGAGCCCCCGCGGCCCGCACATGAACTTCAACCCCTCGCACTACTTCGTCGAGGAGGTGGTCAAG

GGCGTCGACGAGAGCGACCTCCACCGGACATGGATCAAGGTCGTCGCCACACGCAACGCCCGCGAGCGCA

GCACCAGGCTCGAGAACATGTGCTGGCGGATCTGGCATCTCGCGCGTAAGAAGAAACAGCTGGAGCTGGA

GGGCATGCAGAGAATCTCGGCACGCAGGAAGGAACAGGAGCAGGTGCGCCGTGAGGCGACGGAGGACCTG

GCTGAGGATCTGGATGAAGGCGAGAAAGCGGACACCCTCGGCGAGCTTGCGCCGGTTGAGACAGCCAAGA

AGAAGTTCCAGAGGAACTTCTCTGACCTGACCGTCTGGTCTGACGACAATAAGGAGAAGAAGCTTTACAT

TGTGCTCATCAGTGTGCATGGTCTTGTTCGTGGCGAAAACATGGAACTAGGTCGTGATTCTGACACCGGT

GGCCAGGTGAAATATGTTGTCGAACTTGCAAGGGCAATGTCAATGATGCCTGGAGTGTACAGGGTGGACC

TCTTCACTCGTCAAGTGTCATCTCCTGACGTGGACTGGAGCTATGGTGAGCCAACGGAGATGTTATGCTC

CGGTTCCAATGATGGAGAGGGGGCGAGAGTGCCGGAGCCTACATTGTGCGCATACCGTGTGGGCCACGC

GATAAATACCTCAAGAAGGAAGCGCTGTGGCCTTACCTCCAAGAATTTGTCGATGGAGCTCTTGCGCATA

TCCTGAACATGTCCAAGGCTCTGGGAGAGCAGGTTGGAAATGGGAAGCCAGTACTGCCTTACGTGATACA

TGGACACTATGCCGATGCTGGAGATGTTGCTGCTCTCCTCTCCGGTGCGCTGAATGTGCCCATGGTGCTC

ACTGGTCACTCACTTGGGAGGAACAAGCTGGAGCAACTGCTGAAGCAAGGGCGCATGTCTAAAGCGGAGA

TAGATTCAACCTACAAGATCATGAGGCGTATCGAGGGTGAGGAGCTGTCCCTGGATGCGTCAGAGCTTGT

CATCACGAGCACAAGGCAGGAGATTGATGAACAGTGGGGATTATACGATGGATTTGACGTCAAGCTTGAG

AAAGTGTTGAGAGCCCGGGCGAGGCGTGGGGTTAGCTGCCATGGTCGTTTCATGCCTAGGATGGTGGTGA

TTCCTCCAGGAATGGACTTCAGCAATGTTATTCCTGAAGACATTGATGGGGATGGTGACAGCAAAGATGA

TATCGTTGGTTTGGAGGTTGCCTCACCCAAGTCAATGCCTCCAATTTGGGCTGAGGTGATGCGGTTCCTA

ACCAACCCTCACAAGCCGATGATCCTCGCTTTGTCAAGGCCAGACCCGAAGAAGAACATCACTACCCTCG

TCAAAGCGTTTGGAGAGTGCCGCCCACTCAGGGAACTTGCAAACCTTACTCTGATCATGGGGAACAGAGA

TGACATCGACGAAATGTCTGCTGGGAATGCCAGTGTCCTCACCACAGTTCTGAAGCTGATTGACAAGTAT

GATCTGTATGGAAGTGTGGCCTTCCCTAAGCATCACAATCAGGCTGATGTCCCAGAGATCTACCGCCTCG

CGGCCAAAATGAAGGGCGTCTTCATCAACCCTGCTCTCGTTGAGCCGTTCGGTCTCACCCTGATCGAGGC

TGCGGCACACGGACTTCCAATAGTCGCTACCAAGAATGGTGGTCCAGTCGACATTACAACTGCACTGAAC

AATGGACTGCTCGTTGACCCACACGACCAGAACGCCATCGCTGATGCACTGCTGAAGCTTGTGGCGGATA

AGAACCTGTGGCAGGAGTGCCGGAGAAACGGGCTGCGCAACATCCACCTCTACTCATGGCCGGAGCACTG
```

APPENDIX -continued

```
CCGCACTTACCTCACCAGGGTGGCTGGGTGCCGGTTAAGGAACCCGAGGTGGCTGAAGGACACACCGGCA
GATGCTGGAGCTGATGATGAGGAGTTCCTGGAGGATTCCATGGACGCTCAGGACCTGTCACTCCGTCTGT
CCATCGATGGTGAGAAGAGCTCCCTGAACACTAACGACCCACTGTCGTCGGACCCGCAGGATCAGGTGCA
GAAGATCATGAACAAGATCAAGCAGTCATCAGCGCTTCCGCCGTCGATGTCCTCGGGCGGTGACGGTGCC
AAGAATGCAGCCGAGGCCACAGGCGGCACCATGAACAAGTACCCACTCCTGCGCCGGCGCCGGCGCCTGT
TCGTCATAGCTGTGGACTGCTACGAAGACGATGGCCGTGCTAGCAAGAAGATGCTGCAGGTGATCCAAGA
AGTTTTCAGAGCAGTCCGGTCGGACTCCCAGATGTCCAAGATCTCAGGGTTCGCGCTGTCAACTGCGATG
CCGTTGTCCGAGACACTCCAGCTTCTGAAGCTCGGCAAGATCCCAGCGACCGACTTCGACGCCCTCATCT
GTGGCAGTGGCAGCGAGGTGTACTATCCTGGCACGGTGAACTGCATCGACGCTGAAGGAAAGCTGCGCCC
AGACCAGGACTATCTGATGCACATCAGCCACCGCTGGTCCCATGACGGCGCGAGGCAGACCATAGCAAAG
CTCATGGCCAGTCAGGACGGTTCAGACGATGCTGTCGAGCTGGACGTGGCGTCCAGCAATGCACACTGCT
TCGCGTTCCTCATCAAAGATCCCAAAAAGGTGAAAACGGTCGATGAGATGAGAGAGAGGCTGAGGATGCG
TGGTCTCCGGTGCCACATCATGTACTGCAGGAACGCGACAAGACTTCAGGTTGTCCCCCTGCTAGCATCA
AGGTCACAGGCACTCAGGTACCTTTTCGTGCGCTGGGGCCTATCTGTGGGGAACATGTATCTGATCACTG
GGGAACATGGCGATACCGATCTAGAGGAGATGCTATCTGGGTTACACAAGACTGTCATCGTCCGGGGTGT
CACCGAGAAGGGTTCGGAAGCGCTGCTGAGGAGCTCGGGAAGTTACAAGAGGGACGACGTCGTCCCGACT
GAGACCCCCTTGGCTGCGTACACGACTGGTGAGCTGAAGGCCGATGAGATCATGCGGGCTCTGAAGCAGG
TCTCTAAGACTTCCAGCGGCATGTGA
```

4. Genes and their sequences for seed sorting
> proAtOLE1:AtOLE1:RFP(SEQ ID NO: 26)- OLEOSIN1, AT4G25140;
Shintada et al. (2010). The Plant Journal 61, 519-528. *Italicized
bold* is proAtOLE1; regular is cloning vector; bold is AtOLE1 gene,
underline is RFP coding region.

*ATACTGCGTTCCCACATCCCCACCCTACTTAGATCAACACATAAAAGTTAGTAAGTGAAGAACCACAACAACAACAC*

*TAGATTCATCTTCAAGTGTATGTAGGTATAGTAACATGAACAAGAACAGACTCAAGTACAAGATCGCATACGAAAAT*

*GGAAATGGCAATGTCACTTCCACATAATCAAACACGAATCCTCATATCAACAAGGCCTGAGATTCTAACTAGCTCAT*

*AACAACTTAGCCAATAGTTACTTGAGACTACCAAATGTATGTAGAACTAAAGACTAAGGGACAGAGAGTTCGTCTAA*

*ACAGGTGAATCTAGTCGTTGTTATCTAATAAACAATTCAGCCCCAAATGCAGAACACACATAGAGCTCTCTATTGAT*

*TCAAATTACGATCTGATACTGATAACGTCTAGATTTTTAGGGTTAAAGCAATCAATCACCTGACGATTCAAGGTGGT*

*TGGATCATGACGATTCCAGAAAACATCAAGCAAGCTCTCAAAGCTACACTCTTTGGGATCATACTGAACTCTAACAA*

*CCTCGTTATGTCCCGTAGTGCCAGTACAGACATCCTCGTAACTCGGATTGTGCACGATGCCATGGCTATACCCAACC*

*TCGGTCTTGGTCACACCAGGAACTCTCTGGTAAGCTAGCTCCACTCCCCAGAAACAACCGGCGCCAAATTGCGCGAA*

*GACGAGACCCGAATCCGAGTCTGTTGAAAAGGTTGTTCATTGGGGATTTGTATACGGAGATTGGTCGTCGAGAGGTT*

*TGAGGGAAAGGACAAATGGGTTTGGCTCTGGAGAAAGAGAGTGCGGCTTTAGAGAGAGAATTGAGAGGTTTAGAGAG*

*AGATGCGGCGGCGATGAGCGGAGGAGAGACGACGAGGACCTGCATTATCAAAGCAGTGACGTGGTGAAATTTGGAAC*

*CTAAATCCTAAATTTTTCTAATTTTGTTGCCAATAGTGGATATGTGGGCCGTATAGAAGGAATCTATTGAAGGCCCA*

*AACCCATACTGACGAGCCCAAAGGTTCGTTTTGCGTTTTATGTTTCGGTTCGATGCCAACGCCACATTCTGAGCTAG*

*GCAAAAAACAAACGTGTCTTTGAATAGACTCCTCTCGTTAACACATGCAGCGGCTGCATGGTGACGCCATTAACACG*

*TGGCCTACAATTGCATGATGTCTCCATTGACACGTGACTTCTCGTCCTTTCTTAATATATCTAACAAACACTCCT*

*ACCTCTTCCAAAATATATACACATCTTTTTGATCAATCTCTCATTCAAAATCTCATTCTCTCTAGTAAACAAGAACA*

*AAAAAATGGCGGATACAGCTAGAGGAACCCATCACGATATCATCGGCAGAGACCAGTACCCGATGATGGGCCGAGAC*

*CGAGACCAGTACCAGATGTCCGGACGAGGATCTGACTACTCCAAGTCTAGGCAGATTGCTAAAGCTGCAACTGCTGT*

*CACAGCTGGTGGTTCCCTCCTTGTTCTCTCCAGCCTTACCCTTGTTGGAACTGTCATAGCTTTGACTGTTGCAACAC*

APPENDIX -continued

*CTCTGCTCGTTATCTTCAGCCCAATCCTTGTCCCGGCTCTCATCACAGTTGCACTCCTCATCACCGGTTTTCTTTCC*

*TCTGGAGGGTTTGGCATTGCCGCTATAACCGTTTTCTCTTGGATTTACAAGTAAGCACACATTTATCATCTTACTTC*

*ATAATTTTGTGCAATATGTGCATGCATGTGTTGAGCCAGTAGCTTTGGATCAATTTTTTTGGTCGAATAACAAATGT*

*AACAATAAGAAATTGCAAATTCTAGGGAACATTTGGTTAACTAAATACGAAATTTGACCTAGCTAGCTTGAATGTGT*

*CTGTGTATATCATCTATATAGGTAAAATGCTTGGTATGATACCTATTGATTGTGAATAGGTACGCAACGGGAGAGCA*

*CCCACAGGGATCAGACAAGTTGGACAGTGCAAGGATGAAGTTGGGAAGCAAAGCTCAGGATCTGAAAGACAGAGCTC*

*AGTACTACGGACAGCAACATACTGGTGGGGAACATGACCGTGACCGTACTCGTGGTGGCCAGCACACTACT*GCGGTA

CCCCTGATGGCCTCCTCCGAGGACGTCATCAAGGAGTTCATGCGCTTCAAGGTGCGCATGGAGGGCTCCGTGAACGG

CCACGAGTTCGAGATCGAGGGCGAGGGCGAGGGCCGCCCCTACGAGGGCACCCAGACCGCCAAGCTGAAGGTGACCA

AGGGCGGCCCCCTGCCCTTCGCCTGGGACATCCTGTCCCCTCAGTTCCAGTACGGCTCCAAGGCCTACGTGAAGCAC

CCCGCCGACATCCCCGACTACTTGAAGCTGTCCTTCCCCGAGGGCTTCAAGTGGGAGCGCGTGATGAACTTCGAGGA

CGGCGGCGTGGTGACCGTGACCCAGGACTCCTCCCTGCAGGACGGCGAGTTCATCTACAAGGTGAAGCTGCGCGGCA

CCAACTTCCCCTCCGACGGCCCCGTAATGCAGAAGAAGACCATGGGCTGGGAGGCCTCCACCGAGCGGATGTACCCC

GAGGACGGCGCCCTGAAGGGCGAGATCAAGATGAGGCTGAAGCTGAAGGACGGCGGCCACTACGACGCCGAGGTCAA

TGGCCTCCTCCGAGGACGTCATCAAGGAGTTCATGCGCTTCAAGGTGCGCATGGAGGGCTCCGTGAACGG

CCACGAGTTCGAGATCGAGGGCGAGGGCGAGGGCCGCCCCTACGAGGGCACCCAGACCGCCAAGCTGAAG

GTGACCAAGGGCGGCCCCCTGCCCTTCGCCTGGGACATCCTGTCCCCTCAGTTCCAGTACGGCTCCAAGG

CCTACGTGAAGCACCCCGCCGACATCCCCGACTACTTGAAGCTGTCCTTCCCCGAGGGCTTCAAGTGGGA

GCGCGTGATGAACTTCGAGGACGGCGGCGTGGTGACCGTGACCCAGGACTCCTCCCTGCAGGACGGCGAG

TTCATCTACAAGGTGAAGCTGCGCGGCACCAACTTCCCCTCCGACGGCCCCGTAATGCAGAAGAAGACCA

TGGGCTGGGAGGCCTCCACCGAGCGGATGTACCCCGAGGACGGCGCCCTGAAGGGCGAGATCAAGATGAG

GCTGAAGCTGAAGGACGGCGGCCACTACGACGCCGAGGTCAAGACCACCTACATGGCCAAGAAGCCCGTG

CAGCTGCCCGGCGCCTACAAGACCGACATCAAGCTGGACATCACCTCCCACAACGAGGACTACACCATCG

TGGAACAGTACGAGCGCGCCGAGGGCCGCCACTCCACCGGCGCCTAATCTAGAGTCCGCAAAAATCACCA

GTCTCTCTCTACAAATCTATCTCTCTATTTTTCTCCAGAATAATGTGTGAGTAGTTCCCAGATAAGGG

AATTAGGGTTCTTATAGGGTTTCGCTCATGTGTTGAGCATATAAGAAACCCTTAGTATGTATTTGTATTT

GTAAAATACTTCTATCAATAAAATTTCTAATTCCTAAAACCAAAATCCAGTGACCATGGCTATACCCAAC

CTCGGTCTTGGTCACACCAGGAACTCTCTGGTAAGCTAGCTCCACTCCCAGAAACAACCGGCGCCAAAT

TGCGCGAATTGCTGACCTGAAGACGGAACATCATCGTCGGGTCCTTGGGCGATTGCGGCGGAAGATGGGT

CAGCTTGGGCTTGAGGACGAGACCCGAATCCGAGTCTGTTGAAAAGGTTGTTCATTGGGGATTTGTATAC

GGAGATTGGTCGTCGAGAGGTTTGAGGGAAAGGACAAATGGGTTTGGCTCTGGAGAAAGAGAGTGCGGCT

TTAGAGAGAATTGAGAGGTTTAGAGAGAGATGCGGCGGCGATGAGCGGAGGAGAGACGACGAGGACCT

GCATTATCAAAGCAGTGACGTGGTGAAATTTGGAACTTTTAAGAGGCAGATAGATTTATTATTTGTATCC

ATTTTCTTCATTGTTCTAGAATGTCGCGGAACAAATTTTAAAACTAAATCCTAAATTTTTCTAATTTTGT

TGCCAATAGTGGATATGTGGGCCGTATAGAAGGAATCTATTGAAGGCCCAAACCCATACTGACGAGCCCA

AAGGTTCGTTTTGCGTTTTATGTTTCGGTTCGATGCCAACGCCACATTCTGAGCTAGGCAAAAAACAAAC

GTGTCTTTGAATAGACTCCTCTCGTTAACACATGCAGCGGCTGCATGGTGACGCCATTAACACGTGGCCT

ACAATTGCATGATGTCTCCATTGACACGTGACTTCTCGTCTCCTTTCTTAATATATCTAACAAACACTCC

TACCTCTTCCAAAATATATACACATCTTTTTGATCAATCTCTCATTCAAAATCTCATTCTCTCTAGTAAA

CAAGAACAAAAAAATGGCGGATACAGCTAGAGGAACCCATCACGATATCATCGGCAGAGACCAGTACCCG

ATGATGGGCCGAGACCGAGACCAGTACCAGATGTCCGGACGAGGATCTGACTACTCCAAGTCTAGGCAGA

APPENDIX -continued

TTGCTAAAGCTGCAACTGCTGTCACAGCTGGTGGTTCCCTCCTTGTTCTCTCCAGCCTTACCCTTGTTGG

AACTGTCATAGCTTTGACTGTTGCAACACCTCTGCTCGTTATCTTCAGCCCAATCCTTGTCCCGGCTCTC

ATCACAGTTGCACTCCTCATCACCGGTTTTCTTTCCTCTGGAGGGTTTGGCATTGCCGCTATAACCGTTT

TCTCTTGGATTTACAAGTAAGCACACATTTATCATCTTACTTCATAATTTTGTGCAATATGTGCATGCAT

GTGTTGAGCCAGTAGCTTTGGATCAATTTTTTTGGTCGAATAACAAATGTAACAATAAGAAATTGCAAAT

TCTAGGGAACATTTGGTTAACTAAATACGAAATTTGACCTAGCTAGCTTGAATGTGTCTGTGTATATCAT

CTATATAGGTAAAATGCTTGGTATGATACCTATTGATTGTGAATAGGTACGCAACGGGAGAGCACCCACA

GGGATCAGACAAGTTGGACAGTGCAAGGATGAAGTTGGGAAGCAAAGCTCAGGATCTGAAAGACAGAGCT

CAGTACTACGGACAGCAACATACTGGTGGGGAACATGACCGTGACCGTACTCGTGGTGGCCAGCACACTA

CTGCGGTACCCCTGATGGCCTCCTCCGAGGACGTCATCAAGGAGTTCATGCGCTTCAAGGTGCGCATGGA

GGGCTCCGTGAACGGCCACGAGTTCGAGATCGAGGGCGAGGGCGAGGGCCGCCCCTACGAGGGCACCCAG

ACCGCCAAGCTGAAGGTGACCAAGGGCGGCCCCCTGCCCTTCGCCTGGGACATCCTGTCCCCTCAGTTCC

AGTACGGCTCCAAGGCCTACGTGAAGCACCCCGCCGACATCCCCGACTACTTGAAGCTGTCCTTCCCCGA

GGGCTTCAAGTGGGAGCGCGTGATGAACTTCGAGGACGGCGGCGTGGTGACCGTGACCCAGGACTCCTCC

CTGCAGGACGGCGAGTTCATCTACAAGGTGAAGCTGCGCGGCACCAACTTCCCCTCCGACGGCCCCGTAA

TGCAGAAGAAGACCATGGGCTGGGAGGCCTCCACCGAGCGGATGTACCCCGAGGACGGCGCCCTGAAGGG

CGAGATCAAGATGAGGCTGAAGCTGAAGGACGGCGGCCACTACGACGCCGAGGTCAAGACCACCTACATG

GCCAAGAAGCCCGTGCAGCTGCCCGGCGCCTACAAGACCGACATCAAGCTGGACATCACCTCCCACAACG

AGGACTACACCATCGTGGAACAGTACGAGCGCGCCGAGGGCCGCCACTCCACCGGCGCCTAATCTAGAGT

CCGCAAAAATCACCAGTCTCTCTCTACAAATCTATCTCTCTATTTTTCTCCAGAATAATGTGTGAGTA

GTTCCCAGATAAGGGAATTAGGGTTCTTATAGGGTTTCGCTCATGTGTTGAGCATATAAGAAACCCTTAG

TATGTATTTGTATTTGTAAAATACTTCTATCAATAAAATTTCTAATTCCTAAAACCAAAATCCAGTGA

> proSbOLE1:SbOLE1:RFP(SEQ ID NO: 27)—Sobic.006G167700,
ortholog of AtOLE1 in *Arabidopsis*; Shimada et al.
(2010). The Plant Journal 61, 519-528.
ACGGGCCGAGGGAGTAGTATATATGAGATGTTTATTTTTCTTTTTCTTTTTCCAACTTGTTGGGTATTCT

GGTTCTGGGTGGAAAGGGGGGCATCAAAATTCAAAAAGAGAAAAAGGTGTATATGATCCGCCTACTTGCC

GGTCGATCAGTATGGCACCTGACTGAGTACAGGTCATGGGGGCAAAAGCAGGCCACTGTTTCATGAATAG

TGGAGTGGGTCATGAACTCATAATGTGTTTTTATTAGCATGATGAAATGAAAAAGGTACGGAAAGGAGAA

GAGAGCTAGCGATACAAAGGCACGCTTAGTTTGGCATTTTGGAGTGGAAAGGGCTGTACTTCGATTTTTT

TTTCCTTGCAAAAAGGCGTATTTGGTTTAGGCCTTGTTTAGTTCCCCAAAAATTTTGCAAAATTTTTCAC

ATTCTCCGTCACATCGAATCTTTAGACGTATGCATTGAGTATTAAATATAAATAAAAATAAAAACTAATT

GCACAGTTTGGTCGAAATTGACGAGACGAATCTTTTGAGCCTAGTTAGTCTATAATTGGACAATATTTGT

CAAATACAAACGAAAGTGATACTATTCCTATTTTGCAAAAAAAATTGGAAGTAAACAAGCCCTTAATTGG

AGCGGAACTGTTCCCATCGAAGTACTACGGTATAGCACCAAGCAAATGCAGCTGTGCACAGGGCAAGCTG

CCAAAGGAGTGGCAGGGCACCAGCCACATAGGTTTGACGTGGAAGGCATTGTCCTACGCAATGAGAATTT

TAGGTCCCGATTAGCAAAGCTCCCAAGCTTATTGTGGACTAAATCCAATAAGAACTCTGCTAAACAGAGT

TTTTTTTAGAGAGAATTGATTTTCTGTGTTGAATAATTTTTTGAAATGAACTAAGAGGCTGTAAAAGTA

GTTTCTATTGATTCTGTGTAGTCATTCTCTACTGTGATTTTAAGAGTTTATATTAAAGAATCGAAGAGAA

TCACTGTAAGTCACATAATCACTTTTCACCAAGAATCAGAATTAGATAGAGCTTCACCAAACATGCCCTT

TACCACGAACACACTTGAAGCGAAGCAAATTTGCAGCCAAAATCTGGAAGATCGATTTTGACCGGTAGAA

APPENDIX -continued

GAAACTGATCTTATGTGTCACCGCTCCACCTAGTCCAATAAGAACGGGGAGGGACACAATAATGTCGAAA

TTAGGTGCCCAGCTTGATGCTAGTAGTAGCTTAGCTTCAGTGGTTCATCTCGAAAAGCAAGGCATGCTAG

CTGCTAGCAGCGGTTTGAACGGCTCCAAAACGTTGATTCCTGTCTCCCTTTCGCCTAGTATCCTCGTCAG

AGCTTTTCAGTTTCCAAGGCCTCCTGACTTTACACGCCAGCATCGGAATCAGGCGAAGTCCATACTGTAC

CAAACACTTCTTTTTTTAATTAATAAAAAAAAGAAGAAAAATGGAGCATATGGTGTGAGGTGAACGAATG

GGCCAACGGGCACACAAATTATTGCATGGACCCAGACTATTGCAAGCCTGCTAATAGCGAGACACGGAAC

TGGACTTCAGAGACACGCAAGGCAAGAGAGAAAAAAAGCCCAGACTACGGCCCACATGAGATTCGGCCCC

GTCACCTTCACCTCCGTCCTCCGGCAACCAGCGGCCGATCCAAGTGAGCGTCCGTCCACAACCTCGTACG

TATCGCCGCGCGGAAGCGGCGCGATCGCGAACGCACGCCTTGTCGTCTCGTCGACACCCCCCCTACACA

GGTGTCGCGCGGCTCCGGACACGAGTCTCGCATGCGTCCCACGCGGCGGCGCCAGGTCCCGCCTCCGCGC

ATCCCCACGCCCTCTATAAACGCCCCGCTCTCCCTGGCCCTCGTCCACCTCACTCGTAGCCGTAGCATCA

GCTGCAGCAGGCGCTCTGGGCAGTGTGCGCACGTGGTGGTACTACCTAGCTCGCTCTGCTAAGCTAAGCT

AAGCAGCTTGCCATGGCGGATCACCACCGGGGCGGGACGGGAGGTGGCGCGGGTGGCTACGGCGACTACA

ACCGTGGGGCGGCGCCGGCATGTACGGCGAGTCGCAGCAGCAGCAGCAGAAGCAGGGCGCCATGATGAC

GGCGATCAAGGCGGCGACGGCCGCGACCTTCGGCGGGTCGATGCTGGTGCTGTCCGGGCTGATCCTGGCG

GGCACCGTGATCGCGCTCACGGTCGCCACCCCGGTGCTGGTGATCTTCAGCCCGGTGCTGGTGCCGGCCG

CCATCGCGCTGGCGCTCATGGCCGCCGGGTTCGTCACCTCCGGCGGCCTCGGCGTCGCCGCGCTGTCCGT

CTTCTCCTGGATGTACAAGTACCTGACGGGCAAGCACCCGCCGGGCGCCGACCAGCTGGACCACGCCAAG

GCGAGGCTGGCGTCCAAGGCCCGCGACATCAAGGACGCAGCGCAGCACCGCATCGACCAGGCGCAGGGGT

CTgcggtaccCCTGATGGCCTCCTCCGAGGACGTCATCAAGGAGTTCATGCGCTTCAAGGTGCGCATGGA

GGGCTCCGTGAACGGCCACGAGTTCGAGATCGAGGGCGAGGGCGAGGGCCGCCCCTACGAGGGCACCCAG

ACCGCCAAGCTGAAGGTGACCAAGGGCGGCCCCCTGCCCTTCGCCTGGGACATCCTGTCCCCTCAGTTCC

AGTACGGCTCCAAGGCCTACGTGAAGCACCCCGCCGACATCCCCGACTACTTGAAGCTGTCCTTCCCCGA

GGGCTTCAAGTGGGAGCGCGTGATGAACTTCGAGGACGGCGGCGTGGTGACCGTGACCCAGGACTCCTCC

CTGCAGGACGGCGAGTTCATCTACAAGGTGAAGCTGCGCGGCACCAACTTCCCCTCCGACGGCCCCGTAA

TGCAGAAGAAGACCATGGGCTGGGAGGCCTCCACCGAGCGGATGTACCCCGAGGACGGCGCCCTGAAGGG

CGAGATCAAGATGAGGCTGAAGCTGAAGGACGGCGGCCACTACGACGCCGAGGTCAAGACCACCTACATG

GCCAAGAAGCCCGTGCAGCTGCCCGGCGCCTACAAGACCGACATCAAGCTGGACATCACCTCCCACAACG

AGGACTACACCATCGTGGAACAGTACGAGCGCGCCGAGGGCCGCCACTCCACCGGCGCCTAATCTAGAGT

CCGCAAAAATCACCAGTCTCTCTCTACAAATCTATCTCTCTATTTTTCTCCAGAATAATGTGTGTGAGTA

GTTCCCAGATAAGGGAATTAGGGTTCTTATAGGGTTTCGCTCATGTGTTGAGCATATAAGAAACCCTTAG

TATGTATTTGTATTTGTAAAATACTTCTATCAATAAATTTCTAATTCCTAAAACCAAAATCCAGTGAC

> proSbABI3:RFP (SEQ ID NO: 28)—Sobic.002G161600, ortholog of
ABA INSENSITIVE 3(AtABI3) in *Arabidopsis*; Monke et al. (2004).
Planta 219, 158-166

CTACCTGCCGTTGGCTCTAGGATTGGAGGGCGCGAGTAAGGCGAAGCACAGATAAAAAGGGATTGATTCA

TTCTAGGAAGCTTCCACTATGTCATAAAAGCCCGGTAGCTTTGTCCAGTAACTCTCAAAATGGAAGCCAT

GCTTGATATGAATACCATCTTTGAGACCGAGCACCAAGGGGCAATGATCAGAGATATCAAAAGCTTGGCT

CCGCAAGATACACTTTGGAAAGAGTGGTTCCCAATATGTATTGTAGTACAAAGGACCCAATCAAGTTTGA

CCAAAGTGGGTGCTTCCCTCTTTTTCGACCAGGGTTTCTTGTGCTTTGATCGATGTGAAGATATTGTTTC

CTATTTAGAAACAAAAGGAAACAATTTGTATGTTTTTGCTCTTCTCTCCTCTCTTCTCTCTATTCCTTGC

TATATTAGCAAAATACTTATGTAGCACAGTTAGTGCACATAGAAACTATGATAGTTTCTATACTATGAGT

APPENDIX -continued

ACCCTAAGAAAATTGACATTTGTTTAGATGGTTTGCTTGCTAATTTGGATTTCATACTTCTACGAGGCCA

GTCTCAATGTGACTTACAAAAGAATTTCATTCTCATTTCATGATATGACACATCAACAAATTTGTTAGTT

AGCAAGTTATTATGATGTGAAATAGAGAGCATGGGTGATGACCGATCTAATTTATCTCACCAACTAGAAT

GAGAAAAAAGCTCCCTACTGCTGGCAAGGCTGACCTTGACCTTGCTTAGCAAACCCTATCAAATCTTTGG

CAAGAGCTGAAATCAAAGATAGTGACTCATGGCCCGACATCGCTCGGCCCACTGCTATAGAACAAGAGCA

TACACAACAAACCCTCACTCGTTGTGGTTTATGATACCTTAATGACAAGTGGGCCTGTACCTTTCTGGCC

CCATGTCTCTGACAGAGGTATAGGGTGTATGCTATGGGTGAGAAGCAGGATGGCCGAGGAGAGGCTGGCA

TGGGCGGTGGAGTGCTCCCTAGTCCGATAGTCCCTAGTCCTAGTCTCTTCGGTTCCCTCCTATATATGGC

CAAATGGGCCGGACACGATCGGCATGGGCTTGGCACAAAAAAAAGCACAAGCATGATGTAAGGCTGTGC

CTAGGCCGTTGGTTCGGCCCGCAATGCCGACATGGGGCATGACATGGTTAATGGGCCGGCACGACAGCGA

CCCTATTATTTTGCGCCATTGGATAGCCATAGGAGACACCAGCACCGTTGGATCAGCCGAGACTGTCACA

TATAAGGAAAGATGTGCCTGAAACCCTACCTCTCCACCTCTCCTACGCAGGCGCCGCTGCGCTCTCCCTC

TCCCCACTCCCTTTTCCCACATAGGCGCACTATCGCTCTCTCCGACTCCCACTCTTCCTCTCTCCGATCC

CTTCACTTCGCATAGGCGCGTGCGTGGCCTCGCCACTCTCGAAGCTTGTGGCGGCGGCCCCATCCCCGGT

AGTGCGGTGGCAGCCTTCCTACGGTGGTGGGCTAGCCTAACCTGTGATGTGTGGTTTTATATGAGACAAA

CATTTGTTGATCTGTATTTTTGATATGTTTTTCTTTGATTCATCGATCTATTTCTCTTCTCGATCTATGA

TTCTTAAGTTTCTTTTTTCAATCTGTGATGTAGTCACTATGAATTTGAAGATCTCAGCAGGTGTCATGGC

ATAGGTAAAAGGCCATAGTACTGTGCCTAGGTCAAGACGGTGACTTGGTGGCACTATCAGGCAGGCAAGC

TACCGTGCTGCGCAGTGCCGTGTCTAGCCGTGCCCGTGCTGCCGTTTGGCCTCGTATACCTAGTCCCTCT

TCGTCCCCGGTTCCCCCTCCACCTCTTGCTTGTCCAGTTCGTCTCCTCAATAACCACACCCGCACACCTA

CACCGAGAGGCGGCGACAGAGGGAAGACACATACACCGTCTCTTTCCTTCCTTTGTCGTCAACTCGTCGT

GTCTCTCTGCggtaccCCTGATGGCCTCCTCCGAGGACGTCATCAAGGAGTTCATGCGCTTCAAGGTGCG

CATGGAGGGCTCCGTGAACGGCCACGAGTTCGAGATCGAGGGCGAGGGCGAGGGCCGCCCCTACGAGGGC

ACCCAGACCGCCAAGCTGAAGGTGACCAAGGGCGGCCCCCTGCCCTTCGCCTGGGACATCCTGTCCCCTC

AGTTCCAGTACGGCTCCAAGGCCTACGTGAAGCACCCCGCCGACATCCCCGACTACTTGAAGCTGTCCTT

CCCCGAGGGCTTCAAGTGGGAGCGCGTGATGAACTTCGAGGACGGCGGCGTGGTGACCGTGACCCAGGAC

TCCTCCCTGCAGGACGGCGAGTTCATCTACAAGGTGAAGCTGCGCGGCACCAACTTCCCCTCCGACGGCC

CCGTAATGCAGAAGAAGACCATGGGCTGGGAGGCCTCCACCGAGCGGATGTACCCCGAGGACGGCGCCCT

GAAGGGCGAGATCAAGATGAGGCTGAAGCTGAAGGACGGCGGCCACTACGACGCCGAGGTCAAGACCACC

TACATGGCCAAGAAGCCCGTGCAGCTGCCCGGCGCCTACAAGACCGACATCAAGCTGGACATCACCTCCC

ACAACGAGGACTACACCATCGTGGAACAGTACGAGCGCGCCGAGGGCCGCCACTCCACCGGCGCCTAATC

TAGAGTCCGCAAAAATCACCAGTCTCTCTCTACAAATCTATCTCTCTCTATTTTTCTCCAGAATAATGTG

TGAGTAGTTCCCAGATAAGGGAATTAGGGTTCTTATAGGGTTTCGCTCATGTGTTGAGCATATAAGAAAC

CCTTAGTATGTATTTGTATTTGTAAAATACTTCTATCAATAAAATTTCTAATTCCTAAAACCAAAATCCA

GTGACGCGGCCGCACCCATAATACCCATAATAGCTGTTTGCCAGTAATCATGGTCATAGCTGTTTCCTGT

G

> proLTP2:RFP(SEQ ID NO: 29)—lipid transfer protein, LTP2,
HORVU4Hr1G089500 Kalla et al. (1994). The Plant Journal 6(6): 849-860.
GATCTCGATGTGTAGTCTACGAGAAGGGTTAACCGTCTCTTCGTGAGAATAACCGTGGCCTAAAAATAAG

CCGATGAGGATAAATAAAATGTGGTGGTACAGTACTTCAAGAGGTTTACTCATCAAGAGGATGCTTTTCC

GATGAGCTCTAGTAGTACATCGGACCTCACATACCTCCATTGTGGTGAAATATTTTGTGCTCATTTAGTG

APPENDIX -continued

ATGGGTAAATTTTGTTTATGTCACTCTAGGTTTTGACATTTCAGTTTTGCCACTCTTAGGTTTTGACAAA

TAATTTCCATTCCGCGGCAAAAGCAAAACAATTTTATTTTACTTTTACCACTCTTAGCTTTCACAATGTA

TCACAAATGCCACTCTAGAAATTCTGTTTATGCCACAGAATGTGAAAAAAAACACTCACTTATTTGAAGC

CAAGGTGTTCATGGCATGGAAATGTGACATAAAGTAACGTTCGTGTATAAGAAAAAATTGTACTCCTCGT

AACAAGAGACGGAAACATCATGAGACAATCGCGTTTGGAAGGCTTTGCATCACCTTTGGATGATGCGCAT

GAATGGAGTCGTCTGCTTGCTAGCCTTCGCCTACCGCCCACTGAGTCCGGGCGGCAACTACCATCGGCGA

ACCACCCAGATGACCTCTACCGATCGACCGGACATGAATGCGCTACCTTCGTCGGCGACGATGGCCGCGT

ACGCTGGCGACGTGCCCCCGCATGCATGGCGGCACATGGCGAGCTAGGAACCTAGGACCGTGCGTGGCCG

CCGGCTATAAATATCCCATGGTCGTGAGACCACTAGAAGGAAGCAGCACCTGGCACTGCGAGAGCGAGCG

TGCAGTGAGTAGATAGACTAGACCAACGACGACGGCAGGCggtaccCCTGATGGCCTCCTCCGAGGACGT

CATCAAGGAGTTCATGCGCTTCAAGGTGCGCATGGAGGGCTCCGTGAACGGCCACGAGTTCGAGATCGAG

GGCGAGGGCGAGGGCCGCCCCTACGAGGGCACCCAGACCGCCAAGCTGAAGGTGACCAAGGGCGGCCCCC

TGCCCTTCGCCTGGGACATCCTGTCCCCTCAGTTCCAGTACGGCTCCAAGGCCTACGTGAAGCACCCCGC

CGACATCCCCGACTACTTGAAGCTGTCCTTCCCCGAGGGCTTCAAGTGGGAGGGCGTGATGAACTTCGAG

GACGGCGGCGTGGTGACCGTGACCCAGGACTCCTCCCTGCAGGACGGCGAGTTCATCTACAAGGTGAAGC

TGCGCGGCACCAACTTCCCCTCCGACGGCCCCGTAATGCAGAAGAAGACCATGGGCTGGGAGGCCTCCAC

CGAGCGGATGTACCCCGAGGACGGCGCCCTGAAGGGCGAGATCAAGATGAGGCTGAAGCTGAAGGACGGC

GGCCACTACGACGCCGAGGTCAAGACCACCTACATGGCCAAGAAGCCCGTGCAGCTGCCCGGCGCCTACA

AGACCGACATCAAGCTGGACATCACCTCCCACAACGAGGACTACACCATCGTGGAACAGTACGAGCGCGC

CGAGGGCCGCCACTCCACCGGCGCCTAATCTAGAGTCCGCAAAAATCACCAGTCTCTCTCTACAAATCTA

TCTCTCTCTATTTTTCTCCAGAATAATGTGTGAGTAGTTCCCAGATAAGGGAATTAGGGTTCTTATAGGG

TTTCGCTCATGTGTTGAGCATATAAGAAACCCTTAGTATGTATTTGTATTTGTAAAATACTTCTATCAAT

AAAATTTCTAATTCCTAAAACCAAAATCCAGTGACGCGGCCGCACCCATAATACCCATAATAGCTGTTTG

CCAGTAATCATGGTCATAGCTGTTTCCTGTG

5. The cDNA sequence of EsMYB41 (from *Eutrema salsugineum*) for
sorting transgenic plants (seed coat color change)(SEQ ID NO: 30)—
*Eutrema salsugineum* transcription factor MYB114 (LOC18008560)
ATGGAGGGCTCGTCCAAAGGGTTGAGAAAAGGTGCTTGGACTGCTGAAGAAGATAGTCTCTTGAGGCAAT

GCATTGATAAGTATGGAGAAGGCAAATGGCATCAAGTTCCTTTAAGAGCTGGGCTAAATCGGTGCAGGAA

GAGTTGTAGATTAAGATGGTTGAACTACCTGAAGCCAAGTATCAAAAGAGGAAAACTTAGCTCTGATGAG

GTTGATCTTCTTCTTCGCCTTCATAAGCTTCTAGGAAACAGGTGGTCCTTAATTGCTGGTAGATTACCCG

GTCGTACTGCTAATGATGTCAAGAATTACTGGAACACCCATTTGAGTAAGAAGCATGAACCATGTTGTAA

GACAAAGATGAAAAATAGAAACATTCCTTGCTCTTCTACCGCACCAGCCAAAAAAATCGACGTTTTCAAA

CCTCGACCTCGATCCTTCACTGTTAACAACGGCTGCAGTCGTCATCCGCATGGCCTGCCAGAAGCTGACG

TTAGTCCTCCATGCCTTGGACCCAAAAGCATCAGTAATTTTTGTGAAAATATTATCACATGTAGAAAAGA

TGAGGAGAAATATGAGCTTGTTAGTAATTTAATGGTTAATGGAGAGAAGTGGTGGGAGAATTTGTTAGAT

GAGAGCCAAGAGCCAGATTCGCTCGTTCCAGAAGCCACGGTAGCAGAAAAGGGGCAACTTCCGCTTTTG

ACGTTGAGGAACTTTGGAGTTTGTTGGATGGGGACACTGTGGAACTTGATTAG

What is claimed is:

1. A *Sorghum bicolor* seed designated as MS8, wherein a sample of said seed has been deposited as ATCC Patent Deposit No. PTA-127606.

2. A plant, or a part thereof, produced by growing the seed of claim 1.

3. A *Sorghum bicolor* plant having all the physiological and morphological characteristics of the plant of claim 2.

4. A tissue culture of regenerable cells from the plant, or the part thereof, of claim 2.

5. The tissue culture of regenerable cells of claim 4, wherein the regenerable cells are selected from the group consisting of protoplasts and calli, and wherein the regenerable cells are from a leaf, pollen, ovule, cotyledon, hypocotyl, embryo, root, pod, flower, shoot or stalk.

6. A protoplast produced from the tissue culture of claim 4.

7. A *Sorghum bicolor* plant regenerated from the tissue culture of claim 4, wherein the plant has all of the physiological and morphological characteristics of a plant produced by growing a seed designated MS8 and deposited under ATCC Patent Deposit No. PTA-127606.

8. A tissue culture of regenerable cells from the plant, or the part thereof, of claim 7.

9. The tissue culture of claim 8, wherein said regenerable cells are selected from the group consisting of protoplasts and calli, and wherein the regenerable cells are from a leaf, pollen, ovule, cotyledon, hypocotyl, embryo, root, pod, flower, shoot or stalk.

10. A protoplast produced from the tissue culture of claim 9.

11. A method for producing a *Sorghum bicolor* mutant MS8-derived *Sorghum bicolor* L. Moench plant, comprising: (a) crossing MS8 plants grown from MS8 seed, representative seed of which has been deposited under ATCC Patent Deposit No. PTA-127606, with a second *Sorghum bicolor* plant to yield progeny *Sorghum bicolor* seed; and (b) growing the progeny seed to yield a *Sorghum bicolor* mutant MS8-derived *Sorghum bicolor* plant.

12. The method of claim 11, further comprising: (c) crossing the *Sorghum bicolor* mutant MS8-derived *Sorghum bicolor* plant of (b) with itself or a third *Sorghum bicolor* plant to yield a second *Sorghum bicolor* MS8-derived *Sorghum bicolor* progeny seed; and (d) growing the second *Sorghum bicolor* progeny seed of (c) to yield a second *Sorghum bicolor* mutant MS8-derived *Sorghum bicolor* plant.

13. The method of claim 12, wherein (c) and (d) are repeated at least one time to generate an additional *Sorghum bicolor* mutant MS8-derived *Sorghum bicolor* plant.

14. A method of introducing a desired trait into *Sorghum bicolor* MS8 comprising:

(a) crossing MS8 plants grown from MS8 seed, representative seed of which has been deposited under ATCC Patent Deposit No. PTA-127606, with plants of a second *Sorghum bicolor* mutant that comprise a desired trait to produce F1 progeny plants, wherein the desired trait is selected from the group consisting of male sterility, site-specific recombination, increased transformability, abiotic stress tolerance, herbicide resistance, insect resistance, disease resistance, altered phosphorus, altered antioxidants, altered fatty acids, altered essential amino acids and altered carbohydrates;

(b) selecting F1 progeny plants that have the desired trait to produce selected F1 progeny plants;

(c) crossing the selected progeny plants with the MS8 plants to produce backcross progeny plants;

(d) selecting for backcross progeny plants that have the desired trait and physiological and morphological characteristics of *Sorghum bicolor* mutant MS8 to produce selected backcross progeny plants; and (e) repeating steps (c) and (d) three or more times in succession to produce selected fourth or higher backcross progeny plants that comprise the desired trait and all the physiological and morphological characteristics of *Sorghum bicolor* mutant MS8.

15. A plant produced by the method of claim 14, wherein the plant has the desired trait and all of the physiological and all morphological characteristics of said *Sorghum bicolor* mutant MS8.

16. A method for producing a *Sorghum bicolor* mutant plant having an altered agronomic trait comprising introducing a polynucleotide into a MS8 plant grown from MS8 seed, representative seed of which has been deposited under ATCC Patent Deposit No. PTA-127606, wherein the polynucleotide confers an altered agronomic trait to the plant selected from the group consisting of insect resistance, disease resistance, herbicide resistance, abiotic stress resistance, fatty acid metabolism, starch metabolism, carbohydrate metabolism, amino acid metabolism, phosphorus metabolism, antioxidant metabolism, male sterility, site specific DNA integration, plant growth, forage yield and flowering, and wherein the polynucleotide is expressed in the plant.

17. A *Sorghum bicolor* mutant plant produced by the method of claim 16, wherein the plant has the altered agronomic trait and all of the physiological and all morphological characteristics of said *Sorghum bicolor* mutant MS8.

* * * * *